US012760310B2

(12) United States Patent
Yen et al.

(10) Patent No.: US 12,760,310 B2
(45) Date of Patent: Oct. 13, 2026

(54) SYSTEM FOR REGULATING GENE EXPRESSION

(71) Applicant: Baylor College of Medicine, Houston, TX (US)

(72) Inventors: Laising Yen, Pearland, TX (US); Liming Luo, Pearland, TX (US); Jocelyn Duen-Ya Jea, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 1176 days.

(21) Appl. No.: 17/638,619

(22) PCT Filed: Aug. 28, 2020

(86) PCT No.: PCT/US2020/048561
§ 371 (c)(1),
(2) Date: Feb. 25, 2022

(87) PCT Pub. No.: WO2021/041924
PCT Pub. Date: Mar. 4, 2021

(65) Prior Publication Data

US 2022/0290147 A1 Sep. 15, 2022

Related U.S. Application Data

(60) Provisional application No. 63/043,504, filed on Jun. 24, 2020, provisional application No. 62/904,635, filed on Sep. 23, 2019, provisional application No. 62/894,611, filed on Aug. 30, 2019.

(51) Int. Cl.
*C12N 15/115* (2010.01)
*C12N 15/63* (2006.01)

(52) U.S. Cl.
CPC ............ *C12N 15/115* (2013.01); *C12N 15/63* (2013.01); *C12N 2310/16* (2013.01); *C12N 2830/50* (2013.01)

(58) Field of Classification Search
None
See application file for complete search history.

(56) References Cited

U.S. PATENT DOCUMENTS 7,825,229 B2 * 11/2010 Itzhak .................. C12Q 1/6809 435/375
8,090,542 B2 * 1/2012 Khvorova .......... C12N 15/1135 435/6.1
8,178,503 B2 * 5/2012 Rigoutsos ............. G16B 20/20 514/44 A
2005/0221430 A1 10/2005 Prentice
2005/0282190 A1 * 12/2005 Shi ........................ C07H 21/04 435/6.14
2008/0113351 A1 5/2008 Naito et al.
2010/0009410 A1 1/2010 Prentice
2011/0178283 A1 7/2011 Rigoutsos et al.
2013/0157279 A1 * 6/2013 Takoh .................. G01N 33/582 435/6.12
2013/0210897 A1 8/2013 Kay et al.
2013/0239236 A1 * 9/2013 Verhaert .............. A61K 48/005 435/254.2
2015/0141320 A1 5/2015 Krieg et al.
2015/0225717 A1 8/2015 Lee et al.
2015/0284738 A1 10/2015 Marchetti et al.
2018/0327747 A1 11/2018 Yen et al.
2021/0310003 A1 10/2021 Yen et al.

FOREIGN PATENT DOCUMENTS

JP 2007529223 A 10/2007
JP 2018533955 A 11/2018
WO 2016126747 A1 8/2016
WO WO-2017/083747 A1 5/2017
WO WO-2021/041924 A2 3/2021

OTHER PUBLICATIONS

Ashfield et al. EMBO J 13:5656-67 (Year: 1994).*
International Search Report for PCT/US20/48561, 6 pages (mailed Feb. 25, 2021).
Rosenberg, A. B. et al., Learning the Sequence Determinants of Alternative Splicing from Millions of Random Sequences., Cell, 163(3):698-711 (2015).
Written Opinion for PCT/US20/48561, 11 pages (mailed Feb. 25, 2021).
Vogel et al. “A small, portable RNA device for the control of exon skipping in mammalian cells”, Nucleic Acids Research, vol. 46, No. 8, 2018.
Beilstein et al. “Conditoinal control of mammalian gene expression by tetracycline-dependent hammerhead ribozymes”, ACS Synth.. Biol., vol. 4, pp. 526-534, 2015.
Zhong et al. “Rational design of aptazyme riboswitches for efficient control of gene expression in mammalian cells”, eLife, vol. 5, 2016.
Lou et al. “pA regulator: a system for controlling mammalian gene expression via the modulation of polyA signal cleavage”, bioRxiv, 2023.
Daniel et al. “Taping the potential of synthetic riboswitches: reviewing the versatility of the tetracycline aptamer”, RNA Biology, vol. 20, No. 1, pp. 457-468, 2023.
Berens, C. et al., “RNA aptamers as genetic control devices: The potential of riboswitches as synthetic elements for regulating gene expression”, Biotechnology Journal, vol. 10, issue 2, pp. 246-257, Feb. 11, 2015 (Nov. 2, 2015).

* cited by examiner

*Primary Examiner* — Brian Whiteman
(74) *Attorney, Agent, or Firm* — Norton Rose Fulbright US LLP

(57) ABSTRACT

Compositions and methods relating to regulation of gene expression are described. In some embodiments, the present disclosure provides compositions and methods for the regulation of gene expression using nucleic acid constructs. In some embodiments, the present disclosure recognizes the utility of alternative splicing in regulation of gene expression in a nucleic acid construct. In some embodiments, the present disclosure recognizes the utility of regulating gene expression utilizing ligand-binding aptamers.

29 Claims, 73 Drawing Sheets

Specification includes a Sequence Listing.

| | B1 | B2 | B3 | B4 |
|---|---|---|---|---|
| Induction (5ug/mL) | 1 | 1 | 1 | 4 |

| | T1 | T2 | T3 | T4 |
|---|---|---|---|---|
| Induction (5 ug/mL) | 7 | 15 | 13 | 3 |

| | F2 | F3 | F4 | F5 |
|---|---|---|---|---|
| Induction (5 ug/mL) | 2 | 3 | 1 | 1 |

box 1 ---------- box 2

N N

| | | | | | | | |
|---|---|---|---|---|---|---|---|
| Y119 | A-A | Y123 | G-A | Y127 | C-A | Y131 | T-A |
| Y120 | A-T | Y124 | G-T | Y128 | C-T | Y132 | T-T |
| Y121 | A-G | Y125 | G-G | Y129 | C-G | Y133 | T-G |
| Y122 | A-C | Y126 | G-C | Y130 | C-C | Y134 | T-C |

| (1ug/mL) | Y79 | Y119 | Y120 | Y121 | Y122 |
|---|---|---|---|---|---|
| Induction | 21 | 12 | 9 | 10 | 15 |
| | Y79 | Y123 | Y124 | Y125 | Y126 |
| Induction | 16 | 10 | 9 | 5 | 5 |
| | Y79 | Y127 | Y128 | Y129 | Y130 |
| Induction | 16 | 15 | 9 | 7 | 18 |
| | Y79 | Y131 | Y132 | Y133 | Y134 |
| Induction | 12 | 7 | 10 | 11 | 15 |

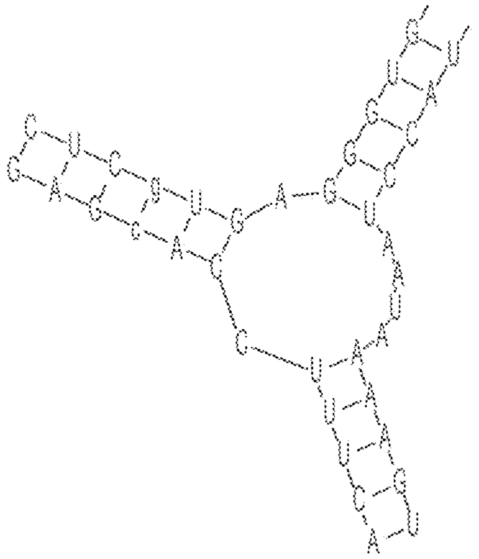
Y174
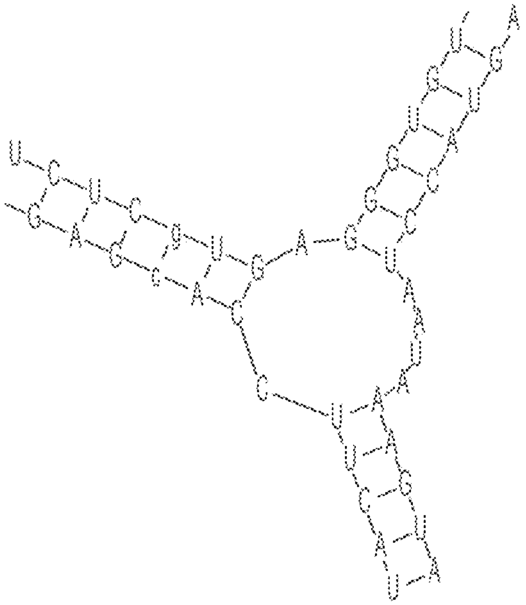
Y176
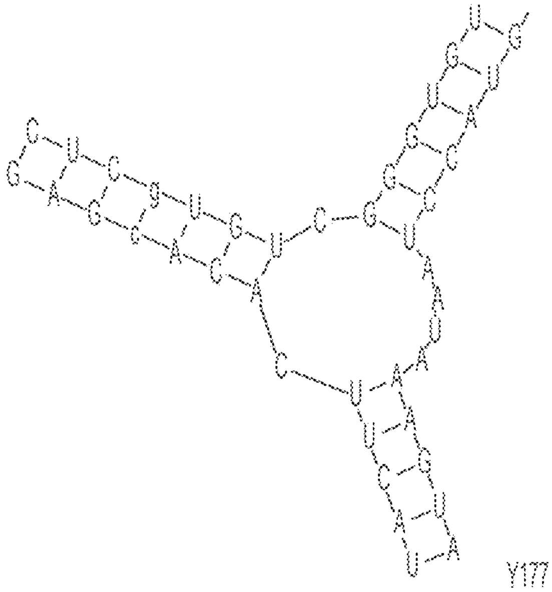
Y177
Fig. 3B

| | Y101mut | Y141 | Y142 | Y143 | Y144 | |
|---|---|---|---|---|---|---|
| Induction (1 ug/mL) | 14 | 10 | 10 | 17 | 6 | |
| | Y101mut | Y145 | Y145 | Y146 | Y147 | Y148 |
| Induction (1 ug/mL) | 14 | 10 | 8 | 12 | 19 | 6 |
| | Y101mut | Y149 | Y150 | Y151 | Y152 | |
| Induction (1 ug/mL) | 14 | 13 | 7 | 8 | 12 | |
| | Y101mut | Y153 | Y153 | Y154 | Y156 | |
| Induction (1 ug/mL) | 14 | 8 | 10 | 14 | 10 | |
| | Y101mut | Y157 | Y158 | Y159 | | |
| Induction (1 ug/mL) | 14 | 2 | 2 | 2 | | |

Fig. 4

| Induction (5ug/mL) | Y35 | Y54 | Y55 | Y56 | Y57 |
|---|---|---|---|---|---|
| | 44 | 2 | 5 | 11 | 2 |

| | Y196CAA | Y240 | Y241 | Y242 | Y243 | Y251 |
|---|---|---|---|---|---|---|
| Induction (1 ug/mL) | 36 | 1 | 1 | 1 | 1 | 1 |

| | Y196CAA | NA | NB | NC | NAB | NBC | NAC |
|---|---|---|---|---|---|---|---|
| Induction (1 ug/mL) | 35 | 37 | 9 | 8 | 8 | 4 | 5 |

| | Y196CAA | NA | NB | NC | NAB | NBC | NAC |
|---|---|---|---|---|---|---|---|
| Induction (5ug/mL) | 273 | 220 | 80 | 60 | 38 | 10 | 32 |

| | Y196CAA | Y230 | Y231 |
|---|---|---|---|
| Induction (1 ug/mL) | 39 | 25 | 23 |

| | Y196CAA | Y230 | Y231 |
|---|---|---|---|
| Induction (5ug/mL) | 279 | 100 | 151 |

Insert CAA repeats into the 5'UTR of Y196, Y208, Y209 and Y211.

Seq: gcggccgccaacaacaacaacaacaacaacaacaacaacaacataacagtgttcactagcaacctcaaacagacaccatg

| | Y196 | Y196-CAA | Y208 | Y208-CAA | Y209 | Y209-CAA | Y211 | Y211-CAA |
|---|---|---|---|---|---|---|---|---|
| Induction (5ug/mL) | 163 | 218 | 125 | 233 | 156 | 207 | 195 | 246 |

Y302: Spacer 39 bases
gcggccTTAATTAAcagtgttcactaggacaacaacaacaacaacaacaacaacaacgacaccATG Y303: Spacer 40 bases
ggcgccTTAATTAAcagtgttcactaggtacaacaacaacaacaacaacaacaacaacgacaccATG Y304 Spacer 39 bases
gcggccgcCTTAATTAAcagtgttcactaggacaacaacaacaacaacaacaacaacaacgacaccATG Y305 Spacer 40 bases
gcggccgcCTTAATTAAcagtgttcactagcatcaacaacaacaacaacaacaacaacaacgacaccATG

| | S222 | Y301 | Y302 | Y303 | Y304 | Y305 |
|---|---|---|---|---|---|---|
| Induction (1ug/mL) | 609 | 368 | 644 | 260 | 450 | 536 |

Fig. 7A

Testing new 5'UTR sequence with strong 3'ss. These are based on S56. A few examples are shown:

S70:
GCGGCCGCCAACAACAACAACAATTCCTGCTCCTCTTCTGCCCAGGAACACGCTTGCCTTCCCCAAGGCTTCCAGAAGCTCTGAGGCAGGAGGCACCAAGTTCTACCTC
ACGTTTGGAGGATCTTGCTAGCTATG

S71:
GCGGCCGCCCAGCAGATCCAGTGCTTCCTGCTCCTCTTCTGCCCAGGAACACGCTTGCCTTCCCCAAGGCTTCCAGAAGCTCTGAGGCAGGAGGCACCAAGTTCTACCT
CACGTTTGGAGGATCTTGCTAGCTATG

S74:
GCGGCCGCCAACAACAACAACAATTCCTGCTCCTCTTCTGCCCTGGAACACGCTTGCCTTCCCCAAGGCTTCCAGAAGCTCTGAGGCAGGAGGCACCAAGTTCTACCTC
ACGTTTGGAGGATCTTGCTAGCTATG

S75:
GCGGCCGCCCAGCAGATCCAGTGCTTCCTGCTCCTCTTCTGCCCTGGAACACGCTTGCCTTCCCCAAGGCTTCCAGAAGCTCTGAGGCAGGAGGCACCAAGTTCTACCT
CACGTTTGGAGGATCTTGCTAGCTATG

S78:
GCGGCCGCCAACAACAACAACAACAACAACAACAACACGCTTGCCTTCCCCAAGCTTCCACAAGCAACCTCAAACAGACACCATG

S79:
GCGGCCGCTACTAACAACACGCTTGCCTTCCCCAAGCTTCCACAAGCAACCTCAAACAGACACCATG

S80:
GCGGCCGCGCTTCCTGCTCCTCTTCTGCCCAGGAACACGCTTGCCTTCCCCAAGCTTCCACAAGCAACCTCAAACAGACACCATG

S81:
GCGGCCGCGCTTCCTGCTCCTCTTCTGCCCTGGAACACGCTTGCCTTCCCCAAGCTTCCACAAGCAACCTCAAACAGACACCATG

S82:
GCGGCCGCTACTAACGCTCCTCTTCTGCCCTGGAACACGCTTGCCTTCCCCAAGCTTCCACAAGCAACCTCAAACAGACACCATG

| | S56-e | S70-e | S71-e | S74-e | S75-e |
|---|---|---|---|---|---|
| Induction (5ug/mL) | 188 | 3 | 76 | 95 | 55 |

| | S56-e | S78-e | S80-e | S81-e | S82-e |
|---|---|---|---|---|---|
| Induction (5ug/mL) | 188 | 25 | 183 | 121 | 21 |

Fig. 7B

New unstructured 5'UTR modified from Y305

Y324: ttaattaacagtgttcactagcatcTAACCACTTACATACCATCTACCACCGACACCATG
Y325: ttaattaacagtgttcactagcatcTAACCACTTACATACCATCTACCACCGCCACCATG
Y326: ttaattaacagtgttcactagcatcTAACCACTTACATAttctgccgcctaccATG

New unstructured 5'UTR modified from Y300

Y328: gcggccgcCataacagtgttcactagcaTccCcaacagACCATCTACCACCGACACCATG
Y329: gcggccgcCataacagtgttcactagcaTccCccagACCATCTACCACCGACACCATG
Y330: gcggccgcCataacagtgttcactagcaTccCcTACCATCTACCACCGACACCATG
Y331: gcggccgcCataacagtgttcactagcaTccCcaacagACTTACATACCATTGACACCATG
Y332: gcggccgcCataacagtgttcactagcaTccCcACTTACATACCATTGACACCATG

| | Y305 | Y324 | Y325 | Y326 | Y328 | Y329 | Y330 | Y331 | Y332 |
|---|---|---|---|---|---|---|---|---|---|
| Induction (1ug/mL) | 599 | 6 | 4 | 3 | 73 | 354 | 33 | 346 | 46 |

Fig. 7C

Y322:
GCGGCCGCCTTAATTAACAACAACAACAACAACAACAACAACAACAACCAGTGTTCACTAGCATCGACAC
CATGATCCCCGGGG

Y323:
GCGGCCGCCCAACAACAACAACAACAACAACAACAACAACTTAATTAACAGTGTTCACTAGCATCGACAC
CATGATCCCCGGGG

| | Y305 | Y322 | Y323 |
|---|---|---|---|
| Induction (1ug/mL) | 599 | 67 | 12 |

Fig. 7D

Parental: Y196CAA (which has 2MAZ (in red))
GTGTGTTGGTTTTTTGTGTGAACGGGGGAGGGGGAGGAAAGGGGGAGGGGGAGCGGCCGCC Y232: identical to Y196CAA, with modified CD44 G-quad (in green) placed before 2MAZ
GTGTGTTGGTTTTTTGTGTG*GTGGTGGATTGGT*TAACGGGGGAGGGGGAGGAAAGGGGGAGGGG
GAGCGGCCGC Y233: identical to Y196CAA, with modified CD44 G-quad (in green) placed after 2MAZ
GTGTGTTGGTTTTTTGTGTGAACGGGGGAGGGGGAGGAAAGGGGGAGGGGGA*GTGGTGGTGGA*
*TTGGT*GCGGCCGC Y196CAA-3MAZ: identical to Y196CAA, with one additional MAZ
GTGTGTTGGTTTTTTGTGTGAACGGGGGAGGGGGAGGAAAGGGGGAGGGGGAGGAAAGGGGG
AGGGGGAGCGGCCGCC Y196CAA-4MAZ: identical to Y196CAA, with two additional MAZ
GTGTGTTGGTTTTTTGTGTGAACGGGGGAGGGGGAGGAAAGGGGGAGGGGGAGGAAAGGGGG
AGGGGGAGGAAAGGGGGAGGGGGAGCGGCCGCC

| | Y196CAA | Y232 | Y233 | Y196CAA3MAZ | Y196CAA4MAZ |
|---|---|---|---|---|---|
| Induction (5ug/mL) | 258 | 261 | 238 | 275 | 569 |

Fig. 8A

S177: based on S56, replacing 4MAZ with one CD44 G-quad: TGGTGGTGGAATGGT
S178: based on S56, replacing 4MAZ with two CD44 G-quad:
TGGTGGTGGAATGGTAAATGGTGGTGGAATGGT
S179: based S56, replacing 4MAZ with four CD44 G-quad:
TGGTGGTGGAATGGTAAATGGTGGTGGAATGGTA
AATGGTGGTGGAATGGTAAATGGTGGTGGAATGGT

| | S56-e | S177-e | S178-e | S179-E |
|---|---|---|---|---|
| Induction (1ug/mL) | 39 | 2 | 2 | 10 |

| | S56-e | S177-e | S178-e | S179-E |
|---|---|---|---|---|
| Induction (5ug/mL) | 139 | 2 | 2 | 46 |

Fig. 8B

S1e-S5e are based on a Y196CAA-4MAZ construct that uses eGFP-luciferase fusion protein as the reporter (indicated by "e") which has shorter half life therefore lower induction levels as compared to luciferase reporter

| | luciferase | With 4MAZ and eGFP/luc | | | | | |
|---|---|---|---|---|---|---|---|
| | Y196CAA-4MAZ | Y196CAA-4MAZ-e | S1e | S2e | S3e | S4e | S5e |
| Induction (5ug/mL) | 698 | 196 | 219 | 44 | 177 | 235 | 2 |

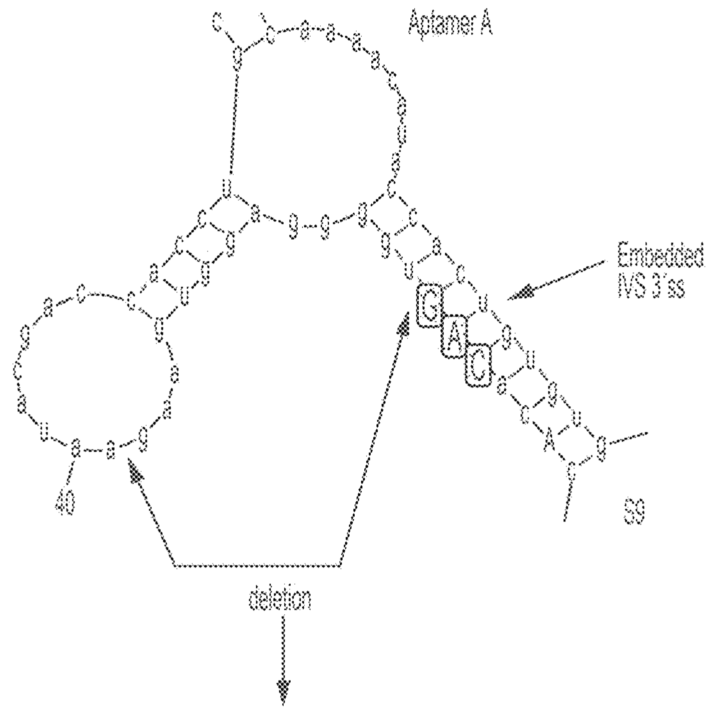
| | Y196CAA-4MAZ-e | S9-e | S9m-e |
|---|---|---|---|
| Induction (5ug/mL) | 203 | 8 | 198 |
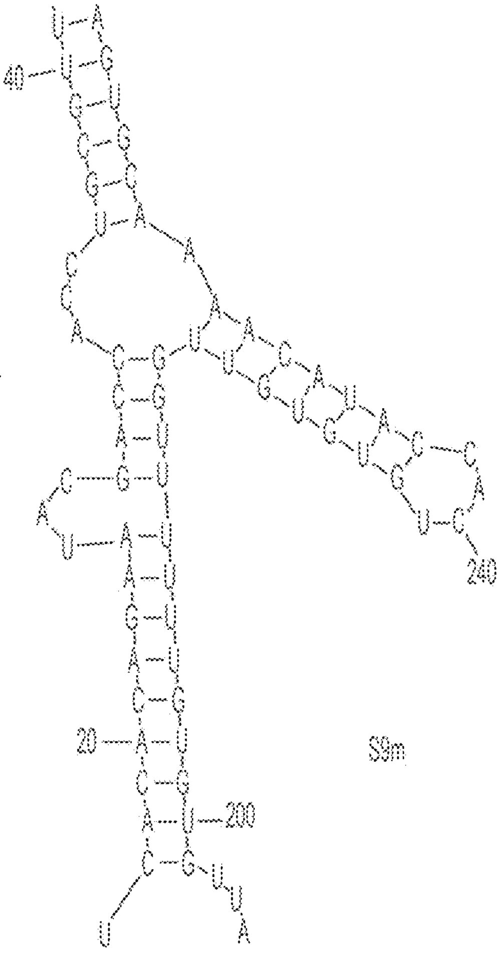
Fig. 10B

| | S9m-e | S15-e | S16-e | S19-e |
|---|---|---|---|---|
| Induction (5ug/mL) | 199 | 143 | 151 | 194 |

| | S19 | S47 | S48 | S49 | S50 |
|---|---|---|---|---|---|
| Induction (1 ug/mL) | 65 | 15 | 29 | 22 | 36 |
| | S19 | S47 | S48 | S49 | S50 |
| Induction (5ug/mL) | 112 | 172 | 164 | 134 | 41 |

S20 to S22 are based on S9m. The predicted splicing strength is indicated by the numbers in blue:
S9m: CACACAGAATACG: 0.76
S20: CACACAGGATACG: 0.88
S21: CACACAGCATACG: 0.46
S22: CACACAGATTACG: 0.92
S23 to S24 are based on Y196CAA-4MAZ, the predicted splicing strength indicated by the numbers in blue:
Y196: ttatcttcctCCCACAGCTCCTGGGCAACgtgctggtctgtgtgctggcccatcactttggcaaagaattggctagc 0.99
S23: ttatcttcctCACACAGAATACGACCgtctgtgtgctggcccatcactttggcaaagaattggctagc: 0.89
S24: ttatcttcctCACACAGCATACGACCgtctgtgtgctggcccatcactttggcaaagaattggctagc: 0.74

| | Y196CAA-4MAZ-e | S9m-e | S20-e | S21-e | S22-e | S23-e | S24-e |
|---|---|---|---|---|---|---|---|
| Induction (5ug/mL) | 182 | 197 | 178 | 202 | 171 | 191 | 195 |

Fig. 10E

Y318: ctgcagCTCCTCACCTACGCCACACACACACAAATCTGGGGA
Y319: ctgcagGCACACACACAAATCTGGGGA
Y320: ctgcagGGCACACACACACAAATCTGGGGA

| | Y302 | Y318 | Y319 | Y320 |
|---|---|---|---|---|
| Induction (1 ug/mL) | 583 | 123 | 177 | 346 |

Min-IVS2 Intron 120 bases:

GtgagtctatgccagctaccattctgcttttatttatggttgggataaggctggattattctgagtccaagctaggccctttgctaatcatCttcatacctctta
tcttcctctg*CAGNNN*aca Best NNN sequences identified by testing:
Y344-based: Y359 (CAT) ,Y360 (TTT), Y361 (TGA), Y362 (TCT)
Y358-based: Y363 (CAT), Y366 (TAC), Y367 (TTT)

| | Y344-based | | | | | Y358-based | | | |
|---|---|---|---|---|---|---|---|---|---|
| | Y344 | Y359 | Y360 | Y361 | Y362 | Y358 | Y363 | Y366 | Y367 |
| Induction (0.5ug/mL) | 200 | 171 | 186 | 156 | 204 | 144 | 172 | 233 | 140 |
| | Y344 | Y359 | Y360 | Y361 | Y362 | Y358 | Y363 | Y366 | Y367 |
| Induction (1ug/mL) | 397 | 445 | 350 | 385 | 688 | 503 | 315 | 574 | 605 |

Fig. 10G

S10: Insert a branch point: caacaacTACTAACataacagtgttcactagcaacctcaaacagacaccATG S11: Insert a PPT: caacaacTCCTGTGCTTataacagtgttcactagcaacctcaaacagacaccATG S12: Mutate CAG to CCC: caacaacataaCCCtgttcactagcaacctcaaacagacaccATG S13: mutate CAG to AAG: caacaacataaAAGtgttcactagcaacctcaaacagacaccATG

| | Y196CAA | S10 | S11 | S12 | S13 |
|---|---|---|---|---|---|
| Induction (5ug/mL) | 620 | 277 | 73 | 157 | 161 |

Fig. 11A

5'UTR sequence: gcggccgccttaattaacagtgttcactagNNNcaacaacaacaacaacaacaacaacaacaacgacaccATG Best NNN sequences identified by testing:

| | | | |
|---|---|---|---|
| R1-4 | TAG | R10-3 | TAG |
| R2-4 | ACA | R10-4 | ACC |
| R4-1 | AAC | R11-4 | AGC |
| R5-2 | TGC | R11-5 | TGA |
| R5-5 | TTG | R12-5 | TGC |
| R6-1 | ACC | R13-3 | TCC |
| R6-2 | CCC | R14-2 | AGC |
| R6-3 | AGC | R14-4 | TGC |
| R7-3 | AGG | R15-4 | CCT |
| | | R15-5 | TCT |

Induction in fold, 1ug/mL

| Y305 | R1-4 | R2-4 | R4-1 | R5-2 | R5-5 | R6-1 | R6-2 |
|---|---|---|---|---|---|---|---|
| 293 | 311 | 158 | 432 | 242 | 230 | 187 | 329 |

| Y305 | R6-3 | R7-3 | R10-4 | R10-5 | R11-5 | R12-1 | R12-5 |
|---|---|---|---|---|---|---|---|
| 216 | 73 | 195 | 248 | 185 | 191 | 162 | 223 |

| Y305 | R14-2 | R14-4 | R15-5 |
|---|---|---|---|
| 250 | 215 | 173 | 239 |

Y305R6-3 renamed as Y358

Example of NNN sequences that lead to much reduced induction:

GGC, GTG, GTC

| | | GGC | GTG | GTC |
|---|---|---|---|---|
| | Y305 | NR7-1 | NR8-1 | NR8-2 |
| Induction (1ug/mL) | 433 | 49 | 58 | 64 |

Fig. 11B inserting the best tagNNN in 5'UTR tested in Y305 into Y329

Parental sequence:
Y329 5'UTR: GcggccgcCataacagtgttcactagCATccCccagACCATCTACCACCGACACCATG
Best tagNNN tested in Y305 backbone: TAG, AAC, ACC, CCC, AGC, CCT, TCT Y341 (identical to Y329 but with NNN= TAG)
gcggccgcCataacagtgttcactagTAGccCccagACCATCTACCACCGACACCATG

Y342 (identical to Y329 but with NNN= AAC)
gcggccgcCataacagtgttcactagAACccCccagACCATCTACCACCGACACCATG

Y343 (identical to Y329 but with NNN=ACC)
gcggccgcCataacagtgttcactagACCccCccagACCATCTACCACCGACACCATG

Y344 (identical to Y329 but with NNN=CCC)
gcggccgcCataacagtgttcactagCCCccCccagACCATCTACCACCGACACCATG

Y345 (identical to Y329 but with NNN= AGC)
gcggccgcCataacagtgttcactagAGCccCccagACCATCTACCACCGACACCATG

Y346 (identical to Y329 but with NNN=CCT)
gcggccgcCataacagtgttcactagCCTccCccagACCATCTACCACCGACACCATG

Y347 (identical to Y329 but with NNN= TCT)
gcggccgcCataacagtgttcactagTCTccCccagACCATCTACCACCGACACCATG

| | Y305 | Y341 | Y342 | Y343 | Y344 | Y345 | Y346 | Y347 |
|---|---|---|---|---|---|---|---|---|
| Induction (1 ug/mL) | 276 | 332 | 406 | 481 | 525 | 246 | 231 | 74 |

Fig. 11C

S159 to S163: Shorten the IVS2 intron length of S56. S56 contains the original full-length IVS2 intron of 476 bases.
S159: Intron Size 120 bases

GTgagtctatgccagctaccattctgcttttattttatggttgggataaggctggattattctgagtccaagctaggccctttgctaatcatCttcatacctcttatcttcctc
tgCAG

S160: Intron Size 140 bases

GTgagtctatgttgctaatagcagctacaatccagctaccattctgcttttattttatggttgggataaggctggattattctgagtccaagctaggccctttgctaatc
atCttcatacctcttatcttcctctgCAG

S161: Intron Size 160 bases

GTgagtctatgctgatgtaagaggtttcatattgctaatagcagctacaatccagctaccattctgcttttattttatggttgggataaggctggattattctgagtccaa
gctaggccctttgctaatcatCttcatacctcttatcttcctctgCAG

S162: Intron Size 180 bases

GTgagtctatgtttctgcatataaattgtaactgatgtaagaggtttcatattgctaatagcagctacaatccagctaccattctgcttttattttatggttgggataaggct
ggattattctgagtccaagctaggccctttgctaatcatCttcatacctcttatcttcctctgCAG

S163: Intron Size 200 bases

GTgagtctatgaatatttctgcatataaatatttctgcatataaattgtaactgatgtaagaggtttcatattgctaatagcagctacaatccagctaccattctgcttttatt
ttatggttgggataaggctggattattctgagtccaagctaggccctttgctaatcatCttcatacctcttatcttcctctgCAG

S164 to S168: similar to S159-S163 but have a branch point TACTAAC inserted at the same location before IVS2 3'ss. The intron sequence of S164 is shown as an example:

GTgagtctatgccagctaccattctgcttttattttatggttgggataaggctggattattctgagtccaagctaggccctttgctaatcatCttcaTACTAACct
cttatcttcctctgCAG

S169 to S173: similar to S159-S163 but have a branch point TACTAAC and one more 3'ss CAG inserted at the same location before IVS2 3'ss. The intron sequence of S169 is shown as an example:

GTgagtctatgccagctaccattctgcttttattttatggttgggataaggctggattattctgagtccaagcTACTAACttttcctgtgcttcttcagacctcttatC
ttcctctgCAG

Fig. 12A

| | S56- | S159 | S160 | S161 | S162 | S163 |
|---|---|---|---|---|---|---|
| Induction (5ug/mL) | 315 | 181 | 150 | 122 | 114 | 119 |

| | S56 | S164 | S166 | S168 | S169 | S170 | S171 | S172 | S173 |
|---|---|---|---|---|---|---|---|---|---|
| Induction (5ug/mL) | 267 | 69 | 45 | 25 | 26 | 12 | 14 | 10 | 11 |

Fig. 12A
CONTINUED

Previously we have showed that CAA repeats may alter the splicing strength of the 3'ss in 5'UTR. Here the CAA repeats (in red) are to be removed from S159, S164, and S169:

Gcggccgc [caacaacaacaacaacaacaacaacaacaacaacaa] cataacagtgttcactagcaacctcaaacagacaccATG

| | S56 | S192 | S193 | S194 |
|---|---|---|---|---|
| Induction (5ug/mL) | 116 | 180 | 58 | 20 |

| | S56 | S192 | S193 | S194 |
|---|---|---|---|---|
| Induction (5ug/mL) | 298 | 279 | 86 | 30 |

Fig. 12B

| | S56 | S192 | S206 |
|---|---|---|---|
| Induction (5ug/mL) | 211 | 319 | 779 |

S206: gcggccgccataacagtgttcactagcaaccTcaaacagacaccATG

S209: gcggccgcCACCATGataacagtgttcactagcaacctcaaacagacaccATG

S210: gcggccgccataacagtgttcactagcaaccCcaaacagacaccATG

S211: gcggccgcCACCataacagtgttcactagcaaccCcaaacagacaccATG

S212: gaggccgcCACCATGataacagtgttcactagcaaccCcaaacagacaccATG

S213: gcggccgcCACCACGataacagtgttcactagcaaccCcaaacagacaccATG

S214: gcggccgcCACCataacagtgttcactagcaTccCcaaacagacaccATG

S215: gcggccgcCACCataacagtgttcacCagcaTccCcaaacagacaccATG

S222: gcggccgccataacagtgttcactagcaTccCcaaacagacaccATG

S223: gcggccgccataacagtgttcacCagcaTccCcaaacagacaccATG

| | S192 | S209 | S210 | S211 | S212 | S213 | S214 | S215 | S222 | S223 |
|---|---|---|---|---|---|---|---|---|---|---|
| Induction (1ug/mL) | 231 | 144 | 290 | 304 | 352 | 279 | 313 | 190 | 402 | 390 |

| | S192 | S209 | S210 | S211 | S212 | S213 | S214 | S215 | S222 | S223 |
|---|---|---|---|---|---|---|---|---|---|---|
| Induction (5ug/mL) | 330 | 545 | 730 | 624 | 554 | 644 | 696 | 488 | 538 | 759 |

Fig. 13B

| | Y196CAA-4MAZ | S222 | Y300 | Y301 |
|---|---|---|---|---|
| Induction (0.5ug/mL) | 33 | 187 | 100 | 285 |

| | Y196CAA-4MAZ | S222 | Y300 | Y301 |
|---|---|---|---|---|
| Induction (1ug/mL) | 117 | 454 | 259 | 311 |

Y362
| Tc con. | 0 | 0.5 | 1 | 2.5 | 5 | 7.5 |
|---|---|---|---|---|---|---|
| Mean induction | 1 | 172 | 471 | 713 | 766 | 797 |
| std | 0 | 44 | 54 | 86 | 77 | 54 |
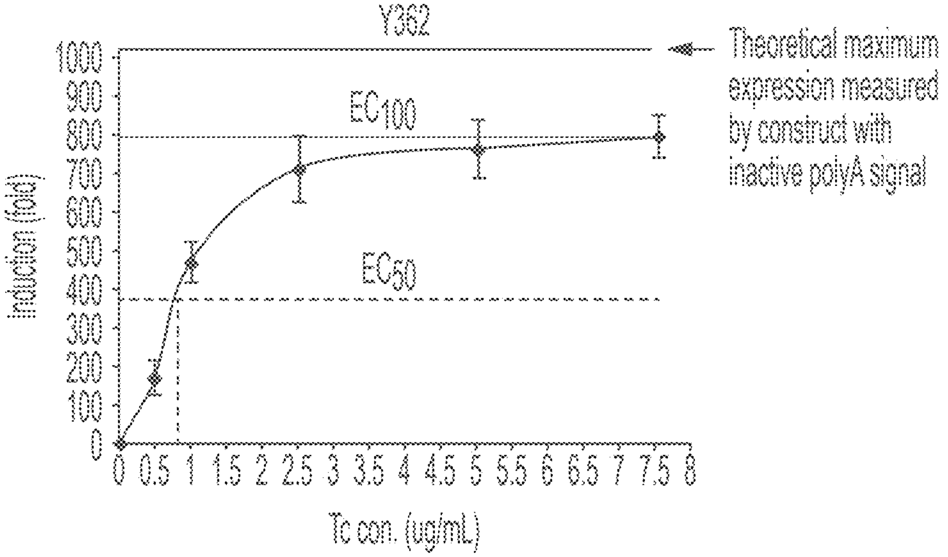
Y367
| Tc con. | 0 | 0.5 | 1 | 2.5 | 5 | 7.5 |
|---|---|---|---|---|---|---|
| Mean induction | 1 | 138 | 496 | 917 | 1071 | 1147 |
| std | 0 | 36 | 96 | 161 | 153 | 147 |
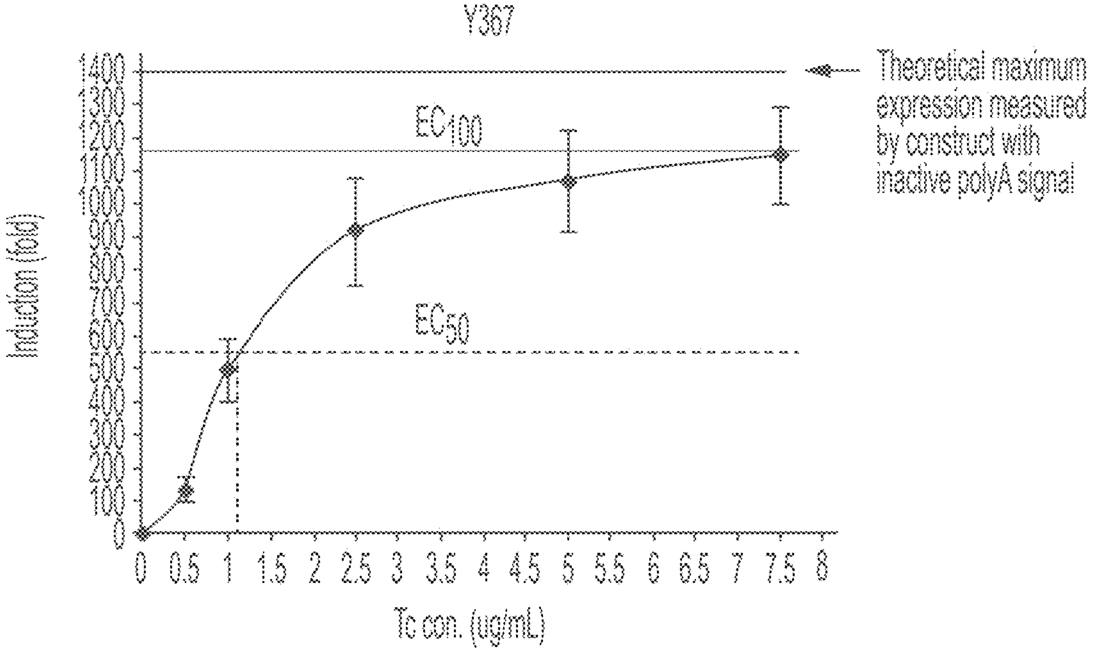
Fig. 14D

| | Y359 | Y392 | Y395 | Y360 | Y393 | Y396 | Y361 | Y394 | Y397 | Y362C | Y362 | Y387 |
|---|---|---|---|---|---|---|---|---|---|---|---|---|
| Mean Induction | 472 | 631 | 925 | 407 | 555 | 775 | 424 | 483 | 922 | 260 | 627 | 735 |
| std | 55 | 64 | 88 | 45 | 45 | 48 | 63 | 53 | 57 | 20 | 19 | 84 |

| Tc [ug/ml] | 0.0 | 0.5 | 1.0 | 2.5 | 5.0 | 7.5 |
|---|---|---|---|---|---|---|
| Y362 | 1 | 332 | 654 | 918 | 896 | 891 |
| Y387 | 1 | 464 | 710 | 854 | 835 | 798 |
| std-Y362 | 0 | 45 | 73 | 139 | 173 | 158 |
| std-Y387 | 0 | 27 | 38 | 74 | 108 | 90 |

| Tc [ug/ml] | 0.0 | 0.5 | 1.0 | 2.5 | 5.0 | 7.5 |
|---|---|---|---|---|---|---|
| Y362 | 0.074% | 23.3% | 46.2% | 65.1% | 63.8% | 65.5% |
| Y387 | 0.104% | 47.5% | 71.7% | 87.0% | 85.6% | 83.3% |
| std-Y362 | 0.013% | 3.8% | 5.2% | 6.1% | 8.8% | 8.9% |
| std-Y387 | 0.014% | 7.5% | 8.8% | 10.8% | 9.4% | 8.5% |

SYSTEM FOR REGULATING GENE EXPRESSION

CROSS REFERENCE TO RELATED APPLICATIONS

This application is a national stage application under 35 U.S.C. § 371 of International Application No. PCT/US2020/048561 filed on Aug. 28, 2020, which claimed the benefit of U.S. Provisional Application No. 62/894,611, filed on Aug. 30, 2019, U.S. Provisional Application No. 62/904,635, filed on Sep. 23, 2019, and U.S. Provisional Application No. 63/043,504, filed Jun. 24, 2020, the contents of each of which are incorporated herein by reference in their entirety.

GOVERNMENT LICENSE RIGHTS

This invention was made with government support under EB013584 awarded by the National Institutes of Health. The government has certain rights in the invention.

REFERENCE TO SEQUENCE LISTING

The application contains a Sequence Listing in compliance with ST. 26 format and is hereby incorporated by reference in its entirety. Said Sequence Listing, created on Feb. 25, 2022 is named Sequence_Listing.txt and is 192,628 bytes in size.

BACKGROUND

Nucleic acid based constructs for modulating expression of genes can be improved by increasing sensitivity and reducing leakiness.

SUMMARY

The present disclosure recognizes a discovery of nucleic acid constructs related to regulatable gene product expression. In some embodiments, the present disclosure provides compositions and methods for the regulation of gene expression using nucleic acid constructs. In some embodiments, the present disclosure recognizes the utility of alternative splicing in regulation of gene expression in a nucleic acid construct. In some embodiments, the present disclosure recognizes the utility of regulating gene expression utilizing ligand-binding aptamers.

In some embodiments, the present disclosure provides a system for modulating gene expression, comprising a polyA aptamer polynucleotide that comprises in a 5' to 3' direction: a 5' splice donor site; an engineered intron; a first 3' splice acceptor site; a polyA switch comprising two or more ligand-binding aptamers with one or more ligand binding pockets, and at least one polyA cleavage signal therein; a second 3' splice acceptor site; and a nucleic acid sequence encoding an expressible polypeptide.

In some embodiments, a polyA aptamer polynucleotide of the present disclosure comprises two ligand-binding aptamers. In some embodiments, a polyA aptamer polynucleotide comprises three ligand-binding aptamers. In some embodiments, a polyA aptamer polynucleotide comprises a polyA switch comprising a three way junction. In some embodiments, a three way junction comprises a junction of one or more RNA double stranded stems. In some embodiments, portions of a three way junction are single stranded. In some embodiments, a RNA double stranded stem comprises a ligand-binding aptamer. In some embodiments, a nucleic acid sequence encoding an expressible polypeptide comprises a 5'UTR.

In some embodiments, the present disclosure provides a method for modulating expression of a gene product in a cell. The method comprises the steps of: introducing into the cell a system comprising in a 5' to 3' direction: a 5' splice donor site; an engineered intron; a first 3' splice acceptor site; a polyA switch comprising two or more ligand-binding aptamers with one or more ligand binding pockets, and at least one polyA cleavage signal therein; a second 3' splice acceptor site. In some embodiments a gene product expressed by the methods described herein is exogenous to the cell. In some embodiments, a gene product expressed by the methods described herein is endogenous to the cell. In some embodiments, a method provided by the present disclosure occurs in one or more cells of an individual, the ligand is glucose, the individual has diabetes, pre-diabetes, or complications from diabetes, and/or the expressible polynucleotide is insulin. In some embodiments, a method provided by the present disclosure occurs in one or more cells of an individual, the expressible polynucleotide is a therapeutic gene product such as human growth hormone, coagulation factor X, or dystrophin. In some embodiments, a method provided by the present disclosure occurs in one or more cells of an individual, the ligand is the gene product of a cancer biomarker, and the expressible polynucleotide is a suicide gene. In some embodiments, a method provided by the present disclosure occurs in an individual, the expressible polynucleotide is a reporter gene, and the location and/or intensity of the expression of the reporter gene provides information about spatial distribution, temporal fluctuation, or both, of a ligand in one or more cells of the individual. In some embodiments, a method provided by the present disclosure occurs in an individual, tissue, or cell, wherein the expressible polynucleotide encodes a detectable gene product, and wherein the respective individual, tissue, or cell is imaged.

BRIEF DESCRIPTION OF THE DRAWING

FIG. 1A depicts mechanism of the 'hybrid' switch based on ligand-inducible alternative splicing and polyA signal cleavage. FIG. 1B depicts configuration of Y-shape polyA switch. The name of different parts of Y-shape structure is labeled. FIG. 1C shows the configuration of a representative Y-shaped polyA switch Y196CAA (SEQ ID NO: 6).

FIGS. 2A and 2B shows alternative Y-shape configurations with three aptamers (aptamer A, B, and C) arranged differently around the 3-way junction. FIG. 2C shows three aptamers stacked on each other without 3-way junction.

FIG. 3B shows the best 3-way junction sequences (SEQ ID NO: 407-413 and 475).

FIG. 4 demonstrate results of modification of a polyA signal relative to the location of a 3-way junction of a polyA aptamer polynucleotide described herein.

FIG. 5A shows the results with the orientation of aptamer B reversed (SEQ ID NO: 46, 181, 413, 191, and 407-413). FIG. 5B shows the results with the orientation of aptamer A orientation reversed (SEQ ID NO: 6, 426, 427, 428, 429, 419, 417, 416, 415, 424, and 425).

FIG. 6A shows the effect of inactivating each aptamer by an A to C point mutation (indicated by the arrow, SEQ ID NO: 432). FIG. 6B shows the effect of deleting aptamer A on induction (SEQ ID NO: 433).

FIGS. 7A-7D demonstrate results of modification of a 5'UTR of the expressible polynucleotide following a polyA aptamer polynucleotide described herein. FIG. 7A shows results of inserting CAA repeats (underlined) in the 5'UTR of the expressible polynucleotide using different parental constructs (SEQ ID Nos: 434-438). FIG. 7B shows results of testing new 5'UTR sequence with strong 3' splice site using S56 as the parental construct (SEQ ID Nos: 439-447). FIG. 7C shows the results of inserting unstructured spacer sequence into 5'UTR of Y305 and Y300 (SEQ ID Nos: 448-455). FIG. 7D shows inserting CAA repeats before the 3' splice site in 5'UTR (SEQ ID Nos: 456 and 457).

FIGS. 8A-8B show the importance of G quad sequences of a polyA aptamer polynucleotide described herein. FIG. 8A shows the effects of G-quad sequence on induction using Y196CAA as the parental construct (SEQ ID Nos: 458-462). FIG. 8B shows results of testing different G-quad sequences to replace 4MAZ G-quad using S56 as the parental construct (SEQ ID Nos: 463-645).

FIGS. 10A-10G demonstrate results of modification of a first 3'splice acceptor site of a polyA aptamer polynucleotide described herein. FIG. 10A shows results of moving IVS2 3' splice site into arm1-1 of Y196CAA-4MAZ (SEQ ID No: 6 and 466-473). FIG. 10B shows that the first 3' splice site is strongly inhibited when completely embedded into the arm1-1 near aptamer A (arrow), resulting in very low induction (SEQ ID NO: 6 and 476-470). Diminishing the clamping effect of aptamer A by deleting part of its sequence restores the induction. FIG. 10C shows results of moving the IVS 3' splice site (box) along the arm 1 of S9m (SEQ ID NO: 6 and 480-486), and FIG. 10D shows results of placing the IVS 3' splice site in the bulge of arm1-2 (SEQ ID NO: 6 and 488-494). FIG. 10E shows results of changing the predicted strength of splicing by mutating the base after IVS2 3' splice site (SEQ ID NO: 495-501). FIG. 10F shows results of moving mini-IVS2 3' splice site further into or away from aptamer A in arm 1-1. FIG. 10G shows randomization of the three bases after the first 3' splice site (CAGNNN) (SEQ ID NO: 521).

FIGS. 11A-11C demonstrate results of modification of a second 3'splice acceptor site of a polyA aptamer polynucleotide described herein. FIG. 11A shows results of modifications of 5'UTR to alter the strength of the alternative 3' splice site (SEQ ID Nos: 522-525). FIG. 11B shows results of randomization of the three bases after 'TAG' in 5'UTR (TAGNNN) to modulate the strength of the alternative 3' splice site in order to improve the induction (SEQ ID NO: 526). FIG. 11C shows the results of incorporating the best TAGNNN sequences selected from randomization into Y329 5'UTR (SEQ ID Nos: 527-534).

FIGS. 12A and 12B demonstrate results of modification of the size of an engineered intron of a polyA aptamer polynucleotide described herein. FIG. 12A shows results of varying the size and splicing elements of the IVS2 intron (SEQ ID Nos: 535-541). FIG. 12B shows results of removing CAA repeats from the constructs (S159, S164 and S169) with the shorter engineered intron (SEQ ID NO: 542).

FIGS. 13A-13C demonstrate results of inclusion of an upstream open reading frame (μORF) in a polyA aptamer polynucleotide described herein. FIG. 13A shows the schematics of inclusion of an upstream open reading frame in a polyA aptamer. The inserted upstream ATG start codon is boxed (SEQ ID NO: 543). FIG. 13B shows results of fine-tuning the 5'UTR sequence of constructs with an upstream open reading frame (SEQ ID NOs: 544-553). FIG. 13C shows one representative hybrid switch with the inclusion of an upstream open reading frame (SEQ ID NO: 554).

FIGS. 14A-14E demonstrate the ability of a polyA aptamer polynucleotide described herein to control the gene expression of an expressible polypeptide in the presence of a ligand. FIG. 14A show the performance of representative S series constructs vs. Y196CAA-4MAZ. FIG. 14B shows dose response of representative S series constructs vs. Y196CAA-4MAZ visualized by microscopy. FIG. 14C shows the performance of Y300 and Y301. FIG. 14D shows the dose response of Y362 and Y367 determined by luciferase reporter assays. FIG. 14E shows the response to 1 ug/ml tetracycline of Y362 and Y367 as determined by fluorescence activated cell sorting (FACS) using eGFP reporter signal. 'Induction in fold' in all results is calculated as the ratio of transgene expression in the presence vs. absence of tetracycline.

FIG. 18A shows that the induction by tetracycline reaches 50% of the maximal level ($EC_{50}$) at as low as 0.5 to 1 μg/ml Tc using the maximum induction in fold as the $EC_{100}$ reference. FIG. 18B shows a similar calculation using the maximum expression level of parental construct (HDM-Luc, which has similar sequence but without the Y-shape structure) as the $EC_{100}$ reference. In this case, $EC_{50}$ is reached by tetracycline as low as 0.5 to 1.2 μg/ml.

DETAILED DESCRIPTION OF CERTAIN EMBODIMENTS

Figure 1A:
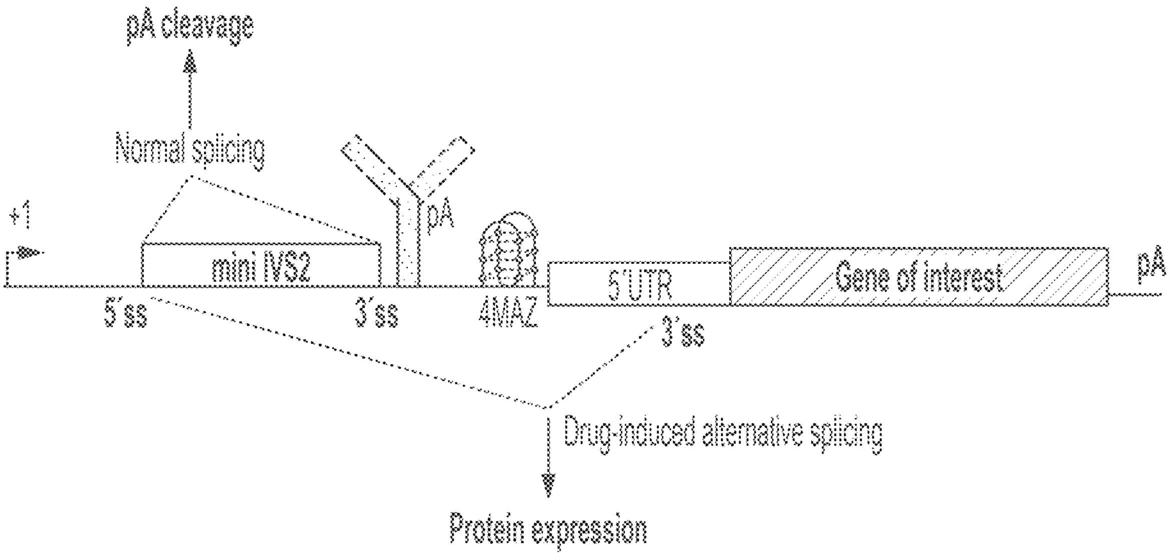
FIGS. 1A-1C provide schematics of aspects of a polyA aptamer polynucleotide described herein.

In some embodiments, the present disclosure provides compositions and methods for regulatable gene product expression. In some embodiments, compositions and methods for regulatable gene product expression comprise a polyA aptamer polynucleotide. In some embodiments, a polyA aptamer polynucleotide comprises, amongst other things, one or more splice donor sites, one or more splice acceptor sites, an engineered intron; a polyA switch; and a nucleic acid sequence encoding an expressible polypeptide. In some embodiments, a polyA switch comprises at least one ligand-binding aptamer. In some embodiments, a polyA switch comprises at least one polyA cleavage signal. In some embodiments, a polyA aptamer polynucleotide comprises RNA double strand stems.

Aptamer

Aptamers are short RNA sequences that fold like receptors and bind to specific ligands. Efficient in vitro evolution methods for generating aptamers with high affinity to specific ligands are well established. The binding affinity of aptamers can often reach nanomolar range, comparable to that of antibodies. In this regard, aptamers can be viewed as antibodies made of RNA. What distinguishes an aptamer from an antibody are its small size (often smaller than 50 bases) and its modular nature. These features enable aptamers to integrate with and control other RNA structures without losing its binding function. It has been demonstrated that aptamers can transform the self-cleaving RNA ribozymes to operate in a ligand-dependent manner, and function like a molecular switch in test tubes and in cells.

In some embodiments, a polyA aptamer polynucleotide comprises one or more RNA double stranded stems. In some embodiments, a RNA double stranded stem is a nucleic acid structure formed by intramolecular base pairing of complementary nucleic acids contained within a single polyA aptamer polynucleotide. In some embodiments, a RNA double stranded stem may also be referred to as an arm. In some embodiments, a polyA aptamer polynucleotide comprises one or more RNA double strand stems. In some embodiments, a polyA aptamer polynucleotide comprises two RNA double strand stems. In some embodiments, a polyA aptamer polynucleotide comprises three RNA double strand stems. In some embodiments, a RNA double stranded stem comprises ligand binding aptamer. In some embodiments, a polyA aptamer polynucleotide comprises two ligand binding aptamers. In some embodiments, a polyA aptamer polynucleotide comprises three ligand binding aptamers.

In some embodiments, at least two RNA double stranded stems are joined to form a junction. In some embodiments, a junction of RNA double stranded stems comprises a single stranded region. In some embodiments, three RNA stems meet to form a three way junction. In some embodiments, a three way junction comprises at least one single stranded region. In some embodiments, a three way junction comprises one, two, or three single stranded regions.

In some embodiments the sequence of a double stranded RNA stem is selected from one of the following:

| SEQ ID NO.: | SEQUENCE (5' to 3') |
|---|---|
| 2 | GGGUGUUUGUGGC |
| 3 | CACGAGAUCUGG |
| 4 | GCGUUUUAUACUU |
| 5 | CUCUGCAGAUGUU |

In some embodiments, a single stranded region formed by a junction of RNA double stranded stems comprises at least one nucleic acid. In some embodiments, a single stranded region formed by a junction of RNA double stranded stems comprises one, two, three, four, five, six, seven, eight, nine, ten, eleven, twelve, or more nucleic acids. In some embodiments, a three way junction comprises a first, second, and third single stranded regions. In some embodiments, a first single stranded region comprises at least one base selected from C and A. In some embodiments, a second single stranded region comprises at least one base selected from C and A.

In some embodiments, a RNA double stranded stem is 30, 20, 10, or 5 base pairs in length. In some embodiments, a RNA double stranded stem is 5 to 30, 10 to 30, 20 to 30, 5 to 10, 5 to 20, 5 to 30, or 10 to 20 base pairs in length. In some embodiments, a RNA double stranded stem is up to 30 base pairs in length. In some embodiments, a RNA double stranded stem is less than 30, 20, or 10 base pairs in length.

In some embodiments, a polyA aptamer polynucleotide comprises one or more aptamers. In some embodiments, a polyA aptamer polynucleotide comprises two aptamers. In some embodiments, a polyA aptamer polynucleotide comprises three aptamers.

In some embodiments, an aptamer included in a polyA aptamer polynucleotide described herein comprises at least one single stranded region and at least one aptamer RNA double stranded stem. In some embodiments, an aptamer RNA double stranded stem comprises a single stranded region. In some embodiments, an aptamer RNA has an RNA double stranded stem with a sequence of AATAAGATTACCGAAAGGCAATCTTATT (e.g., arm2-2). In some embodiments, an aptamer RNA has an RNA double stranded stem with a sequence of CCAGATCGAATTCGATCTGG (e.g., are 3-2). In some embodiments, an aptamer RNA has an RNA double stranded stem with a length ranging from 6-10; 7-11; 8-12; 9-13; 10-14 base pairs in length.

PolyA Cleavage Signal

In accordance with various embodiments, any of a variety of polyA signals (e.g., encoded by a polyA signal sequence) may be used. By way of non-limiting example, a polyA signal sequences used in mammalian cells include: AAUAAA, AUUAAA, AGUAAA, ACUAAA, UAUAAA, CAUAAA, GAUAAA, AAUAUA, AAUACA, and AAUAGA. In some embodiments, a polyA switch may include two or more polyA signal sequences (e.g., 3, 4, 5, 6, 7, 8, 9, 10 or more).

Polyadenylation is a foundational mRNA processing mechanism that is present in all mammalian cells. Typically, mammalian polyA signals are found in the 3' untranslated region (UTR). In contrast, the present disclosure provides compositions and methods that comprise a polyA cleavage signal present in an expression construct at a location other than at the 3' untranslated region (UTR) of an expressible polynucleotide, such as a gene. When a polyA signal is artificially created in the 5' UTR, where it is not normally found in cells, efficient cleavage of the polyA signal leads to the addition of polyA tail at the site. This results in the removal and degradation of the second half of the associated mRNA with transgene sequence, and therefore a loss of gene expression. In some embodiments, the polyA signal is present upstream of the translation start site of a nucleic acid sequence encoding an expressible polynucleotide (mRNA) encoding an expressed polypeptide. In some embodiments, the polyA signal is located in the 5' UTR of the mRNA. In some embodiments, a single stranded region of a 3-way junction comprises all or a portion of the polyA cleavage signal. In some embodiments, the third single stranded region of a 3-way junction comprise all or a portion of the polyA cleavage signal. In some embodiments, a RNA double stranded stem comprises all or a portion of the polyA cleavage signal. In some embodiments, the third RNA double stranded stem comprises all or a portion of the polyA cleavage signal. In some embodiments, a portion of the polyA cleavage signal, as used herein, includes one, two, three, or four nucleotides. In some embodiments, a polyA cleavage signal has a sequence of AAUAAA. In some embodiments, a polyA cleavage signal has a sequence of AUUAAA, AGUAAA, ACUAAA, UAUAAA, CAUAAA, GAUAAA, AAUAUA, AAUACA, AAUAGA, AAAAAG, or ACUAAA. In embodiments wherein two or more polyA signals are utilized in the construct, the polyA signals may be the same or may be different. In particular embodiments, the expressible polynucleotide is able to be transcribed by RNA polymerase II.

In some embodiments, the presence of the polyA cleavage signal in the 5' UTR targets the second half of mRNA after the polyA signal for degradation, and this ability is exploited in the various compositions and methods of the present disclosure. In some embodiments, the presence of the polyA cleavage signal in the 5' UTR results in cleavage of a pre-mRNA/mRNA encoded by a polyA aptamer polynucleotide. In some embodiments, cleavage of a pre-mRNA/mRNA encoded by a polyA aptamer polynucleotide results in degradation of the second half of pre-mRNA/mRNA. In some embodiments, cleavage of a pre-mRNA/mRNA encoded by a polyA aptamer polynucleotide results in no expression of a polypeptide.

In particular embodiments, the polyA cleavage signal is within a polyA aptamer polynucleotide comprising at least one ligand-binding aptamer to which one or more ligands can bind. In some embodiments, binding of the ligand to the ligand-binding aptamer determines whether or not the polyA cleavage signal is present in the pre-mRNA/mRNA after alternative splicing. In some embodiments, binding of the ligand to the ligand-binding aptamer determines whether or not the pre-mRNA/mRNA is cleaved after alternative splicing. In some embodiments, binding of the ligand to the ligand-binding aptamer determines whether or not an expressible polypeptide is expressed after alternative splicing.

Engineered Intron

In some embodiments, a polyA aptamer polynucleotide comprises an engineered intron. In some embodiments, an engineered intron comprises one or more splice sites. In some embodiments, a splice site is or comprises a splice donor site (e.g, comprising a GU sequence). In some embodiments a splice site is or comprises a splice acceptor site (e.g., comprising an AG sequence). In some embodiments, splice sites in an engineered intron function (e.g., in conjunction with each other and/or in conjunction with one or more endogenous splice site(s)) to excise an engineered intron from a polyA aptamer polynucleotide.

In some embodiments, an engineered intron is preceded by a 5' splice donor site. In some embodiments, a polyA aptamer polynucleotide comprises a 5' splice donor site in the region 5' of an engineered intron. In some embodiments, a polyA aptamer polynucleotide comprises a first 3' splice acceptor site 3' of an engineered intron. In some embodiments, an engineered intron of a polyA aptamer polynucleotide described herein comprises a 5' splice donor site and a first 3' splice acceptor site. In some embodiments, a polyA aptamer polynucleotide comprises a nucleic acid sequence encoding an expressible polypeptide. In some embodiments, a polyA aptamer polynucleotide comprises a second 3'splice acceptor site immediately 5' of a nucleic acid sequence encoding an expressible polypeptide.

In some embodiments, a polyA aptamer polynucleotide comprises a promoter 5' of the splice donor site. Exemplary promoters include, e.g., CMV, E1F, VAV, TCRvbeta, MCSV, an SV40 promoter, an RSV promoter, and PGK promoter.

In some embodiments, in the absence of a ligand bound to a ligand-binding aptamer, splicing of the pre-mRNA encoded by a polyA aptamer polynucleotide described herein occurs between the 5' splice donor site and the first 3' splice acceptor site. In some embodiments, splicing between the 5' splice donor site and the first 3' splice acceptor site of a pre-mRNA encoded by a polyA aptamer polynucleotide described herein results in an mRNA comprising a polyA cleavage signal preceding a 5'UTR of a nucleic acid sequence encoding an expressible polypeptide. In some embodiments, presence of a polyA cleavage signal preceding a 5'UTR of a nucleic acid sequence encoding an expressible polypeptide results in cleavage at the polyA cleavage site and degradation of the sequence encoding an expressible polypeptide.

In some embodiments, in the presence of a ligand bound to a ligand-binding aptamer, splicing of the pre-mRNA encoded by a polyA aptamer polynucleotide described herein occurs between the 5' splice donor site and the second 3' splice acceptor site. In some embodiments, splicing of the pre-mRNA encoded by a polyA aptamer polynucleotide described herein between the 5' splice donor site and the second 3' splice acceptor site results in an mRNA comprising a nucleic acid sequence encoding an expressible polypeptide. In some embodiments, splicing of the pre-mRNA encoded by a polyA aptamer polynucleotide described between the 5' splice donor site and the second 3' splice acceptor site results in removal of polyA cleavage signal by splicing it out. In some embodiments, splicing between the 5' splice donor site and the second 3' splice acceptor site of the pre-mRNA encoded by a polyA aptamer polynucleotide described herein results in the expression of an expressible polypeptide.

In some embodiments, a polyA aptamer polynucleotide comprises two or more ligand-binding aptamers. In some embodiments, each of two or more ligand binding aptamers binds a different ligand. In some embodiments, a polyA aptamer polynucleotide comprises two or more separate polyA switches. In some embodiments, a first polyA switch comprises a first aptamer that binds a first ligand, and a second polyA switch comprises a second aptamer that binds a second ligand. In some embodiments the first and second aptamers are non-identical and the first and second ligands are non-identical. In some embodiments, the first and second aptamers are non-identical and the first and second ligands are identical.

In some embodiments, an engineered intron is any sequence. In some embodiments, an engineered intron is approximately 100, 200, 300, 400, or 500 nucleotides in length. In some embodiments, an engineered intron is in the range of 100-200; 110-200; 120-200; 130-200; 140-200; 150-200; 160-200; 170-200; or 180-200 bases in length. In some embodiments, an engineered intron is at most 100, 110, 120, 130, 140, 150, 160, 170, 180, 190, 200, 210, 220 bases in length. In some embodiments, an engineered intron has the following sequence:

(SEQ ID NO.: 1)
GTGAGTCTTAAGCCAGCTACCATTCTGCTTTTATTTTATCGTTGGGATAA

GGCTGGATTATTCTGAGTCCAAGCTAGGCCCTTTTGCTAATCATCTTCAT

ACCTCTTATCTTCCTCTGCAG

In some embodiments, an engineered intron has the following sequence:

(SEQ ID NO.: 49)
GTGAGTCTATGGGACCCTTGATGTTTTCTTTCCCCTTCTTTTCTATGGTT

AAGTTCATGTCATAGGAAGGGGAGAAGTAACAGGGTACACATATTGACCA

AATCAGGGTAATTTTGCATTTGTAATTTTAAAAAATGCTTTCTTCTTTTA

ATATACTTTTTTGTTTATCTTATTTCTAATACTTTCCCTAATCTCTTTCT

TTCAGGGCAATAATGATACAATGTATCATGCCTCTTTGCACCATTCTAAA

GAATAACAGTGATAATTTCTGGGTTAAGGCAATAGCAATATTTCTGCATA

TAAATATTTCTGCATATAAATTGTAACTGATGTAAGAGGTTTCATATTGC

TAATAGCAGCTACAATCCAGCTACCATTCTGCTTTTATTTTATGGTTGGG

ATAAGGCTGGATTATTCTGAGTCCAAGCTAGGCCCTTTTGCTAATCATGT

TCATACCTCTTATCTTCCTCCCACAG

As used herein, an intron can refer to either a DNA sequence or its corresponding RNA sequence.

In some embodiments a polyA aptamer polynucleotide comprises additional sequences to facilitate, regulate or assist polyA signal cleavage within a polyA aptamer polynucleotide. In some embodiments, a polyA aptamer polynucleotide comprises a G-U rich region 5' of the nucleic acid sequence encoding the expressible polypeptide and 3' of the polyA cleavage signal. In some embodiments a polyA aptamer polynucleotide comprises additional sequences to facilitate, regulate or assist splicing within a polyA aptamer polynucleotide. In some embodiments, a polyA aptamer polynucleotide comprises a nucleic acid triplet sequence capable of modulating the strength of alternative splicing. In some embodiments, a nucleic acid triplet sequence is 3' relative to the second 3'acceptor site in the 5'UTR. In some embodiments, a nucleic acid triplet sequence is 3' of an engineered intron. In some embodiments, a sequence of a nucleic acid triplet sequence comprises any three nucleotides. In some embodiments, a sequence of a nucleic acid triplet sequence comprises TAG, TCT, TTC, TTG, TGA, TGC, TCC, ACA, AAC, ACC, AGC, AGG, CCT, CCC, TTT, TGA, TCT, TAC, CAC, or CAT.

In some embodiments, a polyA aptamer polynucleotide comprises a G-U rich region 5' of the nucleic acid sequence encoding the expressible polypeptide and 3' of the polyA cleavage signal. In some embodiments, a polyA aptamer polynucleotide comprises a G rich region 5' of the nucleic acid sequence encoding the expressible polypeptide and 3' of the G-U rich region. In some embodiments, a G rich region is understood in the art to be a MAZ sequence. In some embodiments, a polyA aptamer polynucleotide comprises one or more G rich regions. In some embodiments, a polyA aptamer polynucleotide comprises one or more consecutive G rich regions. In some embodiments, a polyA aptamer polynucleotide comprises one or more MAZ sequences. In some embodiments, a polyA aptamer polynucleotide comprises one or more consecutive MAZ sequences. In some embodiments, a polyA aptamer polynucleotide comprises one, two, three, four, five, six MAZ sequences. The consecutive MAZ may be separated by one or more spacer sequences. In some embodiments the sequence of a G rich region is (SEQ ID NO.: 47)
AACGGGGGAGGGGGAGGAAAGGGGGAGGGGGAGGAAAGGGGGAGGGGGAG

GAAAGGGGGAGGGGGA.

In some embodiments, a polyA aptamer polynucleotide comprises one or more start codons. In some embodiments, a polyA aptamer polynucleotide comprises one or more out of frame start codons. In some embodiments, an out of frame start codon is out of frame relative to the coding sequence of a nucleic acid sequence encoding an expressible polypeptide. In some embodiments, a polyA aptamer polynucleotide comprises at least one out of frame start codon. In some embodiments, a polyA aptamer polynucleotide comprises at least one out of frame start codon 3' of a first 3' splice acceptor site 3' of an engineered intron.

Expressible Polypeptide

In some embodiments, a polyA aptamer polynucleotide comprises a nucleic acid sequence encoding an expressible polypeptide. In some embodiments, a nucleic acid sequence encoding an expressible polypeptide comprises a 5'UTR. In some embodiments, a 5' UTR of a nucleic acid sequence encoding an expressible polypeptide comprises a 3'splice acceptor site. In some embodiments, a 5' UTR of a nucleic acid sequence encoding an expressible polypeptide comprises a branch point and a 3'splice acceptor site. A branch point is understood in the art to comprise a nucleotide or nucleotides involved in initiating a nucleophilic attack on the 5' donor splice site. In some embodiments, a 5' UTR of a nucleic acid sequence encoding an expressible polypeptide does not comprise a branch point. In some embodiments, a 5' UTR of a nucleic acid sequence encoding an expressible polypeptide comprises a spacer sequence. In some embodiments, a spacer sequence comprises at least one CAA repeat. In some embodiments a 5'UTR of a nucleic acid sequence encoding an expressible polypeptide has a sequence of (SEQ ID NO.: 48)
GCGGCCGCCTTAATTAACAGTGTTCACTAGAGCCAACAACAACAACAACA

ACAACAACAACAACGACACC

In some embodiments, a nucleic acid sequence encoding an expressible polypeptide contemplated in the present disclosure can be any nucleic acid sequence or any gene encoding any polypeptide. In some embodiments, a nucleic acid sequence encoding a non-coding RNA. In some embodiments, a nucleic acid sequence encoding an expressible polypeptide contemplated in the present disclosure can be an exogenous nucleic acid. In some embodiments, a nucleic acid sequence encoding an expressible polypeptide contemplated in the present disclosure can be a gene endogenous to a subject to which a polyA aptamer polynucleotide has been introduced. In some embodiments, a polyA aptamer polynucleotide of the present disclosure is introduced into a region of an individual's genome that regulates expression of a gene of interest. Accordingly, in some embodiments, a polyA aptamer polynucleotide of the present disclosure can be used to regulate expression of genes endogenous to an individual. In some embodiments, a nucleic acid sequence encoding an expressible polypeptide of a polyA aptamer polynucleotide of the present disclosure is an endogenous nucleic acid sequence.

In some embodiments, an expressible polypeptide is insulin. In some embodiments, an expressible polypeptide is human growth hormone. In some embodiments, an expressible polypeptide is coagulation factor X. In some embodiments, an expressible polypeptide is dystrophin. In some embodiments, an expressible polypeptide is a suicide protein. In some embodiments, a suicide protein is a protein that induces cell death. Exemplary suicide proteins include Mixed Lineage Kinase Domain Like Pseudokinase (MLKL), Receptor-interacting serine/threonine-protein kinase 3 (RIPK3), Receptor-interacting serine/threonine-protein kinase 1 (RIPK1), Fas-associated protein with death domain (FADD), or gasdermin D (GSDMD), cysteine-aspartic proteases, cysteine aspartases or cysteine-dependent aspartate-directed proteases (CASPASE-1 or CASP-1), CASPASE-4, CASPASE-5, CASPASE-12, PYCARD/ASC (PYD and CARD domain containing/Fas-associated protein with death domain) or variants thereof.

In some embodiments, an expressible polypeptide is a detectable gene product. In some embodiments a detectable gene product is a reporter. In some embodiments a reporter is a protein capable of providing a detectable signal and/or comprise the ability to generate a detectable signal (e.g. by catalyzing reaction converting a compound to a detectable product). Detectable signals can comprise, for example, fluorescence or luminescence. Detectable signals, methods of detecting them, and methods of incorporating them into reagents (e.g. polypeptides comprising a reporter protein) are well known in the art. In some embodiments of any of the aspects, detectable signals can include signals that can be detected by spectroscopic, photochemical, biochemical, immunochemical, electromagnetic, radiochemical, or chemical means, such as fluorescence, chemifluoresence, or chemiluminescence, or any other appropriate means. In some embodiments of any of the aspects, the reporter protein is selected from the group consisting of luciferase, nanoluciferase, beta-lactamase, beta-galactosidase, horseradish peroxidase, alkaline phosphatase, catalase, carbonic anhydrase, green fluorescent protein, red fluorescent protein, cyan fluorescent protein, yellow fluorescent protein, trypsin, a protease, a peptide that complements and activates a truncated reporter protein, a kinase.

In some embodiments, activity or function of a polyA aptamer polynucleotide of the present disclosure is measured by expression of an expressible polypeptide. In some embodiments, activity or function of a polyA aptamer polynucleotide of the present disclosure is measured by fold induction. In some embodiments, fold induction is calculated as the ratio of expressible polypeptide in the presence of a ligand and expressible polypeptide in the absence of a ligand. In some embodiments, fold induction is calculated as the ratio of expressible polypeptide in the presence of an aptamer and expressible polypeptide in the presence of a different aptamer. In some embodiments, fold induction is calculated as the ratio of expressible polypeptide in the presence of an aptamer comprising at least one splice acceptor site and one splice donor site and expressible polypeptide in the presence of a different aptamer with no splice sites. In some embodiments, fold induction is calculated as the ratio of expression of an endogenous gene before introduction of a polyA aptamer polynucleotide and expression of an endogenous gene after introduction of a polyA aptamer polynucleotide regulating expression of the same endogenous gene.

Ligand

In accordance with various embodiments, a ligand may be selected so as to facilitate a desired end purpose of a provided system. Accordingly, a ligand may be or comprise a polypeptide, nucleic acid, small molecule, drug, metabolite, or combination thereof. In some embodiments, a ligand may be or comprise a cellular metabolite, aberrant cellular protein, or a protein expressed by a pathogenic organisms (e.g., a virus, bacteria, or fungus). For example, in some embodiments, a ligand may be an exogenously administered small molecule so that dosing and function of the system can be modulated easily as desired in a particular therapeutic context. For example, in some embodiments, a ligand is tetracycline or its derivatives. In some embodiments, a ligand may be selected such that expression of an expressible polypeptide occurs in response to a particular biological condition (e.g., infection, tumorigenesis, high or low glucose), for example, as a biosensor system that can detect one or more intracellular "signatures" in a cell, tissue, or subject. Accordingly, in some embodiments, a ligand is endogenous to a subject (e.g., an endogenous protein) In some embodiments, a ligand is neomycin or its derivatives. In some embodiments, a ligand is theophylline or its derivatives. In some embodiments, a ligand is glucose. In some embodiments a ligand is a cancer biomarker.

Vectors

In some embodiments, a polyA aptamer polynucleotide of the present disclosure can be introduced by a vector. In some embodiments, a vector can be a viral vector. Suitable viral vectors include, without limitation, lentiviral vectors, retroviral vectors, alphaviral, picornal (e.g., polio) vaccinial, adenoviral, adeno-associated viral, herpes viral, and fowl pox viral vectors.

Exemplary Uses Including Treatment

In accordance with the present disclosure, polyA aptamer polynucleotides and/or systems including one or more polyA aptamer polynucleotides, may be used in any of a variety of applications. For example, in some embodiments, a polyA aptamer polynucleotide of the present disclosure is used for treatment of an individual suffering from a disease, for example, by providing controllable expression of a therapeutic protein encoded by an expressible polynucleotide. In some embodiments, a disease is the lack of certain protein(s) caused by a genetic disorder. In some embodiments, a disease is diabetes, pre-diabetes, or complications from diabetes. In some embodiments, a disease is cancer. In some embodiments, a disease is muscular dystrophy. In some embodiments, a disease is hereditary Factor X deficiency. In some embodiments, a polyA aptamer polynucleotide of the present disclosure is provided in combination with other treatments for a disease. In some embodiments, a polyA aptamer polynucleotide of the present disclosure is used for inducing reprogramming of cells into pluripotent stem cells (induced pluripotent stem cells or iPSCs). In some embodiments, a polyA aptamer polynucleotide of the present disclosure is introduced or administered prior to, during, or subsequent to other treatments for a disease. In some embodiments, a therapeutic protein maybe or comprise insulin, growth hormones, dystrophin, albumin, factor IX, Oct4, Sox2, Klf4, cMyc, and any combination thereof.

In some embodiments, a system comprising a polyA aptamer polynucleotide may be used to provide information regarding whether or not a therapy is effective in a particular subject. In some embodiments wherein it is desirable to determine whether one or more therapies are effective in a subject, a system may be employed in the subject before the therapy is provided, such as to detect the presence or absence of a specific indicative compound for the therapy, and then after the therapy is provided one or more times the system may be employed in the subject to detect the presence or absence of the specific indicative compound. In other embodiments, the system is not employed for monitoring therapy until after the therapy is provided one or more times to the subject, such as to identify the presence or absence of a specific compound that is indicative of the efficacy of the therapy.

In some embodiments, polyA aptamer polynucleotides and/or systems including one or more polyA aptamer polynucleotides may be used as a biosensor. In accordance with various embodiments, provided systems may provide spatial and/or temporal information regarding a particular environment (e.g., an intracellular, extracellular, and/or environmental environment). For example, in some embodiments, a system comprising at least one polyA aptamer polynucleotide may be used to detect one or more specific molecular signatures in a subject and to allow for production of a desired expressible polypeptide in order to achieve a desired biological state in response to the presence of the molecular signature(s). In some embodiments, a molecular signature may be or comprise: the presence of a particular endogenous gene product (e.g., a disease-associated gene product/protein), the presence of a toxin, the presence of an exogenous gene product, the presence of a metabolite (e.g., a metabolite from an environmental contaminant), and any combination thereof.

In some embodiments, a polyA aptamer polynucleotide may comprise one or more reporter moieties (e.g., a reporter gene product, for example, an imaging reporter). In some embodiments, an expressible polynucleotide comprised in a polyA aptamer polynucleotide encodes a reporter gene product (e.g., protein). In some embodiments, a reporter gene product may be or comprise luciferase, green fluorescent protein, red fluorescent protein, β-galactosidase, infrared fluorescent proteins, near-infrared fluorescent proteins, opsin, and any combination thereof.

In some embodiments, a system comprising a polyA aptamer polynucleotide may encode both a reporter gene product and a therapeutic gene product. In some such embodiments, expression of the reporter gene product and the therapeutic gene product may be controlled by the same aptamer. In some embodiments, expression of the reporter gene product and the therapeutic gene product may be controlled by different aptamers.

Exemplification

The present examples describe a highly responsive gene regulation mechanism that harnesses the power of drug-inducible alternative splicing to control polyA cleavage. FIG. 1 provides a representation of some embodiments of the present disclosure. As demonstrated in FIG. 1A, when an engineered short intron (mini-IVS2) and a new polyA signal (pA) are artificially created at the 5' UTR of a transgene, efficient splicing of the intron and the cleavage of polyA signal lead to destruction of the second half of mRNA and therefore loss of gene expression. Binding of a specific ligand to the aptamers engineered as part of the Y-shape switch (dashed line) efficiently induces an alternative splicing. The ligand-induced alternative splicing results in the removal of the Y-shape structure and the artificial 5' UTR polyA signal. This in turn leads to the preservation of the intact mRNA and therefore the induced gene expression. Note, a second 3' splice site (3'ss) is built in the 5'UTR sequence. This 3' splice site is only activated after ligand (e.g., tetracycline, "Tc") binding to the aptamers. The 4MAZ sequence next to the Y structure is to reinforce the alternative splicing upon ligand binding.

Figure 1B:
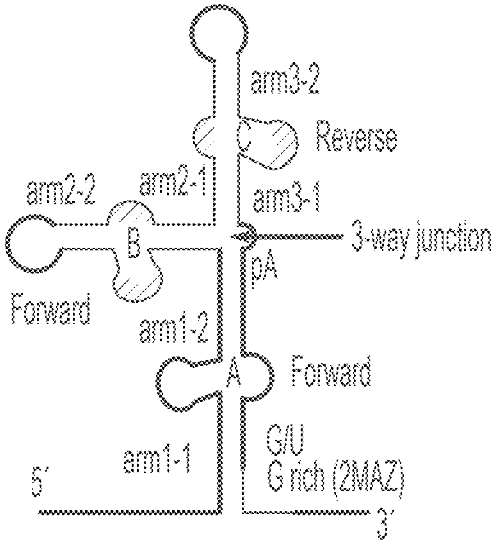

FIG. 1B provides a demonstration of a polyA switch comprising three aptamers as described herein. Each aptamer is located on one arm of the Y shape RNA structure. This Y-shape design has several important advantages: It incorporates 3 aptamers to control the polyA signal (pA) which is strategically placed at the central 3-way junction. By doing so, it harnesses the combined power of Tetracycline-binding effects generated from three different aptamers; The Y-shape structure is compact and requires overall shorter sequences to incorporate 3 aptamers; The Y-shape structure is designed to fold intrinsically during RNA biosynthesis. The three aptamers are arranged in a forward-forward-reverse orientation to minimize the chance of alternative folding between the aptamers. Further, double-stranded RNA stems longer than 35 bp are known to evoke innate immune response in cells. Therefore, all stems in the Y structure are made to be significantly shorter than 35pb to eliminate innate immune response.

Figure 1C:
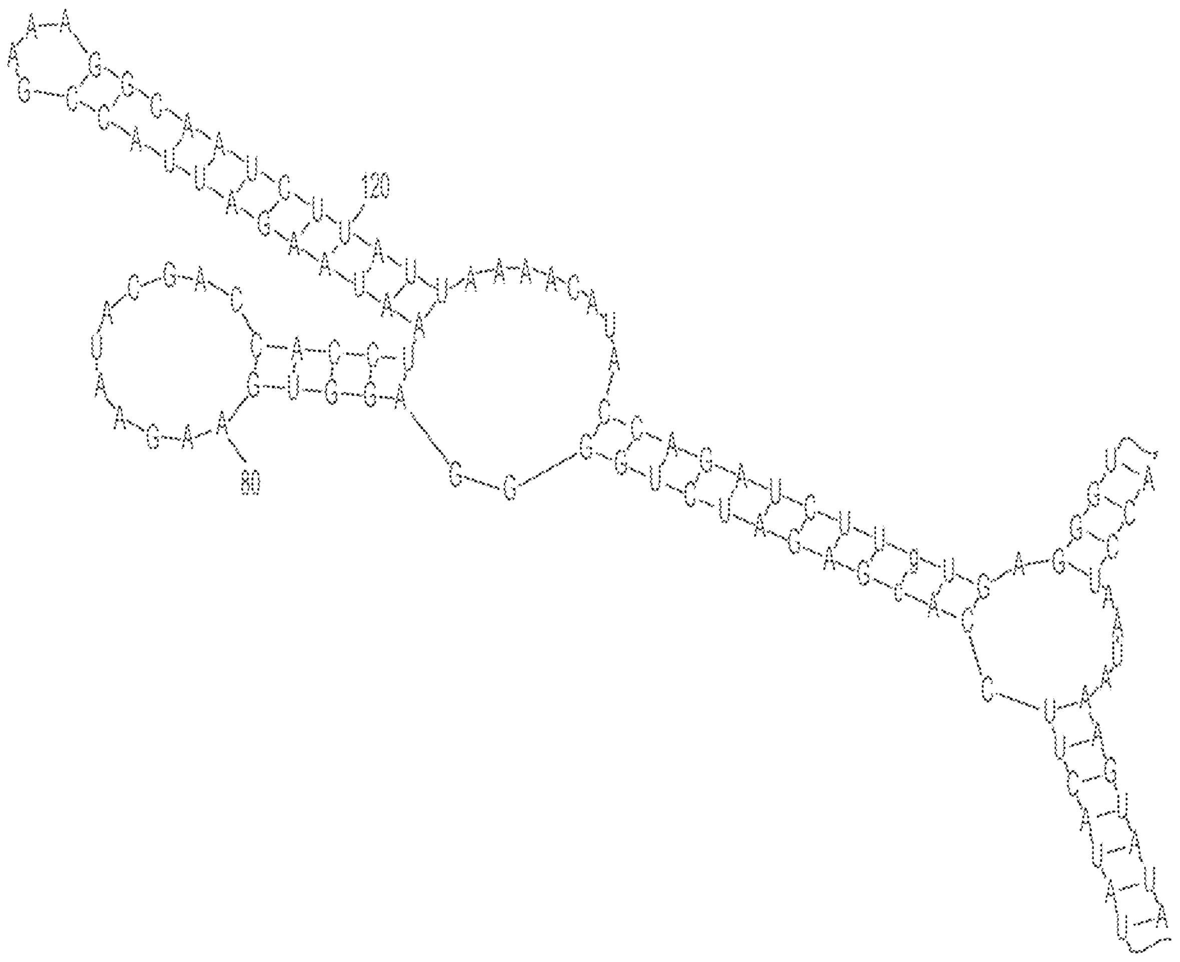
Figure 1C:
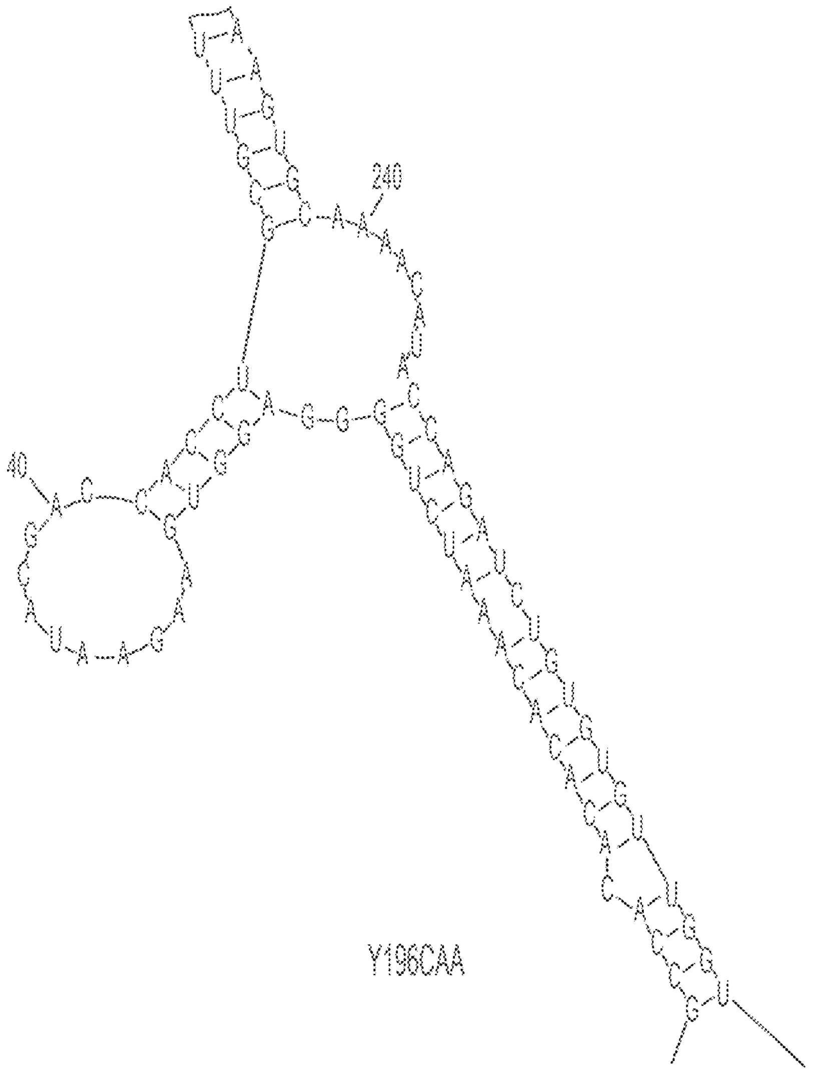
Figure 1C:
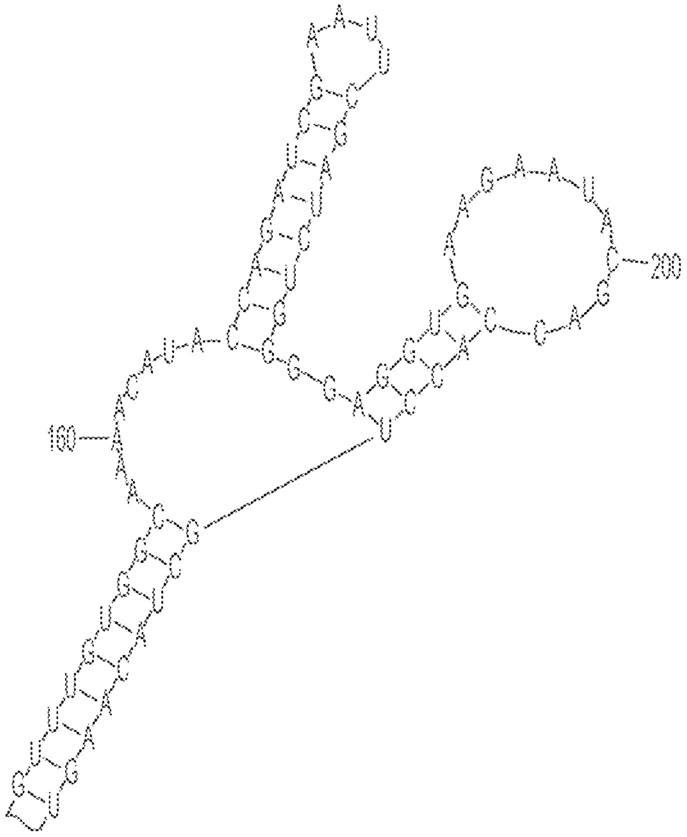

FIG. 1C provides an example (Y196CAA) of the nucleic acid sequence of a polyA switch as described herein. More than 370 constructs were designed and tested to extensively probe the effect of every component of the Y shape structure. These include (1) the length of each arm, (2) the sequence of each arm, (3) the loop of each arm, and (4) the sequence and size of the central 3-way junction where polyA signal is placed. The effect of modifications of those components are described further in these non-limiting examples.

Example 1: Modulation of PolyA Cleavage Signal

Location

Figure 2A:
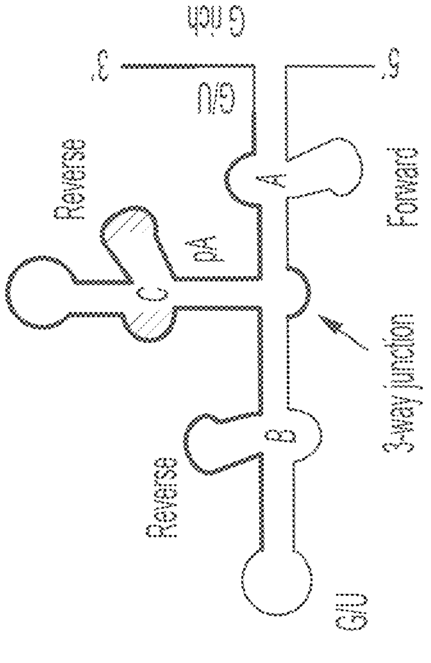
FIGS. 2A-2C demonstrate results of additional Y-shape structures that are configured differently and with the polyA cleavage signal positioned differently. polyA signal is indicated by a bolded line. 3-way junction is labeled.
Figure 2B:
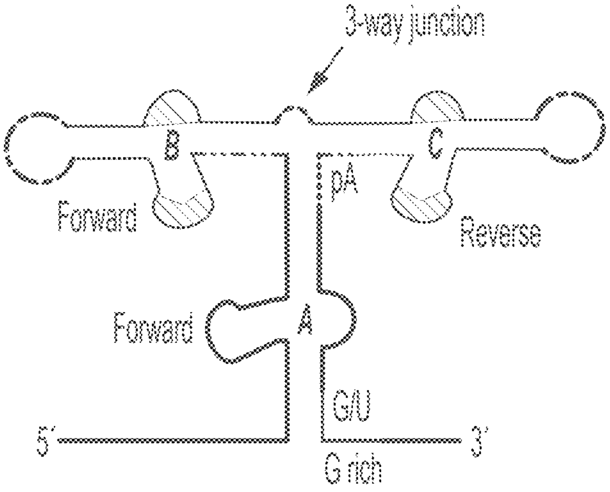
Figure 2C:
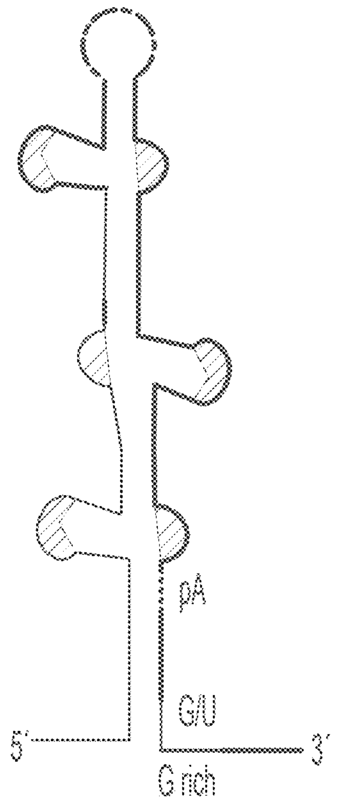

Constructs were made to test additional Y-shape structures that are configured differently and with the polyA cleavage signal positioned differently. Four different constructs were made: B1-B4 where the polyA signal is placed near aptamer C and clamped by the 3-way junction (FIG. 2A; B1 construct is shown). These showed no or minimal induction. An additional four constructs with polyA signal near the 3-way junction were made: T1-T4 (FIG. 2B). These also showed minimal or moderate induction. FIG. 2C exemplifies a polyA switch in which the 3 aptamers are stacked on each other without 3-way junction. Minimal induction was observed for this configuration. The particular Y-shape configuration shown in FIG. 1B, in which polyA signal is placed close to the three way junction, is used for additional testing. In this configuration the three way junction bends with different orientation to provide a unique geometry for clamping the polyA signal. The stability of each arm is determined by two factors: the number of base pair and the composition of base pair (for example, G-C is more stable than A-U or G-U pair).

Number of PolyA Cleavage Signals

Tests were performed to evaluate the optimal number of polyA signal(s) in Y-shape structure. Y1 shows ~12 fold induction, the highest in the three constructs tested. In this group, the majority of arm 3-1 is A-U or G-U pair, so it requires a longer stem to reach certain stability. Arms of the constructs exemplified herein comprise double stranded nucleic acid stems. Shorter arm 3-1 gives lower induction. The length of arms was also tested. Y5 to Y9 have only one polyA signal with variable length of arm3-1 and arm2-1. The length of arm 3-1 and arm2-1 are shortened by 1 bp stepwise from Y5 to Y9. This one polyA configuration leads to better induction. Also tested was when there are 2 polyA signals (Y6mut) in a row in arm1-2, and the induction is reduced by approximately half. Y6mut: is identical to Y6 except that 2 polyA signals (box) are embedded in arm1-2. Based on these results, the optimal number and position of polyA signal are determined: a single polyA signal partially embedded in arm1-2 and in 3-way junction. The configuration is used as the basis for further optimization.

Example 2: Optimization of Three Way Junction

Figure 3A:
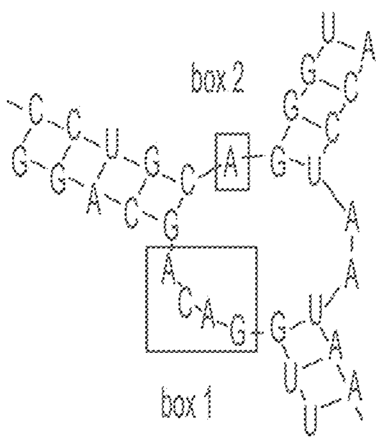
FIGS. 3A and 3B demonstrate results of modification of a 3-way junction of a polyA aptamer polynucleotide described herein (SEQ ID NO: 122, 132, and 115).

Modifying the environment of a 3-way junction directly affects the clamping of polyA signal. Therefore, the performance of Y-shape switch is very sensitive to any change in the 3-way junction. Extensive mutation/insertion/deletion studies around the 3-way junction were performed to identify the best sequences. It was shown that an U to G mutation in Y22 doubles the induction, presumably because this mutation generates a new G-U base pair on arm3-1 that tightens the clamping of polyA signal. The effects of different 3-way junction sequences on induction was also tested. Constructs were tested having 3 bases vs. 1 base in one of the three way junctions. Y107 to Y110 are derivatives of Y79 which has 3 bases. Y107 to Y110 have only one base. Y107 performs similarly to Y79, indicating one unpaired base is sufficient. It was shown that inserting one base into into the 3-way junction, lead to subtle changes of folding in the 3-way junction. The results suggest that the best configuration is one unpaired basein one of the connections of the Y junction. For the constructs in FIG. 3A the single base in box 1 and box2 were randomized. 16 combinations were tested and the results showed that Y127, Y130 and Y134 are the best among them when compared to the parental Y79 tested on the same day. Further optimization of the constructs using Y130 as the basis was done. None of the modifications tested lead to significant improvement. Additional modifications were made relative to Y143 that resulted in little change in induction. Additional modifications were made relative to Y147. Y163 slightly improves induction while Y162 slightly decreases the induction as compared to Y147. Additional modifications were made relative to Y163. Y177 improves induction while Y178 decreases the induction compared to Y163. Modifications were made relative to Y152. These modifications lead to significant improvement compared to Y152. In particular, Y166 nearly doubles the induction. Y166 serves as the new basis for further optimization. Additional modifications were made relative to Y166. These modifications lead to significant improvement as compared to Y166. They also serve as the new bases for optimization.

Figure 3B:
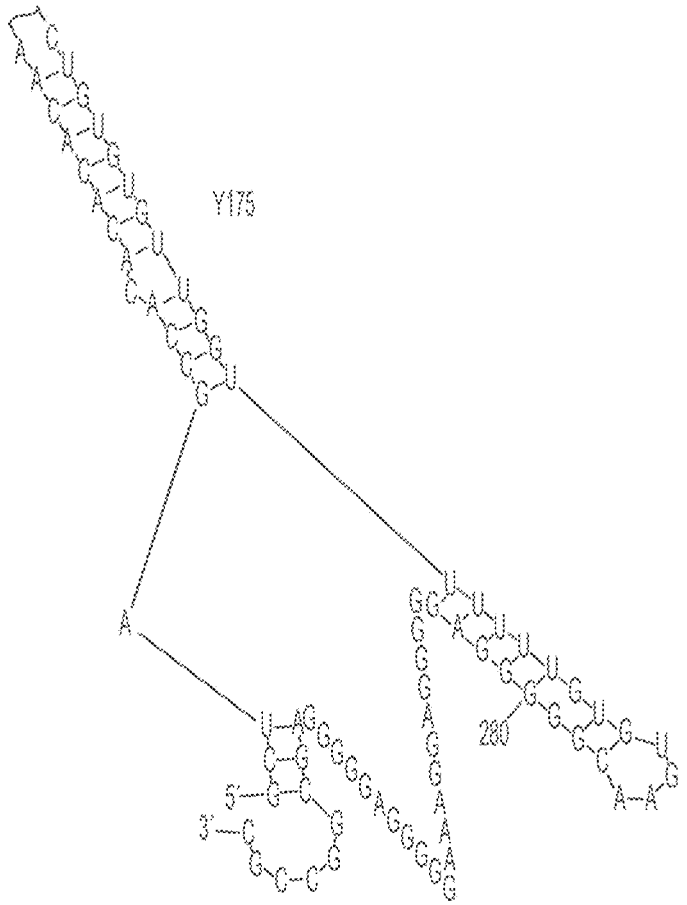

Y174, Y175, Y176, and Y177 (See FIG. 3B) are among the best 3-way junction sequences. All these constructs have a single base C or A in Box1 and Box2. In these constructs, the first 3 bases of polyA signal AAUAAA are open in the pocket of 3-way junction. The last 2 bases of polyA signal are embedded in arm 1-2.

Changing the polyA signal position relative to the pocket of the 3-way junction can alter induction capability (FIG. 4). In Y135-Y140, changes made relative to Y101, the pocket of the 3-way junction is moved along the polyA signal. As a result, the polyA signal is embedded deeper in arm1-2. These modifications lead to lower induction. Y101 mut, a derivative of Y101, contains a flipped C-G pair in arm2-1 that removes a potential 3' splice site. Constructs Y141-Y159 are based on Y101mut. The 3-way junction pocket is moved along the polyA signal. The induction results of moving the 3-way junction pocket along the polyA signal are shown in FIG. 4.

Example 3: Double Strand Stems

PolyA aptamer polynucleotide constructs as described herein comprise nucleic acid (e.g., RNA) double strand stems. Such double stranded regions are also referred to in the present disclosure as arms. Modifications of the length, stability, and nucleotide composition can affect the strength and effectiveness of the polyA aptamer polynucleotide.

Earlier results (using constructs Y1 to Y9) indicated that the stability of arm 3-1 needed to be within certain range. Arm3 is a very sensitive area because it is very close to the polyA signal. Minor changes in stability of arm3 can result in significant change in polyA signal clamping therefore the induction. Using Y35 as the basis, we made many modifications to optimize arm3. The results demonstrate that increasing the length of arm3-2 and changing the loop sequence greatly reduce induction.

The majority of these modifications significantly reduce induction, and none surpasses Y35. Therefore, the arm3 of Y35 represents the optimal arm3 sequence for the Y shape structure of those tested. Some other parental constructs used for arm3 modification, such as Y175, Y197, and Y210, all share the same arm3 sequence of Y35.

Modifications to the double strand stems that are arm 2 (i.e., arm2-1 and arm2-2) alter the stability of arm 2. The modifications include variations in length, sequences, as well as point mutations that create mismatches in the stem.

Modifications were done to arm2-2. Constructs Y48 to Y53 are based on Y35. The results of these modifications indicate that induction is less sensitive to changes in the stability of arm2 as compared to that of arm3. Presumably this is because that arm2 is not directly connected to polyA signal. Nonetheless, arm2 requires certain levels of stability to achieve good induction. Unstable arm2 leads to very low induction. The sequences of arm2 shown in these results are empirically determined. Some of the arm2 sequences are already within the optimal range of stability, and represent near optimal sequences that lead to very efficient induction. Further increase in stability either increases or decreases induction.

Modifications were done to arm 1-2.

Example 4: Orientation of Aptamers

Figure 5A:
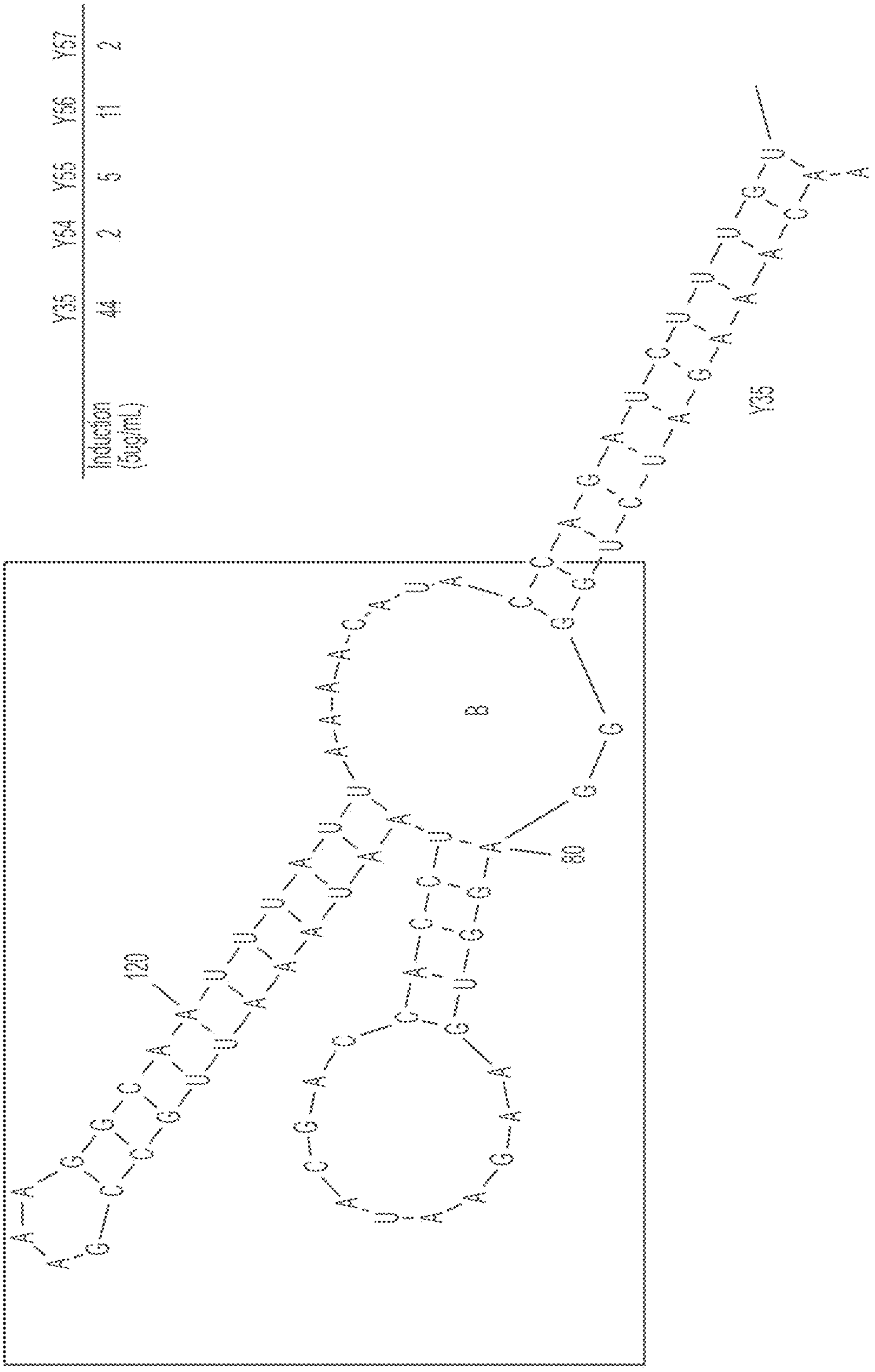
FIGS. 5A-5B demonstrate results of modification of aptamer orientation of a polyA aptamer polynucleotide described herein.
Figure 5A:
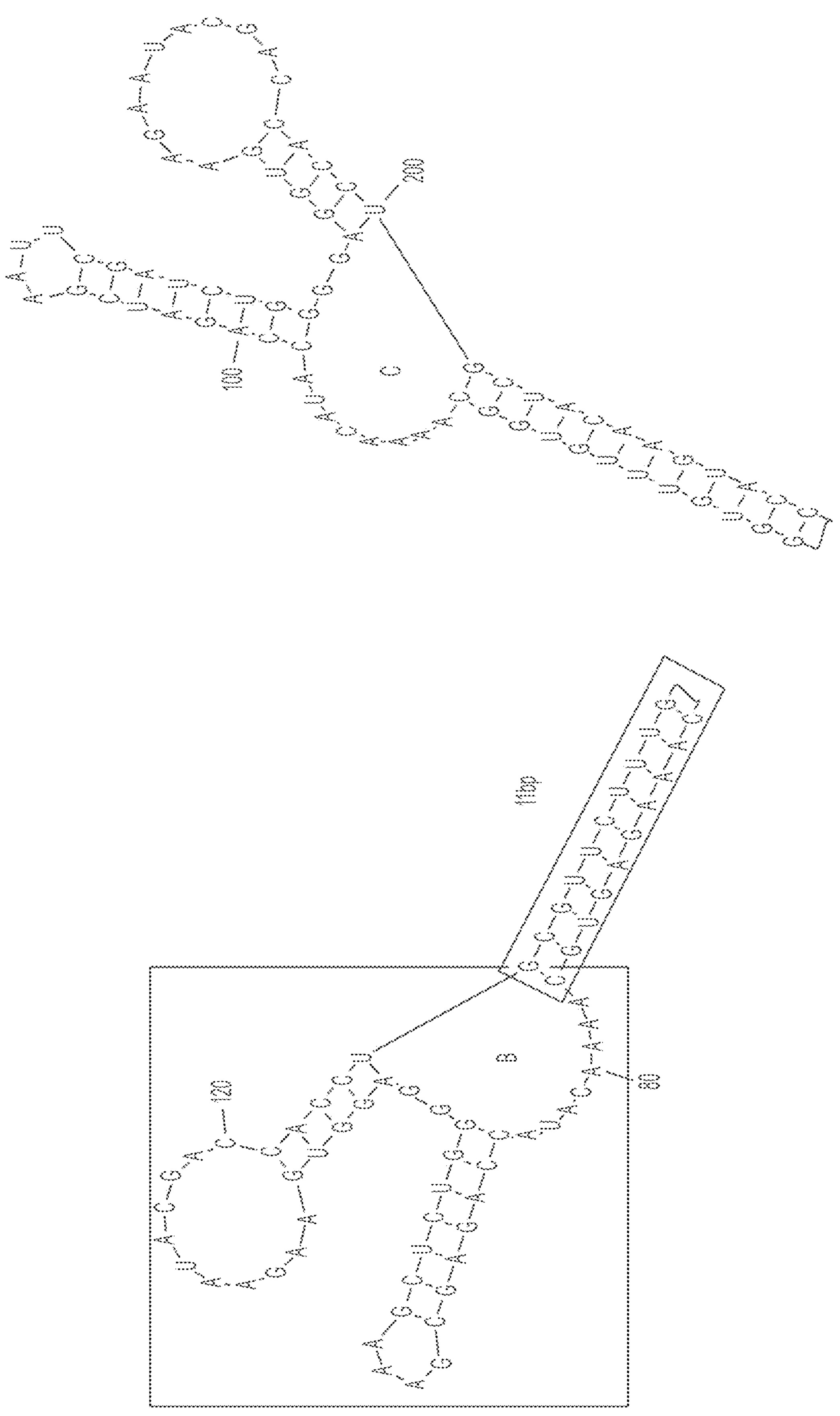
Figure 5A:
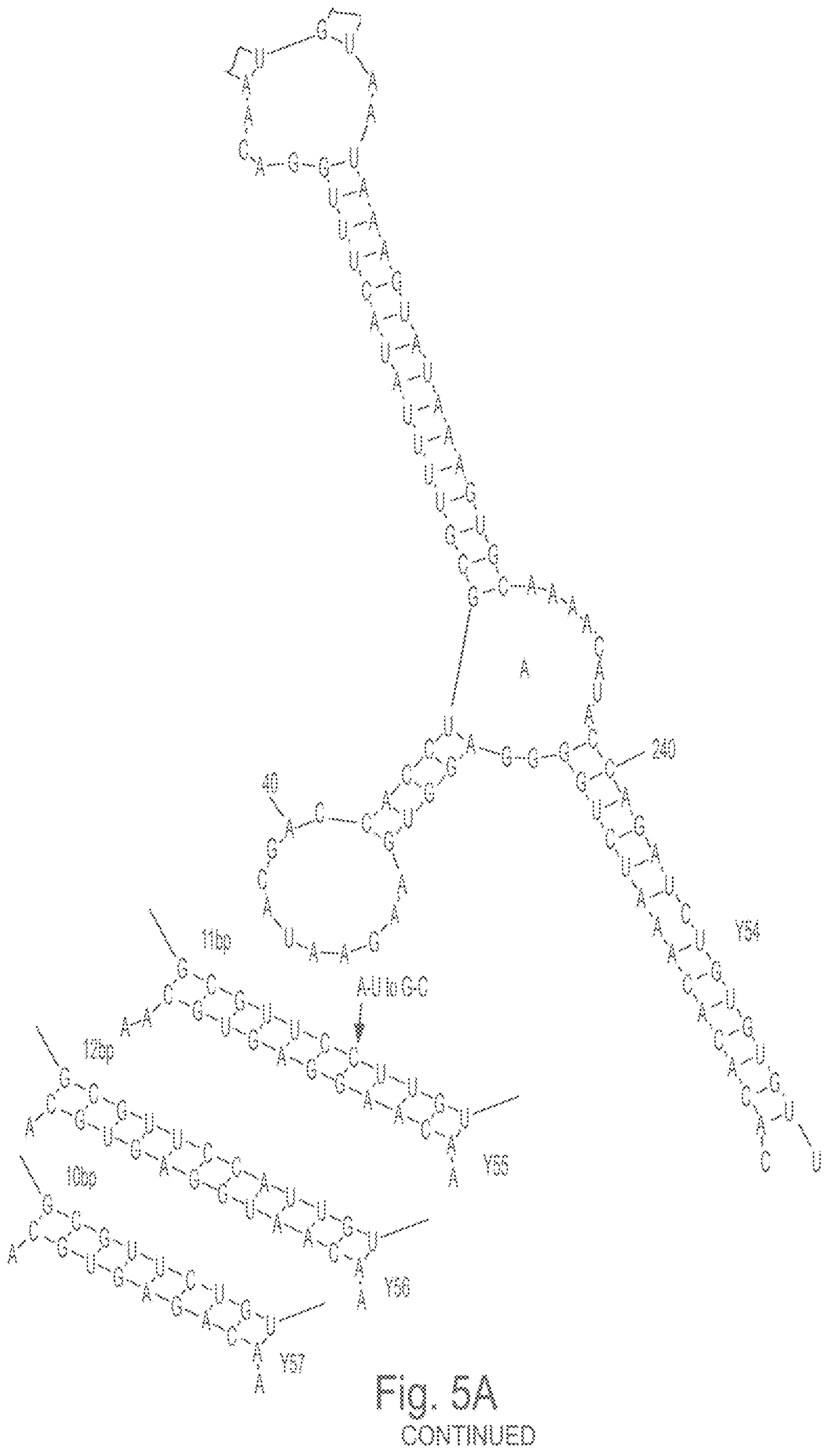
Figure 5B:
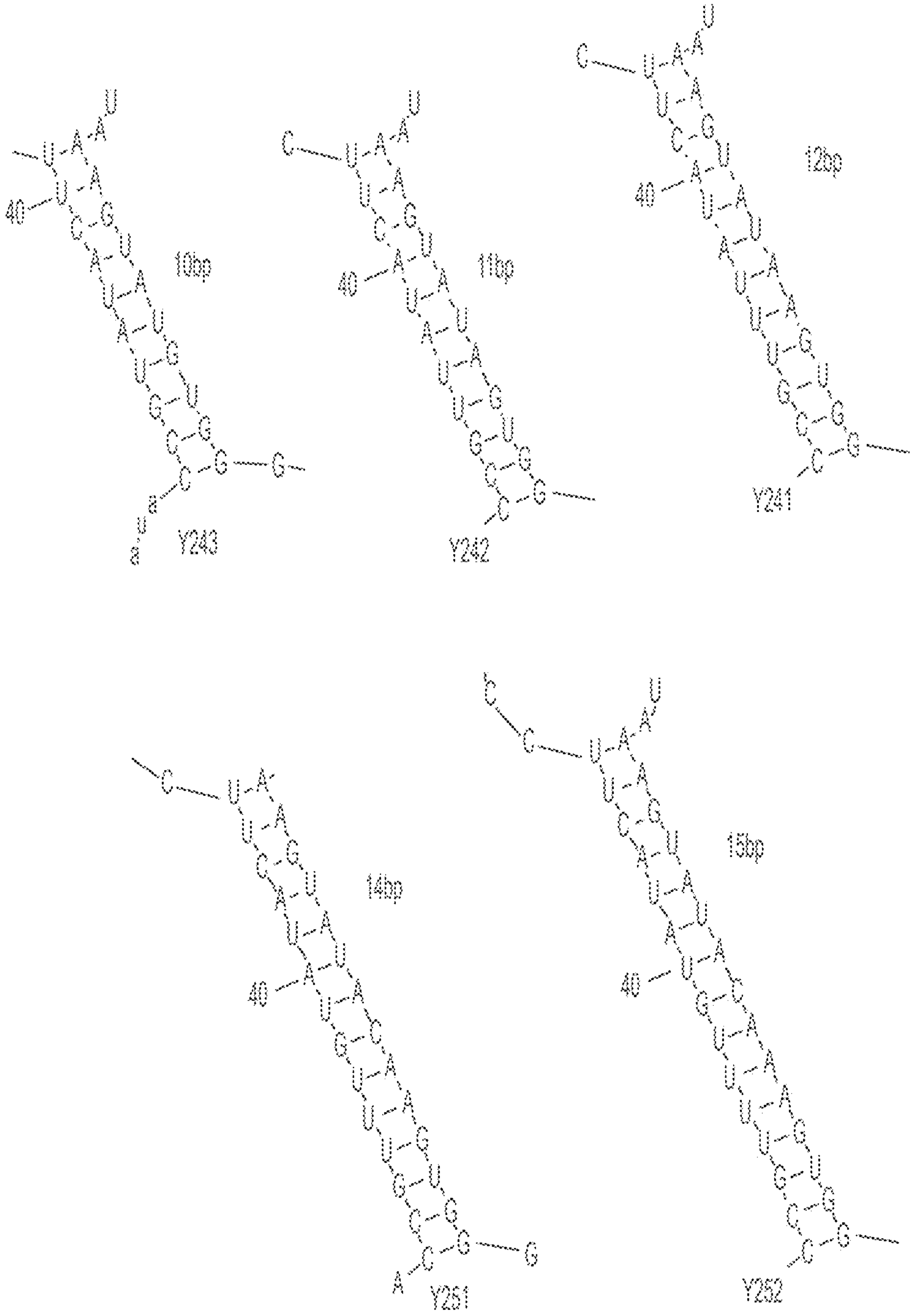
Figure 5B:
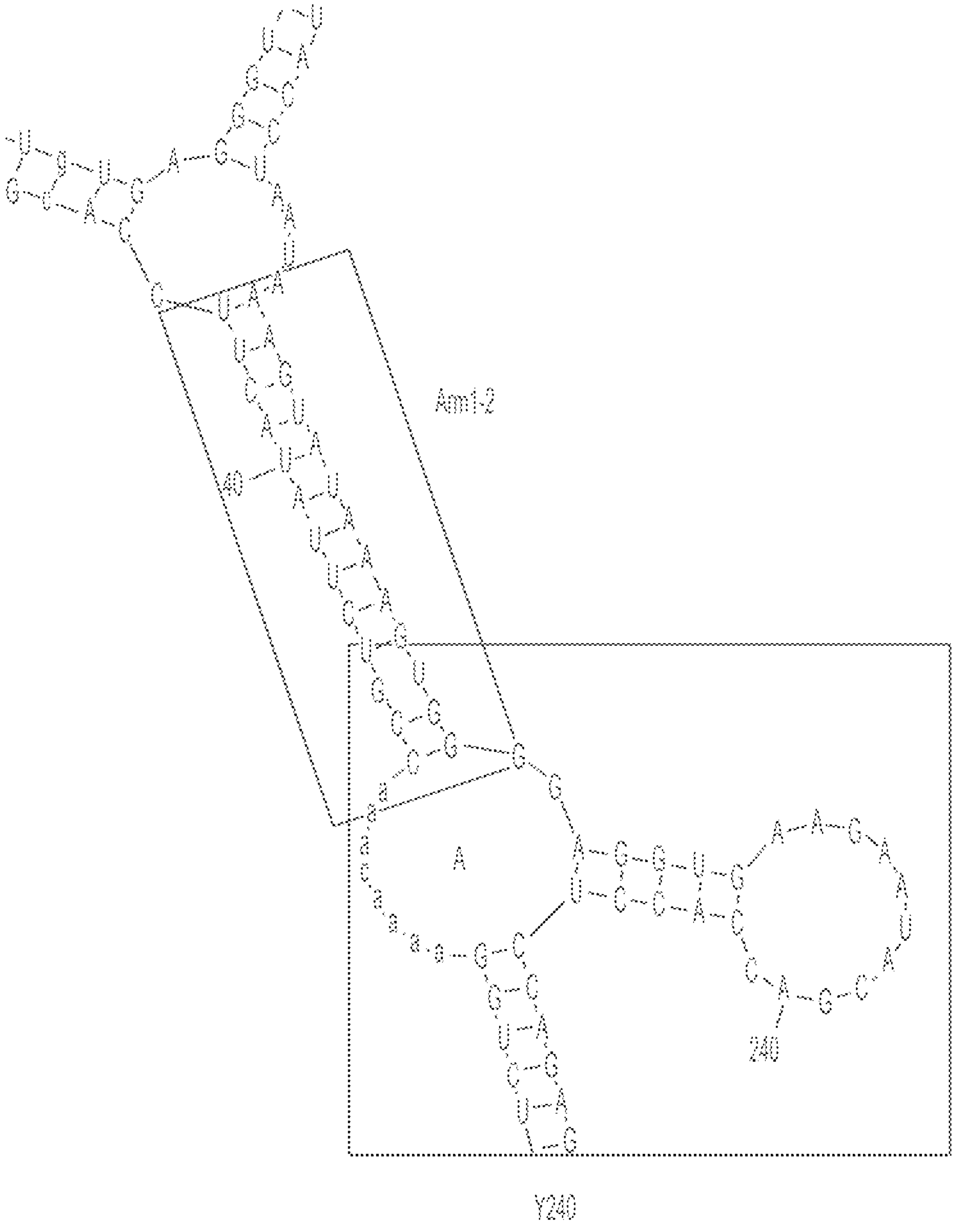
Figure 5B:
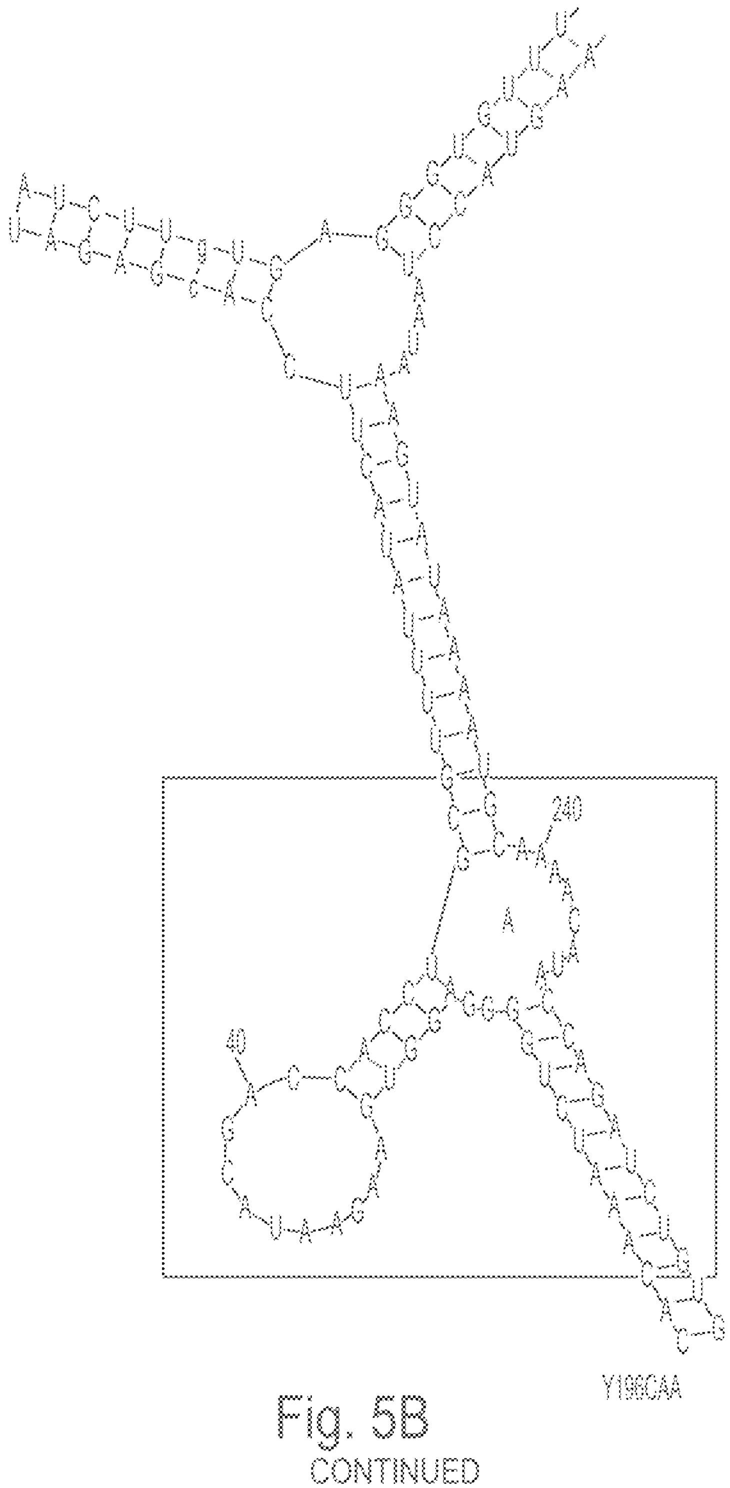

Orientation of each of the aptamers relative to the other aptamers may have an effect of the function of polyA aptamer polynucleotide. FIG. 5A shows the results of constructs Y54 to Y57 which are based on Y35, with aptamer B orientation reversed. Reversing the orientation of aptamer B largely eliminates the induction. FIG. 5B shows induction results of constructs Y240 to Y252 which are based on Y196CAA, with aptamer A orientation reversed. Reversing the orientation of aptamer A completely eliminates the induction regardless of the length of arm1-2.

Example 5: Contribution of Each Aptamer to Induction

Figure 6A:
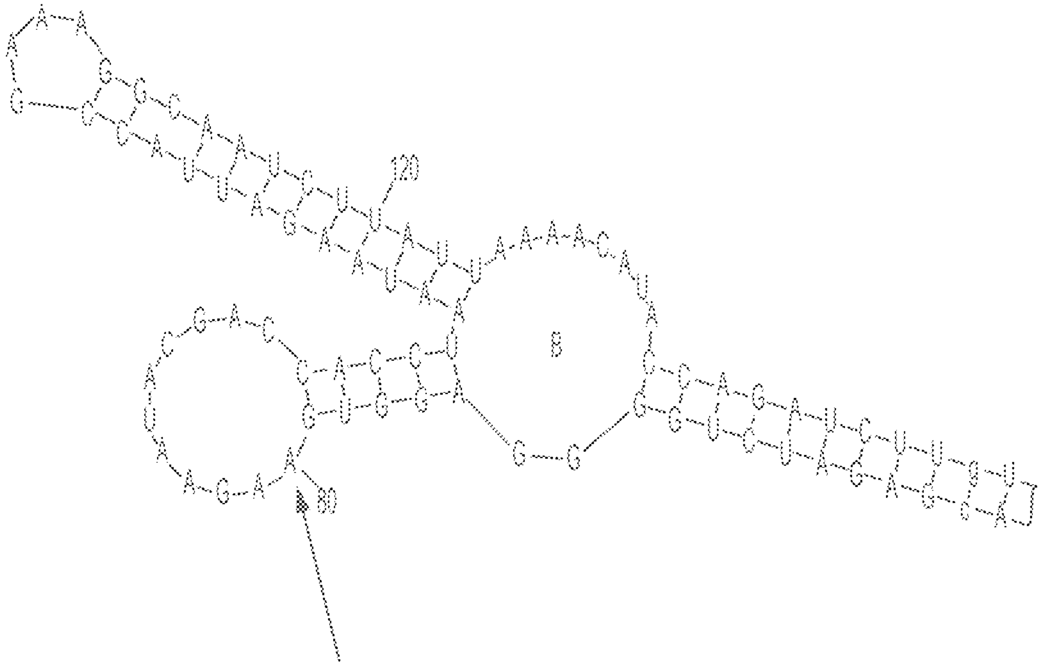
FIGS. 6A-6B demonstrate the contribution of each aptamer in a polyA aptamer polynucleotide described herein.
Figure 6A:
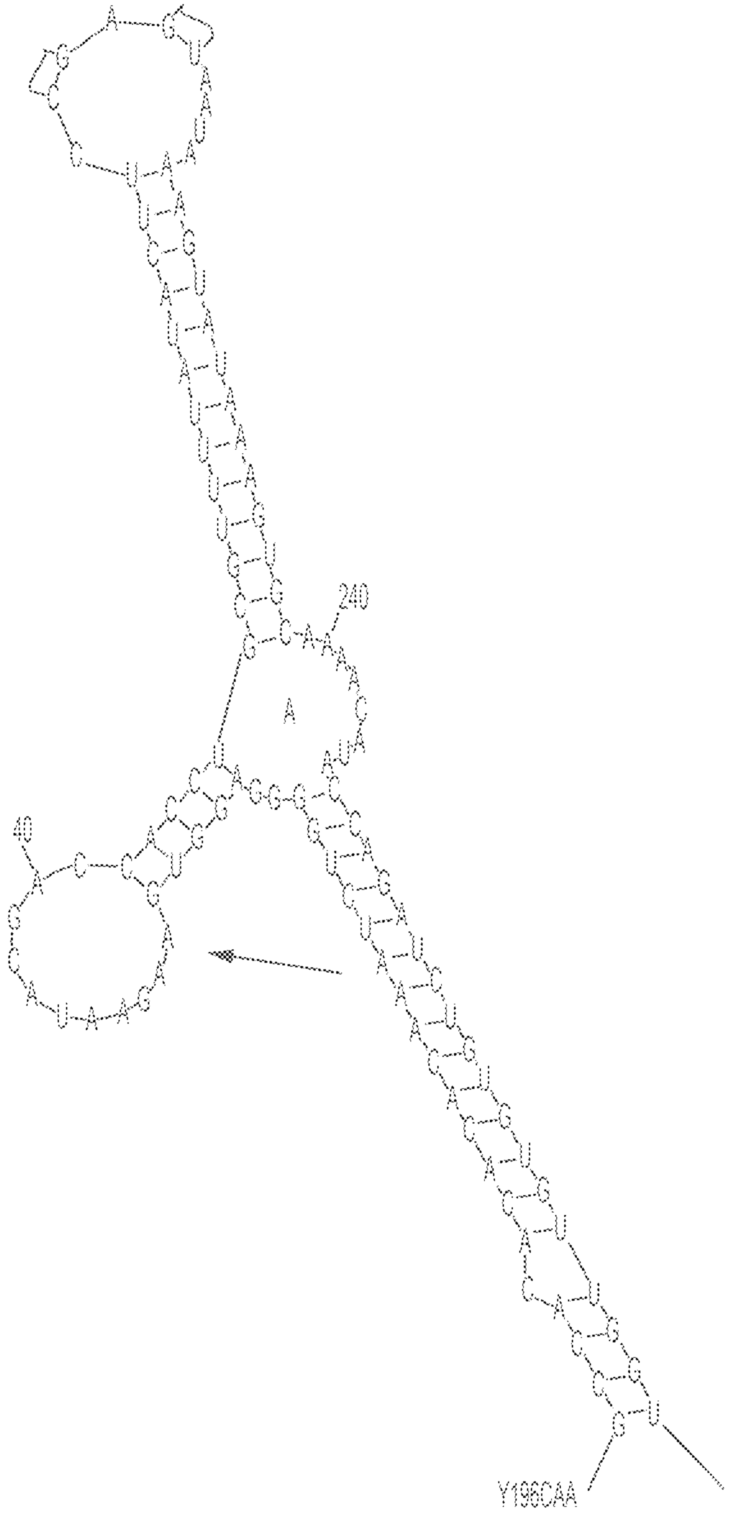
Figure 6A:
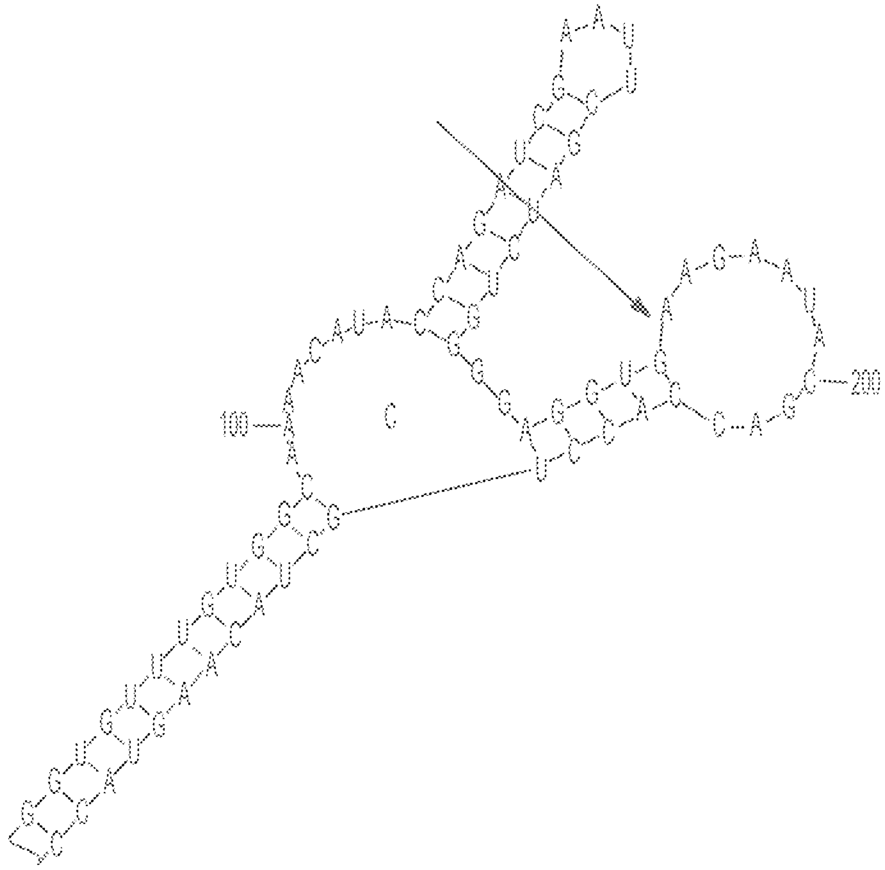

FIG. 6A demonstrates the contribution of each aptamer of the Y-shape structure to induction. Each aptamer of the Y-shape structure can be disabled by an A to C mutation (arrows) in the binding pocket which eliminates the binding to its ligand tetracycline. NA: Aptamer A is disabled; NB: Aptamer B is disabled; NC: Aptamer C is disabled; NAB: Aptamers A and B are disabled; NBC: Aptamers B and C are disabled; NAC: Aptamers A and C are disabled. These results indicate that aptamer C contributes most significantly to the final induction. This is followed by aptamer B, then by aptamer A.

Figure 6B:
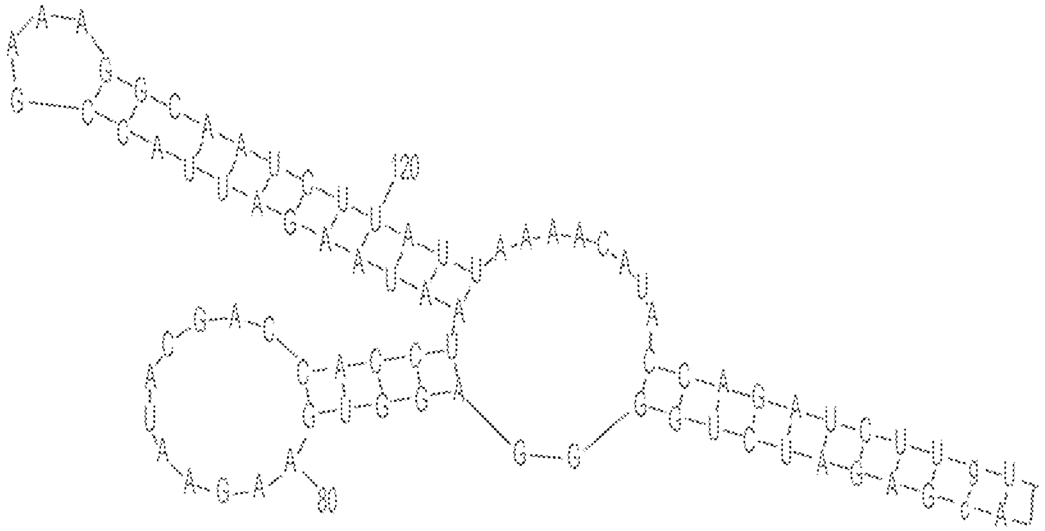
Figure 6B:
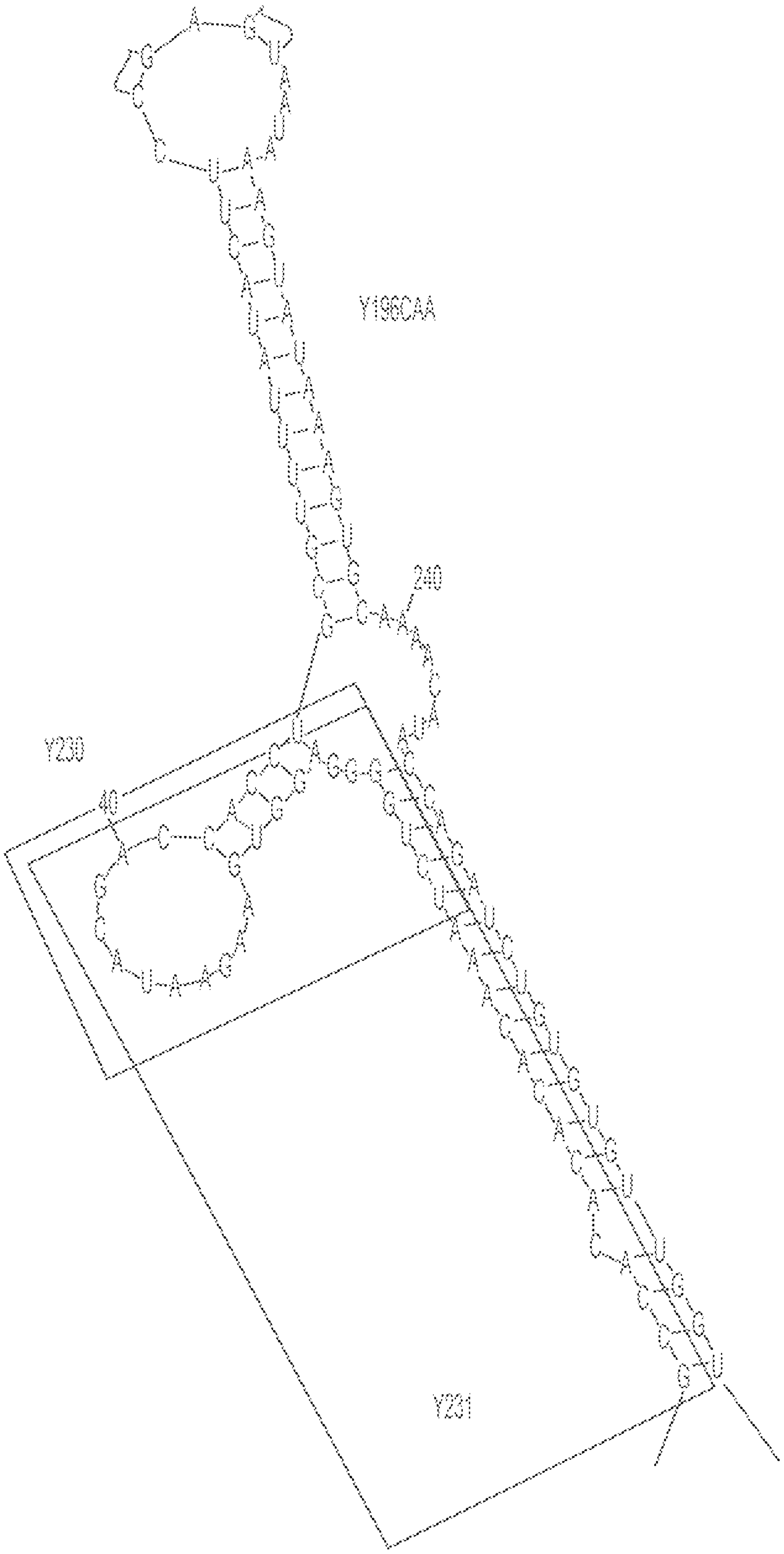
Figure 6B:
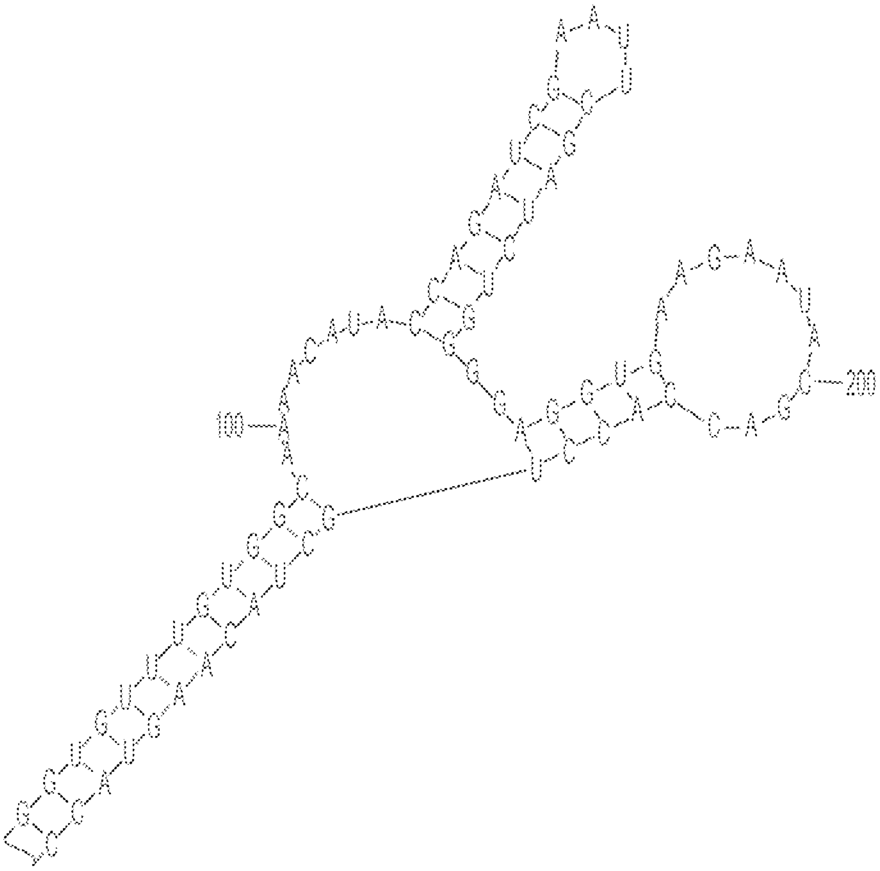

FIG. 6B demonstrates the effect of removing aptamer A from the Y-shape structure. The boxes indicate the sequence removed for each construct. Removing aptamer A retains moderate induction, although the level is significantly reduced compared to the parental Y196CAA.

Example 6: Modifications of 5'UTR

FIG. 7A demonstrates that inserting CAA repeats (underlined) in the 5'UTR can alter induction levels. Here inserting CAA repeats in Y196, Y208, Y209, and Y211 all lead to higher induction. Inserting spacer sequences that contain CAA repeats into 5'UTR of Y301 results in variable effect on induction. These spacer sequences are only slightly different from each other, yet resulting in large difference in induction, indicating that this area is very sensitive to changes. FIG. 7B shows some examples of testing a new 5'UTR sequence with a strong 3' splice site using S56 as parental construct. FIG. 7C shows the results of adding intrinsically unstructured RNA sequences to the 5'UTR near the translational start ATG without using CAA repeats. These constructs are based on Y300 and Y305. Of the Y300-based constructs, Y329 is the best. While it does not surpass the performance of Y305, it has the advantage of not using the CAA repeats. FIG. 7D shows that the insertion location of CAA repeats also significantly affects induction.

Example 7: Importance of G Quad Sequence

Figure 9:
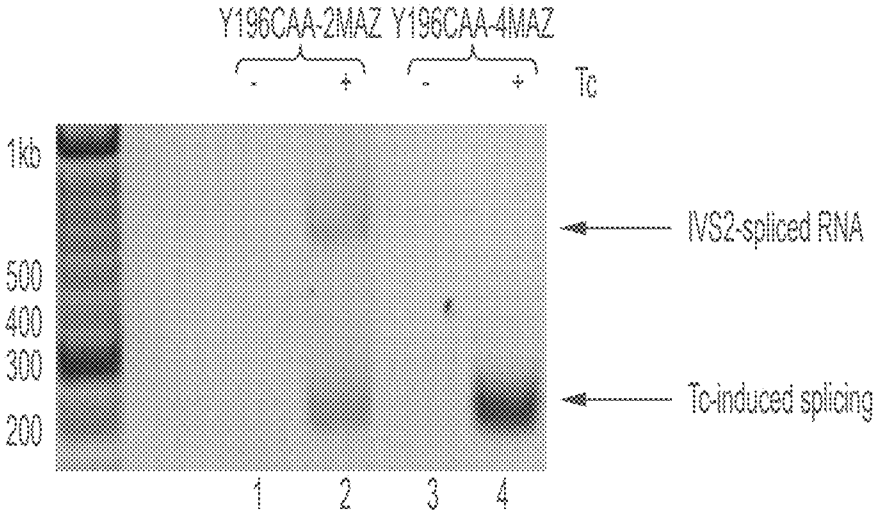
FIG. 9 demonstrates confirmation of tetracycline-induced alternative splicing of a polyA aptamer polynucleotide described herein. In the absence of Tc, IVS2-spliced RNA is degraded by polyA cleavage (lane 1 and 3). The presence of Tc induces alternative splicing in both Y196CAA-2MAZ and Y196CAA-4MAZ (lane 2 and 4). Ligand-induced alternative splicing is much more pronounced with the presence of 4MAZ.

We tested the effects of G-quad sequence on induction. FIG. 8A shows 3MAZ or CD44 G-quad reaches a similar induction level as compared to 2MAZ using Y196CAA as the parental. However, 4MAZ dramatically doubled the induction due to its ability to effectively induce alternative splicing. FIG. 8B shows induction results when different G-quad sequences were tested to replace 4MAZ G-quad using the S56 construct as the parental. In these constructs, 4MAZ is replaced by the following: one CD44 G-quad 'TGGTGGTGGAATGGT' (S177), two CD44 G-quad 'TGGTGGTGGAATGGTAAATGGTGGTGGAATGGT' (S178), or four CD44 G-quad 'TGGTGGTGGAATGGTAAATGGTGGTGGAATGGTAAATGGTGGTGGAATGGTAAATGGT GGTGGAATGGT' (S179). The results indicate that the effect of 4MAZ is unique and cannot be replaced by other G-quad sequences. The 4MAZ sequence possesses unique properties and is a key element of the hybrid switch that requires both efficient polyA signal cleavage and Tc-induced alternative splicing. FIG. 9 further demonstrates the importance of the 4MAZ sequence. RT-PCR revealed the mechanism of drug-induced alternative splicing. In the absence of Tc, IVS2-spliced RNA is degraded by polyA cleavage (lane 1 and 3). The presence of Tc induces alternative splicing in both Y196CAA-2MAZ and Y196CAA-4MAZ (lane 2 and 4). Sanger sequencing confirmed that the Tc-induced band (lower band) contains the expected alternative splices RNA junction. Tc-induced alternative splicing is far more pronounced in Y196CAA-4MAZ as compared to Y196CAA-2MAZ (lane 4 vs. 2). With this induced alternative splicing, both the polyA signal and the Y-shape structure are removed in the presence of Tc, and the induction of protein expression is significantly increased.

Example 8: Modulating First 3' Splice Acceptor Site

Figure 10A:
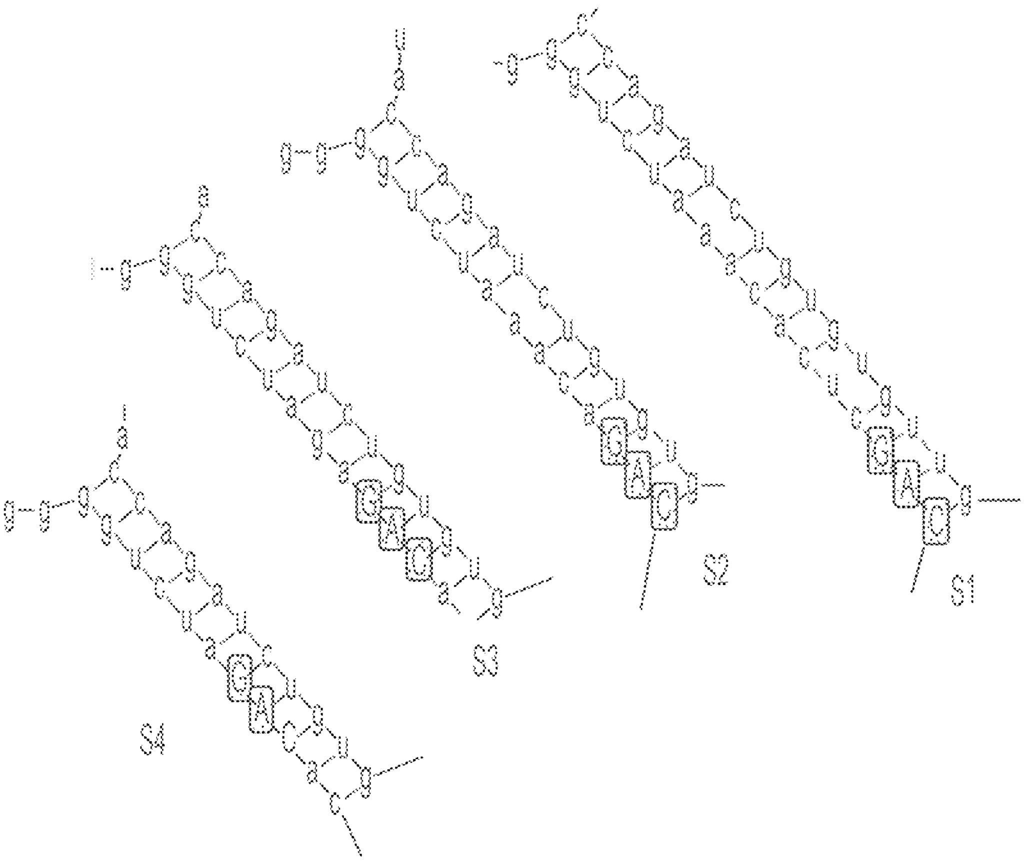
Figure 10A:
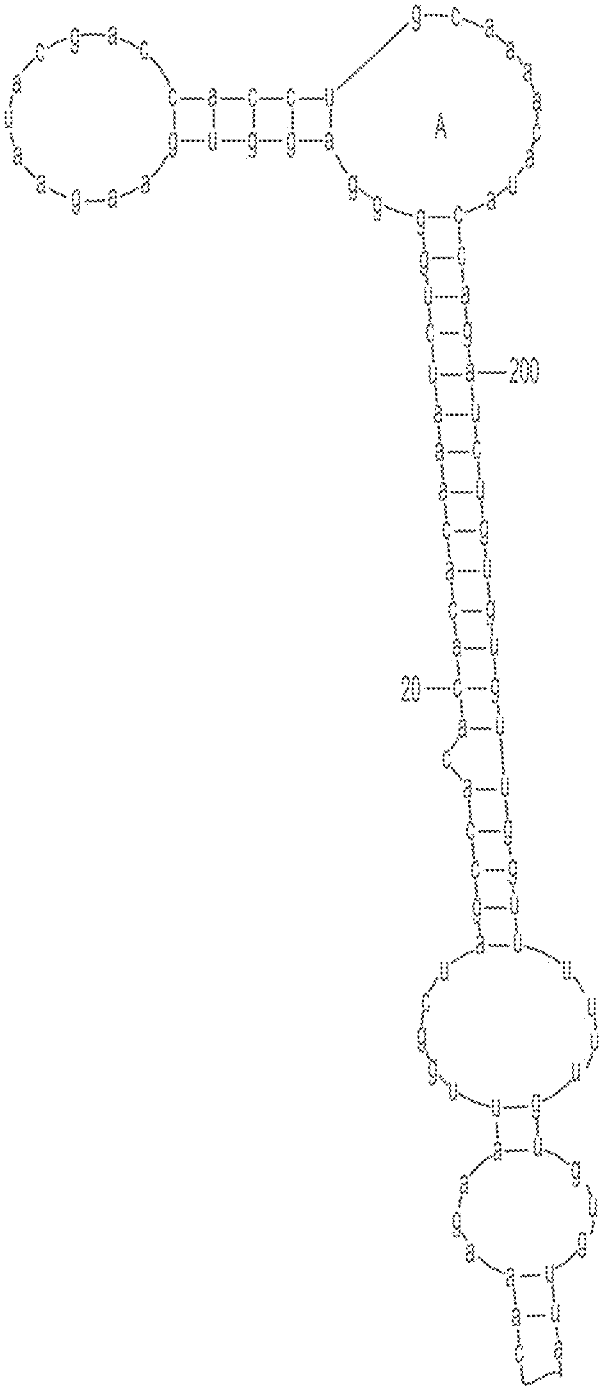
Figure 10A:
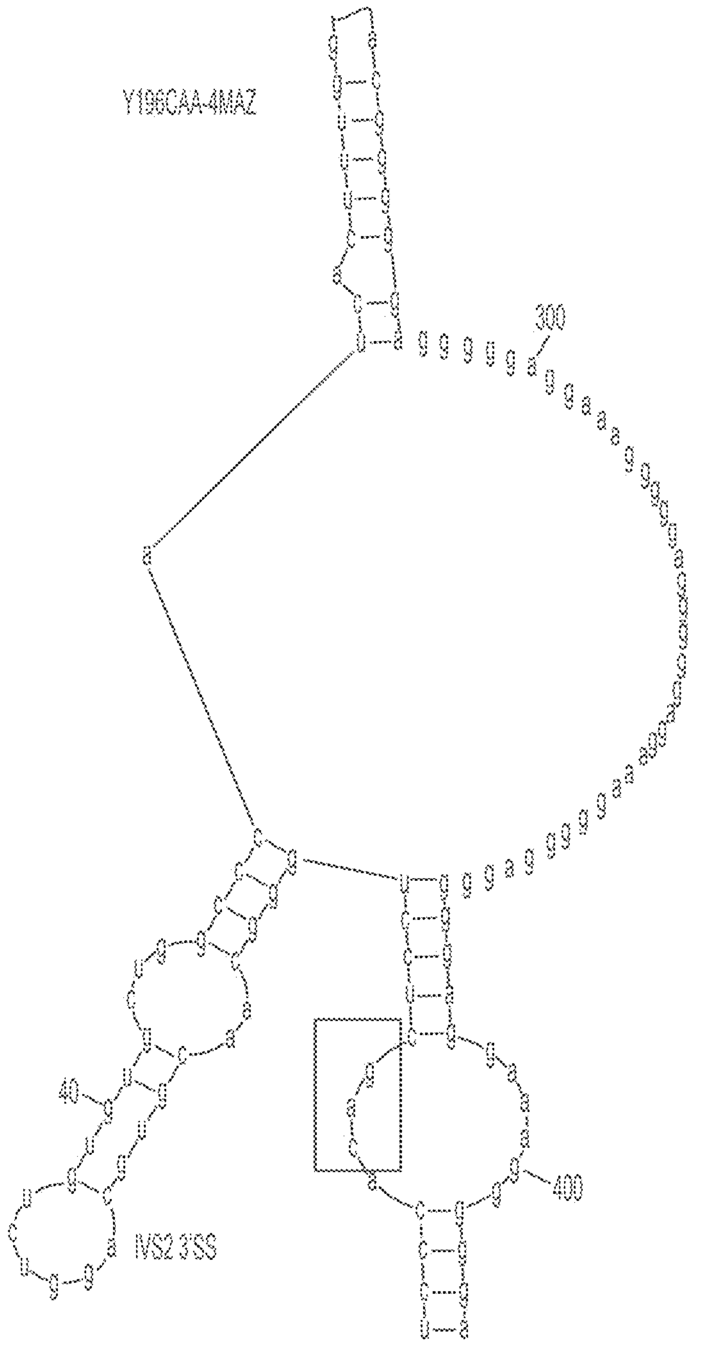
Figure 10C:
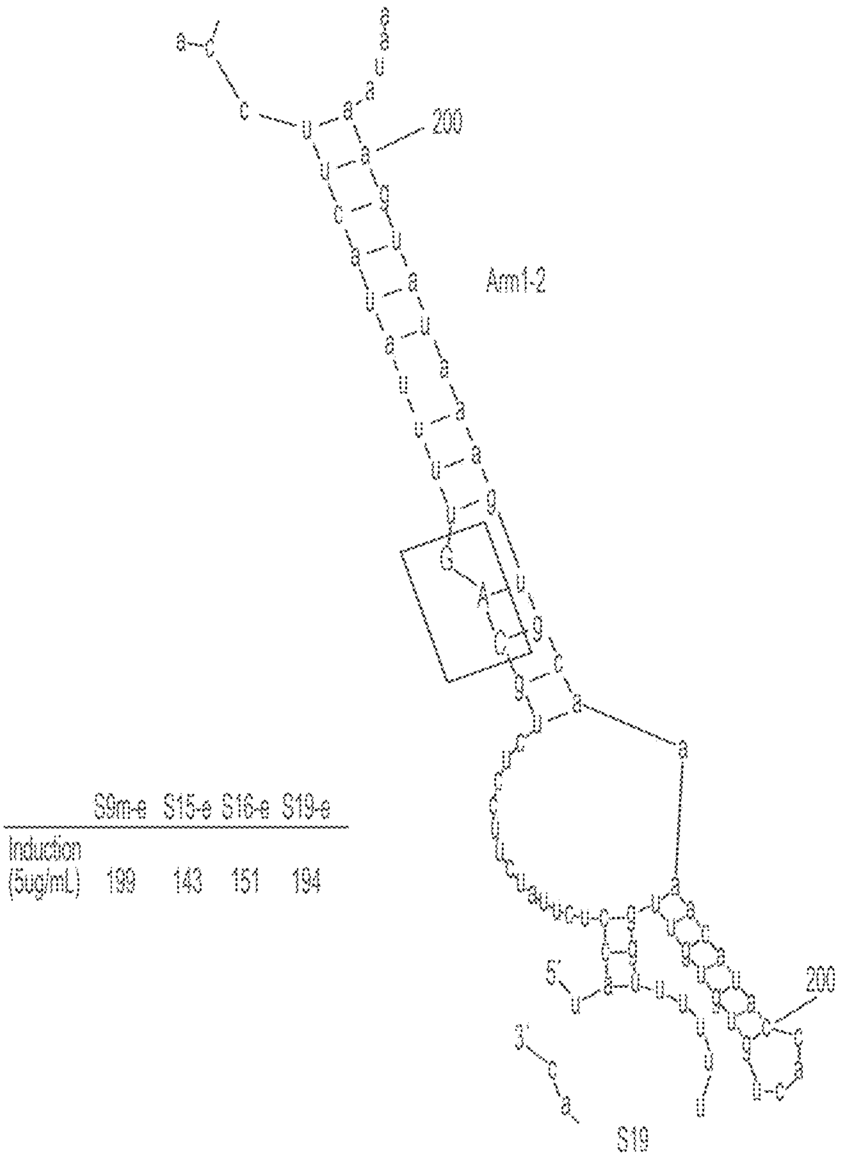
Figure 10C:
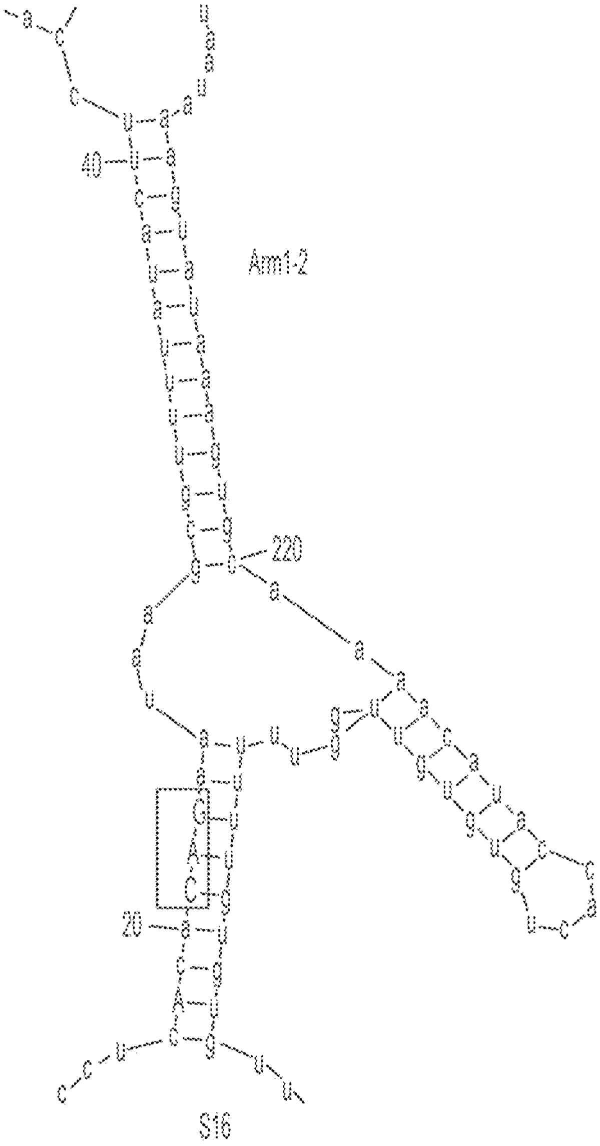
Figure 10C:
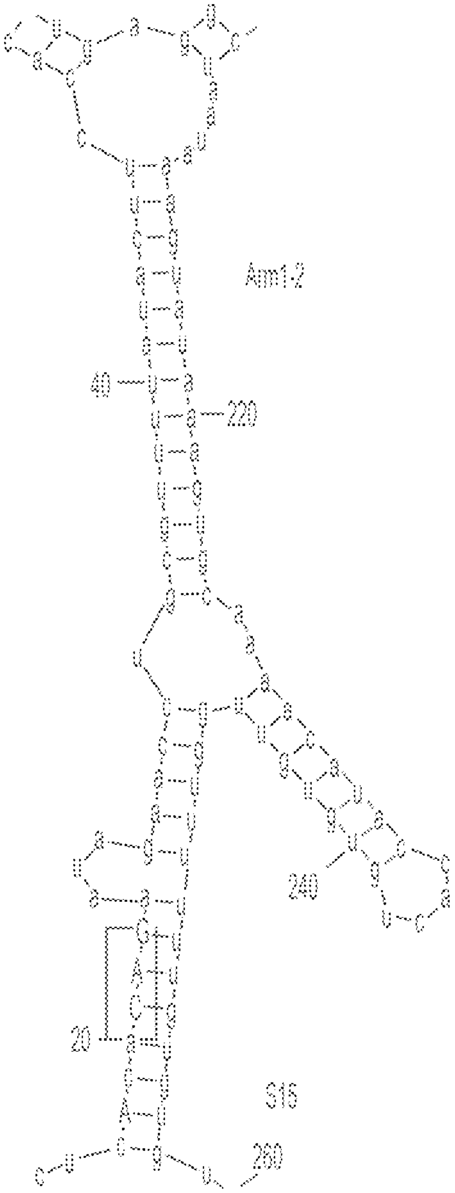
Figure 10C:
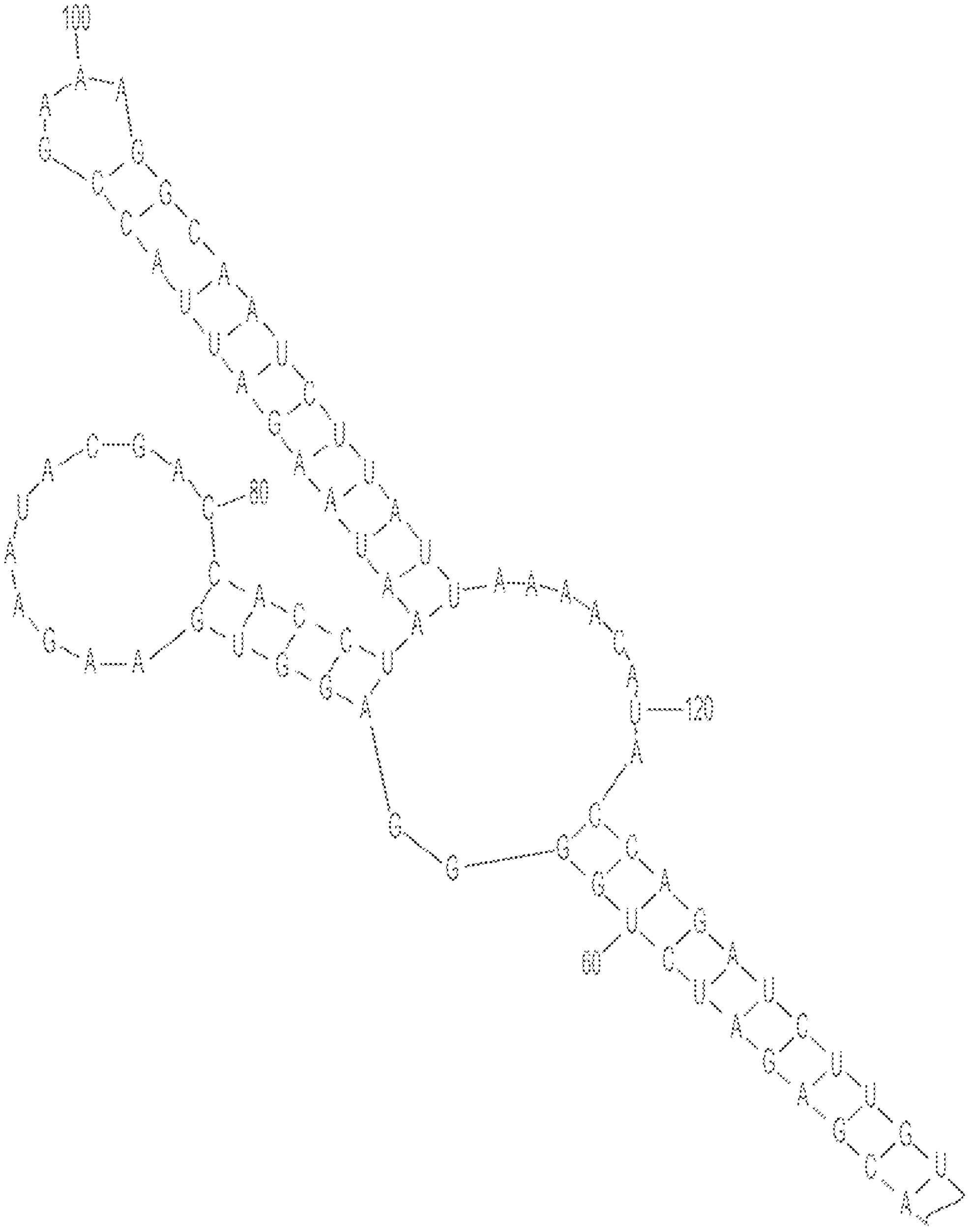
Figure 10C:
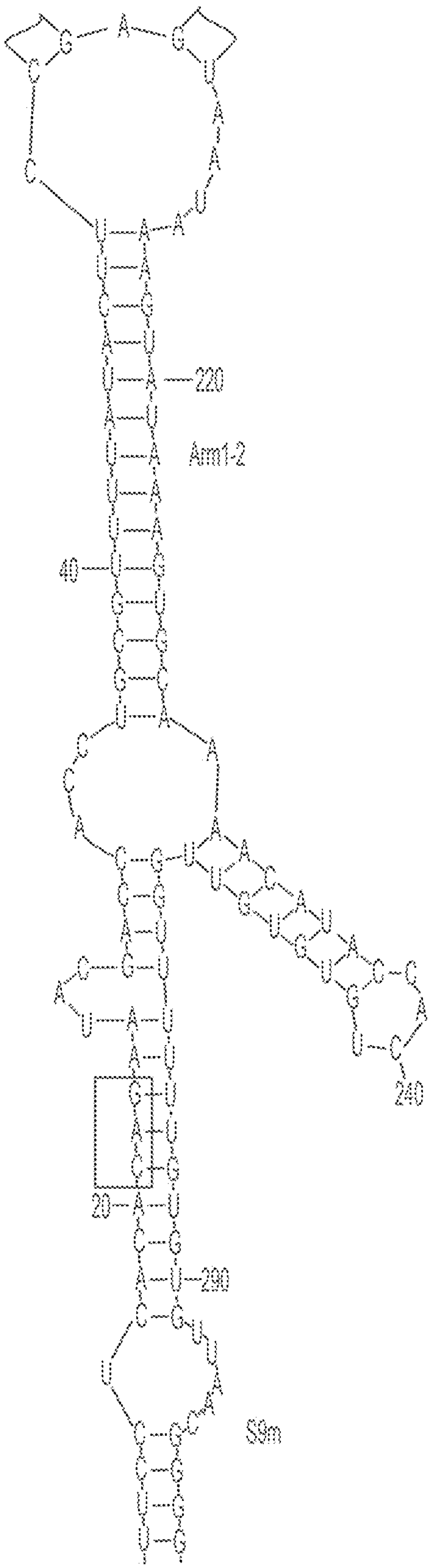
Figure 10C:
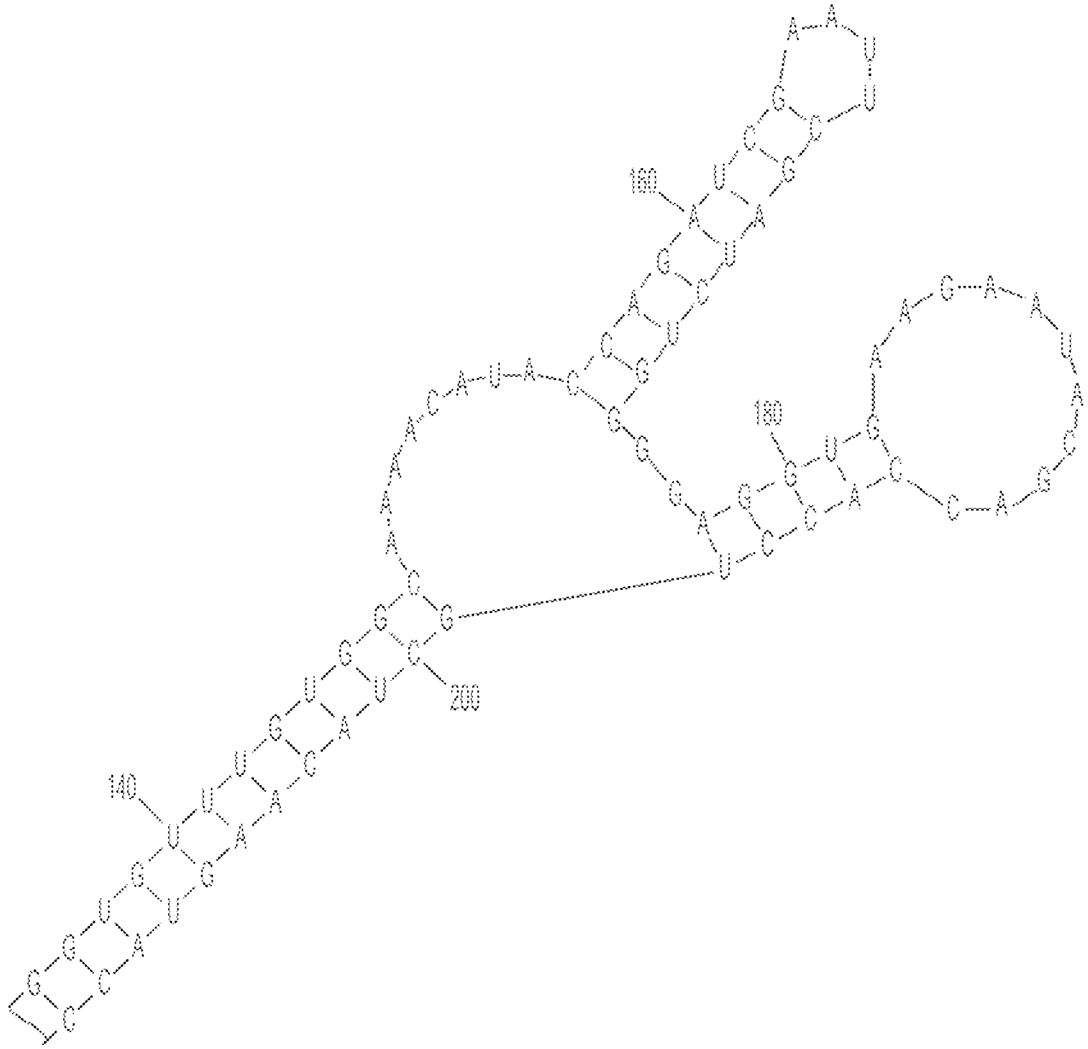
Figure 10D:
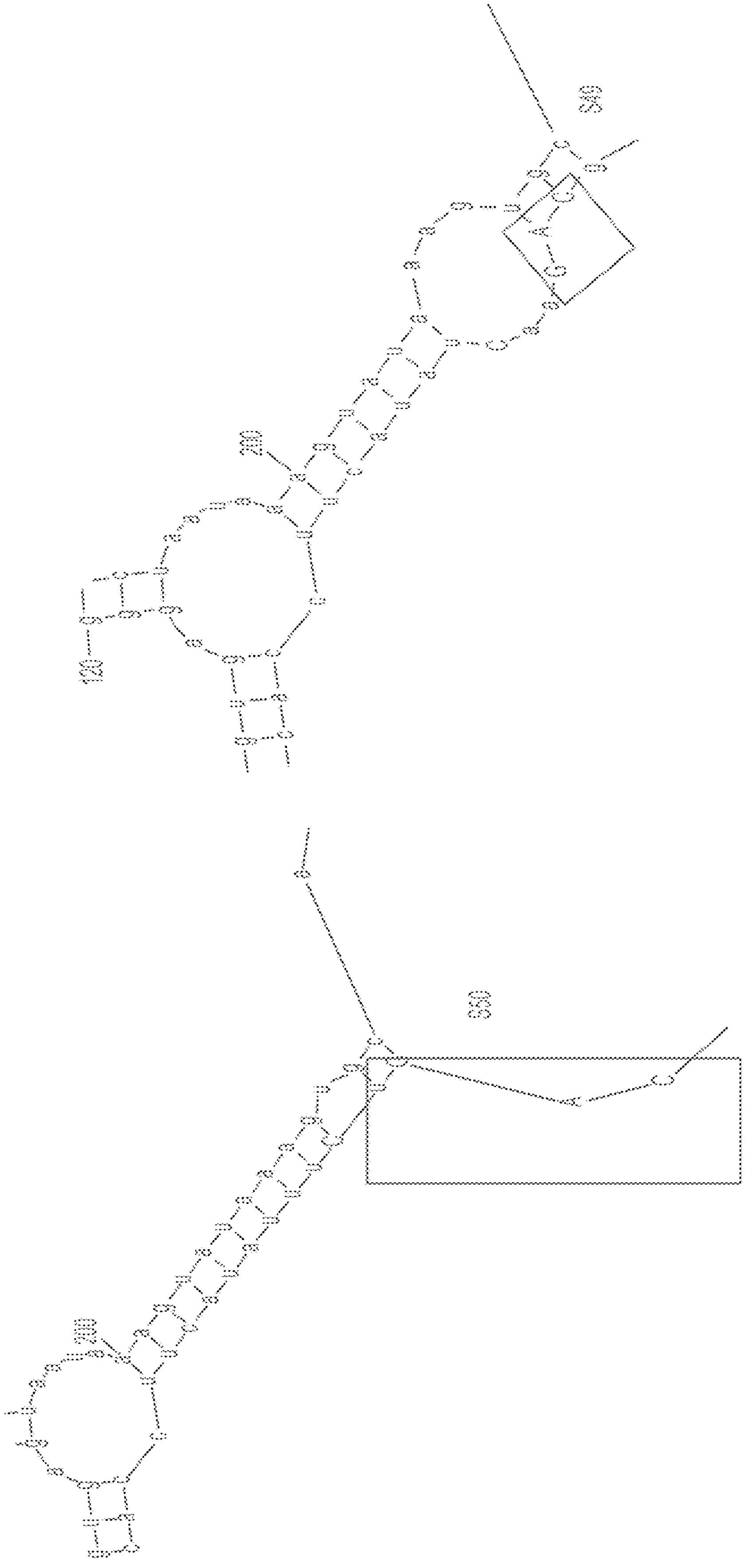
Figure 10D:
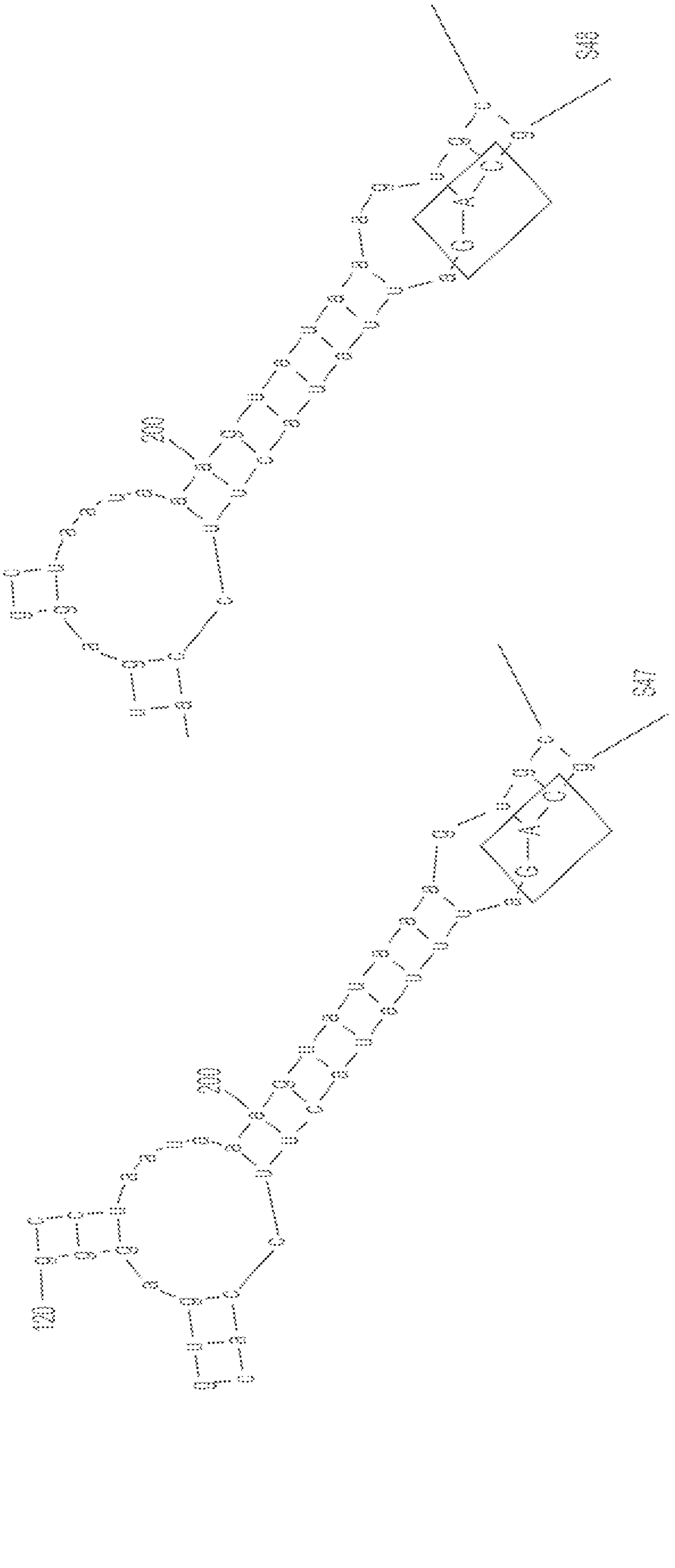
Figure 10D:
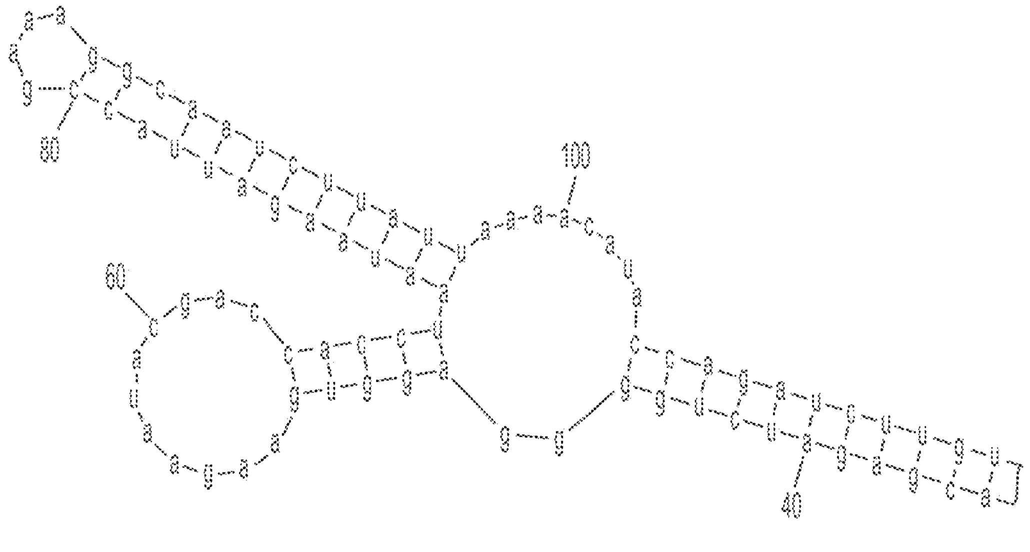
Figure 10D:
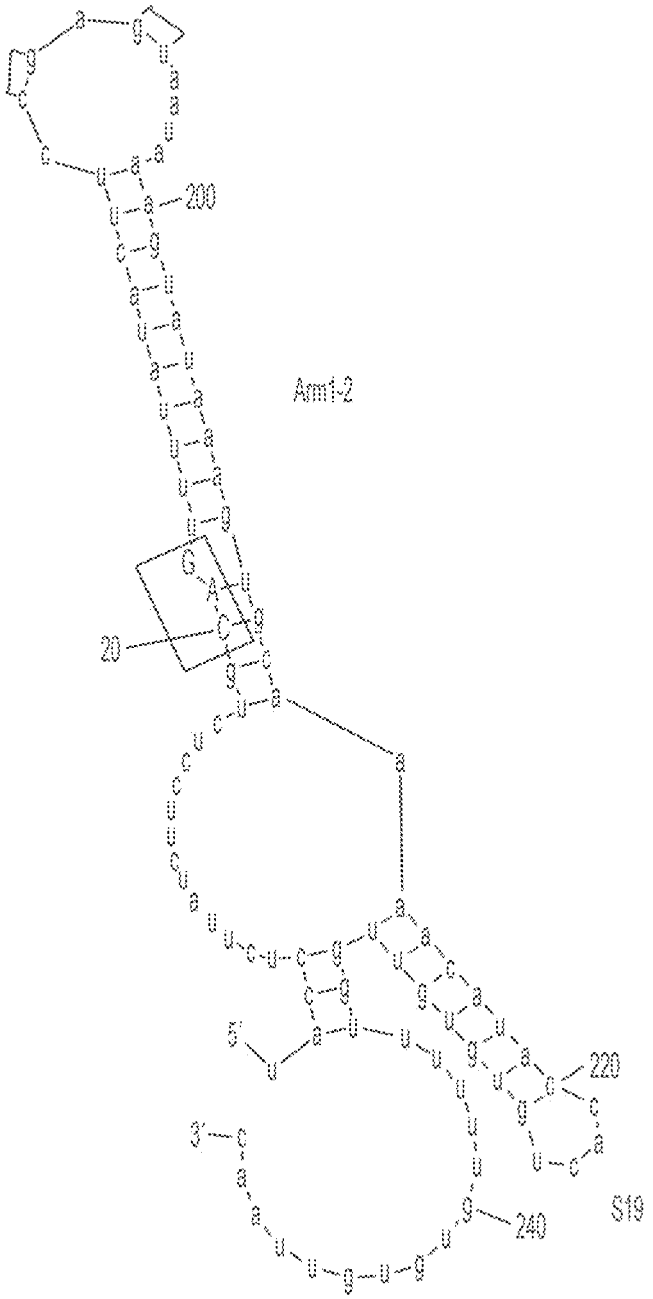
Figure 10D:
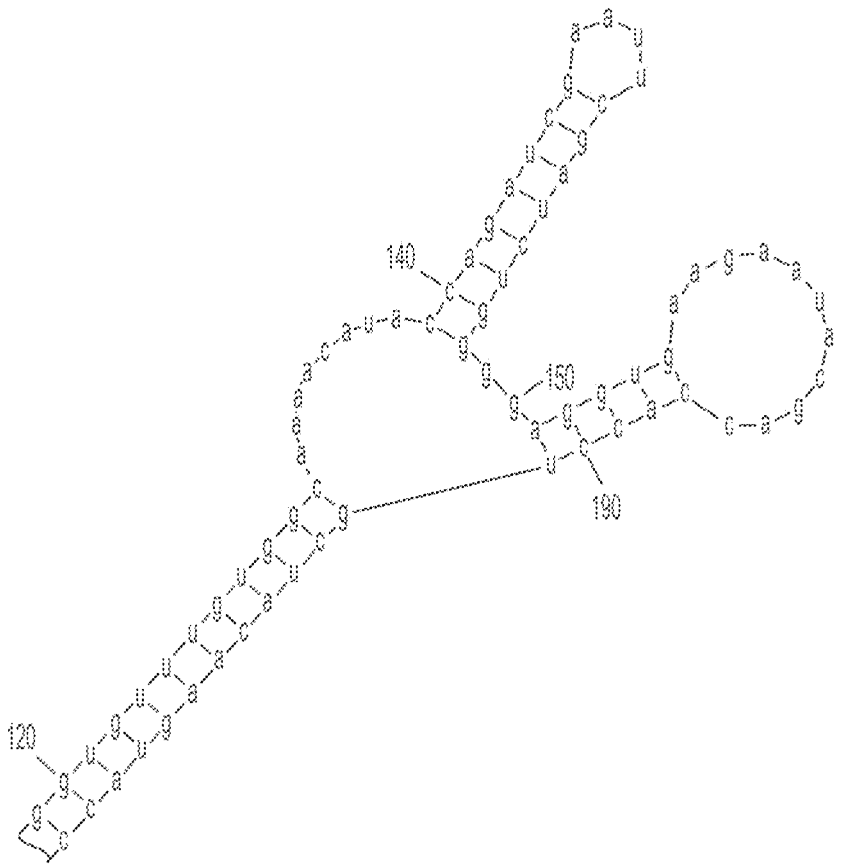
Figure 10F:
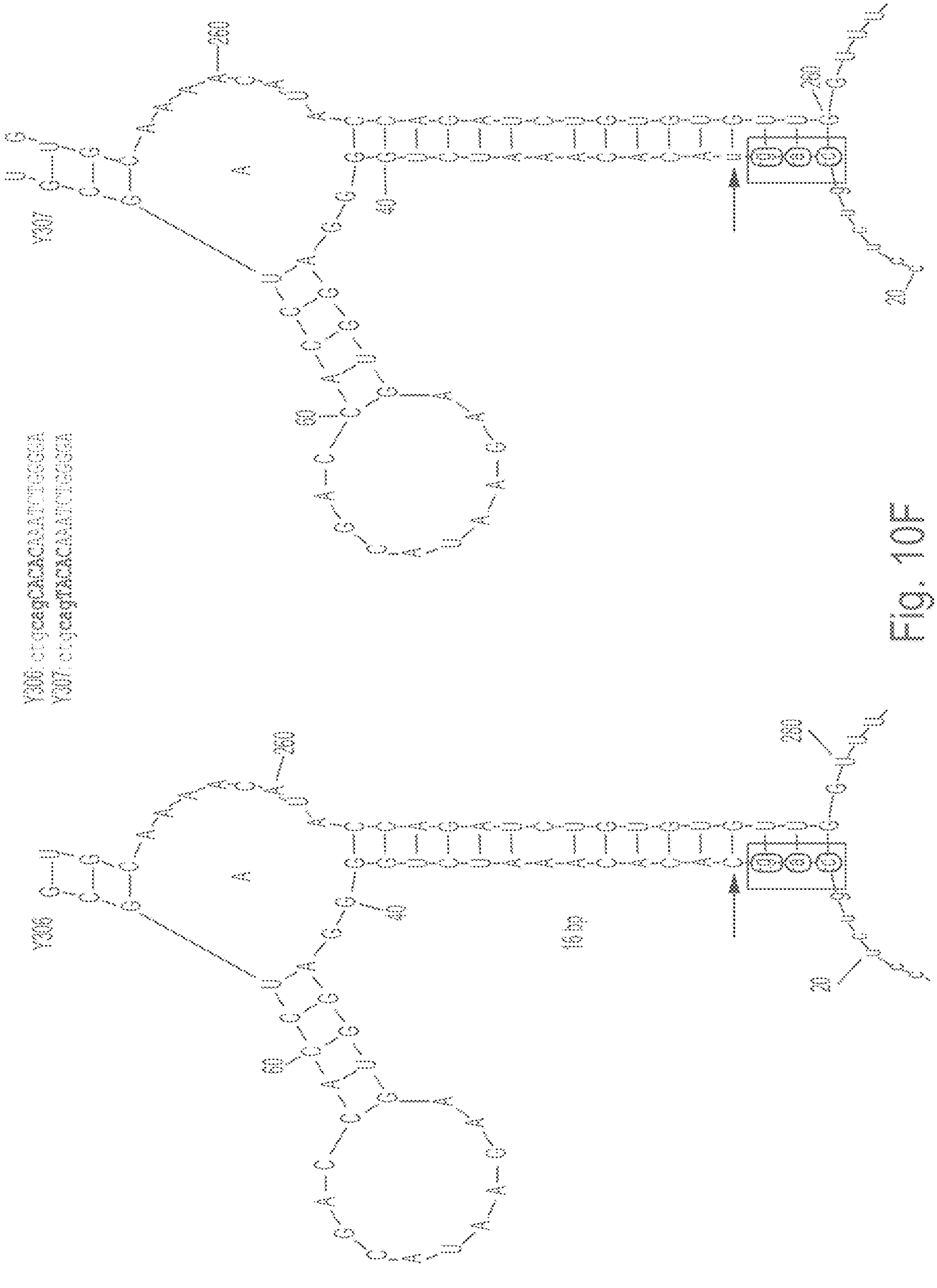
Figure 10F:
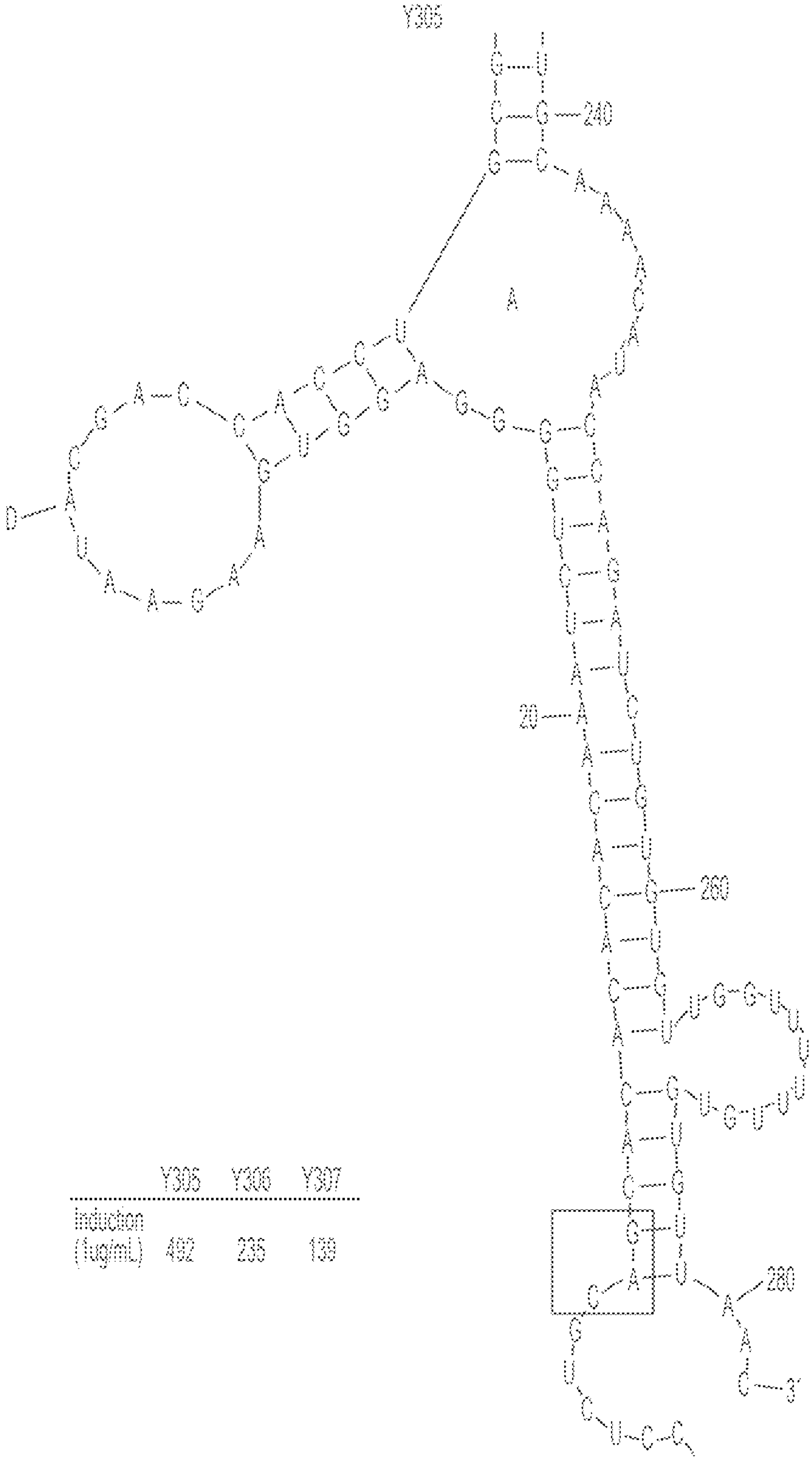
Figure 10F:
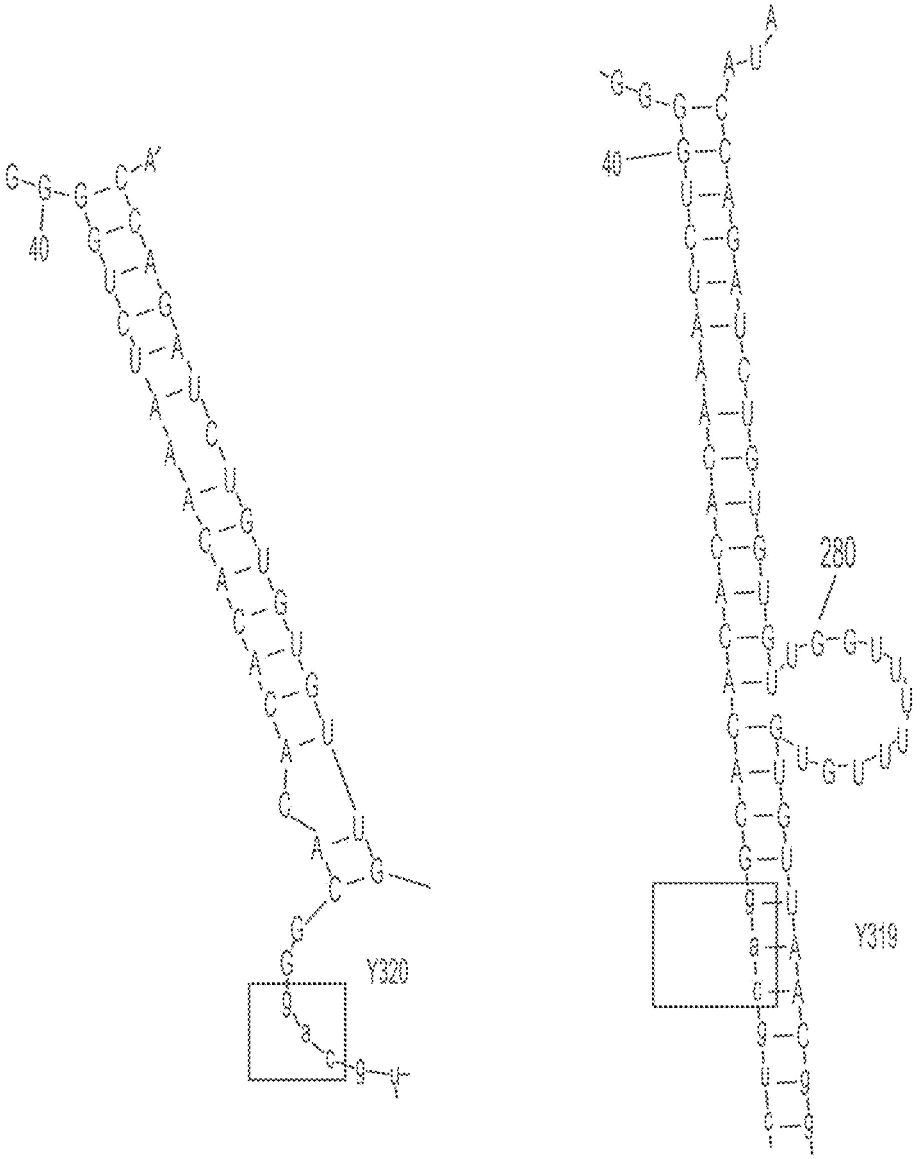
Figure 10F:
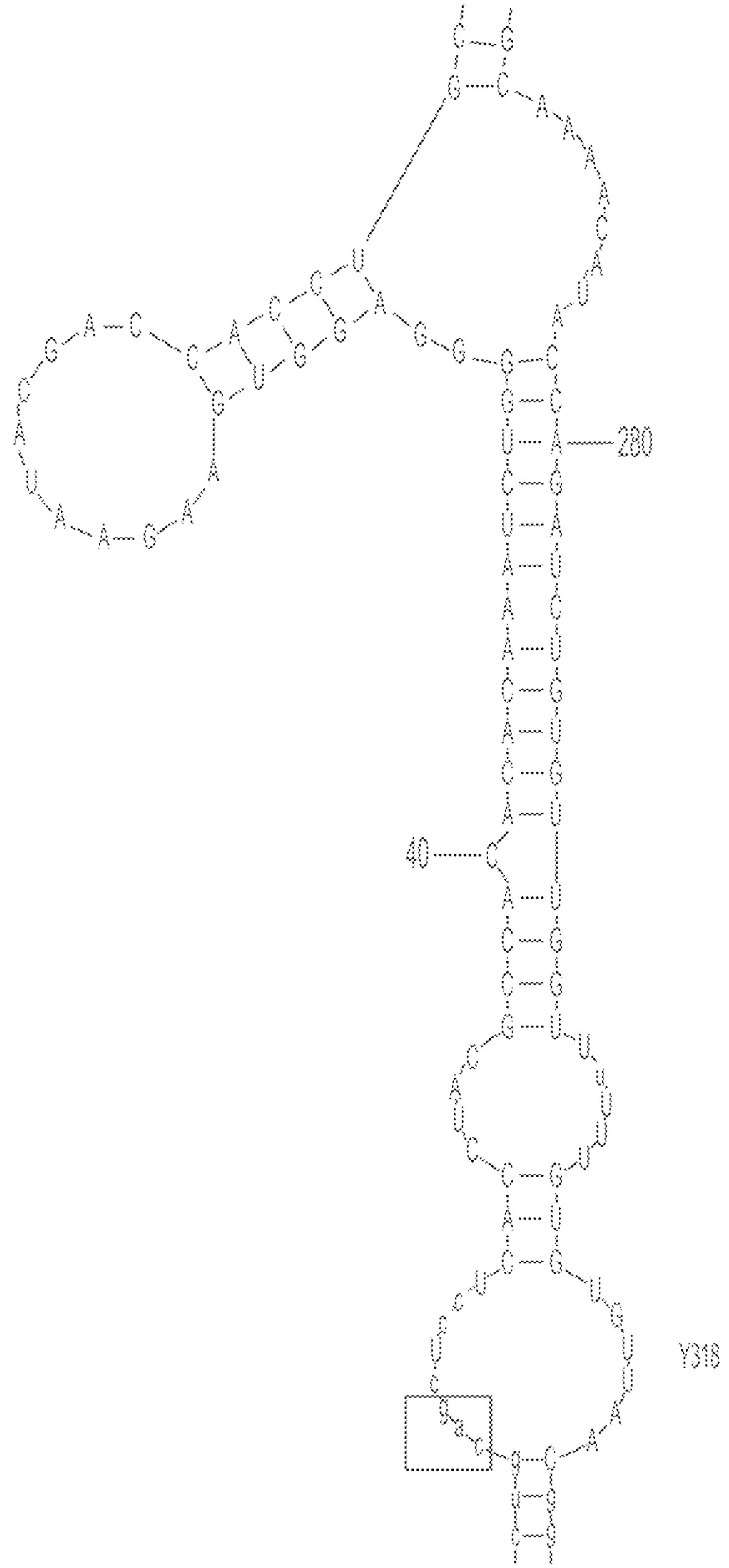
Figure 10F:
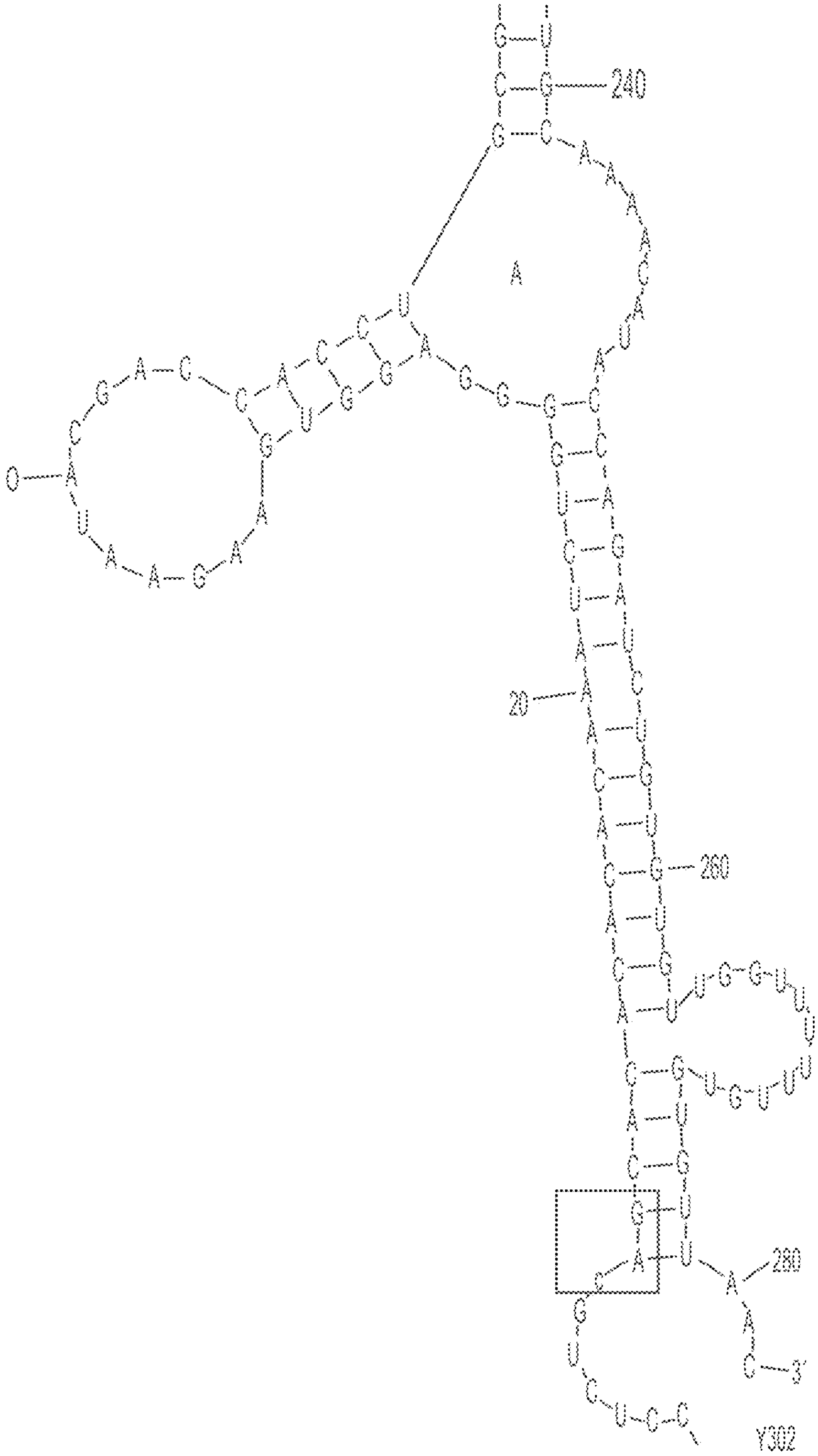

To further optimize the mechanism of Tc-induced alternative splicing, we have extensively probed the effects of IVS2 3' splice site location and surrounding sequence/structure. The modifications include: embed IVS23' splice site into the arm1; move IVS2 3' splice site closer or further away from the aptamers binding site; put IVS2 3' splice site in a loose bulge in the arm1; change the length or stability of the arm1 that hosts IVS2 3' splice site; change splicing strength of IVS2 3' splice site. FIG. 10A shows the results of gradually moving IVS2 3' splice site into arm1-1 of Y196CAA-4MAZ (S1-S4). It shows also that when the IVS2 3' splice site is mutated from CAG to CCC (S5), the induction is nearly eliminated. FIG. 10B demonstrates that when IVS 3' splice site is completely embedded into the arm1-1 near the Tc binding pocket of aptamer A (arrow; S9), this splice site is strongly inhibited, resulting in very low induction. This indicates that clamping of IVS2 3' splice site by aptamer cannot be too strong. Further, diminishing the clamping effect of aptamer A by deleting part of its sequence (S9m) restores the induction. Moving the IVS 3' splice site along the arm 1 of S9m leads to S19 which is shorter and has similar induction levels compared to the parental S9m (FIG. 10C). FIG. 10D demonstrate the effect on induction when the IVS2 3' splice site CAG is placed in the bulge of arm1-2. S47 to S50 are based on S19. At 1 ug/mL Tc, most of them yield lower induction. At 5 ug/mL Tc, they give similar or higher induction compared to S19 with the exception of S50. FIG. 10E shows results of changing the predicted strength of splicing by mutating the base after IVS2 3' splice site. Changing the strength of IVS2 3' splice site does not significantly alter the induction in the S9m-based and Y196CAA-4MAZ based configurations. FIG. 10F shows results of moving mini-IVS2 3' splice site further into or away from stem, which all lead to lower induction. FIG. 10G shows effects of randomization of the three bases after the cag of the 3' splice site of mini-IVS2 to select the sequences with the highest performance. This group of constructs (in particular Y362, Y366, and Y367) exhibited superb switching efficiency, surpassing the performance of Y300 and Y301. Best NNN sequences identified by testing: Y344-based: Y359 (CAT), Y360 (TTT), Y361 (TGA), Y362 (TCT); Y358-based: Y363 (CAT), Y366 (TAC), Y367 (TTT)

Example 9: Modulating a Second 3' Splice Acceptor Site in 5'UTR

Assays were performed to test the effect of modulating the strength second 3' splice acceptor site in the 5'UTR. The 5'UTR sequence of Y196CAA-4MAZ located after 4MAZ and before the start codon ATG has the following sequence: gcggccgccaacaacaacaacaacaacaacaacaacaacaacaacaacat-aacagtgttcactagcaacctcaaacag acaccATG. Adding an additional branch point (S10), ppt (S11), or mutating CAG to CCC (S12) or AAG (S13) all lead to reduced induction (FIG. 11A). To activate the correct 3' splice site (IVS2 3' splice site) in the absence of Tc, and in the presence of Tc (the second alternative 3' splice site), we used the constructs with short introns as the starting point and used a randomization approach to select the best three bases after the TAG in 5'UTR (TAGNNN) to improve the induction (FIG. 11B). We also inserted these best three bases (NNN) intothe 5'UTR of Y329 to assess the performance (FIG. 11C). Among these, Y344 performed best.

Example 10: Intron Size

We tested the effect of shortening the overall size of the hybrid switch by reducing the size of IVS2 intron. FIG. 12A shows exemplary intron sequences. Constructs S164 to S168 are similar to S159-S163 but have a branch point TACTAAC inserted at the same location before IVS2 3' splice site. The intron sequence of S164 is shown as an example: Gtgagtc-tatgccagctaccattctgcttttattttatggttgggataaggctggattattct-gagtccaagctaggcccttttgctaatc atCttcaTACTAACctct-tatcttcctctgCAG. Constructs S169 to S173 are similar to S159-S163 but have a branch point TACTAAC and one more 3' splice site CAG inserted at the same location before IVS2 3' splice site. The intron sequence of S169 is shown as an example: GTgagtctatgccagctaccattctgcttttattttatggttggga-taaggctggattattctgagtccaagcTACTAACttttcctg tgcttcttca-gacctcttatcttcctctgCAG. Reducing the IVS2 intron size from 476 bases to 120-200 bases reduced the induction significantly (FIG. 12B). The results from Y164 to Y173, which have different splicing elements added to enforce IVS2 intron splicing, lead to even lower induction compared to the ones without those added elements. This indicates that shortening or adding elements to IVS2 intron alter the choice of 3' splice site activation in the presence of Tc. Previously we have shown that CAA repeats alter the splicing strength of the 3' splice site in 5'UTR. Here the CAA repeats are to be removed from S159, S164, and S169. As compared to S56, S192 (with 120 bases intron) gave better induction at 1 μg/mL Tc, and similar induction at 5 μg/mL Tc. S192, which is more compact due to shorter intron, is used as a new basis for further modification.

Example 11: Addition of an Upstream Out-of-Frame AUG (HORF)

Figure 13A:
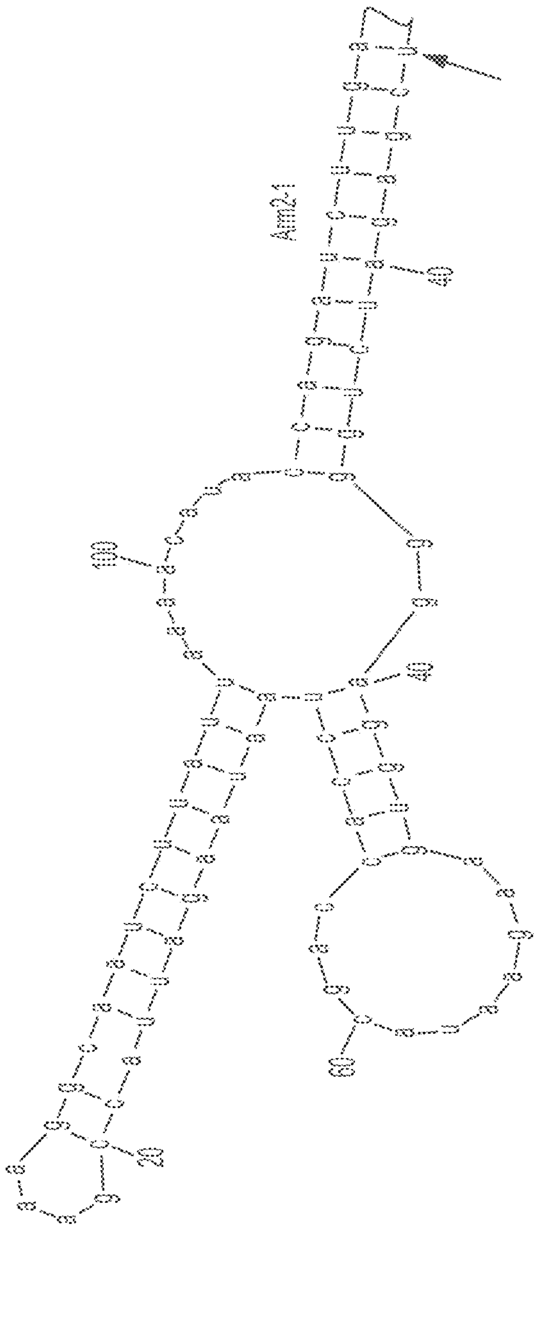
Figure 13A:
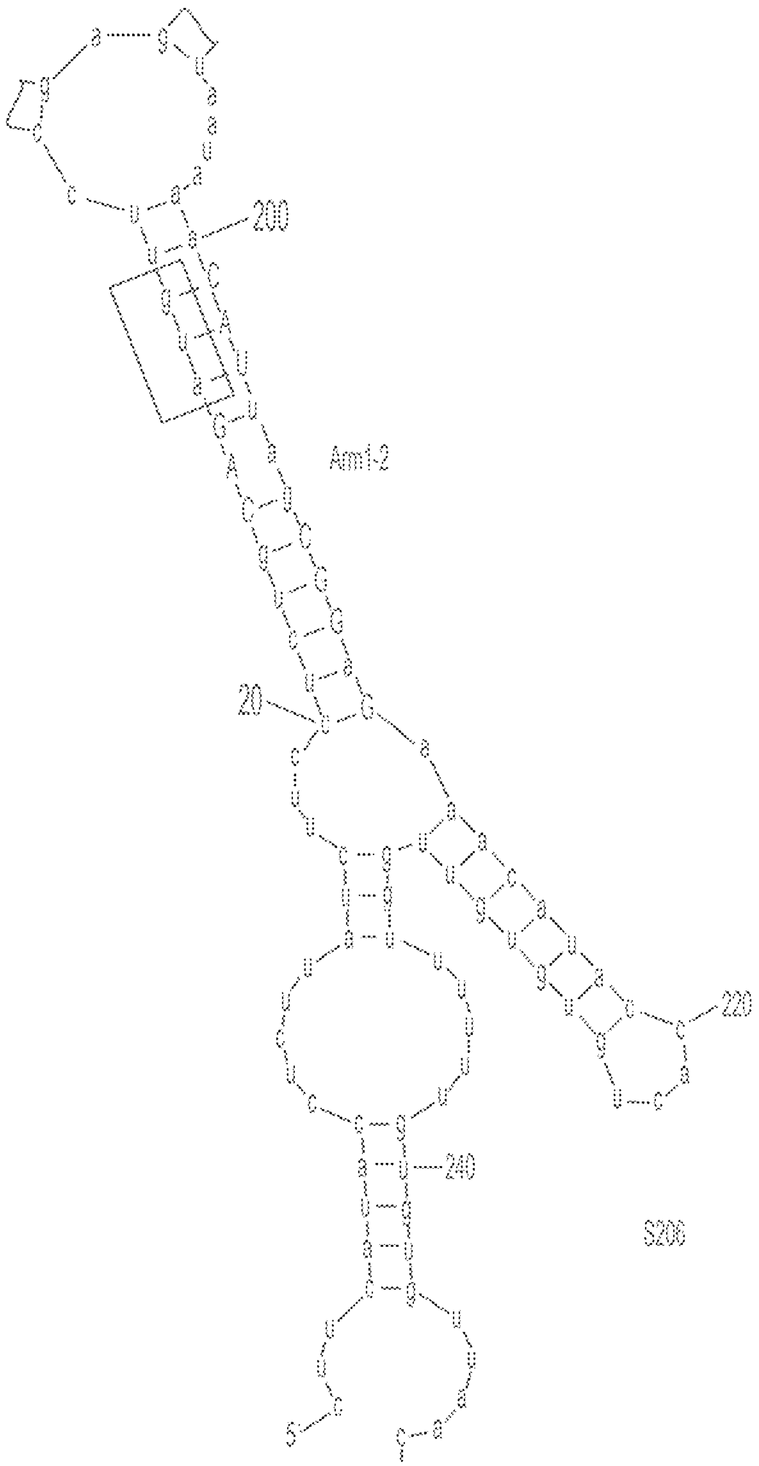
Figure 13A:
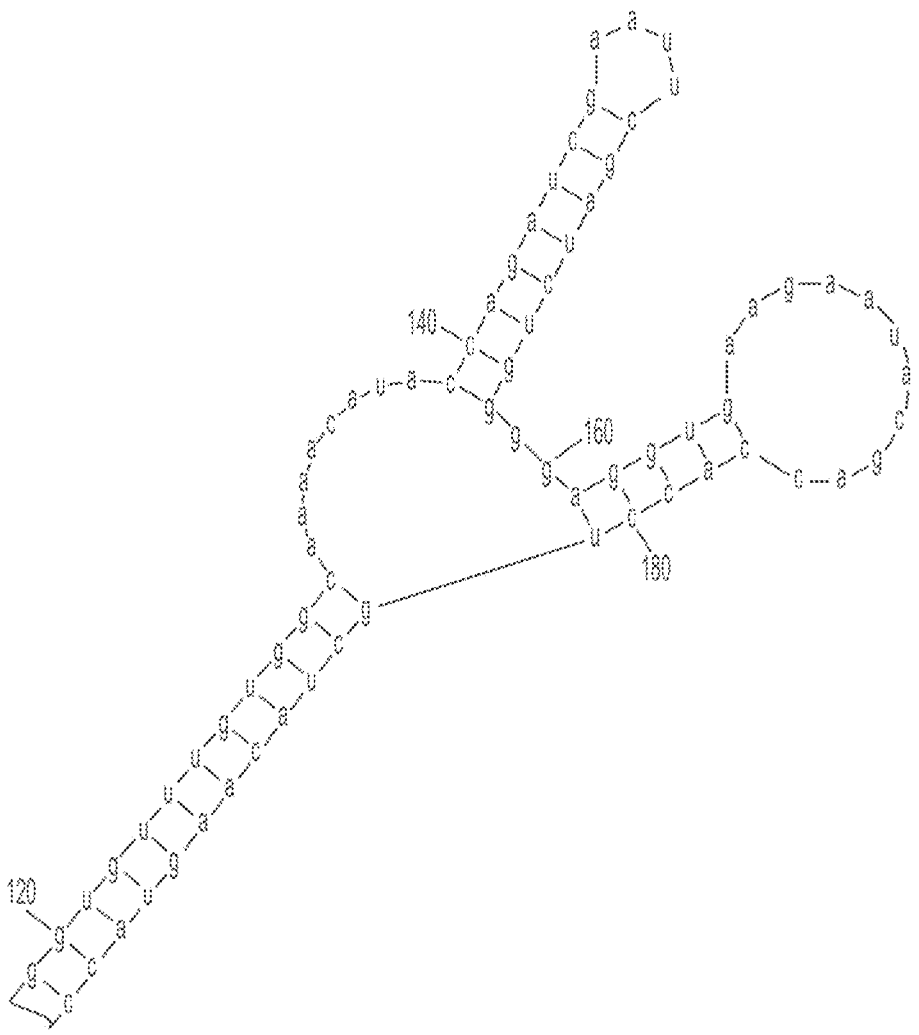

An upstream out-of-frame AUG was introduce to construct S192 to test the effect on reporter gene translation from IVS2-spliced transcript. The modifications include: (1) changing TAC to ATG immediately after IVS2 3' splice site to create a new start codon (box), (2) changing the corresponding base on the other side of arm1 to maintain the base paring in the stem, and (3) mutating an in-frame stop codon tga into aga in arm2-1 (arrow), so the translation from this new ATG can produce fairly long protein. See FIG. 13A.

The sequence after IVS2 3' splice site CAG is shown. The new μORF is underlined: ctgCAGATGttcctcgagatctggg-gaggtgaagaatacgaccacctaataagattaccgaaaggcaatcttattaaaaca taccagatcttgagagggtgtttgtggcaaaacataccagatcgaattc-gatctggggaggtgaagaatacgaccacctgctac aagtacctaataaaCATt-agCGGaGaaacataccactgtgtgttggtttttgtgtgttaacgggggagggg-gaggaaagg gggagggggaggaaagggggagggggaggaaagggggagggg-gagcggccgccataacagtgttcactagcaaccT caaacagacaccATG. This approach significantly lowers the leakage expression from IVS2-spliced transcript, therefore significantly increases the induction as demonstrated by the result of S206.

This construct is further optimized by fine-tuning the 5'UTR sequence based on S206 (FIG. 13B). All of these constructs demonstrate very good induction. These constructs are more compact due to shorter intron and partially deleted aptamer A. They perform very well at Tc concentration as low as 1 ug/mL, and reach as high as ~700 fold induction at 5 ug/mL.

Figure 13C:
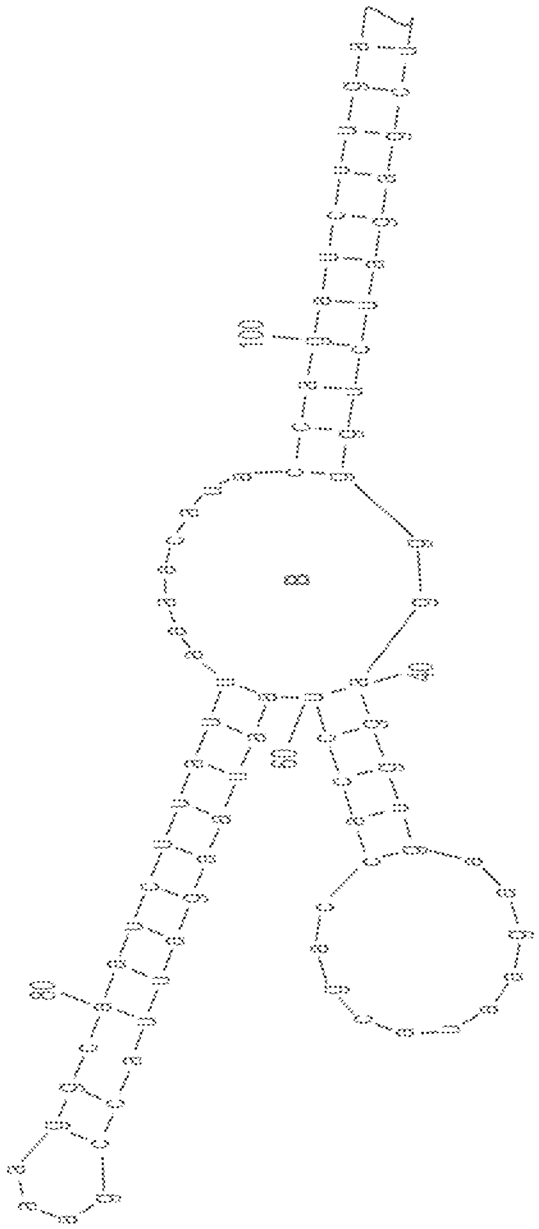
Figure 13C:
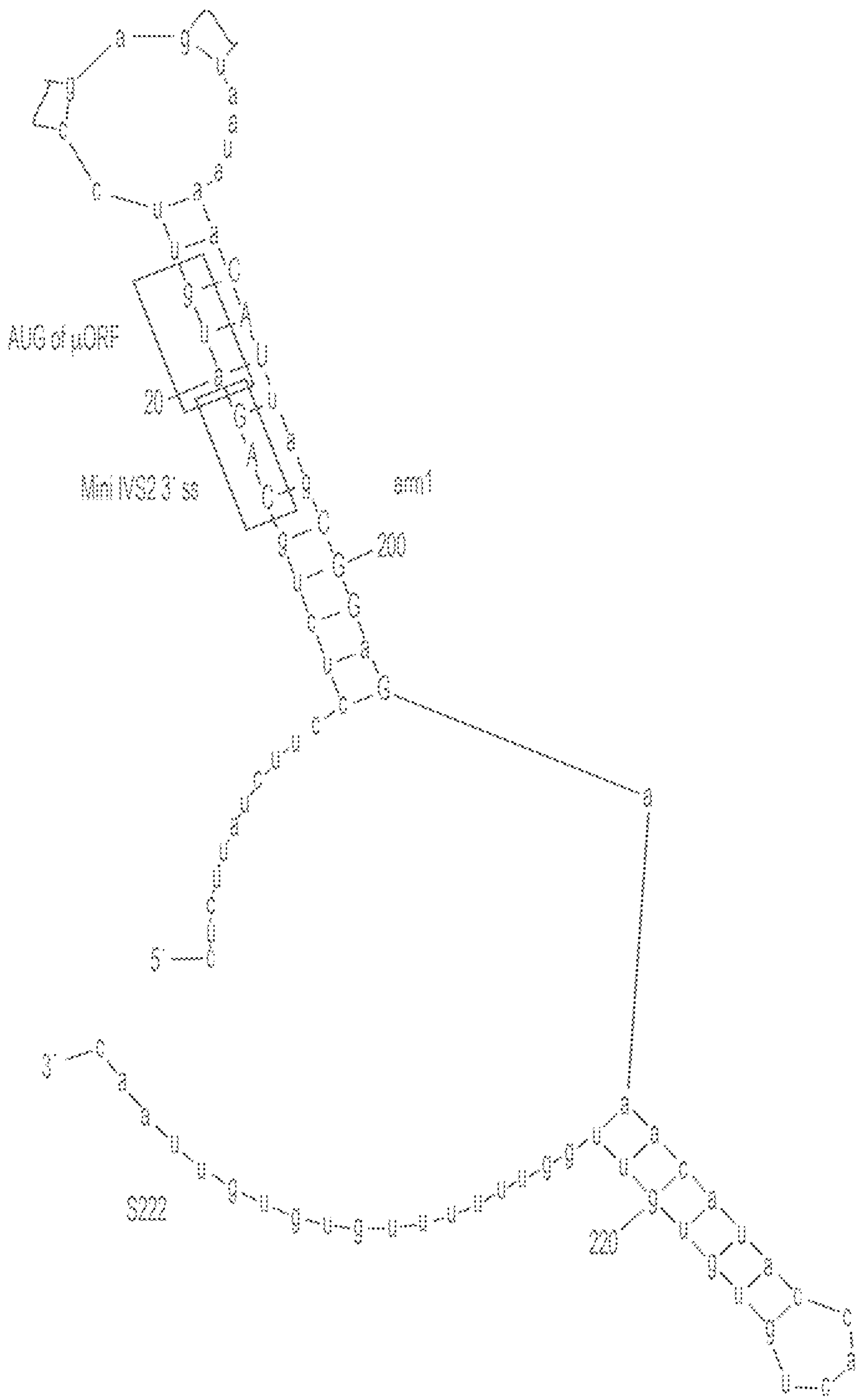
Figure 13C:
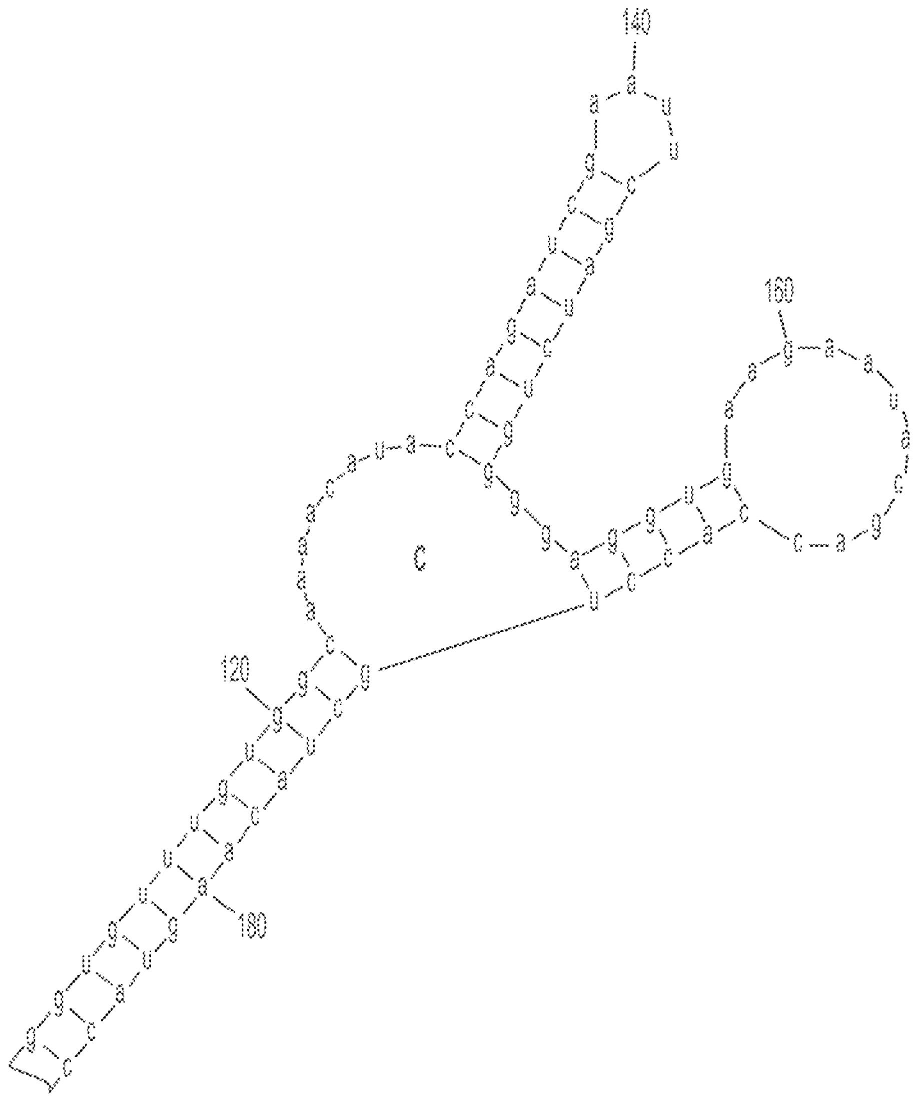

In summary, in the process of optimizing Tc effects on splicing choice between IVS2 3' splice site and the alternative 3' splice site, we found that the best location for placing IVS2 3' splice site is to embed it inside the arm1 of Y structure. In order to place IVS2 3' splice site in that location, the aptamer A is deleted from the Y structure. Creating an upstream out-of-frame AUG (μORF) which eliminates reporter gene translation from IVS2-spliced transcript decreases leakage expression. Compared to Y196CAA-4MAZ, S222 (FIG. 13C) shows higher induction in fold at lower drug concentration, higher gene expression levels, and perhaps more important, S222 is highly sensitive to Tc and performs well at low Tc concentrations.

Construct Performance

Figure 14A:
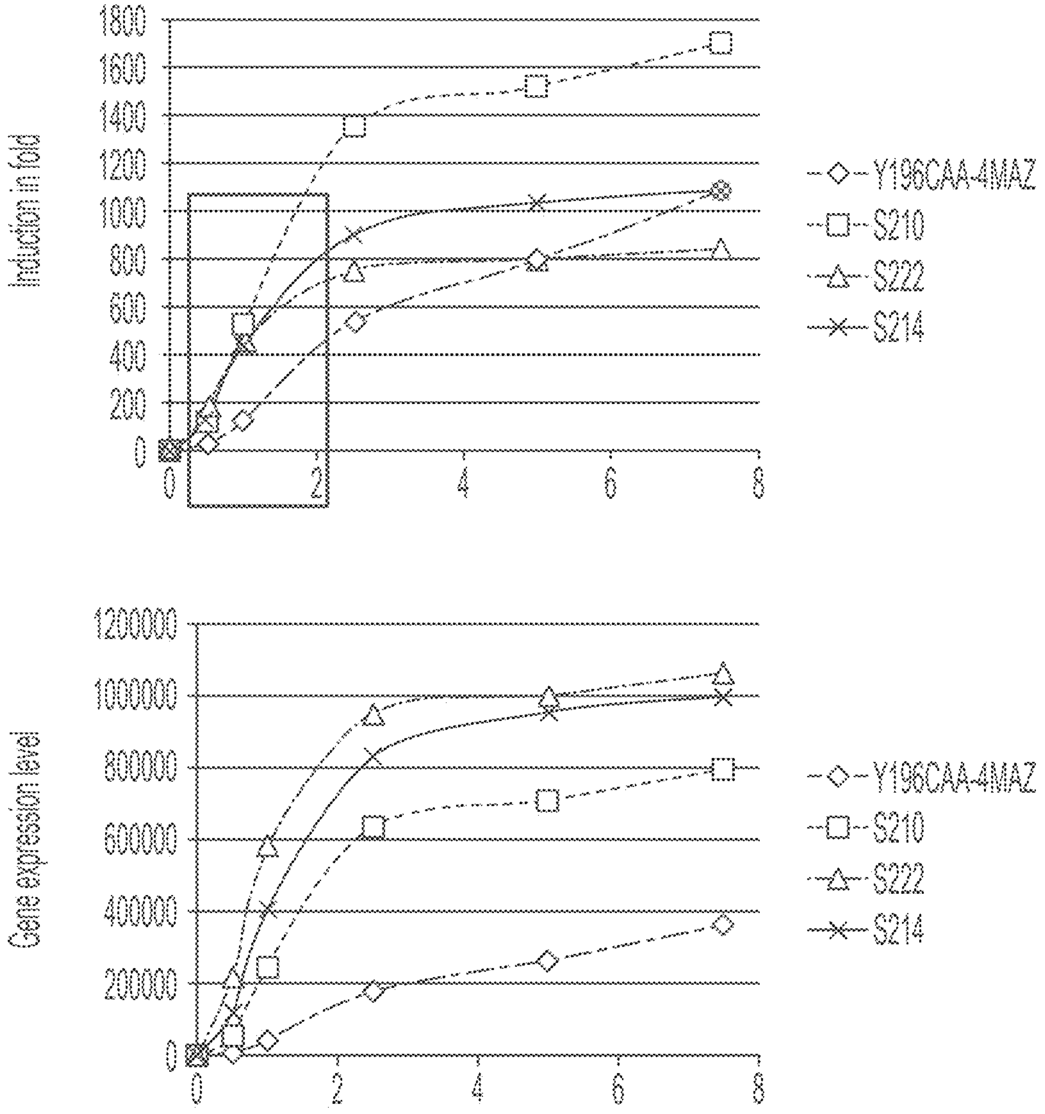
Figure 14B:
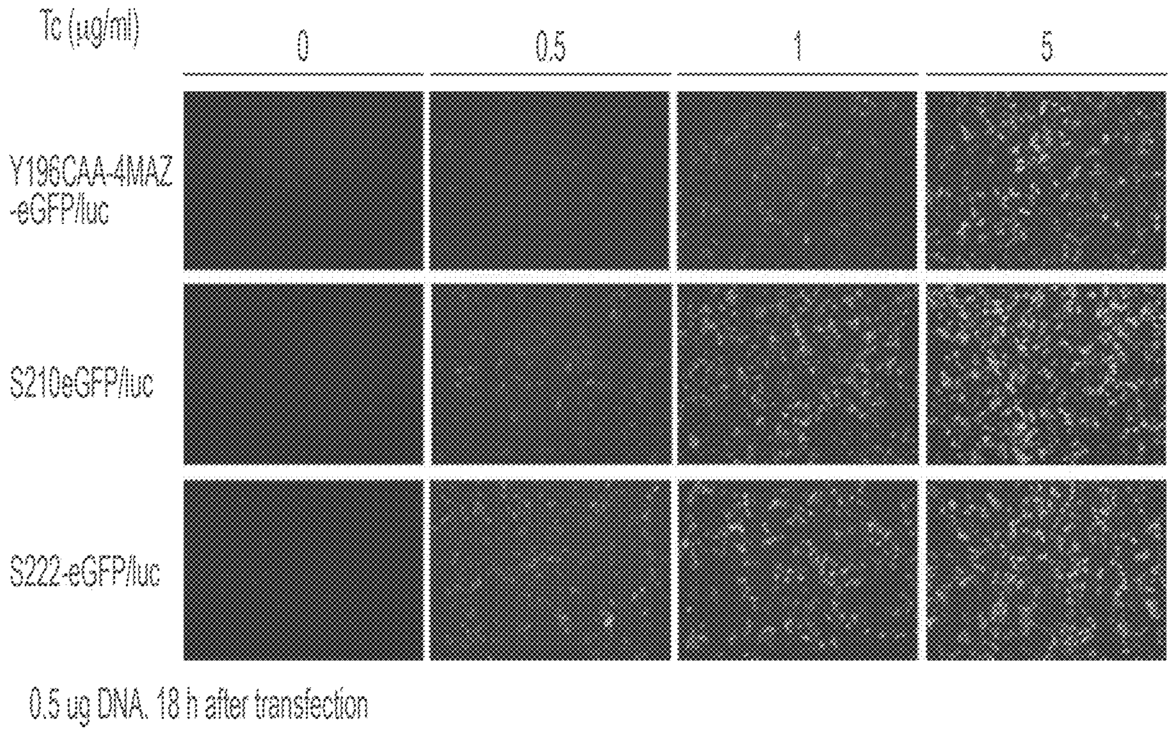

FIG. 14A demonstrates comparison of performance of representative S series constructs relative to Y196CAA-4MAZ. FIG. 14B shows a dose response of expression from the hybrid switch constructs visualized by microscopy.

Figure 14C:
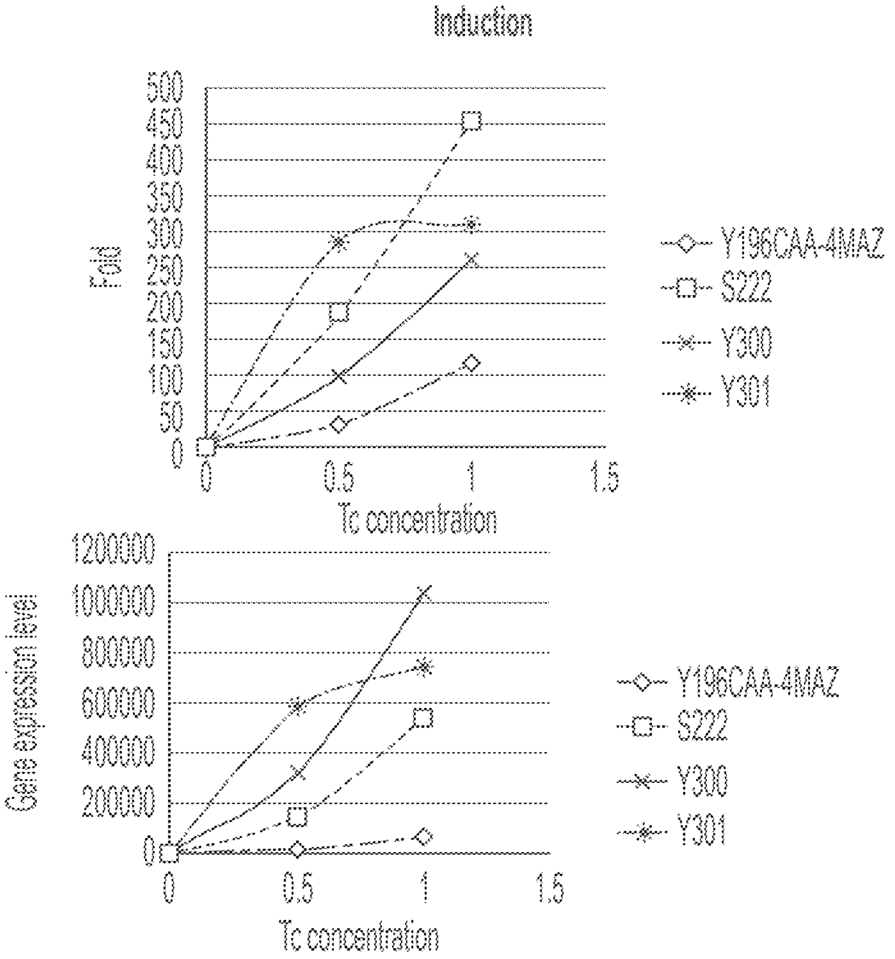

To avoid potential immunogenicity generated by the protein translation of upstream open reading frames (μORF), we built another hybrid switch without the μORF aimed at surpassing the performance of S222. To build this new hybrid switch, we returned to the Y196CAA-4MAZ design as it has 3 aptamers as compared to 2 aptamers in S222. To further improve Y196CAA-4MAZ, we (1) use the mini-IVS2 intron with 120 bases, (2) optimizing the 3' splice site of mini-IVS2 sequence, (3) optimizing the 5'UTR sequence containing the downstream alternative 3' splice site. These efforts led to a group of constructs surpassing S222 in performance. The induction by tetracycline is so efficient that they induce gene expression to 50% of the maximal level ($EC_{50}$) at a drug concentration as low as 0.5 to 1 μg/ml. This concentration of tetracycline can be routinely achieved in human serum using FDA-approved dosage, and is an order of magnitude lower than what has been previously achieved using any RNA-based gene regulation technology. FIG. 14C demonstrates a comparison of the performance of these new constructs to that of S222. 5'UTR sequence of Y300: gcggccgcCataacagtgttcactagcaTccCcaaacagacac-cATG. Y301: based on Y300 with modified 5'UTR gcggccT-TaATtaacagtgttcactaggacaccATG.

Figure 14E:
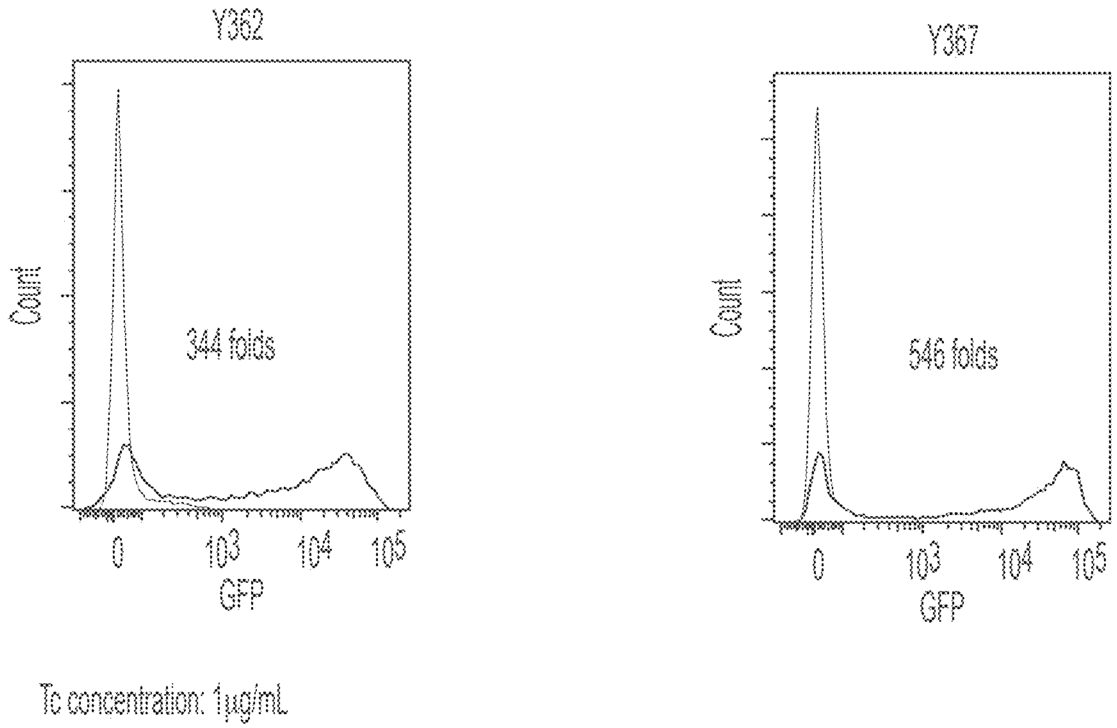

FIG. 14D demonstrates the performance of Y362 and Y367 determined by luciferase assays. FIG. 14E shows the response to 1 ug/ml tetracycline of Y362 and Y367 as determined by fluorescence activated cell sorting (FACS) using eGFP reporter signal. 'Induction in fold' in all results is calculated as the ratio of transgene expression in the presence vs. absence of tetracycline.

Example 12: Insertion of Riboswitch at Endogenous Location

Figure 15:
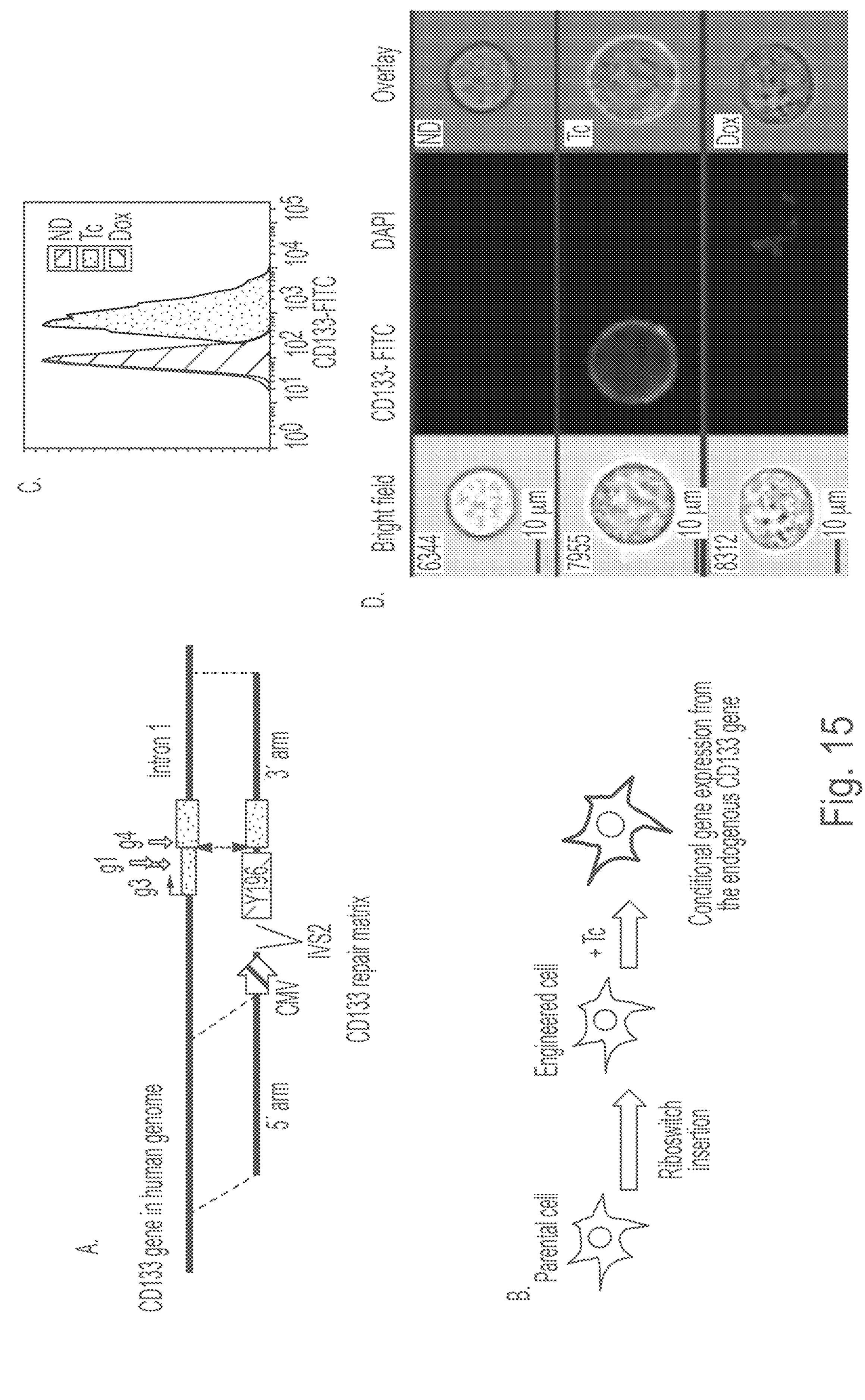
FIG. 15 demonstrates the ability of a polyA aptamer polynucleotide described herein to function as an endogenous switch to control the expression of an endogenous gene in the genome.

The Y-shape polyA switch, when combined with CRISPR, creates a powerful technology platform to control the expression of any endogenous gene in mammalian genome. FIG. 15 provides a schematic of using CD133, a stem cell membrane protein, to demonstrate the principle. The conditional gene expression of endogenous CD133 is achieved by inserting Y196 riboswitch at the 5'UTR of CD133 using CRISPR-Cas9 and a repair matrix. FIG. 15A Top: three gRNAs (g1, g2, and g3) are used to specify the locations for CRISPR-Cas9 cleavage near the translational start of CD133. FIG. 15A Bottom: repair matrix containing mini-CMV promoter, IVS2 intron, and Y196 riboswitch flanked by upstream and downstream homologous sequences to CD133 is used for repair. FIG. 15B provides schematics of experimental procedures. Y196 riboswitch was first inserted into parental CD133; cells by CRISPR-Cas9. The successfully engineered cells then respond to Tc in a dose-dependent manner to turn on CD133 expression.

FITC-conjugated antibody against CD133 protein was used to label and isolate the cells responding to Tc. FIG. 15C shows that conditional expression of endogenous CD133 was regulated by Tc. CD133 expression in engineered cell clone (293T cell in this case) showed little or no background leakage. The CD133 expression is specifically induced by Tc, but not its analog Doxy. ND: no drug treatment, Tc: Tetracycline, Doxy: Doxycycline. Cell clone was treated with or without drug for 2 days and then harvested for flow analysis. X-axis showed the intensity of antibody staining of individual cells. FIG. 15D shows as expected, the CD133 protein induced by Tc (as revealed by FITC-anti CD133 antibody) was localized to cell membrane as normal endogenous CD133 protein would. The stable cell clone was treated with or without drug at 2 μg/ml for 2 days and then harvested for Image flow analysis (Amnis). Again, the induction is clearly specific to Tc but not Doxy.

The data described represent a highly responsive gene regulation mechanism that harnesses the power of drug-inducible alternative splicing to control polyA cleavage. The combination engineered creates a sensitive RNA-based switch that can be controlled by small molecule drugs and enables tight regulation of gene expression in mammalian cells. In contrast to other reported methods, this hybrid switch technology described herein exhibits very low leaky expression, and effectively turns on the transgene expression close to 700-folds in human cells. Furthermore, the induction by tetracycline is so efficient that it induces gene expression to 50% of the maximal level ($EC_{50}$) at a drug concentration as low as 0.5 to 1 μg/ml. This concentration of tetracycline can be routinely achieved in human serum using FDA-approved dosage, and is an order of magnitude lower than what has been previously achieved using other RNA-based gene regulation technology.

This hybrid switch technology therefore is advantageously safe to use in human patients for controlling the expression of a therapeutic gene or transgene. The present disclosure thus satisfies a long-felt need in the art to provide a highly efficient and non-immunogenic technology to regulate genes of interest in cells at a drug concentration that is safe for human consumption.

Example 13: Combination of Single Base Changes at Three Locations

Figure 16:
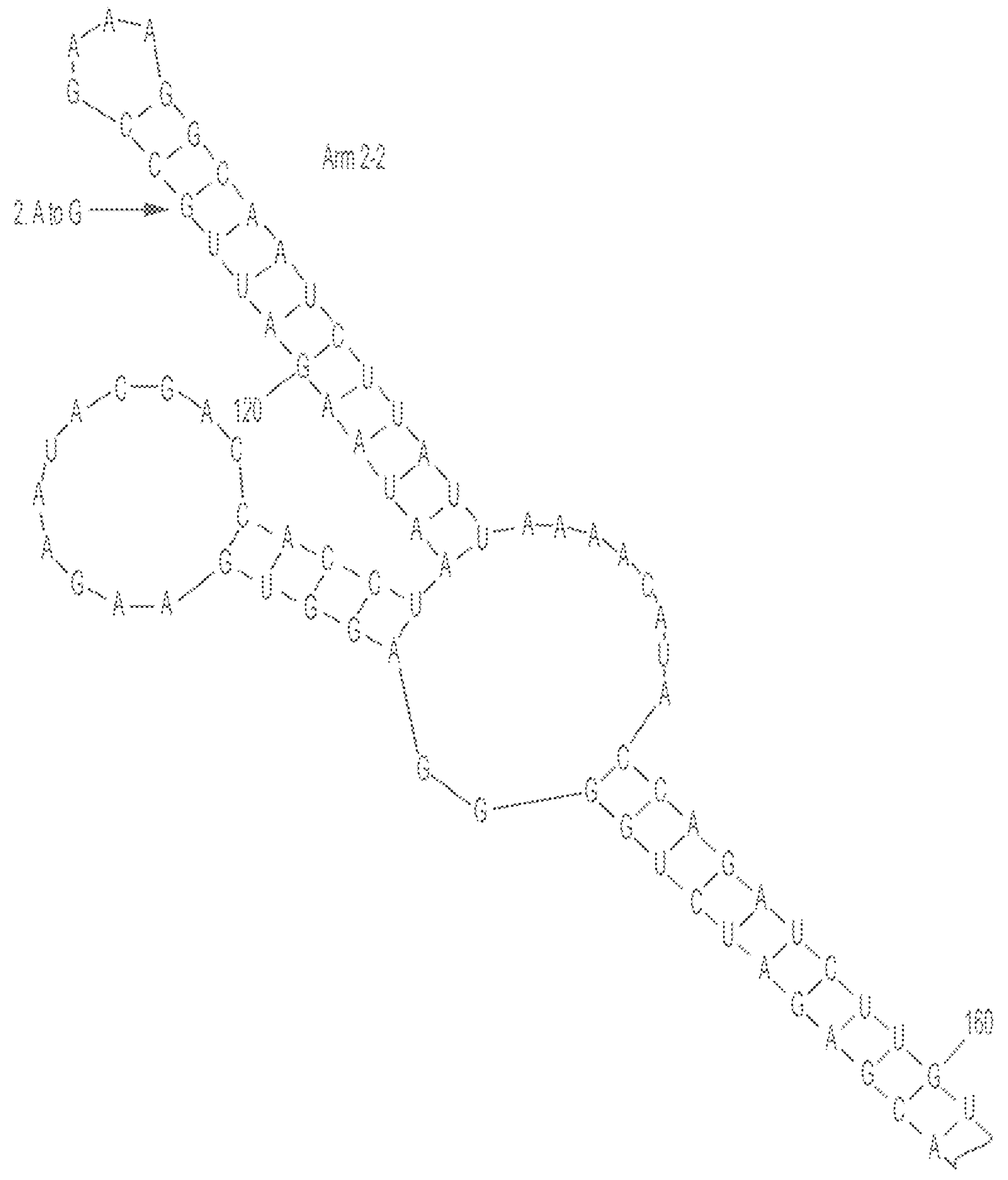
FIG. 16 depicts configuration of a Y-shape polyA switch combining single base changes at three locations. The Y387 construct shown here contains all the three changes (SEQ ID NO: 50).
Figure 16:
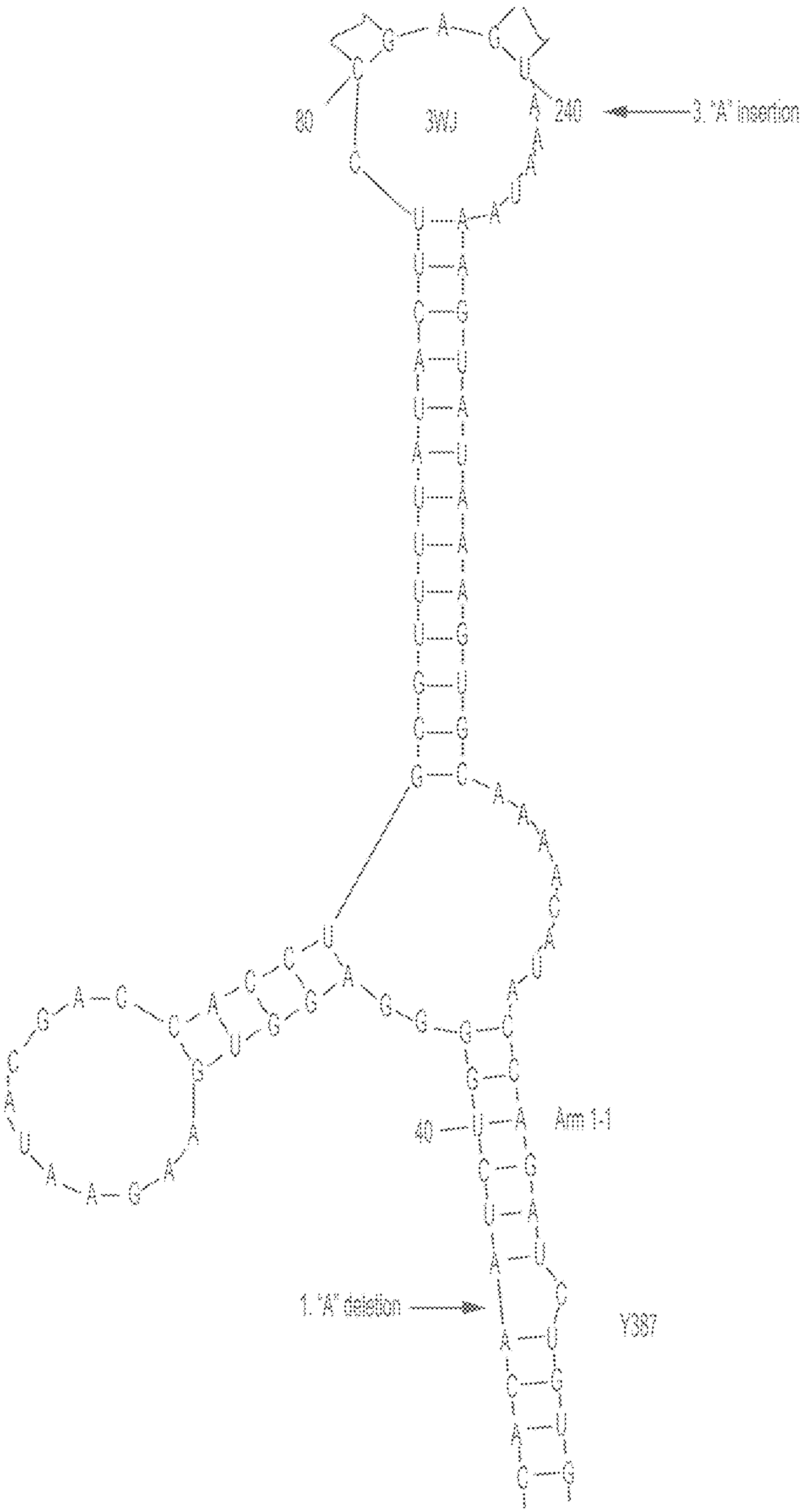
Figure 16:
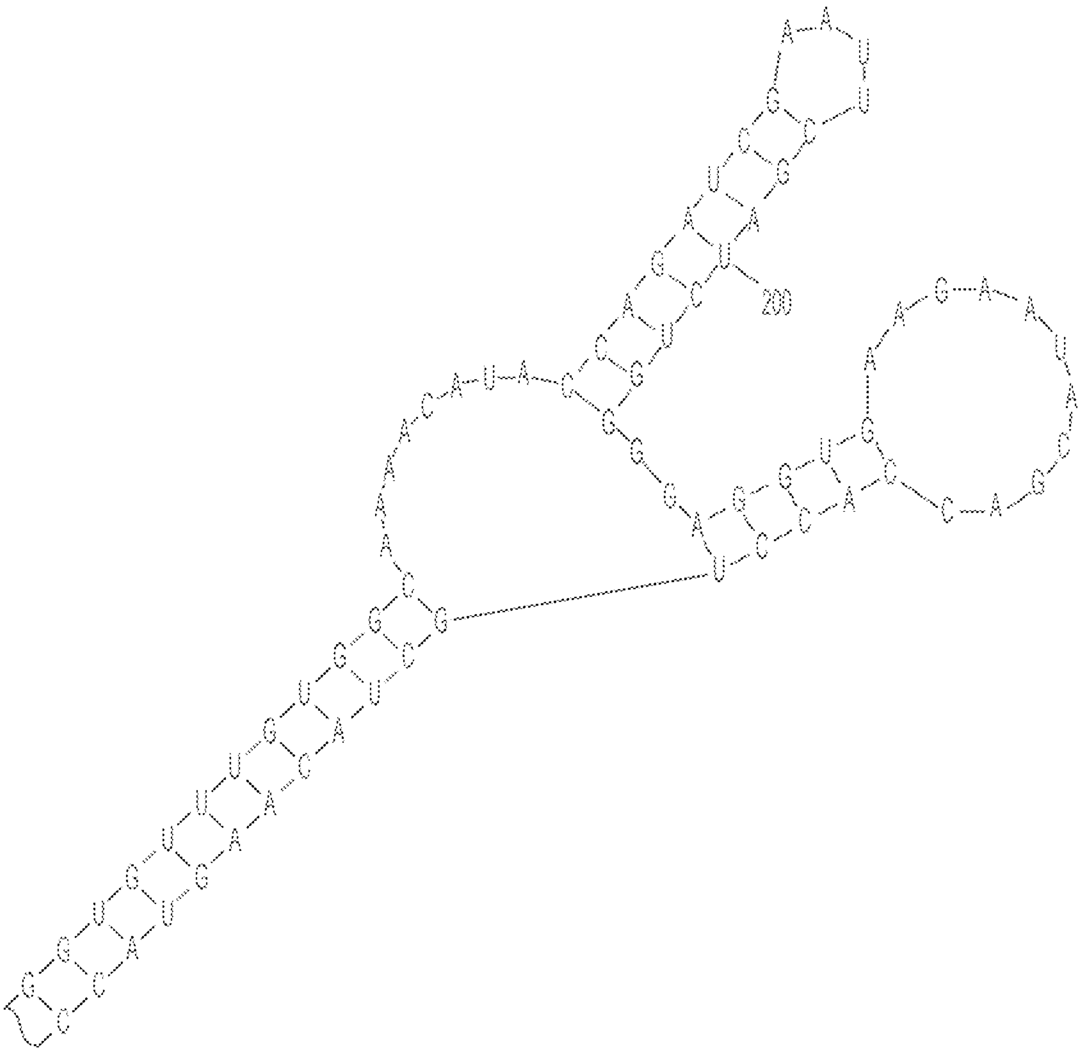

A combination of three base changes to the sequence of the Y-shape structure was tested to determine the cumulative effects on induction performance of the poly A aptamer. The three mutations, as noted in FIG. 16, consist of an ‘A’ deletion in Arm1-1; an ‘A’ to ‘G’ change to close the unpaired break in Arm2-2; and an “A” insertion in the 3-way junction preceding the polyA signal. These mutations were implemented using four different parental constructs that have different bases posterior to mini-IVS2 intron. In all, 12 constructs, described in Table 1, were designed to probe the cumulative effects.

TABLE 1

| | Y359 | Y392 | Y395 | Y360 | Y393 | Y396 | Y361 | Y394 | Y397 | Y362C | Y362 | Y387 |
|---|---|---|---|---|---|---|---|---|---|---|---|---|
| ‘A’ deletion in Arm1-1 | No | Yes | Yes | No | Yes | Yes | No | Yes | Yes | No | Yes | Yes |
| ‘A’ to to ‘G’ change in Arm2-2 | No | No | Yes | No | No | Yes | No | No | Yes | No | No | Yes |
| “A” insertion in 3 way junction | No | No | Yes | No | No | Yes | No | No | Yes | No | No | Yes |
| Bases after mini-IVS2 | CAT | CAT | CAT | TTT | TTT | TTT | TGA | TGA | TGA | TCT | TCT | TCT |

Figure 17:
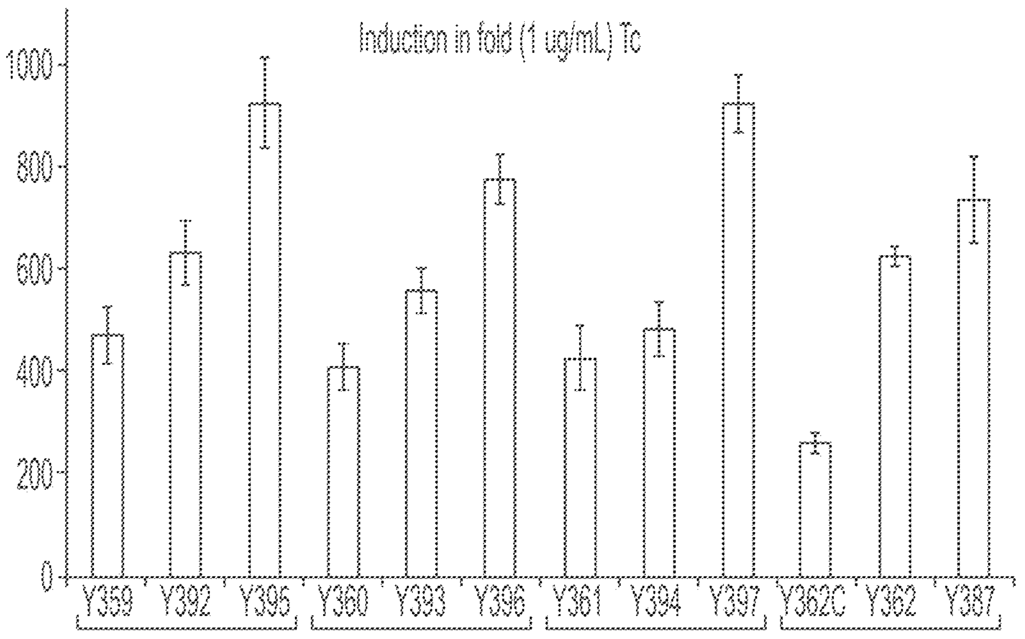
FIG. 17 demonstrates that the combination of three single base changes significantly increase the induced expression of an expressible polypeptide at low drug concentration. Four different parental constructs (Y359, Y360, Y361, Y362C) were used to demonstrate the effects of single base changes on induction. The effects on induction by these single base changes are similar across all four different parental constructs. Upper panel shows the induction in fold with standard variation. Lower panel plots the induction in fold for each construct.
Figure 18A:
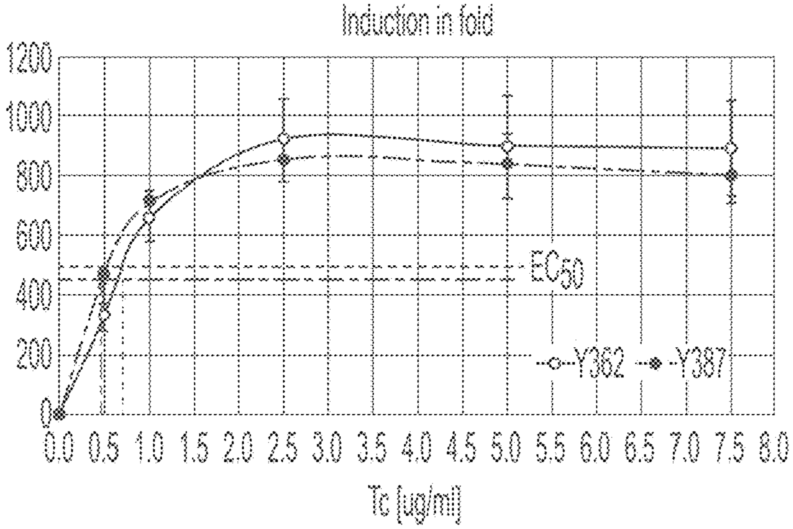
FIGS. 18A and 18B demonstrate a dose response analysis of induction of expression from constructs Y362 and Y386 comprising a Y-shape polyA switch combining single base changes at three locations.
Figure 18B:
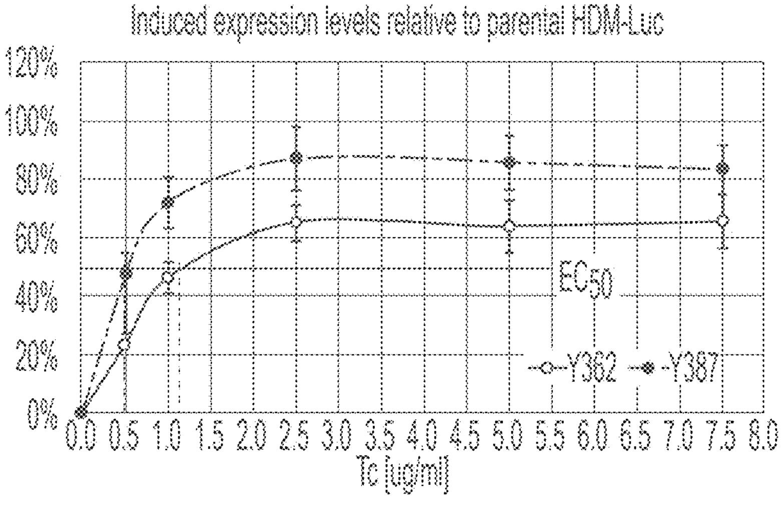

FIG. 17 demonstrates that the combination of the three single base changes significantly increase induction at lower drug concentration. Additionally, FIGS. 18A and 18B demonstrate dose response analysis for constructs Y362 and Y387. Y362 and Y387 effectively turn on the transgene expression up to 650~700-folds in 293T cells using only 1 ug/ml of tetracycline. For both constructs, the induction by tetracycline reaches 50% of the maximal level ($EC_{50}$) at as low as 0.5 to 1 μg/ml Tc using the maximum induction in fold as the $EC_{100}$ reference (FIG. 18A). Calculations using the maximum expression level of parental construct (HDM-Luc, which has similar sequence but without the Y-shape structure) as the $EC_{100}$ reference also show similar $EC_{50}$ values as low as 0.5 to 1.2 μg/ml (FIG. 18B). Y387 is a particularly effective design as it exhibits an $EC_{50}$ value of 0.5 μg/ml regardless of the $EC_{100}$ references used.

Example 14: Methods

Assays described in the figures filed herewith were performed as follows:

Luciferase Assay

Cells were seeded in 96-well plates at a density of 25000-30000 cells/well. After 24 hours of incubation, each well was transfected with 50 ng of DNA vectors and were incubated with culture medium containing none or various concentration of tetracycline for an additional 18 hours. Luciferase activity was measured in relative light units (RLU) with a Polarstar Omega plate reader (BMG Labtech, USA). To make 36 mL of assay buffer, 144 μL 1M DTT, 108 μL 0.1 M ATP, 252 μL 0.1M luciferin and 360 μl 0.05M CoA were added to 35 mL of basic buffer (25 mM Tricine, 0.5 mM EDTA-Na2, 0.54 mM Na-triphosphate, 16.3 mM $MgSO4 \cdot 7H_2O$, and 0.8% Triton X-100). After the cell medium was removed, 40 μL of assay buffer was added to each well, and luciferase activity was read twice with the Polarstar Omega plate reader. Induction in fold is calculated as the ratio of transgene expression in the presence vs absence of tetracycline.

RT-PCR

Cells transfected with the respective constructs were grown 18 hours at 37° C. in medium in the absence or presence of tetracycline. Total RNA was isolated according to the protocol supplied with RiboPure™ RNA Purification Kit (Ambion, Austin, TX). For RT-PCR, RT was performed using SuperScript III (invitrogen, Carlsbad, CA) according to manufacturer’s protocol and PCR was performed using the primers targeting the beginning of the transcript and reporter gene.

Fluorescence Microscopy

Cells were seeded in 12-well plates at a density of $1.2\times10^5$ cells/well. After 24 hours of incubation, each well was transfected with 500 ng of DNA vectors and were incubated with culture medium containing none or various concentration of tetracycline for an additional 18 hours. Images were taken on a fluorescence microscope (Zeiss Axiovert 40CFL) at a magnification of 200×.

Example 15: Exemplary Construct Sequences

The following sequences are additional examples of embodiments of components of the system described herein. The sequences are provided as DNA sequences that when transcribed components of form RNA aptamers:

+1: Transcriptional start
Black: 5' leading RNA sequence
Underline: IVS2 intron or mini-IVS2 intron
Bold: Y-shape poly A switch (with 4MAZ underlined)
Italic: 5'UTR
ATG: Translational start in bold
Y196CAA-4MA (SEQ ID NO: 6)

+1TCAGATCGCCTGGAGACGCCATCCACGCTGTTTTGACCTCCATAGAAGACACC
GGGACCGATCCAGCCTCCCCTCGAAGCTGATCCTGAGAACTTCAGGGTGAGTCT
ATGGGACCCTTGATGTTTTCTTTCCCCTTCTTTTCTATGGTTAAGTTCATGTCATA
GGAAGGGGAGAAGTAACAGGGTACACATATTGACCAAATCAGGGTAATTTTGC
ATTTGTAATTTTAAAAAATGCTTTCTTCTTTTAATATACTTTTTTGTTTATCTTATT
TCTAATACTTTCCCTAATCTCTTTCTTTCAGGGCAATAATGATACAATGTATCAT
GCCTCTTTGCACCATTCTAAAGAATAACAGTGATAATTTCTGGGTTAAGGCAAT
AGCAATATTTCTGCATATAAATATTTCTGCATATAAATTGTAACTGATGTAAGAG
GTTTCATATTGCTAATAGCAGCTACAATCCAGCTACCATTCTGCTTTTATTTTAT
GGTTGGGATAAGGCTGGATTATTCTGAGTCCAAGCTAGGCCCTTTTGCTAATCAT
GTTCATACCTCTTATCTTCCTCCCACAGCTCCTGGGCAACGTGCTGGTCTGTGTG
CTGGCCCATCACTTTGGCAAAGAATTGGCTAGCCACACACACAAATCTGGGG
AGGTGAAGAATACGACCACCTGCGTTTTATACTTCCACGAGATCTGGGGAG
GTGAAGAATACGACCACCTAATAAGATTACCGAAAGGCAATCTTATTAAAA
CATACCAGATCTTGTGAGGGTGTTTGTGGCAAAACATACCAGATCGAATTC
GATCTGGGGAGGTGAAGAATACGACCACCTGCTACAAGTACCTAATAAAGT
ATAAAGTGCAAAACATACCAGATCTGTGTGTTGGTTTTTTGTGTGTTAACG
GGGGAGGGGGAGGAAAGGGGGAGGGGGAGGAAAGGGGGAGGGGGAGGA
AAGGGGGAGGGGGA*GCGGCCGCCAACAACAACAACAACAACAACAACAACAACAA*
*CAACAACATAACAGTGTTCACTAGCAACCTCAAACAGACACC*ATG

Y208

(SEQ ID NO: 7)

+1TGGAGACGCCATCCACGCTGTTTTGACCTCCATAGAAGACACCGGGACCGAT
CCAGCCTCCCCTCGAAGCTGATCCTGAGAACTTCAGGGTGAGTCTATGGGACCC
TTGATGTTTTCTTTCCCCTTCTTTTCTATGGTTAAGTTCATGTCATAGGAAGGGGA
GAAGTAACAGGGTACACATATTGACCAAATCAGGGTAATTTTGCATTTGTAATT
TTAAAAAATGCTTTCTTCTTTTAATATACTTTTTTGTTTATCTTATTTCTAATACTT
TCCCTAATCTCTTTCTTTCAGGGCAATAATGATACAATGTATCATGCCTCTTTGC
ACCATTCTAAAGAATAACAGTGATAATTTCTGGGTTAAGGCAATAGCAATATTT
CTGCATATAAATATTTCTGCATATAAATTGTAACTGATGTAAGAGGTTTCATATT
GCTAATAGCAGCTACAATCCAGCTACCATTCTGCTTTTATTTTATGGTTGGGATA
AGGCTGGATTATTCTGAGTCCAAGCTAGGCCCTTTTGCTAATCATGTTCATACCT
CTTATCTTCCTCCCACAGCTCCTGGGCAACGTGCTGGTCTGTGTGCTGGCCCATC

-continued

ACTTTGGCAAAGAATTGGCTAGCCACACACACAAATCTGGGGAGGTGAAGA

ATACGACCACCTGCGTTTTATACTTCCGcGAGATCTGGGGAGGTGAAGAAT

ACGACCACCTAATAAGATTACCGAAAGGCAATCTTATTAAAACATACCAGA

TCTTGCCGAGGGTGTTTGTGGCAAAACATACCAGATCGAATTCGATCTGGGG

AGGTGAAGAATACGACCACCTGCTACAAGTACCTAATAAAGTATAAAGTGC

AAAACATACCAGATCTGTGTGTTGGTTTTTTGTGTGTTAACGGGGGAGGGG

GAGGAAAGGGGGAGGGGGAGGAAAGGGGGAGGGGGAGGAAAGGGGGAG

GGGGA*GCGGCCGCCAACAACAACAACAACAACAACAACAACAACAACAACAACATAA*

*CAGTGTTCACTAGCAACCTCAACAGACACC*ATG

Y209

(SEQ ID NO: 8)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

ATGGGACCCTTGATGTTTTCTTTCCCCTTCTTTTCTATGGTTAAGTTCATGTCATA

GGAAGGGGAGAAGTAACAGGGTACACATATTGACCAAATCAGGGTAATTTTGC

ATTTGTAATTTTAAAAAATGCTTTCTTCTTTTAATATACTTTTTTGTTTATCTTATT

TCTAATACTTTCCCTAATCTCTTTCTTTCAGGGCAATAATGATACAATGTATCAT

GCCTCTTTGCACCATTCTAAAGAATAACAGTGATAATTTCTGGGTTAAGGCAAT

AGCAATATTTCTGCATATAAATATTTCTGCATATAAATTGTAACTGATGTAAGAG

GTTTCATATTGCTAATAGCAGCTACAATCCAGCTACCATTCTGCTTTTATTTTAT

GGTTGGGATAAGGCTGGATTATTCTGAGTCCAAGCTAGGCCCTTTTGCTAATCAT

GTTCATACCTCTTATCTTCCTCCCACAGCTCCTGGGCAACGTGCTGGTCTGTGTG

CTGGCCCATCACTTTGGCAAAGAATTGGCTAGCCACACACACAAATCTGGGG

AGGTGAAGAATACGACCACCTGCGTTTTATACTTCCGcGAGATCTGGGGAG

GTGAAGAATACGACCACCTAATAAGATTACCGAAAGGCAATCTTATTAAAA

CATACCAGATCTTGCCGAGGGTGTTTGTGGCAAAACATACCAGATCGAATTC

GATCTGGGGAGGTGAAGAATACGACCACCTGCTACAAGTACCTAAATAAAG

TATAAAGTGCAAAACATACCAGATCTGTGTGTTGGTTTTTTGTGTGTTAACG

GGGGAGGGGGAGGAAAGGGGGAGGGGGAGGAAAGGGGGAGGGGGAGGA

AAGGGGGAGGGGGA*GCGGCCGCCAACAACAACAACAACAACAACAACAACAACAA*

*CAACAACATAACAGTGTTCACTAGCAACCTCAAACAGACACC*ATG

Y211

(SEQ ID NO: 9)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

ATGGGACCCTTGATGTTTTCTTTCCCCTTCTTTTCTATGGTTAAGTTCATGTCATA

GGAAGGGGAGAAGTAACAGGGTACACATATTGACCAAATCAGGGTAATTTTGC

ATTTGTAATTTTAAAAAATGCTTTCTTCTTTTAATATACTTTTTTGTTTATCTTATT

TCTAATACTTTCCCTAATCTCTTTCTTTCAGGGCAATAATGATACAATGTATCAT

GCCTCTTTGCACCATTCTAAAGAATAACAGTGATAATTTCTGGGTTAAGGCAAT

AGCAATATTTCTGCATATAAATATTTCTGCATATAAATTGTAACTGATGTAAGAG

-continued

GTTTCATATTGCTAATAGCAGCTACAATCCAGCTACCATTCTGCTTTTATTTTAT

GGTTGGGATAAGGCTGGATTATTCTGAGTCCAAGCTAGGCCCTTTTGCTAATCAT

GTTCATACCTCTTATCTTCCTCCCACAGCTCCTGGGCAACGTGCTGGTCTGTGTG

CTGGCCCATCACTTTGGCAAAGAATTGGCTAGCCACACACACAAATCTGGGG

AGGTGAAGAATACGACCACCTGCGTTTTATACTTCCAcGAGATCTGGGGAG

GTGAAGAATACGACCACCTAATAAGATTACCGAAAGGCAATCTTATTAAAA

CATACCAGATCTTgTGAGGGTGTTTGTGGCAAAACATACCAGATCGAATTC

GATCTGGGGAGGTGAAGAATACGACCACCTGCTACAAGTACCTAAATAAAG

TATAAAGTGCAAAACATACCAGATCTGTGTGTTGGTTTTTTGTGTGTTAACG

GGGGAGGGGGAGGAAAGGGGGAGGGGGAGGAAAGGGGGAGGGGGAGGA

AAGGGGGAGGGGGA*GCGGCCGCCAACAACAACAACAACAACAACAACAACAACAA*

*CAACAACATAACAGTGTTCACTAGCAACCTCAAACAGACACC*ATG

Y226

(SEQ ID NO: 10)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

ATGGGACCCTTGATGTTTTCTTTCCCCTTCTTTTCTATGGTTAAGTTCATGTCATA

GGAAGGGGAGAAGTAACAGGGTACACATATTGACCAAATCAGGGTAATTTTGC

ATTTGTAATTTTAAAAAATGCTTTCTTCTTTTAATATACTTTTTTGTTTATCTTATT

TCTAATACTTTCCCTAATCTCTTTCTTTCAGGGCAATAATGATACAATGTATCAT

GCCTCTTTGCACCATTCTAAAGAATAACAGTGATAATTTCTGGGTTAAGGCAAT

AGCAATATTTCTGCATATAAATATTTCTGCATATAAATTGTAACTGATGTAAGAG

GTTTCATATTGCTAATAGCAGCTACAATCCAGCTACCATTCTGCTTTTATTTTAT

GGTTGGGATAAGGCTGGATTATTCTGAGTCCAAGCTAGGCCCTTTTGCTAATCAT

GTTCATACCTCTTATCTTCCTCCCACAGCTCCTGGGCAACGTGCTGGTCTGTGTG

CTGGCCCATCACTTTGGCAAAGAATTGGCTAGCCACACACACAAACCTGGGG

AGGTGAAGAATACGACCACCTGCGTTTTATACTTCCACGAGATCTGGGGAG

GTGAAGAATACGACCACCTAATAAGATTACCGAAAGGCAATCTTATTAAAA

CATACCAGATCTTGTGAGGGTGTTTGTGGCAAAACATACCAGATCGAATTC

GATCTGGGGAGGTGAAGAATACGACCACCTGCTACAAGTACCTAATAAAGT

ATAAAGTGCAAAACATACCAGGTCTGTGTGTTGGTTTTTTGTGTGTTAACG

GGGGAGGGGGAGGAAAGGGGGAGGGGGAGGAAAGGGGGAGGGGGAGGA

AAGGGGGAGGGGGA*GCGGCCGCCAACAACAACAACAACAACAACAACAACAACAA*

*CAACAACATAACAGTGTTCACTAGCAACCTCAAACAGACACC*ATG

Y227

(SEQ ID NO: 11)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

ATGGGACCCTTGATGTTTTCTTTCCCCTTCTTTTCTATGGTTAAGTTCATGTCATA

GGAAGGGGAGAAGTAACAGGGTACACATATTGACCAAATCAGGGTAATTTTGC

ATTTGTAATTTTAAAAAATGCTTTCTTCTTTTAATATACTTTTTTGTTTATCTTATT

TCTAATACTTTCCCTAATCTCTTTCTTTCAGGGCAATAATGATACAATGTATCAT

-continued

GCCTCTTTGCACCATTCTAAAGAATAACAGTGATAATTTCTGGGTTAAGGCAAT

AGCAATATTTCTGCATATAAATATTTCTGCATATAAATTGTAACTGATGTAAGAG

GTTTCATATTGCTAATAGCAGCTACAATCCAGCTACCATTCTGCTTTTATTTTAT

GGTTGGGATAAGGCTGGATTATTCTGAGTCCAAGCTAGGCCCTTTTGCTAATCAT

GTTCATACCTCTTATCTTCCTCCCACAGCTCCTGGGCAACGTGCTGGTCTGTGTG

CTGGCCCATCACTTTGGCAAAGAATTGGCTAGCCACACACACAAACCTGGGG

AGGTGAAGAATACGACCACCTGCGTTTTATACTTCCAcGAGATCTGGGGAG

GTGAAGAATACGACCACCTAATAAGATTACCGAAAGGCAATCTTATTAAAA

CATACCAGATCTTgTGAGGGTGTTTGTGGCAAAACATACCAGATCGAATTC

GATCTGGGGAGGTGAAGAATACGACCACCTGCTACAAGTACCTAAATAAAG

TATAAAGTGCAAAACATACCAGGTCTGTGTGTTGGTTTTTTGTGTGTTAAC

GGGGGAGGGGGAGGAAAGGGGGAGGGGGAGGAAAGGGGGAGGGGGAGG

AAGGGGGAGGGGGA*GCGGCCGCCAACAACAACAACAACAACAACAACAACAACAA*

*ACAACAACATAACAGTGTTCACTAGCAACCTCAAACAGACACC*ATG

Y300

(SEQ ID NO: 12)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCACACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCATAACAGTG*

*TTCACTAGCATCCCCAAACAGACACC*ATG

Y329

(SEQ ID NO: 13)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCACACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCATAACAGTG*

*TTCACTAGCATCCCCCAGACCATCTACCACCGACACC*ATG

Y305

-continued (SEQ ID NO: 14)

+1TCAGATCGCCTGGAGACGCCATCCACGCTGTTTTGACCTCCATAGAAGACACC

GGGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCTTAATTAAC*

*AGTGTTCACTAGCATCAACAACAACAACAACAACAACAACAACAACGACACC*ATG

Y305D1

(SEQ ID NO: 15)

+1TCAGATCGCCTGGAGACGCCATCCACGCTGTTTTGACCTCCATAGAAGACAC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCTTAATTAAC*

*AGTGTTCACTAGTAGCAACAACAACAACAACAACAACAACAACAACGACACC*ATG

Y305D2

(SEQ ID NO: 16)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCTTAATTAAC*

*AGTGTTCACTAGACACAACAACAACAACAACAACAACAACAACAACGACACC*ATG

Y305D3

(SEQ ID NO: 17)

+1TCAGATCGCCTGGAGACGCCATCCACGCTGTTTTGACCTCCATAGAAGACACC

-continued

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCTTAATTAAC*

*AGTGTTCACTAGAACCAACAACAACAACAACAACAACAACAACAACGACACC*ATG

Y305D4

(SEQ ID NO: 18)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCTTAATTAAC*

*AGTGTTCACTAGTGCCAACAACAACAACAACAACAACAACAACAACGACACC*ATG

Y305D5

(SEQ ID NO: 19)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCTTAATTAAC*

*AGTGTTCACTAGTTGCAACAACAACAACAACAACAACAACAACAACGACACC*ATG

Y305D6

(SEQ ID NO: 20)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

-continued

TGAGTCCAAGCTAGGCCCTTTTGCTAATCATCTTCATACCTCTTATCTTCCTCTGC

AGCACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCTTAATTAAC*

*AGTGTTCACTAGACCCAACAACAACAACAACAACAACAACAACAACGACACCATG*

Y305D7

(SEQ ID NO: 21)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCTTAATTAAC*

*AGTGTTCACTAGCCCCAACAACAACAACAACAACAACAACAACAACGACACC*ATG

Y301

(SEQ ID NO: 22)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGAGCGGCC*TTAATTAACAGT*

*GTTCACTAGGACACCATG*

Y305D9

(SEQ ID NO: 23)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCACACACACAAATCTGGGGAGGTGAAGAATACGACCACCTGCGTTTTAT

-continued

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCTTAATTAAC*

*AGTGTTCACTAGAGGCAACAACAACAACAACAACAACAACAACAACAACGACACC*ATG

Y305D10

(SEQ ID NO: 24)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCACACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCTTAATTAAC*

*AGTGTTCACTAGTGACAACAACAACAACAACAACAACAACAACAACAACGACACC*ATG

Y305D11

(SEQ ID NO: 25)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCACACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCTTAATTAAC*

*AGTGTTCACTAGTCCCAACAACAACAACAACAACAACAACAACAACAACGACACC*ATG

Y305D12

(SEQ ID NO: 26)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCACACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

-continued

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA_GCGGCCGCCTTAATTAAC_

_AGTGTTCACTAGCCTCAACAACAACAACAACAACAACAACAACAACAACGACACC_ATG

Y305D13

(SEQ ID NO: 27)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCACACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA_GCGGCCGCCTTAATTAAC_

_AGTGTTCACTAGTCTCAACAACAACAACAACAACAACAACAACAACAACGACACC_ATG

Y344

(SEQ ID NO: 28)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCACACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA_GCGGCCGCCATAACAGTG_

_TTCACTAGCCCCCCCCAGACCATCTACCACCGACACC_ATG

Y359

(SEQ ID NO: 29)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCATACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

-continued

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCATAACAGTG*

*TTCACTAGCCCCCCCCAGACCATCTACCACCGACACC*ATG

Y360

(SEQ ID NO: 30)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGTTTACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCATAACAGTG*

*TTCACTAGCCCCCCCCAGACCATCTACCACCGACACC*ATG

Y361

(SEQ ID NO: 31)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGTGAACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCATAACAGTG*

*TTCACTAGCCCCCCCCAGACCATCTACCACCGACACC*ATG

Y362

(SEQ ID NO: 32)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGTCTACACACAATCTGGGGAGGTGAAGAATACGACCACCTGCGTTTTATA

CTTCCACGAGATCTGGGGAGGTGAAGAATACGACCACCTAATAAGATTACC

GAAAGGCAATCTTATTAAAACATACCAGATCTTGTGAGGGTGTTTGTGGCA

AAACATACCAGATCGAATTCGATCTGGGGAGGTGAAGAATACGACCACCTG

CTACAAGTACCTAATAAAGTATAAAGTGCAAAACATACCAGATCTGTGTGT

-continued

TGGTTTTTTGTGTGTTAACGGGGGAGGGGGAGGAAAGGGGGAGGGGGAGG

AAAGGGGGAGGGGGAGGAAAGGGGGAGGGGGA*GCGGCCGCCATAACAGTGT*

*TCACTAGCCCCCCCCAGACCATCTACCACCGACACC*ATG

Y358

(SEQ ID NO: 33)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCTTAATTAAC*

*AGTGTTCACTAGAGCCAACAACAACAACAACAACAACAACAACAACGACACC*ATG

Y363

(SEQ ID NO: 34)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGCATACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCTTAATTAAC*

*AGTGTTCACTAGAGCCAACAACAACAACAACAACAACAACAACAACGACACC*ATG

Y366

(SEQ ID NO: 35)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGTACACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCTTAATTAAC*

-continued

*AGTGTTCACTAGAGCCAACAACAACAACAACAACAACAACAACAACAACGACACC*ATG
Y367
(SEQ ID NO: 36)
+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGTTTACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCTTAATTAAC*

*AGTGTTCACTAGAGCCAACAACAACAACAACAACAACAACAACAACAACGACACC*ATG
Y375
+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGTCTACACACAAATCTGGGGAGGTGAAGAATACGACCACCTGCGTTTTAT

ACTTCCACGAGATCTGGGGAGGTGAAGAATACGACCACCTAATAAGATTAC

CGAAAGGCAATCTTATTAAAACATACCAGATCTTGTGAGGGTGTTTGTGGC

AAAACATACCAGATCGAATTCGATCTGGGGAGGTGAAGAATACGACCACCT

GCTACAAGTACCTAATAAAGTATAAAGTGCAAAACATACCAGATCTGTGTG

TTGGTTTTTTGTGTGTTAACGGGGGAGGGGGAGGAAAGGGGGAGGGGGAG

GAAAGGGGGAGGGGGAGGAAAGGGGGAGGGGGA*GCGGCCGCCATAACAGTG*

*TTCACTAGCCCCCCCCAGACCATCTACCACCGACACC*ATG
Y376
+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGTTTACACACAATCTGGGGAGGTGAAGAATACGACCACCTGCGTTTTATA

CTTCCACGAGATCTGGGGAGGTGAAGAATACGACCACCTAATAAGATTACC

GAAAGGCAATCTTATTAAAACATACCAGATCTTGTGAGGGTGTTTGTGGCA

AAACATACCAGATCGAATTCGATCTGGGGAGGTGAAGAATACGACCACCTG

CTACAAGTACCTAATAAAGTATAAAGTGCAAAACATACCAGATCTGTGTGT

TGGTTTTTTGTGTGTTAACGGGGGAGGGGGAGGAAAGGGGGAGGGGGAGG

AAAGGGGGAGGGGGAGGAAAGGGGGAGGGGGA*GCGGCCGCCTTAATTAACA*

*GTGTTCACTAGAGCCAACAACAACAACAACAACAACAACAACAACAACGACACC*ATG
S206
(SEQ ID NO: 37)
+1TCAGATCGCCTGGAGACGCCATCCACGCTGTTTTGACCTCCATAGAAGACACC

-continued

GGGACCGATCCAGCCTCCCCTCGAAGCTGATCCTGAGAACTTCAGGGTGAGTCT

ATGCCAGCTACCATTCTGCTTTTATTTTATGGTTGGGATAAGGCTGGATTATTCT

GAGTCCAAGCTAGGCCCTTTTGCTAATCATCTTCATACCTCTTATCTTCCTCTGC

AGATGTTCCTCGAGATCTGGGGAGGTGAAGAATACGACCACCTAATAAGAT

TACCGAAAGGCAATCTTATTAAAACATACCAGATCTTGAGAGGGTGTTTGT

GGCAAAACATACCAGATCGAATTCGATCTGGGGAGGTGAAGAATACGACCA

CCTGCTACAAGTACCTAATAAACATTAGCGGAGAAACATACCACTGTGTGT

TGGTTTTTTGTGTGTTAACGGGGGAGGGGGAGGAAAGGGGGAGGGGGAGG

AAAGGGGGAGGGGGAGGAAAGGGGGAGGGGGA*GCGGCCGCCATAACAGTGT*

*TCACTAGCAACCTCAAACAGACACC*ATG

S210

(SEQ ID NO: 38)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

ATGCCAGCTACCATTCTGCTTTTATTTTATGGTTGGGATAAGGCTGGATTATTCT

GAGTCCAAGCTAGGCCCTTTTGCTAATCATCTTCATACCTCTTATCTTCCTCTGC

AGATGTTCCTCGAGATCTGGGGAGGTGAAGAATACGACCACCTAATAAGAT

TACCGAAAGGCAATCTTATTAAAACATACCAGATCTTGAGAGGGTGTTTGT

GGCAAAACATACCAGATCGAATTCGATCTGGGGAGGTGAAGAATACGACCA

CCTGCTACAAGTACCTAATAAACATTAGCGGAGAAACATACCACTGTGTGT

TGGTTTTTTGTGTGTTAACGGGGGAGGGGGAGGAAAGGGGGAGGGGGAGG

AAAGGGGGAGGGGGAGGAAAGGGGGAGGGGGA*GCGGCCGCCATAACAGTGT*

*TCACTAGCAACCCCAAACAGACACCATG*

S211

(SEQ ID NO: 39)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

ATGCCAGCTACCATTCTGCTTTTATTTTATGGTTGGGATAAGGCTGGATTATTCT

GAGTCCAAGCTAGGCCCTTTTGCTAATCATCTTCATACCTCTTATCTTCCTCTGC

AGATGTTCCTCGAGATCTGGGGAGGTGAAGAATACGACCACCTAATAAGAT

TACCGAAAGGCAATCTTATTAAAACATACCAGATCTTGAGAGGGTGTTTGT

GGCAAAACATACCAGATCGAATTCGATCTGGGGAGGTGAAGAATACGACCA

CCTGCTACAAGTACCTAATAAACATTAGCGGAGAAACATACCACTGTGTGT

TGGTTTTTTGTGTGTTAACGGGGGAGGGGGAGGAAAGGGGGAGGGGGAGG

*AAAGGGGGAGGGGGAGGAAAGGGGGAGGGGGA**GCGCCGCCACCATAACAG*

*TGTTCACTAGCAACCCCAAACAGACACC*ATG

S212

(SEQ ID NO: 40)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

ATGCCAGCTACCATTCTGCTTTTATTTTATGGTTGGGATAAGGCTGGATTATTCT

GAGTCCAAGCTAGGCCCTTTTGCTAATCATCTTCATACCTCTTATCTTCCTCTGC

AGATGTTCCTCGAGATCTGGGGAGGTGAAGAATACGACCACCTAATAAGAT

-continued

TACCGAAAGGCAATCTTATTAAAACATACCAGATCTTGAGAGGGTGTTTGT

GGCAAAACATACCAGATCGAATTCGATCTGGGGAGGTGAAGAATACGACCA

CCTGCTACAAGTACCTAATAAACATTAGCGGAGAAACATACCACTGTGTGT

TGGTTTTTTGTGTGTTAACGGGGGAGGGGGAGGAAAGGGGGAGGGGGAGG

*AAAGGGGGAGGGGGAGGAAAGGGGGAGGGGGA**GCGGCCGCCCACCATGATAA*

*CAGTGTTCACTAGCAACCTCAAACAGACACC*ATG

S213

(SEQ ID NO: 41)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

ATGCCAGCTACCATTCTGCTTTTATTTTATGGTTGGGATAAGGCTGGATTATTCT

GAGTCCAAGCTAGGCCCTTTTGCTAATCATCTTCATACCTCTTATCTTCCTCTGC

AGATGTTCCTCGAGATCTGGGGAGGTGAAGAATACGACCACCTAATAAGAT

TACCGAAAGGCAATCTTATTAAAACATACCAGATCTTGAGAGGGTGTTTGT

GGCAAAACATACCAGATCGAATTCGATCTGGGGAGGTGAAGAATACGACCA

CCTGCTACAAGTACCTAATAAACATTAGCGGAGAAACATACCACTGTGTGT

TGGTTTTTTGTGTGTTAACGGGGGAGGGGGAGGAAAGGGGGAGGGGGAGG

AAAGGGGGAGGGGGAGGAAAGGGGGAGGGGGA*GCGGCCGCCCACCACGATAA*

*CAGTGTTCACTAGCAACCTCAAACAGACACC*ATG

S214

(SEQ ID NO: 42)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

ATGCCAGCTACCATTCTGCTTTTATTTTATGGTTGGGATAAGGCTGGATTATTCT

GAGTCCAAGCTAGGCCCTTTTGCTAATCATCTTCATACCTCTTATCTTCCTCTGC

AGATGTTCCTCGAGATCTGGGGAGGTGAAGAATACGACCACCTAATAAGAT

TACCGAAAGGCAATCTTATTAAAACATACCAGATCTTGAGAGGGTGTTTGT

GGCAAAACATACCAGATCGAATTCGATCTGGGGAGGTGAAGAATACGACCA

CCTGCTACAAGTACCTAATAAACATTAGCGGAGAAACATACCACTGTGTGT

TGGTTTTTTGTGTGTTAACGGGGGAGGGGGAGGAAAGGGGGAGGGGGAGG

*AAAGGGGGAGGGGGAGGAAAGGGGGAGGGGGA**GCGGCCGCCCACCATAACAG*

*TGTTCACTAGCATCCCCAAACAGACACC*ATG

S215

(SEQ ID NO: 43)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

ATGCCAGCTACCATTCTGCTTTTATTTTATGGTTGGGATAAGGCTGGATTATTCT

GAGTCCAAGCTAGGCCCTTTTGCTAATCATCTTCATACCTCTTATCTTCCTCTGC

AGATGTTCCTCGAGATCTGGGGAGGTGAAGAATACGACCACCTAATAAGAT

TACCGAAAGGCAATCTTATTAAAACATACCAGATCTTGAGAGGGTGTTTGT

GGCAAAACATACCAGATCGAATTCGATCTGGGGAGGTGAAGAATACGACCA

CCTGCTACAAGTACCTAATAAACATTAGCGGAGAAACATACCACTGTGTGT

TGGTTTTTTGTGTGTTAACGGGGGAGGGGGAGGAAAGGGGGAGGGGGAGG

-continued

**AAAGGGGGAGGGGGAGGAAAGGGGGA*GGGGGA*** *GCGGCCGCCACCATAACAG*

*TGTTCACTAGCATCCCCAAACAGACACC*ATG

S222

(SEQ ID NO: 44)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

ATGCCAGCTACCATTCTGCTTTTATTTTATGGTTGGGATAAGGCTGGATTATTCT

GAGTCCAAGCTAGGCCCTTTTGCTAATCATCTTCATACCTCTTATCTTCCTCTGC

AGATGTTCCTCGAGATCTGGGGAGGTGAAGAATACGACCACCTAATAAGAT

TACCGAAAGGCAATCTTATTAAAACATACCAGATCTTGAGAGGGTGTTTGT

GGCAAAACATACCAGATCGAATTCGATCTGGGGAGGTGAAGAATACGACCA

CCTGCTACAAGTACCTAATAAACATTAGCGGAGAAACATACCACTGTGTGT

TGGTTTTTTGTGTGTTAACGGGGGAGGGGGAGGAAAGGGGGAGGGGGAGG

AAAGGGGGAGGGGGAGGAAAGGGGGAGGGGGA*GCGGCCGCCATAACAGTGT*

*TCACTAGCATCCCCAAACAGACACC*ATG

S223

(SEQ ID NO: 45)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

ATGCCAGCTACCATTCTGCTTTTATTTTATGGTTGGGATAAGGCTGGATTATTCT

GAGTCCAAGCTAGGCCCTTTTGCTAATCATCTTCATACCTCTTATCTTCCTCTGC

AGATGTTCCTCGAGATCTGGGGAGGTGAAGAATACGACCACCTAATAAGAT

TACCGAAAGGCAATCTTATTAAAACATACCAGATCTTGAGAGGGTGTTTGT

GGCAAAACATACCAGATCGAATTCGATCTGGGGAGGTGAAGAATACGACCA

CCTGCTACAAGTACCTAATAAACATTAGCGGAGAAACATACCACTGTGTGT

TGGTTTTTTGTGTGTTAACGGGGGAGGGGGAGGAAAGGGGGAGGGGGAGG

AAAGGGGGAGGGGGAGGAAAGGGGGAGGGGGA*GCGGCCGCCATAACAGTGT*

*TCACCAGCATCCCCAAACAGACACC*ATG

S272

(SEQ ID NO: 46)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCT

TAAGCCAGCTACCATTCTGCTTTTATTTTATCGTTGGGATAAGGCTGGATTATTC

TGAGTCCAAGCTAGGCCCTTTTGCTAATCATCTTCATACCTCTTATCTTCCTCTGC

AGATTTTCCACGAGATCTGGGGAGGTGAAGAATACGACCACCTAATAAGAT

TACCGAAAGGCAATCTTATTAAAACATACCAGATCTTGTGAGGGTGTTTGT

GGCAAAACATACCAGATCGAATTCGATCTGGGGAGGTGAAGAATACGACCA

CCTGCTACAAGTACCTAATAAAAATTAGCGGAGAAACATACCACTGTGTGT

TGGTTTTTTGTGTGTTAACGGGGGAGGGGGAGGAAAGGGGGAGGGGGAGG

AAAGGGGGAGGGGGAGGAAAGGGGGAGGGGGA*GCGGCCGCCATAACAGTGT*

*TCACTAGCATCCCCAAACAGACACC*ATG

Y387

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCTT

-continued

AAGCCAGCTACCATTCTGCTTTTATTTTATCGTTGGGATAAGGCTGGATTATTCTGA

GTCCAAGCTAGGCCCTTTTGCTAATCATCTTCATACCTCTTATCTTCCTCTGCAGT

CTACACACAATCTGGGGAGGTGAAGAATACGACCACCTGCGTTTTATACTTC

CACGAGATCTGGGGAGGTGAAGAATACGACCACCTAATAAGATTGCCGAAA

GGCAATCTTATTAAAACATACCAGATCTTGTGAGGGTGTTTGTGGCAAAACA

TACCAGATCGAATTCGATCTGGGGAGGTGAAGAATACGACCACCTGCTACA

AGTACCTAAATAAAGTATAAAGTGCAAAACATACCAGATCTGTGTGTTGGTT

TTTTGTGTGTTAACGGGGGAGGGGGAGGAAAGGGGGAGGGGGAGGAAAG

GGGGAGGGGGAGGAAAAGGGGGAGGGGGA_GCGGCCGCCATAACAGTGTTCACT_

_AGCCCCCCCCAGACCATCTACCACCGACACC_ATG

Y392

(SEQ ID NO: 51)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCTT

AAGCCAGCTACCATTCTGCTTTTATTTTATCGTTGGGATAAGGCTGGATTATTCTGA

GTCCAAGCTAGGCCCTTTTGCTAATCATCTTCATACCTCTTATCTTCCTCTGCAGC

ATACACACAATCTGGGGAGGTGAAGAATACGACCACCTGCGTTTTATACTTC

CACGAGATCTGGGGAGGTGAAGAATACGACCACCTAATAAGATTACCGAAA

GGCAATCTTATTAAAACATACCAGATCTTGTGAGGGTGTTTGTGGCAAAACA

TACCAGATCGAATTCGATCTGGGGAGGTGAAGAATACGACCACCTGCTACA

AGTACCTAATAAAGTATAAAGTGCAAAACATACCAGATCTGTGTGTTGGTTTT

TTGTGTGTTAACGGGGGAGGGGGAGGAAAGGGGGAGGGGGAGGAAAGGG

GGAGGGGGAGGAAAGGGGGAGGGGGA_GCGGCCGCCATAACAGTGTTCACTAGC_

_CCCCCCCAGACCATCTACCACCGACACC_ATG

Y393

(SEQ ID NO: 52)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCTT

AAGCCAGCTACCATTCTGCTTTTATTTTATCGTTGGGATAAGGCTGGATTATTCTGA

GTCCAAGCTAGGCCCTTTTGCTAATCATCTTCATACCTCTTATCTTCCTCTGCAGTT

TACACACAATCTGGGGAGGTGAAGAATACGACCACCTGCGTTTTATACTTCC

ACGAGATCTGGGGAGGTGAAGAATACGACCACCTAATAAGATTACCGAAAG

GCAATCTTATTAAAACATACCAGATCTTGTGAGGGTGTTTGTGGCAAAACAT

ACCAGATCGAATTCGATCTGGGGAGGTGAAGAATACGACCACCTGCTACAA

GTACCTAATAAAGTATAAAGTGCAAAACATACCAGATCTGTGTGTTGGTTTTT

TGTGTGTTAACGGGGGAGGGGGAGGAAAGGGGGAGGGGGAGGAAAGGGG

GAGGGGGAGGAAAGGGGGAGGGGGA_GCGGCCGCCATAACAGTGTTCACTAGCC_

_CCCCCCAGACCATCTACCACCGACACCATG_

Y394

(SEQ ID NO: 53)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCTT

-continued

AAGCCAGCTACCATTCTGCTTTTATTTTATCGTTGGGATAAGGCTGGATTATTCTGA

GTCCAAGCTAGGCCCTTTTGCTAATCATCTTCATACCTCTTATCTTCCTCTGCAGT

GAACACACAATCTGGGGAGGTGAAGAATACGACCACCTGCGTTTTATACTT

CCACGAGATCTGGGGAGGTGAAGAATACGACCACCTAATAAGATTACCGAA

AGGCAATCTTATTAAAACATACCAGATCTTGTGAGGGTGTTTGTGGCAAAAC

ATACCAGATCGAATTCGATCTGGGGAGGTGAAGAATACGACCACCTGCTACA

AGTACCTAATAAAGTATAAAGTGCAAAACATACCAGATCTGTGTGTTGGTTTT

TTGTGTGTTAACGGGGGAGGGGGAGGAAAGGGGGAGGGGGAGGAAAGGG

GGAGGGGGAGGAAAGGGGGAGGGGGA*GCGGCCGCCATAACAGTGTTCACTAGC*

*CCCCCCCAGACCATCTACCACCGACACC*ATG

Y395

(SEQ ID NO: 54)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCTT

AAGCCAGCTACCATTCTGCTTTTATTTTATCGTTGGGATAAGGCTGGATTATTCTGA

GTCCAAGCTAGGCCCTTTTGCTAATCATCTTCATACCTCTTATCTTCCTCTGCAGCA

TACACACAATCTGGGGAGGTGAAGAATACGACCACCTGCGTTTTATACTTCC

ACGAGATCTGGGGAGGTGAAGAATACGACCACCTAATAAGATTGCCGAAAG

GCAATCTTATTAAAACATACCAGATCTTGTGAGGGTGTTTGTGGCAAAACAT

ACCAGATCGAATTCGATCTGGGGAGGTGAAGAATACGACCACCTGCTACAA

GTACCTAAATAAAGTATAAAGTGCAAAACATACCAGATCTGTGTGTTGGTTT

TTTGTGTGTTAACGGGGGAGGGGGAGGAAAGGGGGAGGGGGAGGAAAGG

GGGAGGGGGAGGAAAGGGGGAGGGGGA*GCGGCCGCCATAACAGTGTTCACTA*

*GCCCCCCCCAGACCATCTACCACCGACACC*ATG

Y396

(SEQ ID NO: 55)

+1TCAGATCGCCTGGAGACGCCATCCACGCTGTTTTGACCTCCATAGAAGACACC

GGGACCGATCCAGCCTCCCCTCGAAGCTGATCCTGAGAACTTCAGGGTGAGTCTT

AAGCCAGCTACCATTCTGCTTTTATTTTATCGTTGGGATAAGGCTGGATTATTCTGA

GTCCAAGCTAGGCCCTTTTGCTAATCATCTTCATACCTCTTATCTTCCTCTGCAGTT

TACACACAATCTGGGGAGGTGAAGAATACGACCACCTGCGTTTTATACTTCC

ACGAGATCTGGGGAGGTGAAGAATACGACCACCTAATAAGATTGCCGAAAG

GCAATCTTATTAAAACATACCAGATCTTGTGAGGGTGTTTGTGGCAAAACAT

ACCAGATCGAATTCGATCTGGGGAGGTGAAGAATACGACCACCTGCTACAA

GTACCTAAATAAAGTATAAAGTGCAAAACATACCAGATCTGTGTGTTGGTTT

TTTGTGTGTTAACGGGGGAGGGGGAGGAAAGGGGGAGGGGGAGGAAAGG

GGGAGGGGGAGGAAAGGGGGAGGGGGA*GCGGCCGCCATAACAGTGTTCACTA*

*GCCCCCCCCAGACCATCTACCACCGACACC*ATG

Y397

(SEQ ID NO 56)

+1TCAGATCGCCTGGAGACGCCATCCACGCTGTTTTGACCTCCATAGAAGACACC

-continued

GGGACCGATCCAGCCTCCCCTCGAAGCTGATCCTGAGAACTTCAGGGTGAGTCTT

AAGCCAGCTACCATTCTGCTTTTATTTTATCGTTGGGATAAGGCTGGATTATTCTGA

GTCCAAGCTAGGCCCTTTTGCTAATCATCTTCATACCTCTTATCTTCCTCTGCAGT

GAACACACAATCTGGGGAGGTGAAGAATACGACCACCTGCGTTTTATACTT

CCACGAGATCTGGGGAGGTGAAGAATACGACCACCTAATAAGATTGCCGAA

AGGCAATCTTATTAAAACATACCAGATCTTGTGAGGGTGTTTGTGGCAAAAC

ATACCAGATCGAATTCGATCTGGGGAGGTGAAGAATACGACCACCTGCTACA

AGTACCTAAATAAAGTATAAAGTGCAAAACATACCAGATCTGTGTGTTGGTT

TTTTGTGTGTTAACGGGGGAGGGGGAGGAAAGGGGGAGGGGGAGGAAAG

GGGGAGGGGGAGGAAAGGGGGAGGGGGA*GCGCCGCCATAACAGTGTTCACT*

*AGCCCCCCCCAGACCATCTACCACCGACACC*ATG

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A system for modulating gene expression, comprising a polyA aptamer polynucleotide, that comprises in a 5' to 3' direction:

a) a 5' splice donor site;

b) an engineered intron with a a first 3' splice acceptor site on the 3' side of the engineered intron; and, a polyA switch comprising three ligand-binding aptamers each with one or more ligand binding pockets, a three way junction, and at least one polyA cleavage signal therein;

wherein the first 3' splice acceptor site is either located 5' of the polyA switch or in the polyA switch;

c) a second 3' splice acceptor site; and d) a nucleic acid sequence encoding an expressible polypeptide;

wherein absence of a ligand allows splicing between the 5' splice donor site and the first 3' splice acceptor site, resulting in degradation of mRNA encoding for the expressible polypeptide due to the polyA cleavage signal, and wherein presence of the ligand allows splicing between the 5' splice donor site and the second 3' splice acceptor site, resulting in expression of the expressible polypeptide due to splicing out of the polyA cleavage signal.

2. The system of claim 1, wherein the three way junction comprises a junction of a first, a second, and a third double stranded RNA stem.

3. The system of claim 2, wherein the first double stranded RNA stem does not comprise a ligand-binding aptamer.

4. The system of claim 2, wherein each of the first, second, and third double stranded RNA stems comprises a ligand-binding aptamer.

5. The system of claim 2, wherein the three way junction comprises at least one single stranded region.

6. The system of claim 5, wherein the three way junction comprises a first, a second, and a third single stranded region.

7. The system of claim 6, wherein the first single stranded region is located between the first double stranded RNA stem and the second double stranded RNA stem.

8. The system of claim 6, wherein the second single stranded region is located between the second double stranded RNA stem and the third double stranded RNA stem.

9. The system of claim 6, wherein the third single stranded region is located between the third double stranded RNA stem and the first double stranded RNA stem of the first aptamer.

10. The system of claim 6, wherein one or more nucleotides of the polyA cleavage signal are within the three way junction, the third double stranded RNA stem, the third single stranded region, or the first double stranded RNA stem.

11. The system of claim 10, wherein:

(a) the third single stranded region comprises the first four bases of the polyA cleavage signal;

(b) the first double stranded RNA stem comprises the last two bases of the polyA cleavage signal; or (c) the first double stranded RNA stem comprises the entirety of the polyA cleavage signal.

12. The system of claim 2, wherein the double stranded RNA stem between the binding pocket of the third aptamer and the three way junction is between 10 and 15 base pairs in length.

13. The system of claim 2, wherein:

(a) the sequence of the first double stranded RNA stem is SEQ ID NO: 4, or SEQ ID NO: 5;

(b) the sequence of the second double stranded RNA stem is SEQ ID NO: 3; or (c) the sequence of the third double stranded RNA stem is SEQ ID NO: 2.

14. The system of claim 1, wherein the first aptamer and the second aptamer, in a 5' to 3' orientation, are in the same orientation.

15. The system of claim 1, wherein the third aptamer, in a 5' to 3' orientation, is in the opposite orientation relative to the first and second aptamers.

16. The system of claim 1, wherein the nucleic acid sequence encoding the expressible polypeptide further comprises a 5'UTR.

17. The system of claim 16, wherein the 5'UTR further comprises a CAA repeat.

18. The system of claim 16, wherein the 5'UTR further comprises one or more 3' splice acceptor sites.

19. The system of claim 1, further comprising a G-U rich region 5' of the nucleic acid sequence encoding the expressible polypeptide and 3' of the polyA cleavage signal.

20. The system of claim 19, further comprising a G rich region 5' of the nucleic acid sequence encoding the expressible polypeptide and 3' of the G-U rich region.

21. The system of claim 20, wherein the G rich-region comprises 4 MAZ sequences.

22. The system of claim 1, wherein the engineered intron has a sequence of between 100 and 200 bases in length.

23. The system of claim 1, where the engineered intron is followed by a nucleic acid triplet sequence comprising the sequence TAG, TCT, TTC, TTG, TGA, TGC, TCC, ACA, AAC, ACC, AGC, AGG, CCT, CCC, TTT, TGA, TCT, TAC, CAC, or CAT.

24. The system of claim 1, wherein the system comprises a sequence selected from the group consisting of SEQ ID NO: 6 to SEQ ID NO: 56.

25. A vector for delivery of the system of claim 1, wherein the vector comprises the polyA aptamer polynucleotide.

26. The vector of claim 25, wherein the vector is a viral vector.

27. A nucleic acid molecule encoding a poly A aptamer polynucleotide comprising in a 5' to 3' direction:

a) a 5' splice donor site;

b) an engineered intron with a a first 3' splice acceptor site on the 3' side of the engineered intron; and, a polyA switch comprising three ligand-binding aptamers each with one or more ligand binding pockets, a three way junction, and at least one polyA cleavage signal therein;

wherein the first 3' splice acceptor site is either located 5' of the polyA switch or in the polyA switch;

d) a second 3' splice acceptor site; and e) a nucleic acid sequence encoding an expressible polypeptide;

wherein absence of a ligand allows splicing between the 5' splice donor site and the first 3' splice acceptor site, resulting in degradation of mRNA encoding for the expressible polypeptide due to the polyA cleavage signal, and wherein presence of the ligand allows splicing between the 5' splice donor site and the second 3' splice acceptor site, resulting in expression of the expressible polypeptide due to splicing out of the polyA cleavage signal.

28. A vector for delivery of the nucleic acid of claim 27, wherein the vector comprises the nucleic acid molecule encoding the poly A aptamer polynucleotide.

29. The vector of claim 28, wherein the vector is a viral vector.

* * * * *

SEQUENCE LISTING

```
<160> NUMBER OF SEQ ID NOS: 556

<210> SEQ ID NO 1
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

gtgagtctta agccagctac cattctgctt ttattttatc gttgggataa ggctggatta      60

ttctgagtcc aagctaggcc cttttgctaa tcatcttcat acctcttatc ttcctctgca     120

g                                                                     121


<210> SEQ ID NO 2
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2

ggguguuugu ggc                                                         13


<210> SEQ ID NO 3
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3

cacgagaucu gg                                                          12
```

<210> SEQ ID NO 4
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 4
gcguuuuaua cuu 13

<210> SEQ ID NO 5
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 5
cucugcagau guu 13

<210> SEQ ID NO 6
<211> LENGTH: 1057
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6
tcagatcgcc tggagacgcc atccacgctg ttttgacctc catagaagac accgggaccg 60
atccagcctc ccctcgaagc tgatcctgag aacttcaggg tgagtctatg ggacccttga 120
tgttttcttt ccccttcttt tctatggtta agttcatgtc ataggaaggg gagaagtaac 180
agggtacaca tattgaccaa atcagggtaa ttttgcattt gtaattttaa aaaatgcttt 240
cttcttttaa tatacttttt tgtttatctt atttctaata ctttccctaa tctctttctt 300
tcagggcaat aatgatacaa tgtatcatgc ctctttgcac cattctaaag aataacagtg 360
ataatttctg ggttaaggca atagcaatat ttctgcatat aaatatttct gcatataaat 420
tgtaactgat gtaagaggtt tcatattgct aatagcagct acaatccagc taccattctg 480
cttttatttt atggttggga taaggctgga ttattctgag tccaagctag gcccttttgc 540
taatcatgtt catacctctt atcttcctcc cacagctcct gggcaacgtg ctggtctgtg 600
tgctggccca tcactttggc aaagaattgg ctagccacac acacaaatct ggggaggtga 660
agaatacgac cacctgcgtt ttatacttcc acgagatctg ggaggtgaa gaatacgacc 720 acctaataag attaccgaaa ggcaatctta ttaaaacata ccagatcttg tgagggtgtt 780
tgtggcaaaa cataccagat cgaattcgat ctggggaggt gaagaatacg accacctgct 840
acaagtacct aataaagtat aaagtgcaaa acataccaga tctgtgtgtt ggttttttgt 900
gtgttaacgg gggaggggga ggaaaggggg agggggagga aagggggagg gggaggaaag 960
ggggaggggg agcggccgcc aacaacaaca acaacaacaa caacaacaac aacaacaaca 1020
taacagtgtt cactagcaac ctcaaacaga caccatg 1057

<210> SEQ ID NO 7
<211> LENGTH: 1047
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 7

```
tggagacgcc atccacgctg ttttgacctc catagaagac accgggaccg atccagcctc     60
ccctcgaagc tgatcctgag aacttcaggg tgagtctatg ggacccttga tgttttcttt    120
ccccttcttt tctatggtta agttcatgtc ataggaaggg gagaagtaac agggtacaca    180
tattgaccaa atcagggtaa ttttgcattt gtaattttaa aaaatgcttt cttcttttaa    240
tatacttttt tgtttatctt atttctaata ctttccctaa tctctttctt tcagggcaat    300
aatgatacaa tgtatcatgc ctctttgcac cattctaaag aataacagtg ataatttctg    360
ggttaaggca atagcaatat ttctgcatat aaatatttct gcatataaat tgtaactgat    420
gtaagaggtt tcatattgct aatagcagct acaatccagc taccattctg cttttatttt    480
atggttggga taaggctgga ttattctgag tccaagctag gcccttttgc taatcatgtt    540
catacctctt atcttcctcc cacagctcct gggcaacgtg ctggtctgtg tgctggccca    600
tcactttggc aaagaattgg ctagccacac acacaaatct ggggaggtga agaatacgac    660
cacctgcgtt ttatacttcc gcgagatctg ggaggtgaa gaatacgacc acctaataag    720
attaccgaaa ggcaatctta ttaaaacata ccagatcttg cgagggtgtt tgtggcaaaa    780
cataccagat cgaattcgat ctggggaggt gaagaatacg accacctgct acaagtacct    840
aataaagtat aaagtgcaaa acataccaga tctgtgtgtt ggtttttgt gtgttaacgg    900
gggaggggga ggaaaggggg agggggagga aagggggagg gggaggaaag ggggaggggg    960
agcggccgcc aacaacaaca acaacaacaa caacaacaac aacaacaaca taacagtgtt   1020
cactagcaac ctcaaacaga caccatg                                        1047
```

<210> SEQ ID NO 8
<211> LENGTH: 1058
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8

```
tcagatcgcc tggagacgcc atccacgctg ttttgacctc catagaagac accgggaccg     60
atccagcctc ccctcgaagc tgatcctgag aacttcaggg tgagtctatg ggacccttga    120
tgttttcttt ccccttcttt tctatggtta agttcatgtc ataggaaggg gagaagtaac    180
agggtacaca tattgaccaa atcagggtaa ttttgcattt gtaattttaa aaaatgcttt    240
cttcttttaa tatacttttt tgtttatctt atttctaata ctttccctaa tctctttctt    300
tcagggcaat aatgatacaa tgtatcatgc ctctttgcac cattctaaag aataacagtg    360
ataatttctg ggttaaggca atagcaatat ttctgcatat aaatatttct gcatataaat    420
tgtaactgat gtaagaggtt tcatattgct aatagcagct acaatccagc taccattctg    480
cttttatttt atggttggga taaggctgga ttattctgag tccaagctag gcccttttgc    540
taatcatgtt catacctctt atcttcctcc cacagctcct gggcaacgtg ctggtctgtg    600
tgctggccca tcactttggc aaagaattgg ctagccacac acacaaatct ggggaggtga    660
agaatacgac cacctgcgtt ttatacttcc gcgagatctg ggaggtgaa gaatacgacc    720
acctaataag attaccgaaa ggcaatctta ttaaaacata ccagatcttg cgagggtgtt    780
tgtggcaaaa cataccagat cgaattcgat ctggggaggt gaagaatacg accacctgct    840
```

acaagtacct aaataaagta taaagtgcaa aacataccag atctgtgtgt tggtttttg 900 tgtgttaacg ggggaggggg aggaaagggg gagggggagg aaagggggag ggggaggaaa 960
gggggagggg gagcggccgc caacaacaac aacaacaaca acaacaacaa caacaacaac 1020
ataacagtgt tcactagcaa cctcaaacag acaccatg 1058

<210> SEQ ID NO 9
<211> LENGTH: 1058
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9
tcagatcgcc tggagacgcc atccacgctg ttttgacctc catagaagac accgggaccg 60
atccagcctc ccctcgaagc tgatcctgag aacttcaggg tgagtctatg ggacccttga 120
tgttttcttt ccccttcttt tctatggtta agttcatgtc ataggaaggg gagaagtaac 180
agggtacaca tattgaccaa atcagggtaa ttttgcattt gtaattttaa aaaatgcttt 240
cttcttttaa tatacttttt tgtttatctt atttctaata ctttccctaa tctctttctt 300
tcagggcaat aatgatacaa tgtatcatgc ctctttgcac cattctaaag aataacagtg 360
ataatttctg ggttaaggca atagcaatat ttctgcatat aaatatttct gcatataaat 420
tgtaactgat gtaagaggtt tcatattgct aatagcagct acaatccagc taccattctg 480
cttttatttt atggttggga taaggctgga ttattctgag tccaagctag gcccttttgc 540
taatcatgtt catacctctt atcttcctcc cacagctcct gggcaacgtg ctggtctgtg 600
tgctggccca tcactttggc aaagaattgg ctagccacac acacaaatct ggggaggtga 660
agaatacgac cacctgcgtt ttatacttcc acgagatctg ggaggtgaa gaatacgacc 720 acctaataag attaccgaaa ggcaatctta ttaaaacata ccagatcttg tgagggtgtt 780
tgtggcaaaa cataccagat cgaattcgat ctggggaggt gaagaatacg accacctgct 840
acaagtacct aaataaagta taaagtgcaa aacataccag atctgtgtgt tggtttttg 900 tgtgttaacg ggggaggggg aggaaagggg gagggggagg aaagggggag ggggaggaaa 960
gggggagggg gagcggccgc caacaacaac aacaacaaca acaacaacaa caacaacaac 1020
ataacagtgt tcactagcaa cctcaaacag acaccatg 1058

<210> SEQ ID NO 10
<211> LENGTH: 1057
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10
tcagatcgcc tggagacgcc atccacgctg ttttgacctc catagaagac accgggaccg 60
atccagcctc ccctcgaagc tgatcctgag aacttcaggg tgagtctatg ggacccttga 120
tgttttcttt ccccttcttt tctatggtta agttcatgtc ataggaaggg gagaagtaac 180
agggtacaca tattgaccaa atcagggtaa ttttgcattt gtaattttaa aaaatgcttt 240
cttcttttaa tatacttttt tgtttatctt atttctaata ctttccctaa tctctttctt 300
tcagggcaat aatgatacaa tgtatcatgc ctctttgcac cattctaaag aataacagtg 360

-continued

```
ataatttctg ggttaaggca atagcaatat ttctgcatat aaatatttct gcatataaat    420

tgtaactgat gtaagaggtt tcatattgct aatagcagct acaatccagc taccattctg    480

cttttatttt atggttggga taaggctgga ttattctgag tccaagctag gcccttttgc    540

taatcatgtt catacctctt atcttcctcc cacagctcct gggcaacgtg ctggtctgtg    600

tgctggccca tcactttggc aaagaattgg ctagccacac acacaaacct ggggaggtga    660

agaatacgac cacctgcgtt ttatacttcc acgagatctg ggaggtgaa gaatacgacc     720

acctaataag attaccgaaa ggcaatctta ttaaaacata ccagatcttg tgagggtgtt    780

tgtggcaaaa cataccagat cgaattcgat ctggggaggt gaagaatacg accacctgct    840

acaagtacct aataaagtat aaagtgcaaa acataccagg tctgtgtgtt ggttttttgt    900

gtgttaacgg gggaggggga ggaaaggggg agggggagga aagggggagg gggaggaaag    960

ggggaggggg agcggccgcc aacaacaaca acaacaacaa caacaacaac aacaacaaca   1020

taacagtgtt cactagcaac ctcaaacaga caccatg                            1057
```

<210> SEQ ID NO 11
<211> LENGTH: 1058
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
tcagatcgcc tggagacgcc atccacgctg ttttgacctc catagaagac accgggaccg     60

atccagcctc ccctcgaagc tgatcctgag aacttcaggg tgagtctatg ggacccttga    120

tgttttcttt ccccttcttt tctatggtta agttcatgtc ataggaaggg gagaagtaac    180

agggtacaca tattgaccaa atcagggtaa ttttgcattt gtaattttaa aaaatgcttt    240

cttcttttaa tatacttttt tgtttatctt atttctaata ctttccctaa tctctttctt    300

tcagggcaat aatgatacaa tgtatcatgc ctctttgcac cattctaaag aataacagtg    360

ataatttctg ggttaaggca atagcaatat ttctgcatat aaatatttct gcatataaat    420

tgtaactgat gtaagaggtt tcatattgct aatagcagct acaatccagc taccattctg    480

cttttatttt atggttggga taaggctgga ttattctgag tccaagctag gcccttttgc    540

taatcatgtt catacctctt atcttcctcc cacagctcct gggcaacgtg ctggtctgtg    600

tgctggccca tcactttggc aaagaattgg ctagccacac acacaaacct ggggaggtga    660

agaatacgac cacctgcgtt ttatacttcc acgagatctg ggaggtgaa gaatacgacc     720

acctaataag attaccgaaa ggcaatctta ttaaaacata ccagatcttg tgagggtgtt    780

tgtggcaaaa cataccagat cgaattcgat ctggggaggt gaagaatacg accacctgct    840

acaagtacct aaataaagta taaagtgcaa aacataccag gtctgtgtgt tggttttttg    900

tgtgttaacg ggggaggggg aggaaagggg gagggggagg aaagggggag ggggaggaaa    960

gggggagggg gagcggccgc caacaacaac aacaacaaca acaacaacaa caacaacaac   1020

ataacagtgt tcactagcaa cctcaaacag acaccatg                           1058
```

<210> SEQ ID NO 12
<211> LENGTH: 603
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag cacacacaca aatctgggga 240
ggtgaagaat acgaccacct gcgttttata cttccacgag atctggggag gtgaagaata 300
cgaccaccta ataagattac cgaaaggcaa tcttattaaa acataccaga tcttgtgagg 360
gtgtttgtgg caaaacatac cagatcgaat tcgatctggg gaggtgaaga atacgaccac 420
ctgctacaag tacctaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccataac agtgttcact agcatcccca aacagacacc 600
atg 603

<210> SEQ ID NO 13
<211> LENGTH: 614
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 13
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag cacacacaca aatctgggga 240
ggtgaagaat acgaccacct gcgttttata cttccacgag atctggggag gtgaagaata 300
cgaccaccta ataagattac cgaaaggcaa tcttattaaa acataccaga tcttgtgagg 360
gtgtttgtgg caaaacatac cagatcgaat tcgatctggg gaggtgaaga atacgaccac 420
ctgctacaag tacctaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccataac agtgttcact agcatccccc agaccatcta 600
ccaccgacac catg 614

<210> SEQ ID NO 14
<211> LENGTH: 629
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag cacacacaca aatctgggga 240
ggtgaagaat acgaccacct gcgttttata cttccacgag atctggggag gtgaagaata 300

-continued cgaccaccta ataagattac cgaaaggcaa tcttattaaa acataccaga tcttgtgagg 360
gtgtttgtgg caaaacatac cagatcgaat tcgatctggg gaggtgaaga atacgaccac 420
ctgctacaag tacctaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccttaat taacagtgtt cactagcatc aacaacaaca 600
acaacaacaa caacaacaac gacaccatg 629

<210> SEQ ID NO 15
<211> LENGTH: 629
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag cacacacaca aatctgggga 240
ggtgaagaat acgaccacct gcgttttata cttccacgag atctggggag gtgaagaata 300
cgaccaccta ataagattac cgaaaggcaa tcttattaaa acataccaga tcttgtgagg 360
gtgtttgtgg caaaacatac cagatcgaat tcgatctggg gaggtgaaga atacgaccac 420
ctgctacaag tacctaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccttaat taacagtgtt cactagtagc aacaacaaca 600
acaacaacaa caacaacaac gacaccatg 629

<210> SEQ ID NO 16
<211> LENGTH: 629
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag cacacacaca aatctgggga 240
ggtgaagaat acgaccacct gcgttttata cttccacgag atctggggag gtgaagaata 300
cgaccaccta ataagattac cgaaaggcaa tcttattaaa acataccaga tcttgtgagg 360
gtgtttgtgg caaaacatac cagatcgaat tcgatctggg gaggtgaaga atacgaccac 420
ctgctacaag tacctaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccttaat taacagtgtt cactagacac aacaacaaca 600
acaacaacaa caacaacaac gacaccatg 629

-continued

<210> SEQ ID NO 17
<211> LENGTH: 629
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 17
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag cacacacaca aatctgggga 240
ggtgaagaat acgaccacct gcgttttata cttccacgag atctggggag gtgaagaata 300
cgaccaccta ataagattac cgaaaggcaa tcttattaaa acataccaga tcttgtgagg 360
gtgtttgtgg caaaacatac cagatcgaat tcgatctggg gaggtgaaga atacgaccac 420
ctgctacaag tacctaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccttaat taacagtgtt cactagaacc aacaacaaca 600
acaacaacaa caacaacaac gacaccatg 629

<210> SEQ ID NO 18
<211> LENGTH: 629
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 18
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag cacacacaca aatctgggga 240
ggtgaagaat acgaccacct gcgttttata cttccacgag atctggggag gtgaagaata 300
cgaccaccta ataagattac cgaaaggcaa tcttattaaa acataccaga tcttgtgagg 360
gtgtttgtgg caaaacatac cagatcgaat tcgatctggg gaggtgaaga atacgaccac 420
ctgctacaag tacctaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccttaat taacagtgtt cactagtgcc aacaacaaca 600
acaacaacaa caacaacaac gacaccatg 629

<210> SEQ ID NO 19
<211> LENGTH: 629
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 19
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag cacacacaca aatctgggga 240
ggtgaagaat acgaccacct gcgttttata cttccacgag atctggggag gtgaagaata 300
cgaccaccta ataagattac cgaaaggcaa tcttattaaa acataccaga tcttgtgagg 360
gtgtttgtgg caaaacatac cagatcgaat tcgatctggg gaggtgaaga atacgaccac 420
ctgctacaag tacctaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccttaat taacagtgtt cactagttgc aacaacaaca 600
acaacaacaa caacaacaac gacaccatg 629

<210> SEQ ID NO 20
<211> LENGTH: 629
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 20
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag cacacacaca aatctgggga 240
ggtgaagaat acgaccacct gcgttttata cttccacgag atctggggag gtgaagaata 300
cgaccaccta ataagattac cgaaaggcaa tcttattaaa acataccaga tcttgtgagg 360
gtgtttgtgg caaaacatac cagatcgaat tcgatctggg gaggtgaaga atacgaccac 420
ctgctacaag tacctaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccttaat taacagtgtt cactagaccc aacaacaaca 600
acaacaacaa caacaacaac gacaccatg 629

<210> SEQ ID NO 21
<211> LENGTH: 629
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 21
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag cacacacaca aatctgggga 240
ggtgaagaat acgaccacct gcgttttata cttccacgag atctggggag gtgaagaata 300
cgaccaccta ataagattac cgaaaggcaa tcttattaaa acataccaga tcttgtgagg 360
gtgtttgtgg caaaacatac cagatcgaat tcgatctggg gaggtgaaga atacgaccac 420
ctgctacaag tacctaataa agtataaagt gcaaaacata ccagatctgt gtgttggttt 480

-continued

```
tttgtgtgtt aacgggggag ggggaggaaa gggggagggg gaggaaaggg ggagggggag    540

gaaaggggga gggggagcgg ccgccttaat taacagtgtt cactagcccc aacaacaaca    600

acaacaacaa caacaacaac gacaccatg                                      629
```

<210> SEQ ID NO 22
<211> LENGTH: 592
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
tcagatcgcc tggagacgcc atccacgctg ttttgacctc catagaagac accgggaccg     60

atccagcctc ccctcgaagc tgatcctgag aacttcaggg tgagtcttaa gccagctacc    120

attctgcttt tattttatcg ttgggataag gctggattat tctgagtcca agctaggccc    180

ttttgctaat catcttcata cctcttatct tcctctgcag cacacacaca aatctgggga    240

ggtgaagaat acgaccacct gcgttttata cttccacgag atctggggag gtgaagaata    300

cgaccaccta ataagattac cgaaaggcaa tcttattaaa acataccaga tcttgtgagg    360

gtgtttgtgg caaaacatac cagatcgaat tcgatctggg gaggtgaaga atacgaccac    420

ctgctacaag tacctaataa agtataaagt gcaaaacata ccagatctgt gtgttggttt    480

tttgtgtgtt aacgggggag ggggaggaaa gggggagggg gaggaaaggg ggagggggag    540

gaaaggggga gggggagcgg ccttaattaa cagtgttcac taggacacca tg            592
```

<210> SEQ ID NO 23
<211> LENGTH: 629
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
tcagatcgcc tggagacgcc atccacgctg ttttgacctc catagaagac accgggaccg     60

atccagcctc ccctcgaagc tgatcctgag aacttcaggg tgagtcttaa gccagctacc    120

attctgcttt tattttatcg ttgggataag gctggattat tctgagtcca agctaggccc    180

ttttgctaat catcttcata cctcttatct tcctctgcag cacacacaca aatctgggga    240

ggtgaagaat acgaccacct gcgttttata cttccacgag atctggggag gtgaagaata    300

cgaccaccta ataagattac cgaaaggcaa tcttattaaa acataccaga tcttgtgagg    360

gtgtttgtgg caaaacatac cagatcgaat tcgatctggg gaggtgaaga atacgaccac    420

ctgctacaag tacctaataa agtataaagt gcaaaacata ccagatctgt gtgttggttt    480

tttgtgtgtt aacgggggag ggggaggaaa gggggagggg gaggaaaggg ggagggggag    540

gaaaggggga gggggagcgg ccgccttaat taacagtgtt cactagaggc aacaacaaca    600

acaacaacaa caacaacaac gacaccatg                                      629
```

<210> SEQ ID NO 24
<211> LENGTH: 629
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag cacacacaca aatctgggga 240
ggtgaagaat acgaccacct gcgttttata cttccacgag atctggggag gtgaagaata 300
cgaccaccta ataagattac cgaaaggcaa tcttattaaa acataccaga tcttgtgagg 360
gtgtttgtgg caaaacatac cagatcgaat tcgatctggg gaggtgaaga atacgaccac 420
ctgctacaag tacctaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccttaat taacagtgtt cactagtgac aacaacaaca 600
acaacaacaa caacaacaac gacaccatg 629

<210> SEQ ID NO 25
<211> LENGTH: 629
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 25
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag cacacacaca aatctgggga 240
ggtgaagaat acgaccacct gcgttttata cttccacgag atctggggag gtgaagaata 300
cgaccaccta ataagattac cgaaaggcaa tcttattaaa acataccaga tcttgtgagg 360
gtgtttgtgg caaaacatac cagatcgaat tcgatctggg gaggtgaaga atacgaccac 420
ctgctacaag tacctaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccttaat taacagtgtt cactagtccc aacaacaaca 600
acaacaacaa caacaacaac gacaccatg 629

<210> SEQ ID NO 26
<211> LENGTH: 629
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 26
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag cacacacaca aatctgggga 240
ggtgaagaat acgaccacct gcgttttata cttccacgag atctggggag gtgaagaata 300
cgaccaccta ataagattac cgaaaggcaa tcttattaaa acataccaga tcttgtgagg 360

```
gtgtttgtgg caaaacatac cagatcgaat tcgatctggg gaggtgaaga atacgaccac    420

ctgctacaag tacctaataa agtataaagt gcaaaacata ccagatctgt gtgttggttt    480

tttgtgtgtt aacgggggag ggggaggaaa gggggagggg gaggaaaggg ggagggggag    540

gaaaggggga gggggagcgg ccgccttaat taacagtgtt cactagcctc aacaacaaca    600

acaacaacaa caacaacaac gacaccatg                                      629
```

```
<210> SEQ ID NO 27
<211> LENGTH: 629
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

tcagatcgcc tggagacgcc atccacgctg ttttgacctc catagaagac accgggaccg     60

atccagcctc ccctcgaagc tgatcctgag aacttcaggg tgagtcttaa gccagctacc    120

attctgcttt tattttatcg ttgggataag gctggattat tctgagtcca agctaggccc    180

ttttgctaat catcttcata cctcttatct tcctctgcag cacacacaca aatctgggga    240

ggtgaagaat acgaccacct gcgttttata cttccacgag atctggggag gtgaagaata    300

cgaccaccta ataagattac cgaaaggcaa tcttattaaa acataccaga tcttgtgagg    360

gtgtttgtgg caaaacatac cagatcgaat tcgatctggg gaggtgaaga atacgaccac    420

ctgctacaag tacctaataa agtataaagt gcaaaacata ccagatctgt gtgttggttt    480

tttgtgtgtt aacgggggag ggggaggaaa gggggagggg gaggaaaggg ggagggggag    540

gaaaggggga gggggagcgg ccgccttaat taacagtgtt cactagtctc aacaacaaca    600

acaacaacaa caacaacaac gacaccatg                                      629


<210> SEQ ID NO 28
<211> LENGTH: 614
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

tcagatcgcc tggagacgcc atccacgctg ttttgacctc catagaagac accgggaccg     60

atccagcctc ccctcgaagc tgatcctgag aacttcaggg tgagtcttaa gccagctacc    120

attctgcttt tattttatcg ttgggataag gctggattat tctgagtcca agctaggccc    180

ttttgctaat catcttcata cctcttatct tcctctgcag cacacacaca aatctgggga    240

ggtgaagaat acgaccacct gcgttttata cttccacgag atctggggag gtgaagaata    300

cgaccaccta ataagattac cgaaaggcaa tcttattaaa acataccaga tcttgtgagg    360

gtgtttgtgg caaaacatac cagatcgaat tcgatctggg gaggtgaaga atacgaccac    420

ctgctacaag tacctaataa agtataaagt gcaaaacata ccagatctgt gtgttggttt    480

tttgtgtgtt aacgggggag ggggaggaaa gggggagggg gaggaaaggg ggagggggag    540

gaaaggggga gggggagcgg ccgccataac agtgttcact agcccccccc agaccatcta    600

ccaccgacac catg                                                      614


<210> SEQ ID NO 29
```

<211> LENGTH: 614
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 29
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag catacacaca aatctgggga 240
ggtgaagaat acgaccacct gcgttttata cttccacgag atctggggag gtgaagaata 300
cgaccaccta ataagattac cgaaaggcaa tcttattaaa acataccaga tcttgtgagg 360
gtgtttgtgg caaaacatac cagatcgaat tcgatctggg gaggtgaaga atacgaccac 420
ctgctacaag tacctaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccataac agtgttcact agcccccccc agaccatcta 600
ccaccgacac catg 614

<210> SEQ ID NO 30
<211> LENGTH: 614
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 30
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag tttacacaca aatctgggga 240
ggtgaagaat acgaccacct gcgttttata cttccacgag atctggggag gtgaagaata 300
cgaccaccta ataagattac cgaaaggcaa tcttattaaa acataccaga tcttgtgagg 360
gtgtttgtgg caaaacatac cagatcgaat tcgatctggg gaggtgaaga atacgaccac 420
ctgctacaag tacctaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccataac agtgttcact agcccccccc agaccatcta 600
ccaccgacac catg 614

<210> SEQ ID NO 31
<211> LENGTH: 614
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 31
tcagatcgcc tggagacgcc atccacgctg ttttgacctc catagaagac accgggaccg 60
atccagcctc ccctcgaagc tgatcctgag aacttcaggg tgagtcttaa gccagctacc 120

```
attctgcttt tattttatcg ttgggataag gctggattat tctgagtcca agctaggccc    180

ttttgctaat catcttcata cctcttatct tcctctgcag tgaacacaca aatctgggga    240

ggtgaagaat acgaccacct gcgttttata cttccacgag atctggggag gtgaagaata    300

cgaccaccta ataagattac cgaaaggcaa tcttattaaa acataccaga tcttgtgagg    360

gtgtttgtgg caaaacatac cagatcgaat tcgatctggg gaggtgaaga atacgaccac    420

ctgctacaag tacctaataa agtataaagt gcaaaacata ccagatctgt gtgttggttt    480

tttgtgtgtt aacgggggag ggggaggaaa gggggagggg gaggaaaggg ggagggggag    540

gaaaggggga gggggagcgg ccgccataac agtgttcact agcccccccc agaccatcta    600

ccaccgacac catg                                                      614
```

<210> SEQ ID NO 32
<211> LENGTH: 613
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
tcagatcgcc tggagacgcc atccacgctg ttttgacctc catagaagac accgggaccg     60

atccagcctc ccctcgaagc tgatcctgag aacttcaggg tgagtcttaa gccagctacc    120

attctgcttt tattttatcg ttgggataag gctggattat tctgagtcca agctaggccc    180

ttttgctaat catcttcata cctcttatct tcctctgcag tctacacaca atctggggag    240

gtgaagaata cgaccacctg cgttttatac ttccacgaga tctggggagg tgaagaatac    300

gaccacctaa taagattacc gaaaggcaat cttattaaaa cataccagat cttgtgaggg    360

tgtttgtggc aaaacatacc agatcgaatt cgatctgggg aggtgaagaa tacgaccacc    420

tgctacaagt acctaataaa gtataaagtg caaaacatac cagatctgtg tgttggtttt    480

ttgtgtgtta acgggggagg gggaggaaag ggggaggggg aggaaagggg gagggggagg    540

aaagggggag ggggagcggc cgccataaca gtgttcacta gcccccccca gaccatctac    600

caccgacacc atg                                                       613
```

<210> SEQ ID NO 33
<211> LENGTH: 629
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

```
tcagatcgcc tggagacgcc atccacgctg ttttgacctc catagaagac accgggaccg     60

atccagcctc ccctcgaagc tgatcctgag aacttcaggg tgagtcttaa gccagctacc    120

attctgcttt tattttatcg ttgggataag gctggattat tctgagtcca agctaggccc    180

ttttgctaat catcttcata cctcttatct tcctctgcag cacacacaca aatctgggga    240

ggtgaagaat acgaccacct gcgttttata cttccacgag atctggggag gtgaagaata    300

cgaccaccta ataagattac cgaaaggcaa tcttattaaa acataccaga tcttgtgagg    360

gtgtttgtgg caaaacatac cagatcgaat tcgatctggg gaggtgaaga atacgaccac    420

ctgctacaag tacctaataa agtataaagt gcaaaacata ccagatctgt gtgttggttt    480

tttgtgtgtt aacgggggag ggggaggaaa gggggagggg gaggaaaggg ggagggggag    540
```

-continued

```
gaaaggggga gggggagcgg ccgccttaat taacagtgtt cactagagcc aacaacaaca    600

acaacaacaa caacaacaac gacaccatg                                       629


<210> SEQ ID NO 34
<211> LENGTH: 629
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

tcagatcgcc tggagacgcc atccacgctg ttttgacctc catagaagac accgggaccg     60

atccagcctc ccctcgaagc tgatcctgag aacttcaggg tgagtcttaa gccagctacc    120

attctgcttt tattttatcg ttgggataag gctggattat tctgagtcca agctaggccc    180

ttttgctaat catcttcata cctcttatct tcctctgcag catacacaca aatctgggga    240

ggtgaagaat acgaccacct gcgttttata cttccacgag atctggggag gtgaagaata    300

cgaccaccta ataagattac cgaaaggcaa tcttattaaa acataccaga tcttgtgagg    360

gtgtttgtgg caaaacatac cagatcgaat tcgatctggg gaggtgaaga atacgaccac    420

ctgctacaag tacctaataa agtataaagt gcaaaacata ccagatctgt gtgttggttt    480

tttgtgtgtt aacgggggag ggggaggaaa gggggagggg gaggaaaggg ggagggggag    540

gaaaggggga gggggagcgg ccgccttaat taacagtgtt cactagagcc aacaacaaca    600

acaacaacaa caacaacaac gacaccatg                                       629


<210> SEQ ID NO 35
<211> LENGTH: 629
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

tcagatcgcc tggagacgcc atccacgctg ttttgacctc catagaagac accgggaccg     60

atccagcctc ccctcgaagc tgatcctgag aacttcaggg tgagtcttaa gccagctacc    120

attctgcttt tattttatcg ttgggataag gctggattat tctgagtcca agctaggccc    180

ttttgctaat catcttcata cctcttatct tcctctgcag tacacacaca aatctgggga    240

ggtgaagaat acgaccacct gcgttttata cttccacgag atctggggag gtgaagaata    300

cgaccaccta ataagattac cgaaaggcaa tcttattaaa acataccaga tcttgtgagg    360

gtgtttgtgg caaaacatac cagatcgaat tcgatctggg gaggtgaaga atacgaccac    420

ctgctacaag tacctaataa agtataaagt gcaaaacata ccagatctgt gtgttggttt    480

tttgtgtgtt aacgggggag ggggaggaaa gggggagggg gaggaaaggg ggagggggag    540

gaaaggggga gggggagcgg ccgccttaat taacagtgtt cactagagcc aacaacaaca    600

acaacaacaa caacaacaac gacaccatg                                       629


<210> SEQ ID NO 36
<211> LENGTH: 629
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 36
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag tttacacaca aatctgggga 240
ggtgaagaat acgaccacct gcgttttata cttccacgag atctggggag gtgaagaata 300
cgaccaccta ataagattac cgaaaggcaa tcttattaaa acataccaga tcttgtgagg 360
gtgtttgtgg caaaacatac cagatcgaat tcgatctggg gaggtgaaga atacgaccac 420
ctgctacaag tacctaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccttaat taacagtgtt cactagagcc aacaacaaca 600
acaacaacaa caacaacaac gacaccatg 629

<210> SEQ ID NO 37
<211> LENGTH: 550
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 37
tcagatcgcc tggagacgcc atccacgctg ttttgacctc catagaagac accgggaccg 60
atccagcctc ccctcgaagc tgatcctgag aacttcaggg tgagtctatg ccagctacca 120
ttctgctttt attttatggt tgggataagg ctggattatt ctgagtccaa gctaggccct 180
tttgctaatc atcttcatac ctcttatctt cctctgcaga tgttcctcga gatctgggga 240
ggtgaagaat acgaccacct aataagatta ccgaaaggca atcttattaa aacataccag 300
atcttgagag ggtgtttgtg gcaaaacata ccagatcgaa ttcgatctgg ggaggtgaag 360
aatacgacca cctgctacaa gtacctaata aacattagcg gagaaacata ccactgtgtg 420
ttggtttttt gtgtgttaac gggggagggg gaggaaaggg ggagggggag gaaaggggga 480
gggggaggaa agggggaggg ggagcggccg ccataacagt gttcactagc aacctcaaac 540
agacaccatg 550

<210> SEQ ID NO 38
<211> LENGTH: 550
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 38
tcagatcgcc tggagacgcc atccacgctg ttttgacctc catagaagac accgggaccg 60
atccagcctc ccctcgaagc tgatcctgag aacttcaggg tgagtctatg ccagctacca 120
ttctgctttt attttatggt tgggataagg ctggattatt ctgagtccaa gctaggccct 180
tttgctaatc atcttcatac ctcttatctt cctctgcaga tgttcctcga gatctgggga 240
ggtgaagaat acgaccacct aataagatta ccgaaaggca atcttattaa aacataccag 300
atcttgagag ggtgtttgtg gcaaaacata ccagatcgaa ttcgatctgg ggaggtgaag 360
aatacgacca cctgctacaa gtacctaata aacattagcg gagaaacata ccactgtgtg 420
ttggtttttt gtgtgttaac gggggagggg gaggaaaggg ggagggggag gaaaggggga 480
gggggaggaa agggggaggg ggagcggccg ccataacagt gttcactagc aaccccaaac 540
agacaccatg 550

<210> SEQ ID NO 39
<211> LENGTH: 553
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39
tcagatcgcc tggagacgcc atccacgctg ttttgacctc catagaagac accgggaccg 60
atccagcctc ccctcgaagc tgatcctgag aacttcaggg tgagtctatg ccagctacca 120
ttctgctttt attttatggt tgggataagg ctggattatt ctgagtccaa gctaggccct 180
tttgctaatc atcttcatac ctcttatctt cctctgcaga tgttcctcga gatctgggga 240
ggtgaagaat acgaccacct aataagatta ccgaaaggca atcttattaa aacataccag 300
atcttgagag ggtgtttgtg gcaaaacata ccagatcgaa ttcgatctgg ggaggtgaag 360
aatacgacca cctgctacaa gtacctaata aacattagcg gagaaacata ccactgtgtg 420
ttggtttttt gtgtgttaac gggggagggg gaggaaaggg ggagggggag gaaaggggga 480
gggggaggaa agggggaggg ggagcggccg ccaccataac agtgttcact agcaacccca 540
aacagacacc atg 553

<210> SEQ ID NO 40
<211> LENGTH: 556
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40
tcagatcgcc tggagacgcc atccacgctg ttttgacctc catagaagac accgggaccg 60
atccagcctc ccctcgaagc tgatcctgag aacttcaggg tgagtctatg ccagctacca 120
ttctgctttt attttatggt tgggataagg ctggattatt ctgagtccaa gctaggccct 180
tttgctaatc atcttcatac ctcttatctt cctctgcaga tgttcctcga gatctgggga 240
ggtgaagaat acgaccacct aataagatta ccgaaaggca atcttattaa aacataccag 300
atcttgagag ggtgtttgtg gcaaaacata ccagatcgaa ttcgatctgg ggaggtgaag 360
aatacgacca cctgctacaa gtacctaata aacattagcg gagaaacata ccactgtgtg 420
ttggtttttt gtgtgttaac gggggagggg gaggaaaggg ggagggggag gaaaggggga 480
gggggaggaa agggggaggg ggagcggccg ccaccatgat aacagtgttc actagcaacc 540
ccaaacagac accatg 556

<210> SEQ ID NO 41
<211> LENGTH: 556
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41
tcagatcgcc tggagacgcc atccacgctg ttttgacctc catagaagac accgggaccg 60
atccagcctc ccctcgaagc tgatcctgag aacttcaggg tgagtctatg ccagctacca 120
ttctgctttt attttatggt tgggataagg ctggattatt ctgagtccaa gctaggccct 180
tttgctaatc atcttcatac ctcttatctt cctctgcaga tgttcctcga gatctgggga 240
ggtgaagaat acgaccacct aataagatta ccgaaaggca atcttattaa aacataccag 300
atcttgagag ggtgtttgtg gcaaaacata ccagatcgaa ttcgatctgg ggaggtgaag 360
aatacgacca cctgctacaa gtacctaata aacattagcg gagaaacata ccactgtgtg 420
ttggtttttt gtgtgttaac gggggagggg gaggaaaggg ggagggggag gaaaggggga 480
gggggaggaa agggggaggg ggagcggccg ccaccacgat aacagtgttc actagcaacc 540
ccaaacagac accatg 556

<210> SEQ ID NO 42
<211> LENGTH: 553
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 42
tcagatcgcc tggagacgcc atccacgctg ttttgacctc catagaagac accgggaccg 60
atccagcctc ccctcgaagc tgatcctgag aacttcaggg tgagtctatg ccagctacca 120
ttctgctttt attttatggt tgggataagg ctggattatt ctgagtccaa gctaggccct 180
tttgctaatc atcttcatac ctcttatctt cctctgcaga tgttcctcga gatctgggga 240
ggtgaagaat acgaccacct aataagatta ccgaaaggca atcttattaa aacataccag 300
atcttgagag ggtgtttgtg gcaaaacata ccagatcgaa ttcgatctgg ggaggtgaag 360
aatacgacca cctgctacaa gtacctaata aacattagcg gagaaacata ccactgtgtg 420
ttggtttttt gtgtgttaac gggggagggg gaggaaaggg ggagggggag gaaaggggga 480
gggggaggaa agggggaggg ggagcggccg ccaccataac agtgttcact agcatcccca 540
aacagacacc atg 553

<210> SEQ ID NO 43
<211> LENGTH: 553
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 43
tcagatcgcc tggagacgcc atccacgctg ttttgacctc catagaagac accgggaccg 60
atccagcctc ccctcgaagc tgatcctgag aacttcaggg tgagtctatg ccagctacca 120
ttctgctttt attttatggt tgggataagg ctggattatt ctgagtccaa gctaggccct 180
tttgctaatc atcttcatac ctcttatctt cctctgcaga tgttcctcga gatctgggga 240
ggtgaagaat acgaccacct aataagatta ccgaaaggca atcttattaa aacataccag 300
atcttgagag ggtgtttgtg gcaaaacata ccagatcgaa ttcgatctgg ggaggtgaag 360
aatacgacca cctgctacaa gtacctaata aacattagcg gagaaacata ccactgtgtg 420
ttggtttttt gtgtgttaac gggggagggg gaggaaaggg ggagggggag gaaaggggga 480
gggggaggaa agggggaggg ggagcggccg ccaccataac agtgttcacc agcatcccca 540
aacagacacc atg 553

<210> SEQ ID NO 44
<211> LENGTH: 550
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 44
tcagatcgcc tggagacgcc atccacgctg ttttgacctc catagaagac accgggaccg 60
atccagcctc ccctcgaagc tgatcctgag aacttcaggg tgagtctatg ccagctacca 120
ttctgctttt attttatggt tgggataagg ctggattatt ctgagtccaa gctaggccct 180
tttgctaatc atcttcatac ctcttatctt cctctgcaga tgttcctcga gatctgggga 240
ggtgaagaat acgaccacct aataagatta ccgaaaggca atcttattaa aacataccag 300
atcttgagag ggtgtttgtg gcaaaacata ccagatcgaa ttcgatctgg ggaggtgaag 360
aatacgacca cctgctacaa gtacctaata aacattagcg gagaaacata ccactgtgtg 420
ttggtttttt gtgtgttaac gggggagggg gaggaaaggg ggagggggag gaaaggggga 480
gggggaggaa agggggaggg ggagcggccg ccataacagt gttcactagc atccccaaac 540
agacaccatg 550

<210> SEQ ID NO 45
<211> LENGTH: 550
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 45
tcagatcgcc tggagacgcc atccacgctg ttttgacctc catagaagac accgggaccg 60
atccagcctc ccctcgaagc tgatcctgag aacttcaggg tgagtctatg ccagctacca 120
ttctgctttt attttatggt tgggataagg ctggattatt ctgagtccaa gctaggccct 180
tttgctaatc atcttcatac ctcttatctt cctctgcaga tgttcctcga gatctgggga 240
ggtgaagaat acgaccacct aataagatta ccgaaaggca atcttattaa aacataccag 300
atcttgagag ggtgtttgtg gcaaaacata ccagatcgaa ttcgatctgg ggaggtgaag 360
aatacgacca cctgctacaa gtacctaata aacattagcg gagaaacata ccactgtgtg 420
ttggtttttt gtgtgttaac gggggagggg gaggaaaggg ggagggggag gaaaggggga 480
gggggaggaa agggggaggg ggagcggccg ccataacagt gttcaccagc atccccaaac 540
agacaccatg 550

<210> SEQ ID NO 46
<211> LENGTH: 551
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 46
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag attttccacg agatctgggg 240
aggtgaagaa tacgaccacc taataagatt accgaaaggc aatcttatta aaacatacca 300
gatcttgtga gggtgtttgt ggcaaaacat accagatcga attcgatctg gggaggtgaa 360
gaatacgacc acctgctaca agtacctaat aaaaattagc ggagaaacat accactgtgt 420
gttggttttt tgtgtgttaa cgggggaggg ggaggaaagg gggaggggga ggaaaggggg 480
agggggagga aagggggagg gggagcggcc gccataacag tgttcactag catccccaaa 540
cagacaccat g 551

<210> SEQ ID NO 47
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 47
aacgggggag ggggaggaaa gggggagggg gaggaaaggg ggagggggag gaaaggggga 60
ggggga 66

<210> SEQ ID NO 48
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
gcggccgcct taattaacag tgttcactag agccaacaac aacaacaaca acaacaacaa 60
caacgacacc 70

<210> SEQ ID NO 49
<211> LENGTH: 476
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49
gtgagtctat gggacccttg atgttttctt tccccttctt ttctatggtt aagttcatgt 60
cataggaagg ggagaagtaa cagggtacac atattgacca aatcagggta attttgcatt 120
tgtaatttta aaaaatgctt tcttctttta atatactttt ttgtttatct tatttctaat 180
actttcccta atctctttct ttcagggcaa taatgataca atgtatcatg cctctttgca 240
ccattctaaa gaataacagt gataatttct gggttaaggc aatagcaata tttctgcata 300
taaatatttc tgcatataaa ttgtaactga tgtaagaggt ttcatattgc taatagcagc 360
tacaatccag ctaccattct gcttttattt tatggttggg ataaggctgg attattctga 420
gtccaagcta ggcccttttg ctaatcatgt tcatacctct tatcttcctc ccacag 476

<210> SEQ ID NO 50
<211> LENGTH: 614

-continued

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 50
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag tctacacaca atctggggag 240
gtgaagaata cgaccacctg cgttttatac ttccacgaga tctggggagg tgaagaatac 300
gaccacctaa taagattgcc gaaaggcaat cttattaaaa cataccagat cttgtgaggg 360
tgtttgtggc aaaacatacc agatcgaatt cgatctgggg aggtgaagaa tacgaccacc 420
tgctacaagt acctaaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccataac agtgttcact agcccccccc agaccatcta 600
ccaccgacac catg 614

<210> SEQ ID NO 51
<211> LENGTH: 613
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 51
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag catacacaca atctggggag 240
gtgaagaata cgaccacctg cgttttatac ttccacgaga tctggggagg tgaagaatac 300
gaccacctaa taagattacc gaaaggcaat cttattaaaa cataccagat cttgtgaggg 360
tgtttgtggc aaaacatacc agatcgaatt cgatctgggg aggtgaagaa tacgaccacc 420
tgctacaagt acctaataaa gtataaagtg caaaacatac cagatctgtg tgttggtttt 480
ttgtgtgtta acgggggagg gggaggaaag ggggaggggg aggaaagggg gagggggagg 540
aaagggggag ggggagcggc cgccataaca gtgttcacta gcccccccca gaccatctac 600
caccgacacc atg 613

<210> SEQ ID NO 52
<211> LENGTH: 613
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 52
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180

```
ttttgctaat catcttcata cctcttatct tcctctgcag tttacacaca atctggggag    240

gtgaagaata cgaccacctg cgttttatac ttccacgaga tctggggagg tgaagaatac    300

gaccacctaa taagattacc gaaaggcaat cttattaaaa cataccagat cttgtgaggg    360

tgtttgtggc aaaacatacc agatcgaatt cgatctgggg aggtgaagaa tacgaccacc    420

tgctacaagt acctaataaa gtataaagtg caaaacatac cagatctgtg tgttggtttt    480

ttgtgtgtta acgggggagg gggaggaaag ggggaggggg aggaaagggg gagggggagg    540

aaagggggag ggggagcggc cgccataaca gtgttcacta gcccccccca gaccatctac    600

caccgacacc atg                                                       613
```

```
<210> SEQ ID NO 53
<211> LENGTH: 613
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

tcagatcgcc tggagacgcc atccacgctg ttttgacctc catagaagac accgggaccg     60

atccagcctc ccctcgaagc tgatcctgag aacttcaggg tgagtcttaa gccagctacc    120

attctgcttt tattttatcg ttgggataag gctggattat tctgagtcca agctaggccc    180

ttttgctaat catcttcata cctcttatct tcctctgcag tgaacacaca atctggggag    240

gtgaagaata cgaccacctg cgttttatac ttccacgaga tctggggagg tgaagaatac    300

gaccacctaa taagattacc gaaaggcaat cttattaaaa cataccagat cttgtgaggg    360

tgtttgtggc aaaacatacc agatcgaatt cgatctgggg aggtgaagaa tacgaccacc    420

tgctacaagt acctaataaa gtataaagtg caaaacatac cagatctgtg tgttggtttt    480

ttgtgtgtta acgggggagg gggaggaaag ggggaggggg aggaaagggg gagggggagg    540

aaagggggag ggggagcggc cgccataaca gtgttcacta gcccccccca gaccatctac    600

caccgacacc atg                                                       613
```

```
<210> SEQ ID NO 54
<211> LENGTH: 614
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

tcagatcgcc tggagacgcc atccacgctg ttttgacctc catagaagac accgggaccg     60

atccagcctc ccctcgaagc tgatcctgag aacttcaggg tgagtcttaa gccagctacc    120

attctgcttt tattttatcg ttgggataag gctggattat tctgagtcca agctaggccc    180

ttttgctaat catcttcata cctcttatct tcctctgcag catacacaca atctggggag    240

gtgaagaata cgaccacctg cgttttatac ttccacgaga tctggggagg tgaagaatac    300

gaccacctaa taagattgcc gaaaggcaat cttattaaaa cataccagat cttgtgaggg    360

tgtttgtggc aaaacatacc agatcgaatt cgatctgggg aggtgaagaa tacgaccacc    420

tgctacaagt acctaaataa agtataaagt gcaaaacata ccagatctgt gtgttggttt    480

tttgtgtgtt aacgggggag ggggaggaaa gggggagggg gaggaaaggg ggagggggag    540
```

gaaaggggga gggggagcgg ccgccataac agtgttcact agcccccccc agaccatcta 600
ccaccgacac catg 614

<210> SEQ ID NO 55
<211> LENGTH: 614
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag tttacacaca atctggggag 240
gtgaagaata cgaccacctg cgttttatac ttccacgaga tctggggagg tgaagaatac 300
gaccacctaa taagattgcc gaaaggcaat cttattaaaa cataccagat cttgtgaggg 360
tgtttgtggc aaaacatacc agatcgaatt cgatctgggg aggtgaagaa tacgaccacc 420
tgctacaagt acctaaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccataac agtgttcact agcccccccc agaccatcta 600
ccaccgacac catg 614

<210> SEQ ID NO 56
<211> LENGTH: 614
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag tgaacacaca atctggggag 240
gtgaagaata cgaccacctg cgttttatac ttccacgaga tctggggagg tgaagaatac 300
gaccacctaa taagattgcc gaaaggcaat cttattaaaa cataccagat cttgtgaggg 360
tgtttgtggc aaaacatacc agatcgaatt cgatctgggg aggtgaagaa tacgaccacc 420
tgctacaagt acctaaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccataac agtgttcact agcccccccc agaccatcta 600
ccaccgacac catg 614

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 57
aataagatta ccgaaaggca atcttatt 28

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 58
ccagatcgaa ttcgatctgg 20

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 59
tggtggtgga atggt 15

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 60
tggtggtgga atggtaaatg gtggtggaat ggt 33

<210> SEQ ID NO 61
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 61
tggtggtgga atggtaaatg gtggtggaat ggtaaatggt ggtggaatgg taaatggtgg 60
tggaatggt 69

<210> SEQ ID NO 62
<211> LENGTH: 86
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62
gcggccgcca acaacaacaa caacaacaac aacaacaaca acaacaacat aacagtgttc 60
actagcaacc tcaaacagac accatg 86

<210> SEQ ID NO 63
<211> LENGTH: 124
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 63
gtgagtctat gccagctacc attctgcttt tattttatgg ttgggataag gctggattat     60
tctgagtcca agctaggccc ttttgctaat catcttcata ctaacctctt atcttcctct    120
gcag                                                                 124

<210> SEQ ID NO 64
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
gtgagtctat gccagctacc attctgcttt tattttatgg ttgggataag gctggattat     60
tctgagtcca agctactaac ttttcctgtg cttcttcaga cctcttatct tcctctgcag    120

<210> SEQ ID NO 65
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
ctgcagatgt tcctcgagat ctggggaggt gaagaatacg accacctaat aagattaccg     60
aaaggcaatc ttattaaaac ataccagatc ttgagagggt gtttgtggca aaacatacca    120
gatcgaattc gatctgggga ggtgaagaat acgaccacct gctacaagta cctaataaac    180
attagcggag aaacatacca ctgtgtgttg gtttttgtg tgttaacggg ggagggggag    240
gaaaggggga gggggaggaa agggggaggg ggaggaaagg gggaggggga gcggccgcca    300
taacagtgtt cactagcaac ctcaaacaga caccatg                             337

<210> SEQ ID NO 66
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gcggccgcca taacagtgtt cactagcatc cccaaacaga caccatg                   47

<210> SEQ ID NO 67
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gcggccttaa ttaacagtgt tcactaggac accatg                               36

<210> SEQ ID NO 68
<211> LENGTH: 614
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 68
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag tctacacaca aatctgggga 240
ggtgaagaat acgaccacct gcgttttata cttccacgag atctggggag gtgaagaata 300
cgaccaccta ataagattac cgaaaggcaa tcttattaaa acataccaga tcttgtgagg 360
gtgtttgtgg caaaacatac cagatcgaat tcgatctggg gaggtgaaga atacgaccac 420
ctgctacaag tacctaataa agtataaagt gcaaaacata ccagatctgt gtgttggttt 480
tttgtgtgtt aacgggggag ggggaggaaa gggggagggg gaggaaaggg ggagggggag 540
gaaaggggga gggggagcgg ccgccataac agtgttcact agcccccccc agaccatcta 600
ccaccgacac catg 614

<210> SEQ ID NO 69
<211> LENGTH: 628
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 69
tcagatcgcc tggagacgcc atccacgctg ttttgacctc catagaagac accgggaccg 60
atccagcctc ccctcgaagc tgatcctgag aacttcaggg tgagtcttaa gccagctacc 120
attctgcttt tattttatcg ttgggataag gctggattat tctgagtcca agctaggccc 180
ttttgctaat catcttcata cctcttatct tcctctgcag tttacacaca atctggggag 240
gtgaagaata cgaccacctg cgttttatac ttccacgaga tctggggagg tgaagaatac 300
gaccacctaa taagattacc gaaaggcaat cttattaaaa cataccagat cttgtgaggg 360
tgtttgtggc aaaacatacc agatcgaatt cgatctgggg aggtgaagaa tacgaccacc 420
tgctacaagt acctaataaa gtataaagtg caaaacatac cagatctgtg tgttggtttt 480
ttgtgtgtta acgggggagg gggaggaaag gggggagggg aggaaagggg gagggggagg 540
aaagggggag ggggagcggc cgccttaatt aacagtgttc actagagcca acaacaacaa 600
caacaacaac aacaacaacg acaccatg 628

<210> SEQ ID NO 70
<211> LENGTH: 260
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 70
gccacacaca caaaucuggg gaggugaaga auacgaccac cugcguuuua uacuuccacg 60
agaucugggg aggugaagaa uacgaccacc uaauaagauu accgaaaggc aaucuuauua 120
aaacauacca gaucuuguga ggguguuugu ggcaaaacau accagaucga auucgaucug 180

-continued

```
gggaggugaa gaauacgacc accugcuaca aguaccuaau aaaguauaaa gugcaaaaca    240

uaccagaucu guguguuggu                                                260


<210> SEQ ID NO 71
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71

gccacacaca caaaucuggg gaggugaaga auacgaccac cugcguu                   47


<210> SEQ ID NO 72
<211> LENGTH: 78
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72

aagugcaaaa cauaccagau cugugcgaaa gcacaaaucu ggggaggugua agaauacgac     60

caccugcguu uuaggaca                                                   78


<210> SEQ ID NO 73
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 73

uuuguuaaaa cauaccagau cgaauucgau cuggggaggu gaagaauacg accaccuaau     60

aaacuguaaa augcaaaaca uaccagaucu guguguuggu                          100


<210> SEQ ID NO 74
<211> LENGTH: 56
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74

gccacacaca caaaucuggg gaggugaaga auacgaccac cugcguuuua uacuuu         56


<210> SEQ ID NO 75
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75

cucaaaucug ggaggugaa gaauacgacc accugcagau ucgaaagaau cugcaaaaca     60

uaccagaucu gagucuaac                                                  79


<210> SEQ ID NO 76
<211> LENGTH: 75
<212> TYPE: RNA
```

<213> ORGANISM: Artificial Sequence
<220> FEATURE:
<223> OTHER INFORMATION: Description of Artificial Sequence: Synthetic
oligonucleotide

<400> SEQUENCE: 76
uauacuuugu uaaaacauac cagaucgaau ucgaucuggg gaggugaaga auacgaccac 60
cuaauaaagu auacg 75

<210> SEQ ID NO 77
<211> LENGTH: 40
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 77
aaaguauaaa gugcaaaaca uaccagaucu guguguuggu 40

<210> SEQ ID NO 78
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 78
uuuauacuuu guaaaacaua ccagagaucu gggg 34

<210> SEQ ID NO 79
<211> LENGTH: 49
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 79
accagaucuu uggggaggug aagaauacga ccaccuaaua aaguauaaa 49

<210> SEQ ID NO 80
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 80
accaagaucu ggg 13

<210> SEQ ID NO 81
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 81
accagaucuu ggg 13

<210> SEQ ID NO 82
<211> LENGTH: 14

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 82
accagagauc uggg 14

<210> SEQ ID NO 83
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 83
accagaucuu ugggg 15

<210> SEQ ID NO 84
<211> LENGTH: 77
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 84
gccacacaca caaaucuggg gaggugaaga auacgaccac cugcguuuua uacuuuguua 60
aaacauacca ggagauc 77

<210> SEQ ID NO 85
<211> LENGTH: 55
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 85
aggugaagaa uacgaccacc uaauaaauua ccgaaaggca aauuuauuaa aacau 55

<210> SEQ ID NO 86
<211> LENGTH: 79
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 86
ccagaucucc uggggaggug aagaauacga ccaccuaaua aaguauaaag ugcaaaacau 60
accagaucug uguguuggu 79

<210> SEQ ID NO 87
<211> LENGTH: 72
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 87
cugcuuuguu aaaacauacc agaucgaauu cgaucugggg aggugaagaa uacgaccacc 60
uaauaaagcu aa 72

<210> SEQ ID NO 88
<211> LENGTH: 70
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 88
gccuuuguua aaacauacca gaucgaauuc gaucugggga ggugaagaau acgaccaccu 60
aauaaaggcu 70

<210> SEQ ID NO 89
<211> LENGTH: 258
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 89
gccacacaca caaaucuggg gaggugaaga auacgaccac cugcguuuua uacuuuggac 60
aacucaaauc uggggaggug aagaauacga ccaccugcag auucgaaaga aucugcaaaa 120
cauaccagau cugaguugcu auacuuuguu aaaacauacc agaucgaauu cgaucugggg 180
aggugaagaa uacgaccacc uaauaaagua uagcuaauaa aguauaaagu gcaaaacaua 240
ccagaucugu guguuggu 258

<210> SEQ ID NO 90
<211> LENGTH: 119
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 90
acacacacaa aucuggggag gugaagaaua cgaccaccug cguuuuauac uuuggacaac 60
ucgaucuggg gaggugaaga auacgaccac cugcagauuc gaaagaaucu gcaaaacau 119

<210> SEQ ID NO 91
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 91
ccagaucgag uugcuauacu uggc 24

<210> SEQ ID NO 92
<211> LENGTH: 104
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 92
aaacauacca gaucgaauuc gaucugggga ggugaagaau acgaccaccu gcuaaguaua 60
gcuaauaaag uauaaagugc aaaacauacc agaucugugu guug 104

<210> SEQ ID NO 93
<211> LENGTH: 215
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 93
acacacaaau cuggggaggu gaagaauacg accaccugcg uuuuauucuu uggacagcag 60
aucuggggag gugaagaaua cgaccaccug cagauucgaa agaaucugca aaacauacca 120
gaucugcugc uacuuuggca aaacauacca gaucgaauuc gaucugggga ggugaagaau 180
acgaccaccu gcuaaaguag cuaauaaaga auaaa 215

<210> SEQ ID NO 94
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 94
ugcaaaacau accagaucug ugugu 25

<210> SEQ ID NO 95
<211> LENGTH: 12
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 95
guaccuaaua aa 12

<210> SEQ ID NO 96
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 96
uuuggacaac a 11

<210> SEQ ID NO 97
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 97
uaccuaauaa a 11

<210> SEQ ID NO 98
<211> LENGTH: 11
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 98
uuuggacaac a 11

<210> SEQ ID NO 99
<211> LENGTH: 217
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 99
cacaaaucug gggaggugaa gaauacgacc accugcguuu uauacuuugg acaacaaaga 60
ucuggggagg ugaagaauac gaccaccuaa uaaauugccg aaaggcaauu uauuaaaaca 120
uaccagaucu uugugggugu uuguggcaaa acauaccaga ucgaauucga ucuggggagg 180
ugaagaauac gaccaccugc uacaaguacc uaauaaa 217

<210> SEQ ID NO 100
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
uauaaagugc aaaacauacc agaucugug 29

<210> SEQ ID NO 101
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
uuuggacaac a 11

<210> SEQ ID NO 102
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
uuuggacaac aa 12

<210> SEQ ID NO 103
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
uaccuaauaa a 11

<210> SEQ ID NO 104
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 104
uuggacaaca 10

<210> SEQ ID NO 105
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 105
cuuuggacaa caaa 14

<210> SEQ ID NO 106
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 106
cuuuguuggu gu 12

<210> SEQ ID NO 107
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 107
aguaccaaau aaag 14

<210> SEQ ID NO 108
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 108
uaccuaaaua aagu 14

<210> SEQ ID NO 109
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 109
cuuugugaca acaaa 15

<210> SEQ ID NO 110

-continued

<211> LENGTH: 12
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 110
uuuguuggug uu 12

<210> SEQ ID NO 111
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 111
aguaccuaaa uaaagu 16

<210> SEQ ID NO 112
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 112
cuuugugcag g 11

<210> SEQ ID NO 113
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 113
ccugcgggug 10

<210> SEQ ID NO 114
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 114
guaccuaaua aag 13

<210> SEQ ID NO 115
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 115
accuaauaaa 10

<210> SEQ ID NO 116
<211> LENGTH: 16

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 116
acuuugggca ggagau 16

<210> SEQ ID NO 117
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 117
gaucuccugc ggguguu 17

<210> SEQ ID NO 118
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 118
aaguaccuaa uaaagu 16

<210> SEQ ID NO 119
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 119
uaccuaauaa a 11

<210> SEQ ID NO 120
<211> LENGTH: 51
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 120
acacacaaau cuggggaggu gaagaauacg accaccugcg uuuuauacuu u 51

<210> SEQ ID NO 121
<211> LENGTH: 203
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 121
gacagcagga gaucugggga ggugaagaau acgaccaccu aauaaauugc cgaaaggcaa 60
uuuauuaaaa cauaccagau cuccugcggg uguuuguggc aaaacauacc agaucgaauu 120
cgaucugggg aggugaagaa uacgaccacc ugcuacaagu accuaauaaa guauaaagug 180
caaaacauac cagaucugug ugu 203

<210> SEQ ID NO 122
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 122
uuuggacagc agg 13

<210> SEQ ID NO 123
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 123
uccugccggg 10

<210> SEQ ID NO 124
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 124
ccuaauaaag 10

<210> SEQ ID NO 125
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 125
uggacagcag ga 12

<210> SEQ ID NO 126
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 126
cuccugcggg gug 13

<210> SEQ ID NO 127
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 127
uaccuaauaa 10

-continued

<210> SEQ ID NO 128
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 128
uuuggacagc agg 13

<210> SEQ ID NO 129
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 129
ccugcugggu gu 12

<210> SEQ ID NO 130
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 130
aguaccuaau aaa 13

<210> SEQ ID NO 131
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 131
uuggacagca gg 12

<210> SEQ ID NO 132
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 132
ccugcagggu 10

<210> SEQ ID NO 133
<211> LENGTH: 255
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 133
acacacaaau cuggggaggu gaagaauacg accaccugcg uuuuauacuu uggacagcag 60

-continued

```
gagaucuggg gaggugaaga auacgaccac cuaauaaauu gccgaaaggc aauuuauuaa    120

aacauaccag aucuccugcg ggugguuugug gcaaaacaua ccagaucgaa uucgaucugg    180

ggaggugaag aauacgacca ccugcuacaa guaccuaaua aaguauaaag ugcaaaacau    240

accagaucug ugugu                                                     255
```

<210> SEQ ID NO 134
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 134

```
uuggacagca gg                                                         12
```

<210> SEQ ID NO 135
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 135

```
ccugcagggu                                                            10
```

<210> SEQ ID NO 136
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 136

```
cuuucgcagg                                                            10
```

<210> SEQ ID NO 137
<211> LENGTH: 11
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 137

```
ccugccgggu g                                                          11
```

<210> SEQ ID NO 138
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 138

```
uaccuaaaua aagu                                                       14
```

<210> SEQ ID NO 139
<211> LENGTH: 11
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 139
cuuugcgcag g 11

<210> SEQ ID NO 140
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 140
ccugccgggu 10

<210> SEQ ID NO 141
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 141
uaccuaaaua aagu 14

<210> SEQ ID NO 142
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 142
uauacuuucg caggag 16

<210> SEQ ID NO 143
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 143
cuccugccgg gug 13

<210> SEQ ID NO 144
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 144
guaccuaaua aaguaua 17

<210> SEQ ID NO 145
<211> LENGTH: 134
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 145
acacacaaau cuggggaggu gaagaauacg accaccugcg uuuuauacuu ugcgcaggag 60
aucuggggag gugaagaaua cgaccaccua auaaaauugcc gaaaggcaau uuauuaaaac 120
auaccagauc uccu 134

<210> SEQ ID NO 146
<211> LENGTH: 114
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 146
guguuugugg caaaacauac cagaucgaau ucgaucuggg gaggugaaga auacgaccac 60
cugcuacaag uaccuaauaa aguauaaagu gcaaaacaua ccagaucugu gugu 114

<210> SEQ ID NO 147
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 147
uacuuugaac acg 13

<210> SEQ ID NO 148
<211> LENGTH: 11
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 148
ucgugucggg u 11

<210> SEQ ID NO 149
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 149
uaccuaaaua aagua 15

<210> SEQ ID NO 150
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 150
uacuuuguaa cacgagau 18

<210> SEQ ID NO 151

-continued

<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 151
gaucucgugu cgggguguu 18

<210> SEQ ID NO 152
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 152
aguaccuaaa uaaagua 17

<210> SEQ ID NO 153
<211> LENGTH: 51
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 153
cacacaaauc uggggaggug aagaauacga ccaccugcgu uuuauacuuu g 51

<210> SEQ ID NO 154
<211> LENGTH: 84
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 154
uaacacgaga ucuggggagg ugaagaauac gaccaccuaa uaagauuacc gaaaggcaau 60
cuuauuaaaa cauaccagau cucg 84

<210> SEQ ID NO 155
<211> LENGTH: 115
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 155
guguuugugg caaaacauac cagaucgaau ucgaucuggg gaggugaaga auacgaccac 60
cugcuacaag uaccuaaaua aaguauaaag ugcaaaacau accagaucug ugugu 115

<210> SEQ ID NO 156
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 156
uacuuucaac acgag 15

<210> SEQ ID NO 157
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
cucgugucgg gugu 14

<210> SEQ ID NO 158
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
guaccuaaua aagua 15

<210> SEQ ID NO 159
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
uacuuugaac acga 14

<210> SEQ ID NO 160
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
cucgugucgg gu 12

<210> SEQ ID NO 161
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
uaccuaauaa aguau 15

<210> SEQ ID NO 162
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
acacacaaau cuggggaggu gaagaauacg accaccugcg uuuuauacuu u 51

<210> SEQ ID NO 163
<211> LENGTH: 158
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 163
acgagaucug gggaggugaa gaauacgacc accuaauaag auuaccgaaa ggcaaucuua     60
uuaaaacaua ccagaucucg ugucgggugu uuguggcaaa acauaccaga ucgaauucga    120
ucuggggagg ugaagaauac gaccaccugc uacaagua                            158

<210> SEQ ID NO 164
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
cuaauaaagu auaaagugca aaacauacca gaucugugug u                         41

<210> SEQ ID NO 165
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
acuucacacg                                                            10

<210> SEQ ID NO 166
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
cgugucgggu                                                            10

<210> SEQ ID NO 167
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
uaccuaaaua aagu                                                       14

<210> SEQ ID NO 168
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
uacuucacac gag 13

<210> SEQ ID NO 169
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 169
cucgugucgg gugu 14

<210> SEQ ID NO 170
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 170
guaccuaaua aagua 15

<210> SEQ ID NO 171
<211> LENGTH: 52
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 171
acacaaaucu ggggagguga agaauacgac caccugcguu uuauacuuuc aa 52

<210> SEQ ID NO 172
<211> LENGTH: 198
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 172
acgagaucug gggaggugaa gaauacgacc accuaauaag auuaccgaaa ggcaaucuua 60
uuaaaacaua ccagaucucg ugucgggugu uuguggcaaa acauaccaga ucgaauucga 120
ucuggggagg ugaagaauac gaccaccugc uacaaguacc uaauaaagua uaaagugcaa 180
aacauaccag aucugugu 198

<210> SEQ ID NO 173
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 173
cuuuccacga ga 12

<210> SEQ ID NO 174
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
ucucgugagg gug 13

<210> SEQ ID NO 175
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
guaccuaaua aag 13

<210> SEQ ID NO 176
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
uaccuaauaa a 11

<210> SEQ ID NO 177
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
uauacuuucc acgaga 16

<210> SEQ ID NO 178
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
ucucgugcug ggug 14

<210> SEQ ID NO 179
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
guaccuaaua aaguaua 17

<210> SEQ ID NO 180
<211> LENGTH: 137
<212> TYPE: RNA
<213> ORGANISM: Artificial Sequence
<220> FEATURE:

<223> OTHER INFORMATION: Description of Artificial Sequence: Synthetic
      polynucleotide

<400> SEQUENCE: 180
cacacaaauc uggggaggug aagaauacga ccaccugcgu uuuauacuuu ccacgagauc     60
uggggaggug aagaauacga ccaccuaaua agauuaccga aaggcaaucu uauuaaaaca    120
uaccagaucu cgugauu                                                   137

<210> SEQ ID NO 181
<211> LENGTH: 77
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
gguguuugug gcaaaacaua ccagaucgaa uucgaucugg ggaggugaag aauacgacca     60
ccugcuacaa guaccua                                                    77

<210> SEQ ID NO 182
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
uaaaguauaa agugcaaaac auaccagauc ugugug                               36

<210> SEQ ID NO 183
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
uaccuaauaa agu                                                        13

<210> SEQ ID NO 184
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
cuuuccacga g                                                          11

<210> SEQ ID NO 185
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
cucgugaggg ug                                                         12

-continued

<210> SEQ ID NO 186
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 186
uaccuaaaua aagu 14

<210> SEQ ID NO 187
<211> LENGTH: 12
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 187
uacuuccacg ag 12

<210> SEQ ID NO 188
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 188
cucgugaggg ugu 13

<210> SEQ ID NO 189
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 189
aguaccuaaa uaaagua 17

<210> SEQ ID NO 190
<211> LENGTH: 209
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 190
cacacaaauc uggggaggug aagaauacga ccaccugcgu uuuauacuuu ccacgagauc 60
uggggaggug aagaauacga ccaccuaaua agauuaccga aaggcaaucu uauuaaaaca 120
uaccagaucu cgugagggug uuuguggcaa aacauaccag aucgaauucg aucuggggag 180
gugaagaaua cgaccaccug cuacaagua 209

<210> SEQ ID NO 191
<211> LENGTH: 41
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 191
cuaauaaagu auaaagugca aaacauacca gaucugugug u 41

<210> SEQ ID NO 192
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 192
uacuucacac gag 13

<210> SEQ ID NO 193
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 193
cucgugucgg gugu 14

<210> SEQ ID NO 194
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 194
guaccuaaua aagua 15

<210> SEQ ID NO 195
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 195
uacuuccacg ag 12

<210> SEQ ID NO 196
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 196
cucgugaggg ugu 13

<210> SEQ ID NO 197
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 197
aguaccuaaa uaaagua 17

<210> SEQ ID NO 198
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 198
cuuuccacga g 11

<210> SEQ ID NO 199
<211> LENGTH: 12
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 199
cucgugaggg ug 12

<210> SEQ ID NO 200
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 200
uaccuaaaua aagu 14

<210> SEQ ID NO 201
<211> LENGTH: 56
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 201
gcugccacac acacaaaucu ggggagguga agaauacgac caccugcguu uuauac 56

<210> SEQ ID NO 202
<211> LENGTH: 85
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 202
ccacgagauc uggggaggug aagaauacga ccaccuaaua agauuaccga aaggcaaucu 60
uauuaaaaca uaccagaucu cguga 85

<210> SEQ ID NO 203
<211> LENGTH: 169
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 203
gguguuugug gcaaaacaua ccagaucgaa uucgaucugg ggaggugaag aauacgacca 60
ccugcuacaa guaccuaaua aaguauaaag ugcaaaacau accagaucug uguguugguu 120
uuuuguguga acgggggagg gggaggaaag ggggaggggg agcggccgc 169

<210> SEQ ID NO 204
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 204
uacuuuguua auuacaggag a 21

<210> SEQ ID NO 205
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 205
ucuccuaaug ggugu 15

<210> SEQ ID NO 206
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 206
uaccuaauaa agua 14

<210> SEQ ID NO 207
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 207
uuuguuaggu acaggagau 19

<210> SEQ ID NO 208
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 208
gaucuccuaa ugggugcuug 20

<210> SEQ ID NO 209
<211> LENGTH: 19
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 209
cuuuguuagu uacaggaga 19

<210> SEQ ID NO 210
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 210
ucuccuaaug ggugu 15

<210> SEQ ID NO 211
<211> LENGTH: 12
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 211
uaccuaauaa ag 12

<210> SEQ ID NO 212
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 212
uacuuuggac agcaggagau 20

<210> SEQ ID NO 213
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 213
gaucuccuaa ugggug 16

<210> SEQ ID NO 214
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 214
guaccuaaua aagua 15

<210> SEQ ID NO 215
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 215
acuuuggaca gcagga 16

<210> SEQ ID NO 216
<211> LENGTH: 11
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 216
cuccuaauug g 11

<210> SEQ ID NO 217
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 217
cuaauaaagu 10

<210> SEQ ID NO 218
<211> LENGTH: 254
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 218
acacaaaucu ggggagguga agaauacgac caccugcguu uuauacuuug gacaacagga 60
gaucugggga ggugaagaau acgaccaccu aauaagauua ccgaaaggca aucuuauuaa 120
aacauaccag aucuccugug gguguuugug gcaaaacaua ccagaucgaa uucgaucugg 180
ggaggugaag aauacgacca ccugcuacaa guaccuaaua aaguauaaag ugcaaaacau 240
accagaucug ugug 254

<210> SEQ ID NO 219
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 219
cuuuguuaac acga 14

<210> SEQ ID NO 220
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 220
ucgugucggg ugu 13

<210> SEQ ID NO 221
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 221
guaccuaaau aaag 14

<210> SEQ ID NO 222
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 222
cuuuguuaac acgag 15

<210> SEQ ID NO 223
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 223
ucucgugugg guguu 15

<210> SEQ ID NO 224
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 224
aaguaccuaa uaaagu 16

<210> SEQ ID NO 225
<211> LENGTH: 12
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 225
acuuuguuac ac 12

<210> SEQ ID NO 226
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 226
cgugugggug 10

<210> SEQ ID NO 227
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 227
uaccuaauaa agua 14

<210> SEQ ID NO 228
<211> LENGTH: 265
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 228
ccacacacac aaaucugggg aggugaagaa uacgaccacc ugcguuuuau acuuuggaca 60
acacgagauc uggggaggug aagaauacga ccaccuaaua agauuaccga aaggcaaucu 120
uauuaaaaca uaccagaucu cgugugggug uuuguggcaa aacauaccag aucgaauucg 180
aucuggggag gugaagaaua cgaccaccug cuacaaguac cuaauaaagu auaaagugca 240
aaacauacca gaucugugug uuggu 265

<210> SEQ ID NO 229
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 229
uuuguuaaac ac 12

<210> SEQ ID NO 230
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 230
uaccuuaaua aag 13

<210> SEQ ID NO 231
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 231
cuuuguuaaa cacgag 16

<210> SEQ ID NO 232
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 232
cucgugucgg gug 13

<210> SEQ ID NO 233
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 233
guaccuauaa uaaag 15

<210> SEQ ID NO 234
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 234
acuuuguuac ac 12

<210> SEQ ID NO 235
<211> LENGTH: 11
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 235
ccuaauaaag u 11

<210> SEQ ID NO 236
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 236
uacuuuguaa cacgag 16

<210> SEQ ID NO 237
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 237
cucgugucgg gugu 14

<210> SEQ ID NO 238
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 238
guaccuaaua aagua 15

<210> SEQ ID NO 239
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 239
uacuuuguaa cacg 14

<210> SEQ ID NO 240
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 240
cgugucggug 10

<210> SEQ ID NO 241
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 241
guacuaauaa agua 14

<210> SEQ ID NO 242
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 242
acuuugucac 10

<210> SEQ ID NO 243
<211> LENGTH: 12
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 243
ccuaauaaag ua 12

<210> SEQ ID NO 244
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 244
cuuugaucac g 11

<210> SEQ ID NO 245
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 245
ucgugacugg ugu 13

<210> SEQ ID NO 246
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 246
uacuaauaaa gu 12

<210> SEQ ID NO 247
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 247
uacuuugauc acg 13

<210> SEQ ID NO 248
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 248
ucgugauugg gug 13

<210> SEQ ID NO 249
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 249
guaccuaaua aagua 15

<210> SEQ ID NO 250
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 250
auacuuucca cgag 14

<210> SEQ ID NO 251
<211> LENGTH: 11
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 251
cucgugauug g 11

<210> SEQ ID NO 252
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 252
ccuaauaaag uau 13

<210> SEQ ID NO 253
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 253
uauacuuucc acgag 15

<210> SEQ ID NO 254
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 254
ucucgugauu gguguu 16

<210> SEQ ID NO 255
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 255
aaguacuaau aaaguaua 18

<210> SEQ ID NO 256
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 256
auacuuucac acgaga 16

<210> SEQ ID NO 257
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 257
ucucguguau ugguguu 17

<210> SEQ ID NO 258
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 258
aaguacuaau aaaguaua 18

<210> SEQ ID NO 259
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 259
uauacuuuca cacgag 16

<210> SEQ ID NO 260
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 260
ucucguguau uguguu 16

<210> SEQ ID NO 261
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 261
aaguauaaua aaguaua 17

<210> SEQ ID NO 262
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 262
uauacuuaca cga 13

<210> SEQ ID NO 263
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 263
cucgugcauu gg 12

<210> SEQ ID NO 264
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 264
cuaauaaagu aua 13

<210> SEQ ID NO 265
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 265
uuuauacuua cacgagau 18

<210> SEQ ID NO 266
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 266
aguauaauaa aguauaaa 18

<210> SEQ ID NO 267
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 267
uuauacuuaa cacgagau 18

<210> SEQ ID NO 268
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 268
aucucguguc auuguguuu 19

<210> SEQ ID NO 269
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
aaguauaaua aaguauaa 18

<210> SEQ ID NO 270
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
uuauacuuaa cacgaga 17

<210> SEQ ID NO 271
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
aucucguguu auuguguu 18

<210> SEQ ID NO 272
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
aguauaauaa aguauaa 17

<210> SEQ ID NO 273
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
acuuuggaca acaaagau 18

<210> SEQ ID NO 274
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
gaucuuugug guguuug 17

<210> SEQ ID NO 275
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 275
acaaguacua auaaagu 17

<210> SEQ ID NO 276
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 276
cuuuggacaa caaagau 17

<210> SEQ ID NO 277
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 277
aucuuugugg uguuug 16

<210> SEQ ID NO 278
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 278
acaaguaccu aauaaag 17

<210> SEQ ID NO 279
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 279 gugggguguuu guggca 16

<210> SEQ ID NO 280
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 280
gcuacaagua ucuaaua 17

<210> SEQ ID NO 281

<211> LENGTH: 151
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 281
acacacaaau cuggggaggu gaagaauacg accaccugcg uuuuauacuu uggacaacaa 60
agaucugggg aggugaagaa uacgaccacc uaauaaauug ccgaaaggca auuuauuaaa 120
acauaccaga ucuuugoggg uguuuguggc a 151

<210> SEQ ID NO 282
<211> LENGTH: 101
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 282
aacauaccag aucgaauucg aucuggggag gugaagaaua cgaccaccug cuacaaguac 60
cuaauaaagu auaaagugca aaacauacca gaucugugug u 101

<210> SEQ ID NO 283
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 283
aggguguuug gcaa 14

<210> SEQ ID NO 284
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 284
gcuaaguacc u 11

<210> SEQ ID NO 285
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 285
gaggguguuu uggcaa 16

<210> SEQ ID NO 286
<211> LENGTH: 12
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 286

-continued gcuaaaguac cu 12

<210> SEQ ID NO 287
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 287 gagggguguuu guggcaaa 18

<210> SEQ ID NO 288
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 288
gcuacaagua ccuaa 15

<210> SEQ ID NO 289
<211> LENGTH: 57
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 289
aaacauacca gaucgaggaa agaauucgau cuggggaggu gaagaauacg accaccu 57

<210> SEQ ID NO 290
<211> LENGTH: 62
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 290
gcaaaacaua ccagaucgag ugaaagaauu cgaucugggg aggugaagaa uacgaccacc 60
ug 62

<210> SEQ ID NO 291
<211> LENGTH: 65
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 291
ggcaaaacau accagaucga guugaaagaa uucgaucugg ggaggugaag aauacgacca 60
ccugc 65

<210> SEQ ID NO 292
<211> LENGTH: 174
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 292
acacaaaucu ggggagguga agaauacgac caccugcguu uuauacuucc acgagaucug 60
gggaggugaa gaauacgacc accuaauaag auuaccgaaa ggcaaucuua uuaaaacaua 120
ccagaucucg ugagggugu u uguggcaaaa cauaccagau cgaauucgau cugg 174

<210> SEQ ID NO 293
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 293
gaggugaaga auacgaccac cugcuacaag uaccuaauaa aguauaaagu gcaaaacaua 60
ccagaucugu gug 73

<210> SEQ ID NO 294
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 294
ggguguuugu ggcaa 15

<210> SEQ ID NO 295
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 295
gcuacaagua cuuaauaa 18

<210> SEQ ID NO 296
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 296
gaggguguuu gugguaaaac auacc 25

<210> SEQ ID NO 297
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 297
gcuacaagua ccu 13

<210> SEQ ID NO 298

<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 298
aggguguuug uggcaaaaca 20

<210> SEQ ID NO 299
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 299
gcuacaagua ucuaau 16

<210> SEQ ID NO 300
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 300
guguuugugg caaaac 16

<210> SEQ ID NO 301
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 301
ccugcuauaa guaccuaau 19

<210> SEQ ID NO 302
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 302
ggguguuugu ggcaaaacau ac 22

<210> SEQ ID NO 303
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 303
accaccuguu auaaguaccu aa 22

<210> SEQ ID NO 304
<211> LENGTH: 23

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 304
gguguuugug gcaaaacaua cca 23

<210> SEQ ID NO 305
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 305
ccaccuguua caaguaccua aua 23

<210> SEQ ID NO 306
<211> LENGTH: 260
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 306
gccacacaca caaaucuggg gaggugaaga auacgaccac cugcguuuua uacuuccgcg 60
agaucugggg aggugaagaa uacgaccacc uaauaaagau accgaaaggc aaucuuauua 120
aaacauacca gaucucgcga ggguguuugu ggcaaaacau accagaucga auucgaucug 180
gggaggugaa gaauacgacc accugcuaca aguaccuaau aaaguauaaa gugcaaaaca 240
uaccagaucu guguguuggu 260

<210> SEQ ID NO 307
<211> LENGTH: 57
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 307
aaacauacca gaucgaggaa agaauucgau cuggggaggu gaagaauacg accaccu 57

<210> SEQ ID NO 308
<211> LENGTH: 62
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 308
gcaaaacaua ccagaucgag ugaaagaauu cgaucugggg aggugaagaa uacgaccacc 60
ug 62

<210> SEQ ID NO 309
<211> LENGTH: 65
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 309
ggcaaaacau accagaucga guugaaagaa uucgaucugg ggaggugaag aauacgacca 60
ccugc 65

<210> SEQ ID NO 310
<211> LENGTH: 174
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 310
acacaaaucu ggggagguga agaauacgac caccugcguu uuauacuucc acgagaucug 60
gggaggugaa gaauacgacc accuaauaag auuaccgaaa ggcaaucuua uuaaaacaua 120
ccagaucucg ugagggugu uguggcaaaa cauaccagau cgaauucgau cugg 174

<210> SEQ ID NO 311
<211> LENGTH: 73
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 311
gaggugaaga auacgaccac cugcuacaag uaccuaauaa aguauaaagu gcaaaacaua 60
ccagaucugu gug 73

<210> SEQ ID NO 312
<211> LENGTH: 53
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 312
caaaacauac cagaucgaau ucgauuuggg gaggugaaga auacgaccac cug 53

<210> SEQ ID NO 313
<211> LENGTH: 53
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 313
ggcaaaacau accagcgaau ucgcugggga ggugaagaau acgaccaccu gcu 53

<210> SEQ ID NO 314
<211> LENGTH: 171
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 314
ccacacacac aaaucugggg aggugaagaa uacgaccacc ugcguuuuau acuuccgcga 60
gaucugggga ggugaagaau acgaccaccu aauaagauua ccgaaaggca aucuuauuaa 120
aacauaccag aucuugcgag gguguuugug gcaaaacaua ccagaucgaa u 171

<210> SEQ ID NO 315
<211> LENGTH: 87
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 315
cgaucugggg aggugaagaa uacgaccacc ugcuacaagu accuaauaaa guauaaagug 60
caaaacauac cagaucugug uguuggu 87

<210> SEQ ID NO 316
<211> LENGTH: 78
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 316
acaaagaucu ggggagguga agaauacgac caccuaauaa auuccgaaag gaauuuauua 60
aaacauacca gaucuuug 78

<210> SEQ ID NO 317
<211> LENGTH: 77
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 317
aaagaucugg ggaggugaag aauacgacca ccuaacgaau ugccgaaagg caauucguua 60
aaacauacca gaucuuu 77

<210> SEQ ID NO 318
<211> LENGTH: 72
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 318
aaagaucugg ggaggugaag aauacgacca ccuaauaaau ucgaaagaau uuauuaaaac 60
auaccagauc uu 72

<210> SEQ ID NO 319
<211> LENGTH: 247
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 319
cacaaaucug gggaggugaa gaauacgacc accugcguuu uauacuuugg acaacaaaga 60
ucuggggagg ugaagaauac gaccaccuaa uaaauugccc aaaggcaauu uauuaaaaca 120
uaccagaucu uugugggugu uuguggcaaa acauaccaga ucgaauucga ucuggggagg 180
ugaagaauac gaccaccugc uacaaguacc uaauaaagua uaaagugcaa aacauaccag 240
aucugug 247

<210> SEQ ID NO 320
<211> LENGTH: 69
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 320
ucuggggagg ugaagaauac gaccaccuaa uaaaguugcc gaaaggcaac uuuauuaaaa 60
cauaccaga 69

<210> SEQ ID NO 321
<211> LENGTH: 71
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 321
aucuggggag gugaagaaua cgaccaccua auaagauugc cgaaaggcaa ucuuauuaaa 60
acauaccaga u 71

<210> SEQ ID NO 322
<211> LENGTH: 95
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 322
gccacacaca caaaucuggg gaggugaaga auacgaccac cugcguuuua uacuuuggac 60
aacagaagau cuggggaggu gaagaauacg accac 95

<210> SEQ ID NO 323
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 323
uaauaaauug ccgaaaggca auuuauu 27

<210> SEQ ID NO 324
<211> LENGTH: 140
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 324
aaacauacca gaucuucugu ggguguuugu ggcaaaacau accagaucga auucgaucug 60
gggaggugaa gaauacgacc accugcuaca aguaccuaau aaaguauaaa gugcaaaaca 120
uaccagaucu guguguuggu 140

<210> SEQ ID NO 325
<211> LENGTH: 68
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 325
aucuggggag gugaagaaua cgaccaccua auaaaauugcc uucgggcaau uuauuaaaac 60
auaccaga 68

<210> SEQ ID NO 326
<211> LENGTH: 106
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 326
gccacacaca caaaucuggg gaggugaaga auacgaccac cugcguuuua uacuuuggac 60
aacagaagau cuggggaggu gaagaauacg accaccuaau aaauug 106

<210> SEQ ID NO 327
<211> LENGTH: 150
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 327
caauuuauua aaacauacca gaucuucugu ggguguuugu ggcaaaacau accagaucga 60
auucgaucug gggaggugaa gaauacgacc accugcuaca aguaccuaau aaaguauaaa 120
gugcaaaaca uaccagaucu guguguuggu 150

<210> SEQ ID NO 328
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 328
aucuggggag gugaagaaua cgaccaccua auaagagucu gccgaaaggc agacucuuau 60
uaaaacauac caga 74

<210> SEQ ID NO 329
<211> LENGTH: 67
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 329
cuggggaggu gaagaauacg accaccuaau aagauuaccg aaaggcaauc uuauuaaaac 60
auaccag 67

<210> SEQ ID NO 330
<211> LENGTH: 69
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 330
cuggggaggu gaagaauacg accaccuaau aagaguugcc gaaaggcaac ucuuauuaaa 60
acauaccag 69

<210> SEQ ID NO 331
<211> LENGTH: 91
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 331
acacacaaau cuggggaggu gaagaauacg accaccugcg uuuuauacuu uggacagcag 60
gagaucuggg gaggugaaga auacgaccac c 91

<210> SEQ ID NO 332
<211> LENGTH: 163
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 332
aauaaauugc cgaaaggcaa uuuauuaaaa cauaccagau cuccugcggg uguuuguggc 60
aaaacauacc agaucgaauu cgaucugggg aggugaagaa uacgaccacc ugcuacaagu 120
accuaauaaa guauaaagug caaaacauac cagaucugug ugu 163

<210> SEQ ID NO 333
<211> LENGTH: 82
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 333
acaacaagau cuggggaggu gaagaauacg accaccuaau aaauugccga aaggcaauuu 60
auuaaaacau accagaucuu gu 82

<210> SEQ ID NO 334
<211> LENGTH: 82
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 334
aacgaagauc uggggaggug aagaauacga ccaccuaaua aauugccgaa aggcaauuua 60
uuaaaacaua ccagaucuuc gu 82

<210> SEQ ID NO 335

-continued

<211> LENGTH: 83
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 335
acagaagauc uggggaggug aagaauacga ccaccuaaua aauugccgaa aggcaauuua 60
uuaaaacaua ccagaucuuc ugu 83

<210> SEQ ID NO 336
<211> LENGTH: 247
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 336
cacaaaucug gggaggugaa gaauacgacc accugcguuu uauacuuugg acaacaaaga 60
ucuggggagg ugaagaauac gaccaccuaa uaaauugccg aaaggcaauu uauuaaaaca 120
uaccagaucu uugugggugu uuguggcaaa acauaccaga ucgaauucga ucuggggagg 180
ugaagaauac gaccaccugc uacaaguacc uaauaaagua uaaagugcaa aacauaccag 240
aucugug 247

<210> SEQ ID NO 337
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 337
gcagaagauc ugg 13

<210> SEQ ID NO 338
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 338
accagaucuu cugu 14

<210> SEQ ID NO 339
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 339
acaggcgauc ugg 13

<210> SEQ ID NO 340
<211> LENGTH: 13
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 340
ccagaucgcc ugu 13

<210> SEQ ID NO 341
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 341
acaggcgagc ugg 13

<210> SEQ ID NO 342
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 342
ccagcucgcc ugu 13

<210> SEQ ID NO 343
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 343
acaggagauc ugg 13

<210> SEQ ID NO 344
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 344
ccagaucucc ugu 13

<210> SEQ ID NO 345
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 345
acagacgauc ugg 13

<210> SEQ ID NO 346
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 346
ccagaucguc ugu 13

<210> SEQ ID NO 347
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 347
ccagaagauc ugg 13

<210> SEQ ID NO 348
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 348
ccagaucuuc ugg 13

<210> SEQ ID NO 349
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 349
gcagaagauc ugg 13

<210> SEQ ID NO 350
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 350
ccagaucuuc ugc 13

<210> SEQ ID NO 351
<211> LENGTH: 264
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 351
gccacacaca caaaucuggg gaggugaaga auacgaccac cugcguuuua uacuuuggac 60
aacagaagau cuggggaggu gaagaauacg accaccuaau aaauugccga aaggcaauuu 120
auuaaaacau accagaucuu cugugggugu uuguggcaaa acauaccaga ucgaauucga 180
ucuggggagg ugaagaauac gaccaccugc uacaaguacc uaauaaagua uaaagugcaa 240
aacauaccag aucugugugu uggu 264

<210> SEQ ID NO 352
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 352
acagaacgag cugg 14

<210> SEQ ID NO 353
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 353
ccagaucuuc ucgu 14

<210> SEQ ID NO 354
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 354
aacgagaaga ucugg 15

<210> SEQ ID NO 355
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 355
ccagcucgcu cugu 14

<210> SEQ ID NO 356
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 356
acagagcgag cugg 14

<210> SEQ ID NO 357
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 357
acacgaagau cugg 14

<210> SEQ ID NO 358
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 358
ccagaucguu cugu 14

<210> SEQ ID NO 359
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 359
acagaacgau cugg 14

<210> SEQ ID NO 360
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 360
ccagcucgcg ucugu 15

<210> SEQ ID NO 361
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 361
acagacgcga gcugg 15

<210> SEQ ID NO 362
<211> LENGTH: 264
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 362
gccacacaca caaaucuggg gaggugaaga auacgaccac cugcguuuua uacuuuggac 60
aacagaagau cuggggaggu gaagaauacg accaccuaau aaauugccga aaggcaauuu 120
auuaaaacau accagaucuu cugugggugu uuguggcaaa acauaccaga ucgaauucga 180
ucuggggagg ugaagaauac gaccaccugc uacaaguacc uaauaaagua uaaagugcaa 240
aacauaccag aucugugugu uggu 264

<210> SEQ ID NO 363
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 363
gcgcuuuaua cccac 15

<210> SEQ ID NO 364
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 364
cuaaauaaag uauaaagugc aa 22

<210> SEQ ID NO 365
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 365
gcgcuuuaua cccacg 16

<210> SEQ ID NO 366
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 366
ccuaauaaag uauaaagugc aa 22

<210> SEQ ID NO 367
<211> LENGTH: 249
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 367
cacacaaauc uggggaggug aagaauacga ccaccugcgu uuuauacuuc cacgagaucu 60
ggggagguga agaauacgac caccuaauaa gauuaccgaa aggcaaucuu auuaaaacau 120
accagaucuc gugagggugu uuguggcaaa acauaccaga ucgaauucga ucuggggagg 180
ugaagaauac gaccaccugc uacaaguacc uaauaaagua uaaagugcaa aacauaccag 240
aucugugug 249

<210> SEQ ID NO 368
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 368
gcguuuuaua cuu 13

<210> SEQ ID NO 369
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 369
aaguauaaag ugu 13

<210> SEQ ID NO 370
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 370
gcguuuuaua uuuc 14

<210> SEQ ID NO 371
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 371
auaaaguaua aagugca 17

<210> SEQ ID NO 372
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 372
guguuuuaua cuuc 14

<210> SEQ ID NO 373
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 373
aaaguauaaa gugcaa 16

<210> SEQ ID NO 374
<211> LENGTH: 260
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 374
gccacacaca caaaucuggg gaggugaaga auacgaccac cugcguuuua uacuuccacg 60
agaucugggg aggugaagaa uacgaccacc uaauaagauu accgaaaggc aaucuuauua 120
aaacauacca gaucuuguga gggguguuugu ggcaaaacau accagaucga auucgaucug 180
gggaggugaa gaauacgacc accugcuaca aguaccuaau aaaguauaaa gugcaaaaca 240
uaccagaucu guguguuggu 260

<210> SEQ ID NO 375
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 375
aggguguuug uggcaaaa 18

<210> SEQ ID NO 376
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 376
cugccacaag caccuaauaa 20

<210> SEQ ID NO 377
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 377
ggguguuugu ggcaaaa 17

<210> SEQ ID NO 378
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 378
cugccacaag uaccuaau 18

<210> SEQ ID NO 379
<211> LENGTH: 82
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 379
cgagggugcu uguggcaaaa cauaccagau cgaauucgau cuggggaggu gaagaauacg 60
accaccugcu acaaguaccu aa 82

<210> SEQ ID NO 380
<211> LENGTH: 42
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 380
gccacacaca caaaucuggg gaggugaaga auacgaccac cu 42

<210> SEQ ID NO 381
<211> LENGTH: 191
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 381
cguuuuauac uuccgcgaga ucuggggagg ugaagaauac gaccaccuaa uaagauuacc 60
gaaaggcaau cuuauuaaaa cauaccagau cucgcgaggg uguuuguggc aaaacauacc 120
agaucgaauu cgaucugggg aggugaagaa uacgaccacc ugcuacaagu accuaaauaa 180
aguauaaagu g 191

<210> SEQ ID NO 382
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 382
aaaacauacc agaucugugu guuggu 26

<210> SEQ ID NO 383
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 383
gcguuucaua cuucc 15

<210> SEQ ID NO 384
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 384
auaaaguaua aagugcaa 18

<210> SEQ ID NO 385
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 385
gcguuuuaua cuuc 14

<210> SEQ ID NO 386
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 386
uaaaguauaa agcgcaa 17

<210> SEQ ID NO 387
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 387
gcgcuuuaua cuucca 16

<210> SEQ ID NO 388
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 388
aauaaaguau aaagugc 17

<210> SEQ ID NO 389
<211> LENGTH: 238
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 389
gccacacaca caaaucuggg gaggugaaga auacgaccac cugcguuuua uacuuccacg 60
agaucugggg aggugaagaa uacgaccacc uaauaaagau accgaaaggc aaucuuauua 120
aaacauacca gaucuuguga ggguguuugu ggcaaaacau accagaucga auucgaucug 180
gggaggugaa gaauacgacc accugcuaca aguaccuaau aaaguauaaa gugcaaaa 238

<210> SEQ ID NO 390
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 390
auaccagauc uguguguugg u 21

<210> SEQ ID NO 391
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 391
gcguuuacuu c 11

<210> SEQ ID NO 392
<211> LENGTH: 12
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 392
aaaguaagug ca 12

<210> SEQ ID NO 393
<211> LENGTH: 12
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 393
gcguuauacu uc 12

<210> SEQ ID NO 394
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 394
aaaguauagu gca 13

<210> SEQ ID NO 395
<211> LENGTH: 12
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 395
gcguuuauac uu 12

<210> SEQ ID NO 396
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 396
uaaaguauaa gugca 15

<210> SEQ ID NO 397
<211> LENGTH: 260
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 397
gccacacaca caaaucuggg gaggugaaga auacgaccac cugcguuuua uacuuccacg 60
agaucugggg aggugaagaa uacgaccacc uaauaagauu accgaaaggc aaucuuauua 120
aaacauacca gaucuuguga ggguguuugu ggcaaaacau accagaucga auucgaucug 180
gggaggugaa gaauacgacc accugcuaca aguaccuaau aaaguauaaa gugcaaaaca 240
uaccagaucu guguguuggu 260

<210> SEQ ID NO 398
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 398
acacacaaac cuggg 15

<210> SEQ ID NO 399
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 399
accaggucug ugugu 15

<210> SEQ ID NO 400
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 400
cacacagacc ugg 13

<210> SEQ ID NO 401
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 401
ccaggucugu gug 13

<210> SEQ ID NO 402
<211> LENGTH: 11
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 402
acagaucugg g 11

<210> SEQ ID NO 403

<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 403
ccagaucugu g 11

<210> SEQ ID NO 404
<211> LENGTH: 247
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 404
acacaaaucu ggggagguga agaauacgac caccugcguu uuauacuucc acgagaucug 60
gggaggugaa gaauacgacc accuaauaag auuaccgaaa ggcaaucuua uuaaaacaua 120
ccagaucucg ugagggugu uguggcaaaa cauaccagau cgaauucgau cuggggaggu 180
gaagaauacg accaccugcu acaaguaccu aauaaaguau aaagugcaaa acauaccaga 240
ucugugu 247

<210> SEQ ID NO 405
<211> LENGTH: 258
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 405
gccacacaca caaaccuggg gagugaagaa uacgaccacc ugcguuuuau acuuccacga 60
gaucugggga ggugaagccu acgaccaccu aauaagauua ccgaaaggca aucuuauuaa 120
aacauaccag aucuugugag gguguuugug gcaaaacaua ccagaucgaa uucgaucugg 180
ggaggugaag aauacgacca ccugcuacaa guaccuaaua aaguauaaag ugaaaacaua 240
ccaggucugu guguuggu 258

<210> SEQ ID NO 406
<211> LENGTH: 82
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 406
aacaaagauc uggggaggug aagaauacga ccaccuaaua aauugccgaa aggcaauuua 60
uuaaaacaua ccagaucuuu gu 82

<210> SEQ ID NO 407
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 407
gcguuccuug u 11

<210> SEQ ID NO 408
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 408
aacaaggagu gcaa 14

<210> SEQ ID NO 409
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 409
gcguuccauu gu 12

<210> SEQ ID NO 410
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 410
aacaauggag ugca 14

<210> SEQ ID NO 411
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 411
gcguucuugu 10

<210> SEQ ID NO 412
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 412
aacaagagug caa 13

<210> SEQ ID NO 413
<211> LENGTH: 116
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 413
acacacaaau cuggggaggu gaagaauacg accaccugcg uuuuauacuu uggacaacaa 60
agagugcaaa acauaccaga gcgaaagcuc uggggaggug aagaauacga ccaccu 116

<210> SEQ ID NO 414
<211> LENGTH: 126
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 414
cguucuuugu ggguguuugu ggcaaaacau accagaucga auucgaucug gggaggugaa 60
gaauacgacc accugcuaca aguaccuaau aaaguauaaa gugcaaaaca uaccagaucu 120
gugugu 126

<210> SEQ ID NO 415
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 415
aaguauacaa guggg 15

<210> SEQ ID NO 416
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 416
accguuugua uacuuc 16

<210> SEQ ID NO 417
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 417
aaaguauaag ugg 13

<210> SEQ ID NO 418
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 418
accguuuaua cuuc 14

<210> SEQ ID NO 419
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 419
ucuugugagg gugu 14

<210> SEQ ID NO 420
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 420
aguaccuaau aaaguauaaa gu 22

<210> SEQ ID NO 421
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 421
caaaacauac cagauc 16

<210> SEQ ID NO 422
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 422
acaaaucugg ggaggugaag aauacgacca ccug 34

<210> SEQ ID NO 423
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 423
guuuuauacu uccacgaga 19

<210> SEQ ID NO 424
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 424
ccguuuugua uacuucc 17

<210> SEQ ID NO 425
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 425
uaaaguauac aaaguggg 18

<210> SEQ ID NO 426
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 426
auaccguaua cuu 13

<210> SEQ ID NO 427
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 427
uaaaguaugu ggg 13

<210> SEQ ID NO 428
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 428
ccguuauacu uc 12

<210> SEQ ID NO 429
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 429
uaaaguauag ugg 13

<210> SEQ ID NO 430
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 430
ucuggaaaac auaccgu 17

<210> SEQ ID NO 431
<211> LENGTH: 40
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 431
aguauaaagu ggggagguga agaauacgac caccuccaga 40

<210> SEQ ID NO 432
<211> LENGTH: 260
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 432
gccacacaca caaaucuggg gaggugaaga auacgaccac cugcguuuua uacuuccacg 60
agaucugggg aggugaagaa uacgaccacc uaauaaagauu accgaaaggc aaucuuauua 120
aaacauacca gaucuuguga gggguguuugu ggcaaaacau accagaucga auucgaucug 180
gggaggugaa gaauacgacc accugcuaca aguaccuaau aaaguauaaa gugcaaaaca 240
uaccagaucu guguguuggu 260

<210> SEQ ID NO 433
<211> LENGTH: 260
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 433
gccacacaca caaaucuggg gaggugaaga auacgaccac cugcguuuua uacuuccacg 60
agaucugggg aggugaagaa uacgaccacc uaauaaagauu accgaaaggc aaucuuauua 120
aaacauacca gaucuuguga gggguguuugu ggcaaaacau accagaucga auucgaucug 180
gggaggugaa gaauacgacc accugcuaca aguaccuaau aaaguauaaa gugcaaaaca 240
uaccagaucu guguguuggu 260

<210> SEQ ID NO 434
<211> LENGTH: 86
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 434
gcggccgcca acaacaacaa caacaacaac aacaacaaca acaacaacat aacagtgttc 60
actagcaacc tcaaacagac accatg 86

<210> SEQ ID NO 435
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 435
gcggccttaa ttaacagtgt tcactaggac aacaacaaca acaacaacaa caacaacaac 60
gacaccatg 69

<210> SEQ ID NO 436
<211> LENGTH: 70

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 436
ggcgccttaa ttaacagtgt tcactaggta caacaacaac aacaacaaca acaacaacaa 60
cgacaccatg 70

<210> SEQ ID NO 437
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 437
gcggccgcct taattaacag tgttcactag gacaacaaca acaacaacaa caacaacaac 60
aacgacacca tg 72

<210> SEQ ID NO 438
<211> LENGTH: 73
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 438
gcggccgcct taattaacag tgttcactag catcaacaac aacaacaaca acaacaacaa 60
caacgacacc atg 73

<210> SEQ ID NO 439
<211> LENGTH: 135
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 439
gcggccgcca acaacaacaa caattcctgc tcctcttctg cccaggaaca cgcttgcctt 60
ccccaaggct tccagaagct ctgaggcagg aggcaccaag ttctacctca cgtttggagg 120
atcttgctag ctatg 135

<210> SEQ ID NO 440
<211> LENGTH: 136
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 440
gcggccgccc agcagatcca gtgcttcctg ctcctcttct gcccaggaac acgcttgcct 60
tccccaaggc ttccagaagc tctgaggcag gaggcaccaa gttctacctc acgtttggag 120
gatcttgcta gctatg 136

<210> SEQ ID NO 441
<211> LENGTH: 135

-continued

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 441
gcggccgcca acaacaacaa caattcctgc tcctcttctg ccctggaaca cgcttgcctt 60
ccccaaggct tccagaagct ctgaggcagg aggcaccaag ttctacctca cgtttggagg 120
atcttgctag ctatg 135

<210> SEQ ID NO 442
<211> LENGTH: 136
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 442
gcggccgccc agcagatcca gtgcttcctg ctcctcttct gccctggaac acgcttgcct 60
tccccaaggc ttccagaagc tctgaggcag gaggcaccaa gttctacctc acgtttggag 120
gatcttgcta gctatg 136

<210> SEQ ID NO 443
<211> LENGTH: 85
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 443
gcggccgcca acaacaacaa caacaacaac aacaacacgc ttgccttccc caagcttcca 60
caagcaacct caaacagaca ccatg 85

<210> SEQ ID NO 444
<211> LENGTH: 67
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 444
gcggccgcta ctaacaacac gcttgccttc cccaagcttc cacaagcaac ctcaaacaga 60
caccatg 67

<210> SEQ ID NO 445
<211> LENGTH: 85
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 445
gcggccgcgc ttcctgctcc tcttctgccc aggaacacgc ttgccttccc caagcttcca 60
caagcaacct caaacagaca ccatg 85

<210> SEQ ID NO 446
<211> LENGTH: 85

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 446
gcggccgcgc ttcctgctcc tcttctgccc tggaacacgc ttgccttccc caagcttcca 60
caagcaacct caaacagaca ccatg 85

<210> SEQ ID NO 447
<211> LENGTH: 85
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 447
gcggccgcta ctaacgctcc tcttctgccc tggaacacgc ttgccttccc caagcttcca 60
caagcaacct caaacagaca ccatg 85

<210> SEQ ID NO 448
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 448
ttaattaaca gtgttcacta gcatctaacc acttacatac catctaccac cgacaccatg 60

<210> SEQ ID NO 449
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 449
ttaattaaca gtgttcacta gcatctaacc acttacatac catctaccac cgccaccatg 60

<210> SEQ ID NO 450
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 450
ttaattaaca gtgttcacta gcatctaacc acttacatat tctgccgcct accatg 56

<210> SEQ ID NO 451
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 451
gcggccgcca taacagtgtt cactagcatc cccaacagac catctaccac cgacaccatg 60

<210> SEQ ID NO 452
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 452
gcggccgcca taacagtgtt cactagcatc ccccagacca tctaccaccg acaccatg 58

<210> SEQ ID NO 453
<211> LENGTH: 56
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 453
gcggccgcca taacagtgtt cactagcatc ccctaccatc taccaccgac accatg 56

<210> SEQ ID NO 454
<211> LENGTH: 61
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 454
gcggccgcca taacagtgtt cactagcatc cccaacagac ttacatacca ttgacaccat 60
g 61

<210> SEQ ID NO 455
<211> LENGTH: 56
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 455
gcggccgcca taacagtgtt cactagcatc cccacttaca taccattgac accatg 56

<210> SEQ ID NO 456
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 456
gcggccgcct taattaacaa caacaacaac aacaacaaca acaacaacca gtgttcacta 60
gcatcgacac catgatcccc gggg 84

<210> SEQ ID NO 457
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 457
gcggccgccc aacaacaaca acaacaacaa caacaacaac ttaattaaca gtgttcacta 60
gcatcgacac catgatcccc gggg 84

<210> SEQ ID NO 458
<211> LENGTH: 61
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 458
gtgtgttggt tttttgtgtg aacgggggag ggggaggaaa gggggagggg gagcggccgc 60
c 61

<210> SEQ ID NO 459
<211> LENGTH: 74
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 459
gtgtgttggt tttttgtgtg gtggtggatt ggttaacggg ggagggggag gaaaggggga 60
gggggagcgg ccgc 74

<210> SEQ ID NO 460
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 460
gtgtgttggt tttttgtgtg aacgggggag ggggaggaaa gggggagggg gagtggtggt 60
ggattggtgc ggccgc 76

<210> SEQ ID NO 461
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 461
gtgtgttggt tttttgtgtg aacgggggag ggggaggaaa gggggagggg gaggaaaggg 60
ggagggggag cggccgcc 78

<210> SEQ ID NO 462
<211> LENGTH: 95
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 462
gtgtgttggt tttttgtgtg aacgggggag ggggaggaaa gggggagggg gaggaaaggg 60
ggagggggag gaaaggggga gggggagcgg ccgcc 95

<210> SEQ ID NO 463
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 463
tggtggtgga atggt 15

<210> SEQ ID NO 464
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 464
tggtggtgga atggtaaatg gtggtggaat ggt 33

<210> SEQ ID NO 465
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 465
tggtggtgga atggtaaatg gtggtggaat ggtaaatggt ggtggaatgg taaatggtgg 60
tggaatggt 69

<210> SEQ ID NO 466
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 466
cacagaucug ggg 13

<210> SEQ ID NO 467
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 467
accagaucug ug 12

<210> SEQ ID NO 468
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 468
acagagaucu ggg 13

<210> SEQ ID NO 469
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 469
accagaucug ugug 14

<210> SEQ ID NO 470
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 470
cagacaaauc uggg 14

<210> SEQ ID NO 471
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 471
uaccagaucu gugug 15

<210> SEQ ID NO 472
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 472
cagcucacaa aucuggg 17

<210> SEQ ID NO 473
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 473
ccagaucugu guguug 16

<210> SEQ ID NO 474
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 474
cccacagcuc cugggcaacg ugc 23

<210> SEQ ID NO 475
<211> LENGTH: 182
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 475
ggucugugug cuggcccauc acuuuggcaa agaauuggcu agccacacac acaaaucugg 60
ggaggugaag aauacgacca ccugcaaaac auaccagauc ugugguuugg uuuuuugugu 120
guuaacgggg gagggggagg aaagggggag ggggaggaaa gggggagggg gaggaaaggg 180
gg 182

<210> SEQ ID NO 476
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 476
cacacagugg ggaggugaag aauacgacca ccugc 35

<210> SEQ ID NO 477
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 477
caaaacauac cacugugug 19

<210> SEQ ID NO 478
<211> LENGTH: 41
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 478
agugcaaaac auaccacugu guguugguuu uuugugugu a 41

<210> SEQ ID NO 479
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 479
ucacacagaa uacgaccacc ugcguu 26

<210> SEQ ID NO 480
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 480
uaccucuuau cuuccucugc aguuuuauac uucca 35

<210> SEQ ID NO 481
<211> LENGTH: 45
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 481
aauaaaguau aaagugcaaa acauaccacu gugguuggu uuuuu 45

<210> SEQ ID NO 482
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 482
agaauaagcg uuuuauacuu cca 23

<210> SEQ ID NO 483
<211> LENGTH: 53
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 483
uaauaaagua uaaagugcaa aacauaccac ugugguuugg uuuuuugugu guu 53

<210> SEQ ID NO 484
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 484
aauagaaccu gcguuuuaua cuuccac 27

<210> SEQ ID NO 485
<211> LENGTH: 53
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 485
cuaauaaagu auaaagugca aaacauacca cugugguuug guuuuuugug ugu 53

<210> SEQ ID NO 486
<211> LENGTH: 259
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 486
uuccucacac agaauacgac caccugcguu uuauacuucc acgagaucug gggaggugaa 60
gaauacgacc accuaauaag auuaccgaaa ggcaaucuua uuaaaacaua ccagaucuug 120 ugagggugu ugugcaaaa cauaccagau cgaauucgau cuggggaggu gaagaauacg 180
accaccugcu acaaguaccu aauaaaguau aaagugcaaa acauaccacu guguguuggu 240
uuuuugugug uuaacgggg 259

<210> SEQ ID NO 487
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 487
cuuuauacuu ccac 14

<210> SEQ ID NO 488
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 488
uaauaaagua uaaagugca 19

<210> SEQ ID NO 489
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 489
gcagaacuau acuuccac 18

<210> SEQ ID NO 490
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 490
cuaauaaagu auaaagugc 19

<210> SEQ ID NO 491
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 491
gcagaauuau acuucca 17

-continued

<210> SEQ ID NO 492
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 492
ccuaauaaag uauaaagugc 20

<210> SEQ ID NO 493
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 493
agauuuauac uuccac 16

<210> SEQ ID NO 494
<211> LENGTH: 249
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 494
uaccucuuau cuuccucugc aguuuuauac uuccacgaga ucuggggagg ugaagaauac 60
gaccaccuaa uaagauuacc gaaaggcaau cuuauuaaaa cauaccagau cuugugaggg 120
uguuuguggc aaaacauacc agaucgaauu cgaucugggg aggugaagaa uacgaccacc 180
ugcuacaagu accuaauaaa guauaaagug caaaacauac cacugugugu ugguuuuuug 240
uguguuaac 249

<210> SEQ ID NO 495
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 495
cacacagaat acg 13

<210> SEQ ID NO 496
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 496
cacacaggat acg 13

<210> SEQ ID NO 497
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 497
cacacagcat acg 13

<210> SEQ ID NO 498
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 498
cacacagatt acg 13

<210> SEQ ID NO 499
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 499
ttatcttcct cccacagctc ctgggcaacg tgctggtctg tgtgctggcc catcactttg 60
gcaaagaatt ggctagc 77

<210> SEQ ID NO 500
<211> LENGTH: 68
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 500
ttatcttcct cacacagaat acgaccgtct gtgtgctggc ccatcacttt ggcaaagaat 60
tggctagc 68

<210> SEQ ID NO 501
<211> LENGTH: 68
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 501
ttatcttcct cacacagcat acgaccgtct gtgtgctggc ccatcacttt ggcaaagaat 60
tggctagc 68

<210> SEQ ID NO 502
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 502
ctgcagcaca caaatctggg ga 22

<210> SEQ ID NO 503

<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 503
ctgcagtaca caaatctggg ga 22

<210> SEQ ID NO 504
<211> LENGTH: 48
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 504
ccucugcagc acacaaaucu ggggagguga agaauacgac caccugcg 48

<210> SEQ ID NO 505
<211> LENGTH: 30
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 505
ugcaaaacau accagaucug uguguugguu 30

<210> SEQ ID NO 506
<211> LENGTH: 48
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 506
ccucugcagu acacaaaucu ggggagguga agaauacgac caccugcg 48

<210> SEQ ID NO 507
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 507
gugcaaaaca uaccagaucu guguguuggu uu 32

<210> SEQ ID NO 508
<211> LENGTH: 52
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 508
ccucugcagc acacacacaa aucuggggag gugaagaaua cgaccaccug cg 52

<210> SEQ ID NO 509
<211> LENGTH: 44

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 509
ugcaaaacau accagaucug uguguugguu uuuugugugu uaac 44

<210> SEQ ID NO 510
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 510
ctgcagctcc tcacctacgc cacacacaca aatctgggga 40

<210> SEQ ID NO 511
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 511
ctgcaggcac acacacaaat ctgggga 27

<210> SEQ ID NO 512
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 512
ctgcagggca cacacacaaa tctgggga 28

<210> SEQ ID NO 513
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 513
ugcagggcac acacacaaau cugggg 26

<210> SEQ ID NO 514
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 514
accagaucug uguguug 17

<210> SEQ ID NO 515
<211> LENGTH: 26
<212> TYPE: RNA

-continued

<213> ORGANISM: Artificial Sequence
<220> FEATURE:
<223> OTHER INFORMATION: Description of Artificial Sequence: Synthetic
      oligonucleotide

<400> SEQUENCE: 515
cugcaggcac acacacaaau cugggg 26

<210> SEQ ID NO 516
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
auaccagauc uguguguugg uuuuuugugu guuaacgg 38

<210> SEQ ID NO 517
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 517
cugcagcucc ucaccuacgc cacacacaca aaucugggga ggugaagaau acgaccaccu 60
gc 62

<210> SEQ ID NO 518
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 518
gcaaaacaua ccagaucugu guguugguuu uuugugugu aacgg 45

<210> SEQ ID NO 519
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 519
ccucugcagc acacacacaa aucuggggag gugaagaaua cgaccaccug cg 52

<210> SEQ ID NO 520
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 520
ugcaaaacau accagaucug uguguugguu uuuugugugu uaac 44

<210> SEQ ID NO 521
<211> LENGTH: 126

<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (121)..(123)
<223> OTHER INFORMATION: a, c, t, g, unknown or other

<400> SEQUENCE: 521
gtgagtctat gccagctacc attctgcttt tattttatgg ttgggataag gctggattat 60
tctgagtcca agctaggccc ttttgctaat catcttcata cctcttatct tcctctgcag 120 nnnaca 126

<210> SEQ ID NO 522
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 522
caacaactac taacataaca gtgttcacta gcaacctcaa acagacacca tg 52

<210> SEQ ID NO 523
<211> LENGTH: 55
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 523
caacaactcc tgtgcttata acagtgttca ctagcaacct caaacagaca ccatg 55

<210> SEQ ID NO 524
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 524
caacaacata accctgttca ctagcaacct caaacagaca ccatg 45

<210> SEQ ID NO 525
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 525
caacaacata aaagtgttca ctagcaacct caaacagaca ccatg 45

<210> SEQ ID NO 526
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:

<221> NAME/KEY: modified_base
<222> LOCATION: (31)..(33)
<223> OTHER INFORMATION: a, c, t, g, unknown or other

<400> SEQUENCE: 526
gcggccgcct taattaacag tgttcactag nnncaacaac aacaacaaca acaacaacaa 60
caacgacacc atg 73

<210> SEQ ID NO 527
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 527
gcggccgcca taacagtgtt cactagcatc ccccagacca tctaccaccg acaccatg 58

<210> SEQ ID NO 528
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 528
gcggccgcca taacagtgtt cactagtagc ccccagacca tctaccaccg acaccatg 58

<210> SEQ ID NO 529
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 529
gcggccgcca taacagtgtt cactagaacc ccccagacca tctaccaccg acaccatg 58

<210> SEQ ID NO 530
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 530
gcggccgcca taacagtgtt cactagaccc ccccagacca tctaccaccg acaccatg 58

<210> SEQ ID NO 531
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 531
gcggccgcca taacagtgtt cactagcccc ccccagacca tctaccaccg acaccatg 58

<210> SEQ ID NO 532
<211> LENGTH: 58
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 532
gcggccgcca taacagtgtt cactagagcc ccccagacca tctaccaccg acaccatg 58

<210> SEQ ID NO 533
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 533
gcggccgcca taacagtgtt cactagcctc ccccagacca tctaccaccg acaccatg 58

<210> SEQ ID NO 534
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 534
gcggccgcca taacagtgtt cactagtctc ccccagacca tctaccaccg acaccatg 58

<210> SEQ ID NO 535
<211> LENGTH: 120
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 535
gtgagtctat gccagctacc attctgcttt tattttatgg ttgggataag gctggattat 60
tctgagtcca agctaggccc ttttgctaat catcttcata cctcttatct tcctctgcag 120

<210> SEQ ID NO 536
<211> LENGTH: 140
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 536
gtgagtctat gttgctaata gcagctacaa tccagctacc attctgcttt tattttatgg 60
ttgggataag gctggattat tctgagtcca agctaggccc ttttgctaat catcttcata 120
cctcttatct tcctctgcag 140

<210> SEQ ID NO 537
<211> LENGTH: 160
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 537
gtgagtctat gctgatgtaa gaggtttcat attgctaata gcagctacaa tccagctacc 60
attctgcttt tattttatgg ttgggataag gctggattat tctgagtcca agctaggccc 120
ttttgctaat catcttcata cctcttatct tcctctgcag 160

<210> SEQ ID NO 538
<211> LENGTH: 180
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 538
gtgagtctat gtttctgcat ataaattgta actgatgtaa gaggtttcat attgctaata 60
gcagctacaa tccagctacc attctgcttt tattttatgg ttgggataag gctggattat 120
tctgagtcca agctaggccc ttttgctaat catcttcata cctcttatct tcctctgcag 180

<210> SEQ ID NO 539
<211> LENGTH: 200
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 539
gtgagtctat gaatatttct gcatataaat atttctgcat ataaattgta actgatgtaa 60
gaggtttcat attgctaata gcagctacaa tccagctacc attctgcttt tattttatgg 120
ttgggataag gctggattat tctgagtcca agctaggccc ttttgctaat catcttcata 180
cctcttatct tcctctgcag 200

<210> SEQ ID NO 540
<211> LENGTH: 124
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 540
gtgagtctat gccagctacc attctgcttt tattttatgg ttgggataag gctggattat 60
tctgagtcca agctaggccc ttttgctaat catcttcata ctaacctctt atcttcctct 120
gcag 124

<210> SEQ ID NO 541
<211> LENGTH: 120
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 541
gtgagtctat gccagctacc attctgcttt tattttatgg ttgggataag gctggattat 60
tctgagtcca agctactaac ttttcctgtg cttcttcaga cctcttatct tcctctgcag 120

<210> SEQ ID NO 542
<211> LENGTH: 86
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 542
gcggccgcca acaacaacaa caacaacaac aacaacaaca acaacaacat aacagtgttc 60
actagcaacc tcaaacagac accatg 86

<210> SEQ ID NO 543
<211> LENGTH: 248
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 543
cuucauaccu cuuaucuucc ucugcagaug uuccucgaga ucuggggagg ugaagaauac 60
gaccaccuaa uaagauuacc gaaaggcaau cuuauuaaaa cauaccagau cuugagaggg 120
uguuuguggc aaaacauacc agaucgaauu cgaucugggg aggugaagaa uacgaccacc 180
ugcuacaagu accuaauaaa cauuagcgga gaaacauacc acuguguguu gguuuuuugu 240
guguuaac 248

<210> SEQ ID NO 544
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 544
gcggccgcca taacagtgtt cactagcaac ctcaaacaga caccatg 47

<210> SEQ ID NO 545
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 545
gcggccgcca ccatgataac agtgttcact agcaacctca aacagacacc atg 53

<210> SEQ ID NO 546
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 546
gcggccgcca taacagtgtt cactagcaac cccaaacaga caccatg 47

<210> SEQ ID NO 547
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 547
gcggccgcca ccataacagt gttcactagc aaccccaaac agacaccatg 50

<210> SEQ ID NO 548
<211> LENGTH: 53
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 548
gcggccgcca ccatgataac agtgttcact agcaacccca aacagacacc atg 53

<210> SEQ ID NO 549
<211> LENGTH: 53
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 549
gcggccgcca ccacgataac agtgttcact agcaacccca aacagacacc atg 53

<210> SEQ ID NO 550
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 550
gcggccgcca ccataacagt gttcactagc atccccaaac agacaccatg 50

<210> SEQ ID NO 551
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 551
gcggccgcca ccataacagt gttcaccagc atccccaaac agacaccatg 50

<210> SEQ ID NO 552
<211> LENGTH: 47
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 552
gcggccgcca taacagtgtt cactagcatc cccaaacaga caccatg 47

<210> SEQ ID NO 553
<211> LENGTH: 47
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 553

-continued gcggccgcca taacagtgtt caccagcatc cccaaacaga caccatg 47

<210> SEQ ID NO 554
<211> LENGTH: 240
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 554
cucuuaucuu ccucugcaga uguuccucga gaucugggga ggugaagaau acgaccaccu 60
aauaagauua ccgaaaggca aucuuauuaa aacauaccag aucuugagag gguguuugug 120
gcaaaacaua ccagaucgaa uucgaucugg ggaggugaag aauacgacca ccugcuacaa 180
guaccuaaua aacauuagcg gagaaacaua ccacugugug uugguuuuuu guguguuaac 240

<210> SEQ ID NO 555
<211> LENGTH: 245
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 555
cacaaucugg ggaggugaag aauacgacca ccugcguuuu auacuuccac gagaucuggg 60
gaggugaaga auacgaccac cuaauaagau ugccgaaagg caaucuuauu aaaacauacc 120
agaucuugug agggguguuug uggcaaaaca uaccagaucg aauucgaucu ggggagguga 180
agaauacgac caccugcuac aaguaccuaa auaaaguaua aagugcaaaa cauaccagau 240
cugug 245

<210> SEQ ID NO 556
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 556
uggggaggug 10